US011311575B2

(12) United States Patent
Galetto et al.

(10) Patent No.: US 11,311,575 B2
(45) Date of Patent: *Apr. 26, 2022

(54) METHODS FOR ENGINEERING HIGHLY ACTIVE T CELL FOR IMMUNOTHERAPY

(71) Applicant: CELLECTIS, Paris (FR)

(72) Inventors: Roman Galetto, Paris (FR); Agnes Gouble, Paris (FR); Stephanie Grosse, Saint Cyr sur Morin (FR); Cécile Schiffer-Mannioui, Villiers sur Marne (FR); Laurent Poirot, Paris (FR); Andrew Scharenberg, Seattle, WA (US); Julianne Smith, Le Plessis Robinson (FR)

(73) Assignee: CELLECTIS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,426

(22) PCT Filed: May 13, 2014

(86) PCT No.: PCT/IB2014/061412
§ 371 (c)(1),
(2) Date: Nov. 27, 2015

(87) PCT Pub. No.: WO2014/184744
PCT Pub. Date: Nov. 20, 2014

(65) Prior Publication Data
US 2016/0120906 A1    May 5, 2016

Related U.S. Application Data

(63) Continuation-in-part of application No. 13/892,805, filed on May 13, 2013, and a continuation-in-part of application No. PCT/US2013/040755, filed on May 13, 2013, and a continuation-in-part of application No. PCT/US2013/040766, filed on May 13, 2013.

(60) Provisional application No. 61/907,858, filed on Nov. 22, 2013.

(51) Int. Cl.
| A61K 48/00 | (2006.01) |
| C07H 21/04 | (2006.01) |
| A61K 35/17 | (2015.01) |
| C12N 9/22 | (2006.01) |
| C12N 5/0783 | (2010.01) |
| A01K 67/00 | (2006.01) |
| A61K 35/12 | (2015.01) |

(52) U.S. Cl.
CPC ............ *A61K 35/17* (2013.01); *C12N 5/0636* (2013.01); *C12N 9/22* (2013.01); *A61K 2035/124* (2013.01); *C07K 2319/80* (2013.01); *C12N 2501/39* (2013.01); *C12N 2501/51* (2013.01); *C12N 2501/515* (2013.01); *C12N 2501/599* (2013.01); *C12N 2502/99* (2013.01); *C12N 2510/00* (2013.01)

(58) Field of Classification Search
CPC combination set(s) only.
See application file for complete search history.

(56) References Cited

U.S. PATENT DOCUMENTS

| 8,906,682 | B2 * | 12/2014 | June et al. | |
| 9,597,357 | B2 * | 3/2017 | Gregory | A61K 35/26 |
| 10,426,795 | B2 * | 10/2019 | Galetto | C07K 14/70578 |
| 2007/0286857 | A1 * | 12/2007 | Arthaud | C07K 16/2893 |
| | | | | 424/133.1 |
| 2010/0055102 | A1 | 3/2010 | Langermann | |
| 2011/0301073 | A1 | 12/2011 | Gregory et al. | |
| 2013/0071403 | A1 * | 3/2013 | Rolland | A61K 39/39558 |
| | | | | 424/142.1 |
| 2013/0196373 | A1 | 8/2013 | Gregory et al. | |
| 2013/0315884 | A1 | 11/2013 | Galetto et al. | |
| 2014/0349402 | A1 * | 11/2014 | Cooper | A61K 39/0011 |
| | | | | 435/455 |

OTHER PUBLICATIONS

Carrasco et al. An endoplasmic reticulum retention function of the cytoplasmic tail of the human pre-T cell receptor (TCR) alpha chain. J. Exp. Med. 193:1045-1057, 2001.*
Barber et al. Cutting edge: The expression in vivo of a second isoform of pTalpha. J. immunol. 161:11-16, 1998.*
John et al. Blockade of PD-1 immunosuppression boosts CAR T-cell therapy. Oncolmmunology 2: e26286-1 to e26286-3, (Year: 2013).*
Cartellieri et al. Chimeric Antigen Receptor-Engineered T Cells for Immunotherapy of Cancer. Journal of Biomedicine and Biotechnology, vol. 2010, Article ID 956304, pp. 1-13, (Year: 2010).*
Sadelain et al., Jan. 2003, Nature Reviews.*
Mizogucehi et al: "Pathogenic role of IL-4, but not IFN-gamma in colitis of TCR alpha knockout mice", GASTROENTEROLOGY, vol. 114, Apr. 15, 1998, p. A104.

(Continued)

*Primary Examiner* — Quang Nguyen
(74) *Attorney, Agent, or Firm* — Arrigo, Lee, Guttman & Mouta-Bellum LLP

(57) ABSTRACT

The present invention relates to methods for developing engineered T-cells for immunotherapy and more specifically to methods for modifying T-cells by inactivating at immune checkpoint genes, preferably at least two selected from different pathways, to increase T-cell immune activity. This method involves the use of specific rare cutting endonucleases, in particular TALE-nucleases (TAL effector endonuclease) and polynucleotides encoding such polypeptides, to precisely target a selection of key genes in T-cells, which are available from donors or from culture of primary cells. The invention opens the way to highly efficient adoptive immunotherapy strategies for treating cancer and viral infections.

Figure 1:
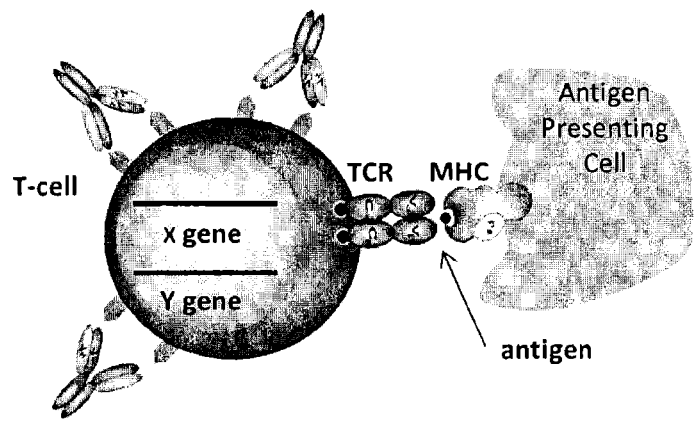

15 Claims, 41 Drawing Sheets
Specification includes a Sequence Listing.

(56) References Cited

OTHER PUBLICATIONS

Torkiai et al: "A foundation for universal T-cell based immunotherapy:T cells engineered to express a CD 19-specific chimeric-antigen-receptor and eliminate expression of endogenous TCR", Blood, vol. 119, No. 24, Jun. 14, 2012, pp. 5697-570.
Cooper et al: "Combining checkpoint inhibitors and BRAF-targeted agents against metastatic melanoma", ONCOIMMUNOLOGY, vol. 2, No. 5, May 1, 2013, p. e2432.
Miller et al: A Tale nuclease architecture for efficient genome editing, Nature Biotechnology, vol. 29, No. 2, Feb. 1, 2011 (Feb. 1, 2011), pp. 143-14.
Mahfouz et al: "De novo-engineered transcription activator-like effector (TALE) hybrid nuclease with novel DNA binding specificity creates double-strand breaks", Proceedings of the National Acadamy of Sciences, vol. 108, No. 6, Feb. 8, 2011, pp. 2623-262.
Kebriaei et al: "Infusing CD19-Directed T Cells to Augment Disease Control in Patients Undergoing Autologous Hematopoietic Stem-Cell Transplantation for Advanced B-Lymphoid Malignancies", Human Gene Therapy, vol. 23 No. 5, May 1, 2012 , pp. 444-450.
Kim et al., "Synergistic Inhibition of T-cell Activation by a Cell-permeable ZAP-70 Mutant and ctCTLA-4", Biochem and Biophys Res Comm, 381(3):355-360 (2009).
Osterborg et al., "Clonal CD*+ and CD52-T Cels are Induced in Responding B Cell Lymphoma Patients Treated with Campath-1H (anti-CD52)", European Journal of Haematology, 58(1):5-13 (1997).
Greenwald et al., Negative Co-Receptors on Lymphocytes, Current Opinion in Immunology, 14(3): 391-396 (2002).
Ahmadzadeh et al., Tumor antigen-specific CD8 T cells infiltrating the tumor express high levels of PD-1 and are functionally impaired, BLOOD, Aug. 20, 2009, vol. 114, No. 8, 1537-1544.
Beatty et al., Chimeric antigen receptor T cells are vulnerable to immunosuppressive mechanisms present within the tumor microenvironment, Oncolmmunology 3:11, e970027; Nov. 1, 2014, 1-3.
Long et al., 4-1BB Costimulation Ameliorates T Cell Exhaustion Induced by Tonic Signaling of Chimeric Antigen Receptors, Nat Med. Jun. 2015 ; 21(6): 581-590.
Chmielewski et al., Antigen-specific T-cell activation independently of the MHC: chimeric antigen receptor-redirected T cells, Frontiers in Immunology—Tumor Immunity, Nov. 2013, vol. Article 371, 1-7.
Stone et al, T-cell receptor binding affinities and kinetics: impact on T-cell activity and specificity, Immunology, 126, 165-176.
Nicholson et al., Construction and Characterisation of a Functional CD19 Specific Single Chain Fv Fragment for Immunotherapy of B Lineage Leukaemia and Lymphoma, Molecuiur Immunology, vol. 34, No. 1617, pp. 1157-1165, 1997.
Francisco et al., The PD-1 Pathway in Tolerance and Autoimmunity, Immunol Rev. Jul. 2010 ; 236: 219-242, 2009.
Sadelain et al., The basic principles of chimeric antigen receptor (CAR) design, Cancer Discov. Apr. 2013 ; 3(4): 388-398.
Finney et al., Activation of Resting Human Primary T Cells with Chimeric Receptors: Costimulation from CD28, Inducible Costimulator, CD134, and CD137 in Series with Signals from the TCR Chain, J Immunol 2004; 172:104-113.
Imai et al., Chimeric receptors with 4-1BB signaling capacity provoke potent cytotoxicity against acute lymphoblastic leukemia, Leukemia (2004) 18, 676-684.
Milone et al., Chimeric Receptors Containing CD137 Signal Transduction Domains Mediate Enhanced Survival of T Cells and Increased Antileukemic Efficacy In Vivo, Molecular Therapy vol. 17 No. 8, 1453-1464 Aug. 2009.
Freeman et al., Engagement of the PD-1 Immunoinhibitory Receptor by a Novel B7 Family Member Leads to Negative Regulation of Lymphocyte Activation, J. Exp. Med., vol. 192, No. 7, Oct. 2, 2000 1027-1034.
John et al., Anti-PD-1 Antibody Therapy Potently Enhances the Eradication of Established Tumors By Gene-Modified T Cells, Clin Cancer Res; 19(20) Oct. 15, 2013, 5636-5646.
Moon et al., Multifactorial T-cell Hypofunction That Is Reversible Can Limit the Efficacy of Chimeric Antigen Receptor-Transduced Human T cells in Solid Tumors, Clin Cancer Res; 20(16) Aug. 15, 2014, 4262-4273.

* cited by examiner

| | LEFT HALF TARGET | Spacer size (bp) | RIGHT HALF TARGET | |
|---|---|---|---|---|
| TRAC | TTGTCCCACAGATATCC | 15 | CCGTGTACCCAGCTGAGA | |
| CD52 | TTCCTCCTACTCACCAT | 15 | GGTACAGGTAAGAGCAA | |
| Potential offsite targets | Left matched sequence | Spacer size (bp) | Right matched sequence | Mismatches |
| 1 | ttgctctCaccAgtaTA | 25 | TTtTcaggtaagTgcaa | 8 |
| 2 | tCActcttacctgGacc | 19 | CCtacaggttaagGgcCa | 7 |
| 3 | tctcagAtgAtacacCC | 24 | AgtacaggCaTgagcCa | 8 |
| 4 | tGAtcccacagaAatAc | 18 | gCatTtctgtgggaTCa | 8 |
| 5 | ttCctctAacctgtaTT | 25 | gAtCcaggtaagGTcaa | 8 |
| 6 | tAgtcccCcagatatGA | 19 | aAggtgTgGaTgaggaa | 8 |
| 7 | ttgtcAcacaTataCcG | 21 | TgGtatTtgtgTgacaa | 8 |
| 8 | tAActcttacctgtaGT | 16 | AgatTtctCtgggGcaa | 8 |
| 9 | ttActccAactAacTat | 16 | ccgtTtaccGgctTaga | 7 |
| 10 | tGgctcAtacctgtaGT | 14 | aGgAtgagGTggaggaa | 8 |
| 11 | ttgctcAtacAtgtGcA | 21 | atgCtgTgtaggTggTa | 8 |
| 12 | ttgtcccacagaCatTc | 18 | ccACgtaGcagctgGga | 6 |
| 13 | tcAcaCctggtacaTAg | 27 | GtgTtTagtaggGggaa | 8 |
| 14 | ttgtcccacagCtaCcc | 29 | gAgtCtTtgtAggacaa | 6 |
| 15 | tctcaActgAAacaAgg | 23 | TgtaAtgTCaagagcaa | 8 |

*Fig. 9A*

|  | Control transfection (no RNA) | | | CD52-TALEN+TRAC-TALEN transfection | | |
|---|---|---|---|---|---|---|
|  | Nb seq analyzed | Nb indels | Frequency indels(less than) | Nb seq analyzed | Nb indels | Frequency indels(less than) |
|  | 3965 | 0 | 2.52E-04 | 7560 | 3371 | 0.44 |
|  | 1046 | 0 | 9.56E-04 | 2266 | 1056 | 0.47 |
| Matched sequence |  |  |  |  |  |  |
| CD52-R_TRAC-R | 7132 | 0 | 1.4E-04 | 7644 | 1 | 1.3E-04 |
| CD52-R_TRAC-R | 6431 | 0 | 1.6E-04 | 7377 | 2 | 2.7E-04 |
| CD52-R_TRAC-R | 2771 | 0 | 3.6E-04 | 2704 | 0 | 3.7E-04 |
| TRAC-L_CD52-L | 5525 | 0 | 1.8E-04 | 4739 | 0 | 2.1E-04 |
| CD52-R_TRAC-R | 27958 | 0 | 3.6E-05 | 16646 | 0 | 6.0E-05 |
| TRAC-L_CD52-L | 22456 | 0 | 4.5E-05 | 32912 | 10 | 3.0E-04 |
| TRAC-L_CD52-L | 8275 | 0 | 1.2E-04 | 5629 | 0 | 1.8E-04 |
| TRAC-L_CD52-R | 23253 | 0 | 4.3E-05 | 22054 | 16 | 7.3E-04 |
| CD52-L_TRAC-R | 13371 | 0 | 7.5E-05 | 13688 | 1 | 7.3E-05 |
| CD52 | 22856 | 0 | 4.4E-05 | 31292 | 0 | 3.2E-05 |
| CD52 | 3238 | 1 | 3.1E-04 | 3064 | 0 | 3.3E-04 |
| TRAC | 4530 | 0 | 2.2E-04 | 4652 | 0 | 2.1E-04 |
| CD52-L_TRAC-R | 17361 | 0 | 5.8E-05 | 14454 | 0 | 6.9E-05 |
| TRAC-L_CD52-L | 32823 | 0 | 3.0E-05 | 33911 | 1 | 2.9E-05 |
| CD52-R_TRAC-R | 6479 | 0 | 1.5E-04 | 6088 | 0 | 1.6E-04 |

*Fig. 9B*

METHODS FOR ENGINEERING HIGHLY ACTIVE T CELL FOR IMMUNOTHERAPY

FIELD OF THE INVENTION

The present invention relates to methods for developing engineered T-cells for immunotherapy and more specifically to methods for modifying T-cells by inactivating, immune checkpoint genes, preferably at least two selected from different pathways, to circumvent inhibitory mechanisms and enhance T-cell immune activity. This method involves the use of specific rare cutting endonucleases, in particular TALE-nucleases (TAL effector endonuclease) and polynucleotides encoding such polypeptides, to precisely target a selection of key genes in T-cells, which are available from donors or from culture of primary cells. The invention opens the way to highly efficient adoptive immunotherapy strategies for treating cancer and viral infections.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors (Jena, Dotti et al. 2010).

T-cell mediated immunity includes multiple sequential steps regulated by a balance between co-stimulatory and inhibitory signals that fine-tune the immune response. The inhibitory signals referred to as immune checkpoints are crucial for the maintenance of self-tolerance and also to limit immune-mediated collateral tissue damage. The ability of tumours to co-opt these inhibitory pathways represents an important mechanism in immune resistance and limits the success of immunotherapy. One of the promising approaches to activate a therapeutic T-cell immune response is the blockade of these immune checkpoints (Pardoll 2012). Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics.

Cytotoxic-T-lymphocyte-associated antigen 4 (CTLA-4; also known as CD152) downregulates the amplitude of T cell activation and treatment with antagonist CTLA4 antibodies (ipilimumab) has shown a survival benefit in patients with melanoma (Robert and Mateus 2011). Programmed cell death protein 1 (PD1 or PDCD1 also known as CD279) represents another very promising target for immunotherapy (Pardoll and Drake 2012; Pardoll 2012). In contrast to CTLA-4, PD1 limits T cell effector functions in peripheral tissue at the time of an inflammatory response to infection and limits autoimmunity. The first clinical trial with PD1 antibody shows some cases of tumour regression (Brahmer, Drake et al. 2010). Multiple additional immune checkpoint proteins represent promising targets for therapeutic blockade based on recent studies.

Although the precise molecular pathways by which these immune checkpoint proteins signal are poorly understood, immune-checkpoint proteins seem to use distinct mechanisms to inhibit T-cell activation and are potentially non-redundant. Use of at least two different antibodies to block multiple immune checkpoint ligands or receptors has been shown to produce synergic antitumor activities. Nevertheless, the rate of adverse events was increased among patients treated with a combination CTLA-4/PD-1 antibody therapy (Wolchok, Kluger et al.).

To avoid the adverse events of antibody tumor treatments, the inventors sought to engineer highly active T-cells for immunotherapy by inactivating at least two genes encoding immune-checkpoint proteins. Contrary to the immune-checkpoint blockade mediated by antibody treatment, checkpoint signal pathways are blocked specifically in engineered T-cells used for immunotherapy and the adverse events due to non-specific effects of the antibodies on the patient's immune system are avoided.

In particular, this was made possible by gene inactivation using specific TALE-nucleases directed against at least two immune checkpoint proteins, such as PD1 and CTLA-4. Inactivation of immune checkpoint genes in T lymphocytes permits significant proliferation and activity of the introduced lymphocytes. Thus, these modified T cells are expected to be highly active in patient's blood, where they can target tumor cells or infected cells.

In addition to the above conception of genetically modified T cells, which can be highly active, the inventors, by the use and design of specific TALE-nucleases, have concomitantly inactivated different genes in T-cells, thereby obtaining at least double mutants. As a matter of fact, double gene targeting by double-strand break has been so far unachieved in T cells due to the difficulty of yielding and maintaining T-cells in culture over time, to their low transformation rates, and loss during selection procedures. These difficulties result in a low probability of success for obtaining such cells.

Thus, one significant part of the invention is to have designed specific TALE-nucleases, allowing higher rates of DSB events within T-cells, which are well tolerated by the cells (especially upon co-transfection) and are able to target the selection of genes according to the invention. By using rare-cutting endonucleases, such as the TALE-nucleases described therein, the probability of obtaining double inactivation of the genes in the transfected T-cells was significantly increased, so that it now appears possible to produce engineered T cells available from donors on a regular basis, using standard procedures.

SUMMARY OF THE INVENTION

In one aspect, the present invention discloses methods to engineer T cells to make them suitable for immunotherapy purposes. The methods of the present invention more particularly allow the precise modification of the genome of cells relevant for immunotherapy by inactivating or replacing genes encoding immune checkpoint proteins. In certain embodiments, the modified cells relevant for immunotherapy further comprise exogenous recombinant polynucleotides encoding Chimeric Antigen Receptors (CAR) for specific cell recognition. In another aspect, the present invention relates to the polypeptides and the polynucleotides, which encode the rare-cutting endonucleases, to precisely target the above genes encoding immune checkpoint proteins, thereby enabling the genetic modification of the T-cells for immunotherapy. The present invention provides more particularly specific target sequences within these genes and TALE-nucleases designed to respectively target those genes.

The present invention also relates to the isolated cells or cell lines comprising any of the proteins, polypeptides or vectors described herein. In certain embodiments, the T cells of the present invention comprise inactivated immune checkpoint genes for their use in immunotherapy In a preferred embodiment, the modified T cells are used as a therapeutic product, ideally as an "off the shelf" product. In this respect, the T-cells according to the invention can be further genetically modified, for instance by inactivating at least one gene encoding a component of TCR (T cell receptor), to make the cells allogeneic and thereby suited for treating different patients from one donor's sample.

In a further aspect, the present invention concerns the method for treating or preventing cancer or infections in the patient by administrating an engineered T-cell obtainable by the above methods.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Schematic representation of the normal relationship between T-cells and antigen presenting cell.

Figure 2:
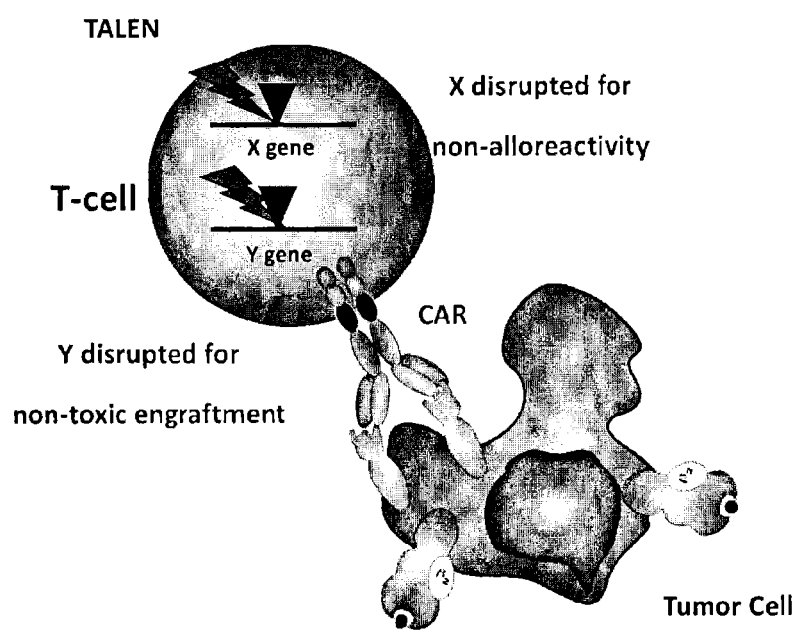

FIG. 2: Schematic representation of the genetically modified therapeutic T-cells according to the invention and the patient's tumor cells.

Figure 3:
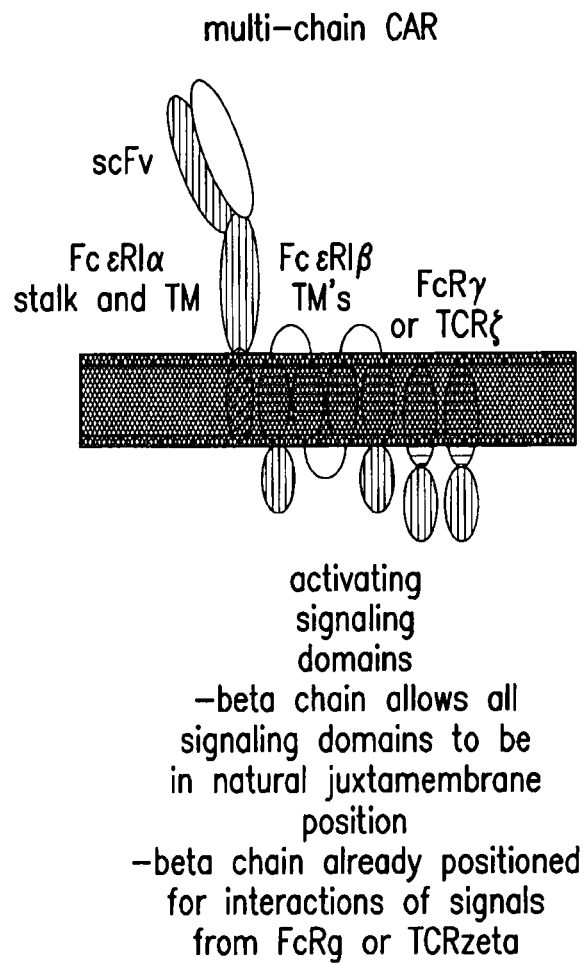

FIG. 3: Schematic representation of multi-chain CAR.

FIG. 4: Schematic of different versions of multi-chain CARs. A. Schematic of the FcεRI receptor. B-C Different versions of multi-chain CARs (csm1 to csm10) comprising a scFv and a CD8 stalk region fused to the transmembrane domain of FcεRI alpha chain. At least one 41BB, CD28 and/or CD3 zeta domains can be fused to a FcεRI alpha, beta and/or gamma chain.

Figure 5:
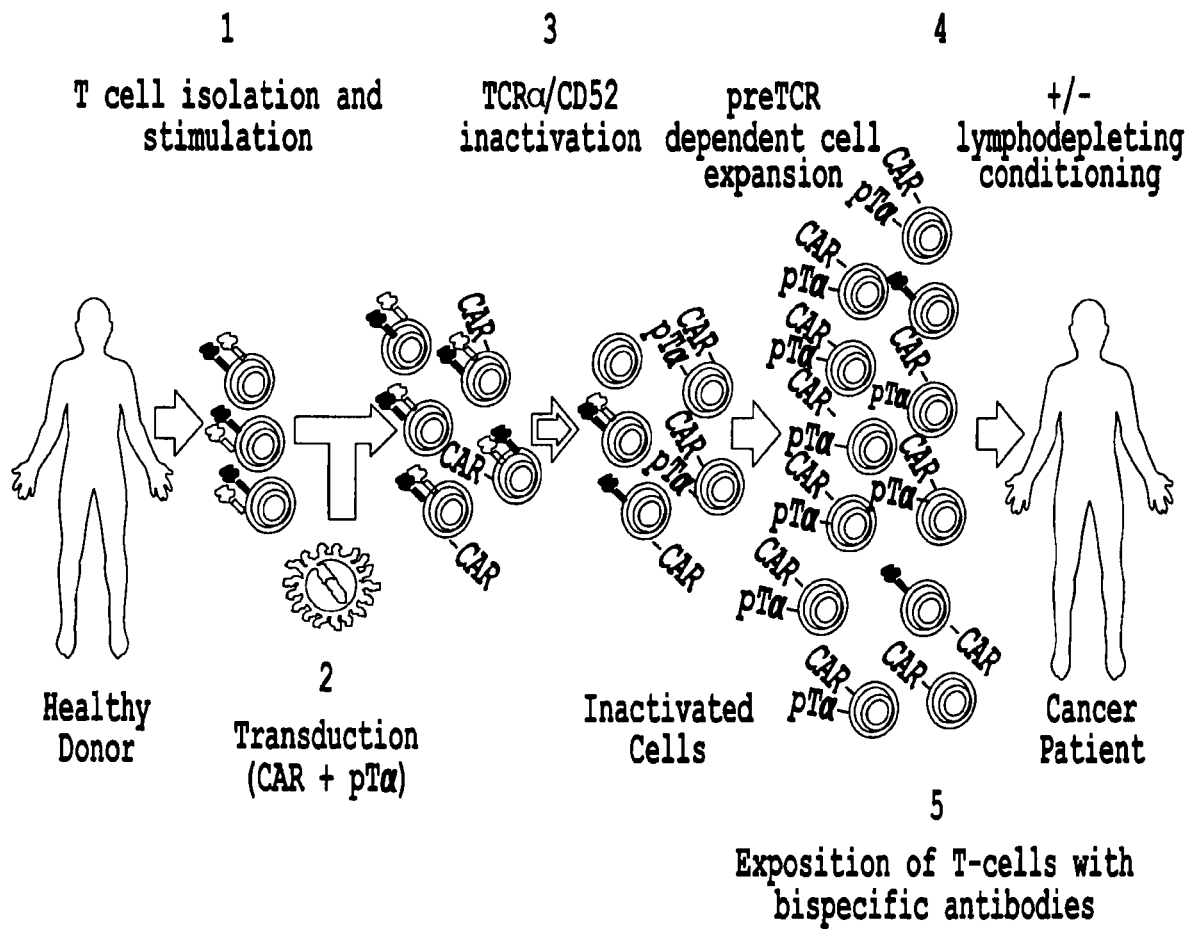

FIG. 5: Schematic representation of one example of the method of engineering human allogenic cells for immunotherapy FIG. 6: Concentration in cells per milliliter of live CD52-positive or CD52-negative cells after treatment with anti-CD52 antibody (CAMPATH1-H) with complement or controls.

Figure 7:
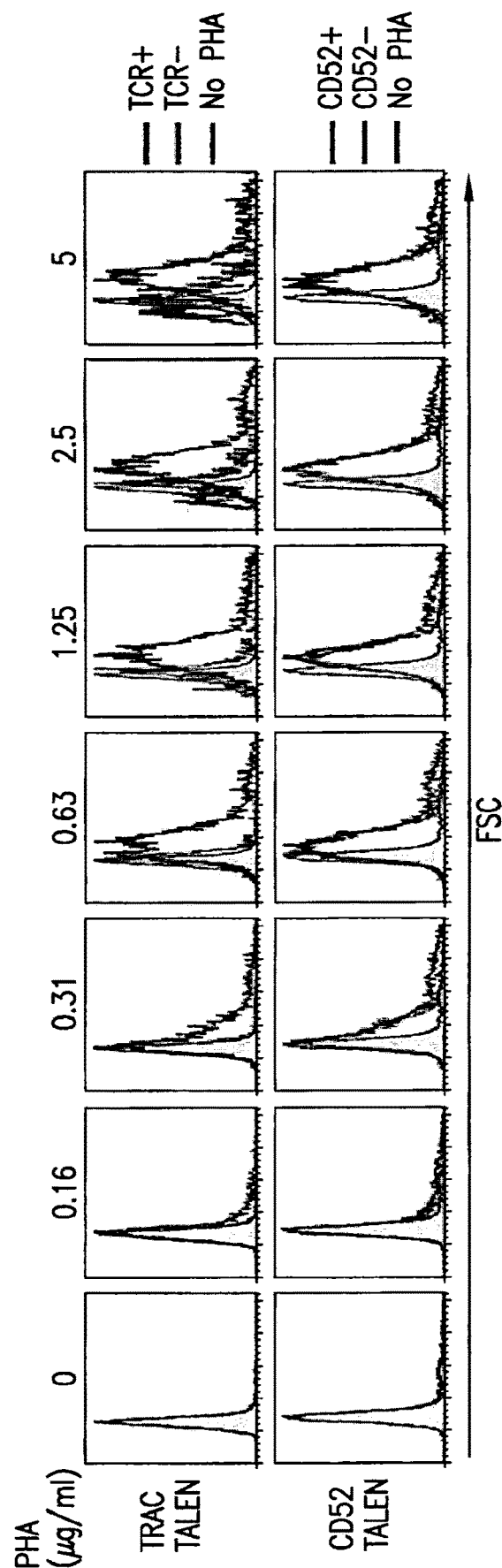
Figure 8A:
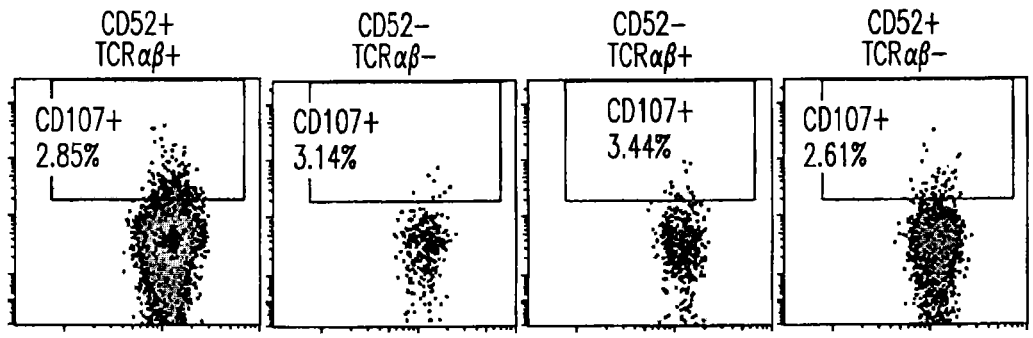
Figure 8B:
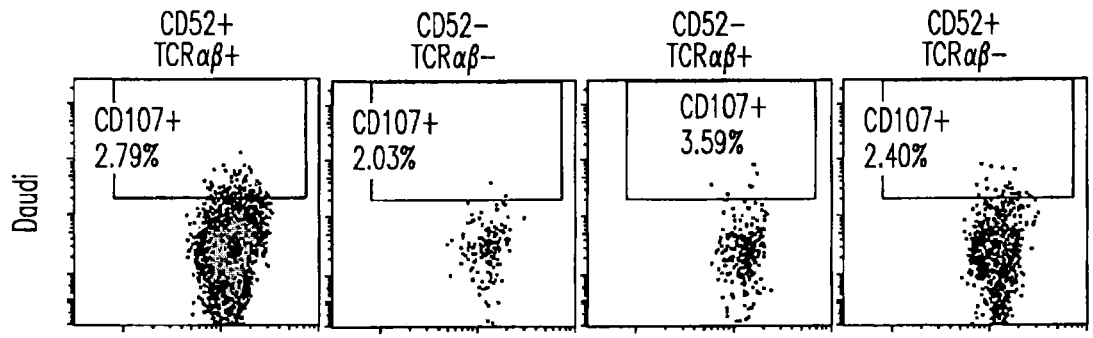
Figure 8C:
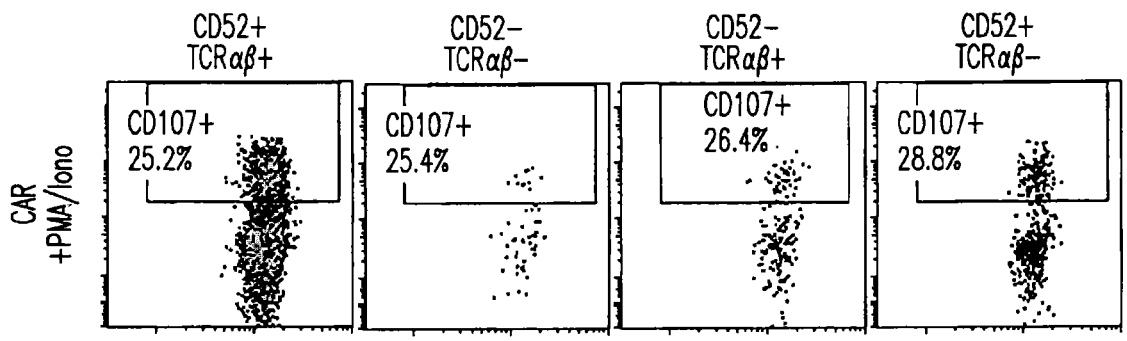
Figure 8D:
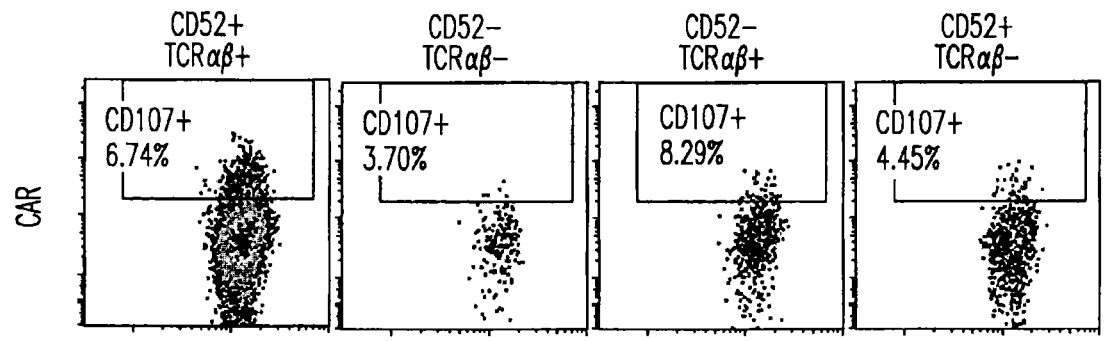
Figure 8E:
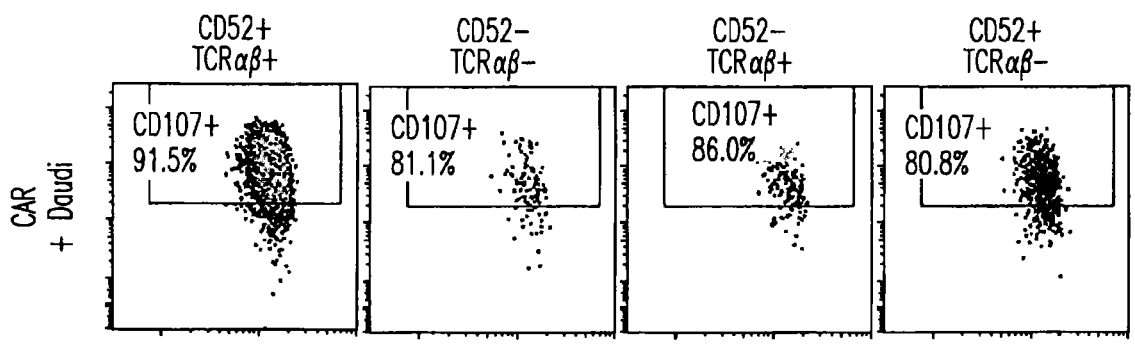

FIG. 7: Comparison of the forward side scatter (FSC) distribution, an indicator of cell size, between TCR-positive and TCR-negative cells, or between CD52-positive and CD52-negative cells, and non activated cells as control.

FIG. 8: Flow cytometry analysis of CD107a expression (marker of degranulation) on targeted CD52 and TCRalpha inactivated T cells. CD107 expression is analyzed on CD52+ TCRαβ+ cells (first column), CD52-TCRαβ– cells (second column), CD52-TCRαβ+ cells (third column) and CD52+ TCRαβ– cells (fourth column) before (A) and after incubation with Daudi cells (B); C) represents flow cytometry analysis of T cells further transfected with a CAR and incubated with Daudi cells; D) represents flow cytometry analysis of T cells transfected with a CAR but not incubated with Daudi cells and E) represents flow cytometry analysis of T cells transfected with a CAR and treated to PMA/ionomycin (positive control).

FIG. 9: Deep sequencing analysis of CD52 and TRAC TALE-nucleases potential off-site targets.

Figure 10:
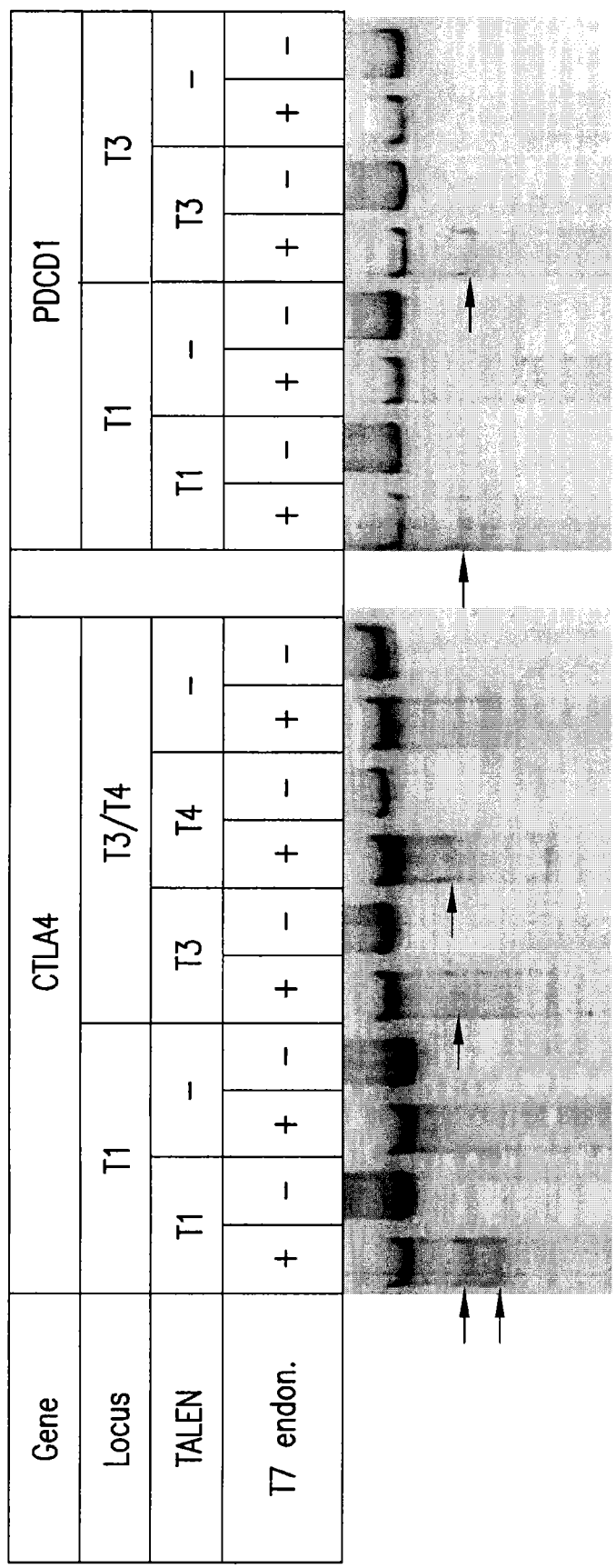

FIG. 10: Analysis of PDCD1 and CTLA-4 genomic locus by T7-endonuclease assay. Arrows point to digested PCR products.

Figure 11:
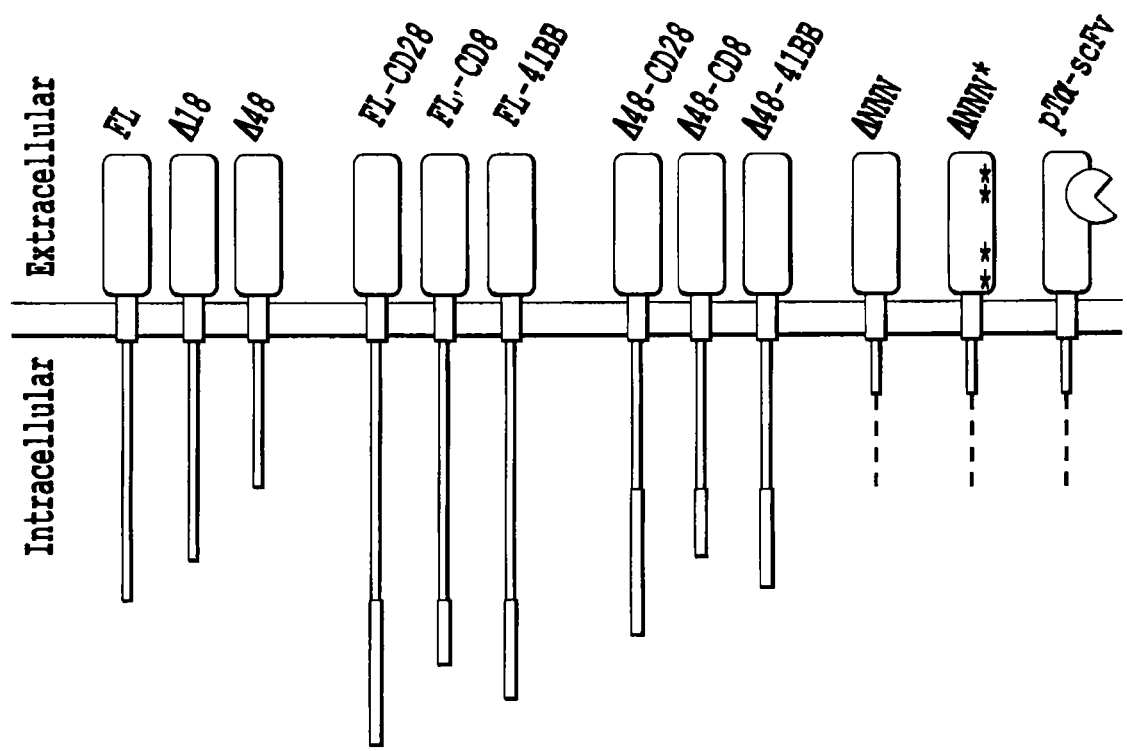

FIG. 11: Schematic representation of some examples of preTalpha constructs.

Figure 12:
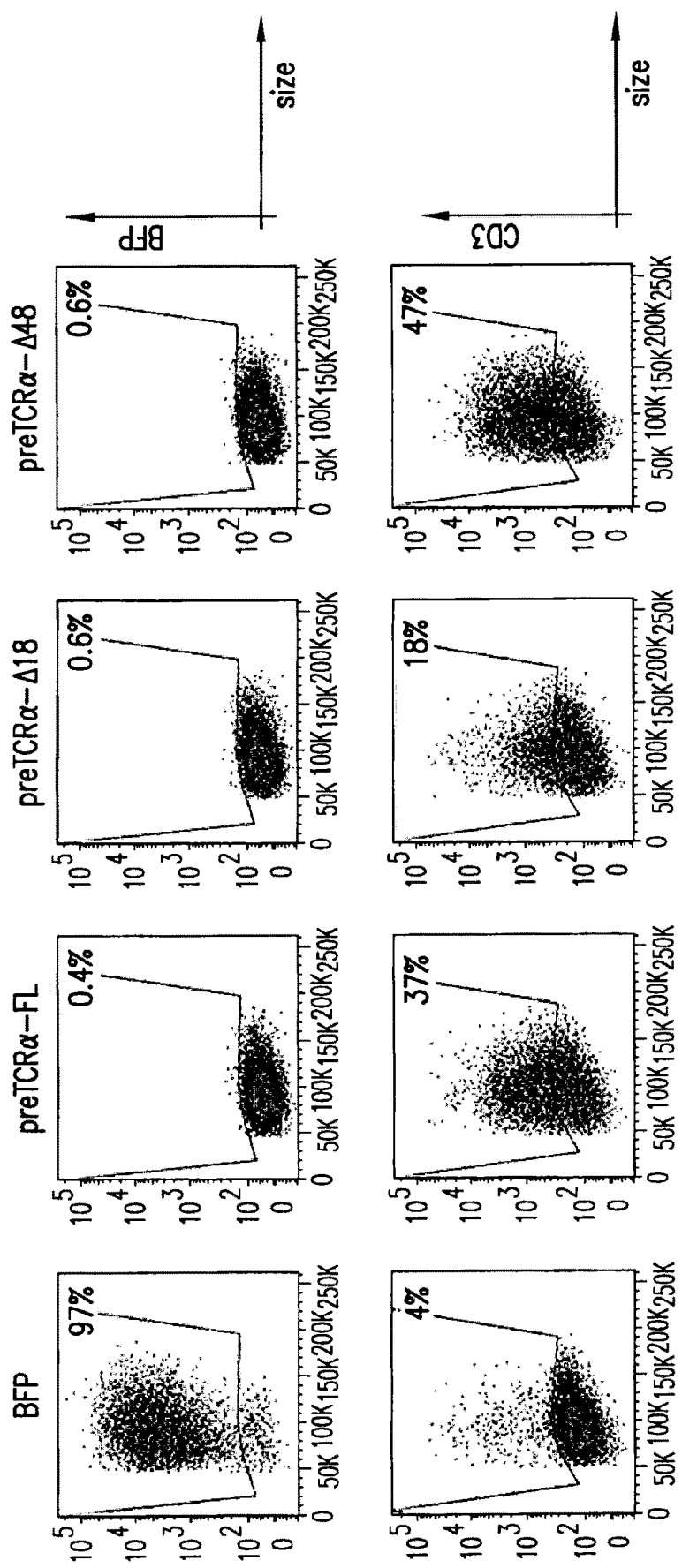

FIG. 12: Flow cytometry analysis of transduction efficiency (% BFP+ cells) and activity of the FL, Δ18, Δ48 pTalpha constructs (% CD3 surface expression) in TCR alpha inactivated Jurkat cells.

Figure 13:

FIG. 13: Schematic representation of a lentiviral construct coding for pTalpha protein (preTCRα).

Figure 14A:
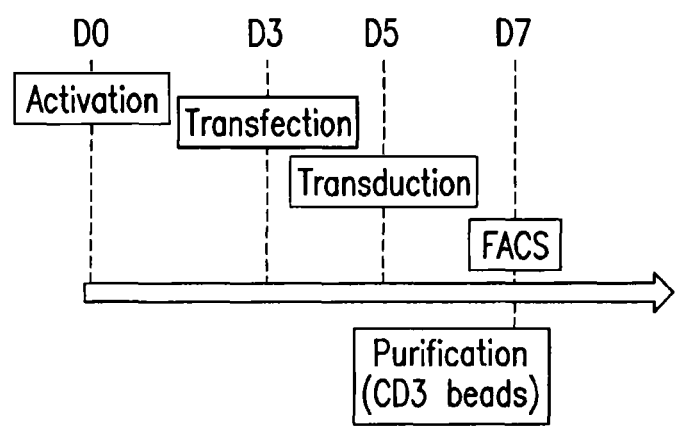
Figure 14B:
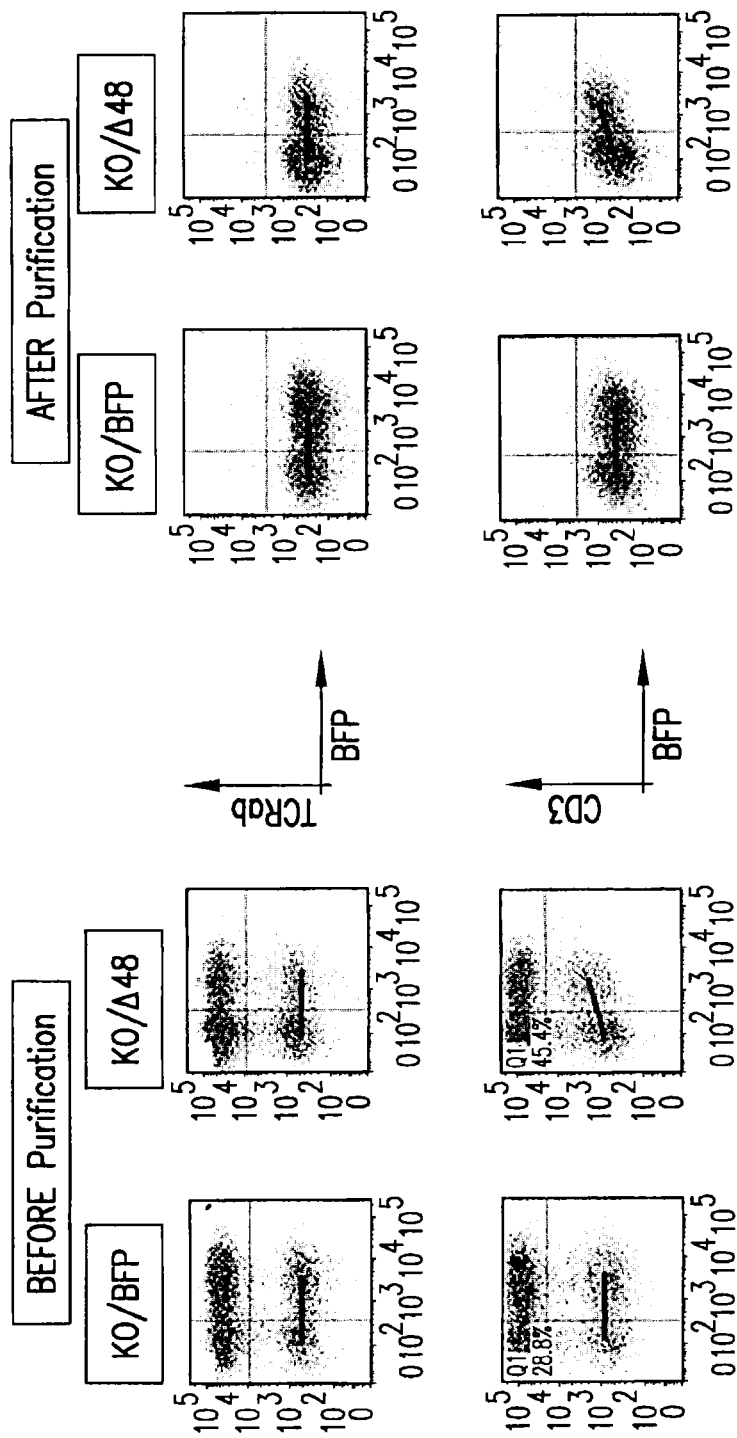
Figure 14C:
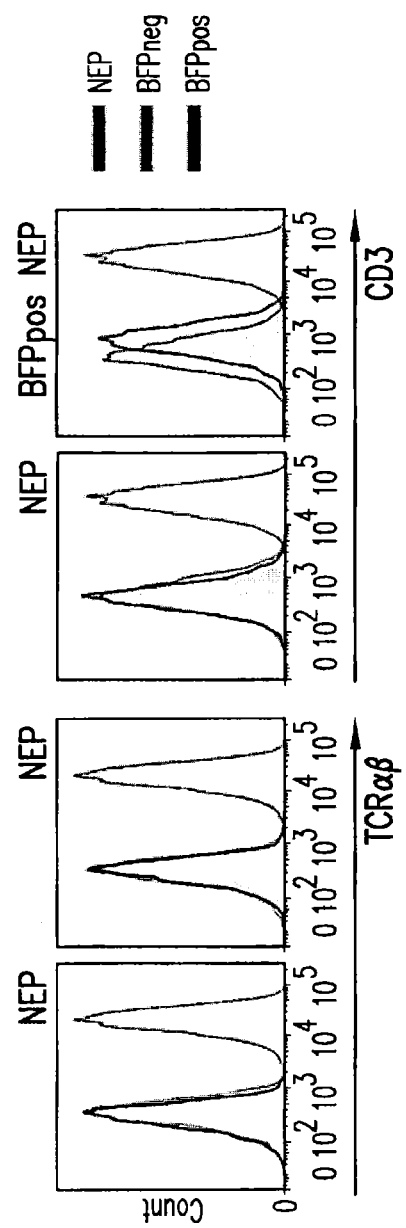

FIG. 14: A. Representation of the experimental protocol. B. Flow cytometry analysis of TCR alpha/beta, CD3 expression and BFP expression on TCRalpha inactivated T cells (KO) transduced with either BFP-2A-pTalphaΔ48 (KO/Δ48) or control BFP lentiviral vector (KO/BFP) before and after purification. C. Flow cytometry analysis of TCR alpha/beta and CD3 expression on purified TCR alpha inactivated cells transduced (BFPpos) or not (BFPneg) with BFP-2A-pTalphaΔ48 lentiviral vector. NEP represents non electroporated cells with TRAC TALE-nucleases.

FIG. 15: A-B. Flow cytometry analysis of early activation marker CD69 (A), late activation marker CD25 (B) expression 24 and 48 hours after re-activation with anti-CD3/CD28 beads respectively on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). pTα-Δ48 histograms correspond to the signal detected in TCR inactivated cells expressing pTα-Δ48 (BFP+ cells) while the KO histograms correspond to TCRalpha inactivated cells which do not express pTα-Δ48 (BFP– cells) pTα-Δ48.BB histograms correspond to the signal detected in TCR inactivated cells expressing pTα-Δ48.41BB (BFP+ cells) while the KO histograms correspond to TCRalpha inactivated cells which do not express pTα-Δ48.41BB (BFP– cells). NEP (non electroporated) histograms correspond to signal detected in non engineered cells. C. Flow cytometry analysis of the size of cells 72 hours after re-activation with anti-CD3/CD28 beads on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). The values indicated in the upper part of each graph correspond to the geometrical mean of the fluorescence of each population.

Figure 16A:
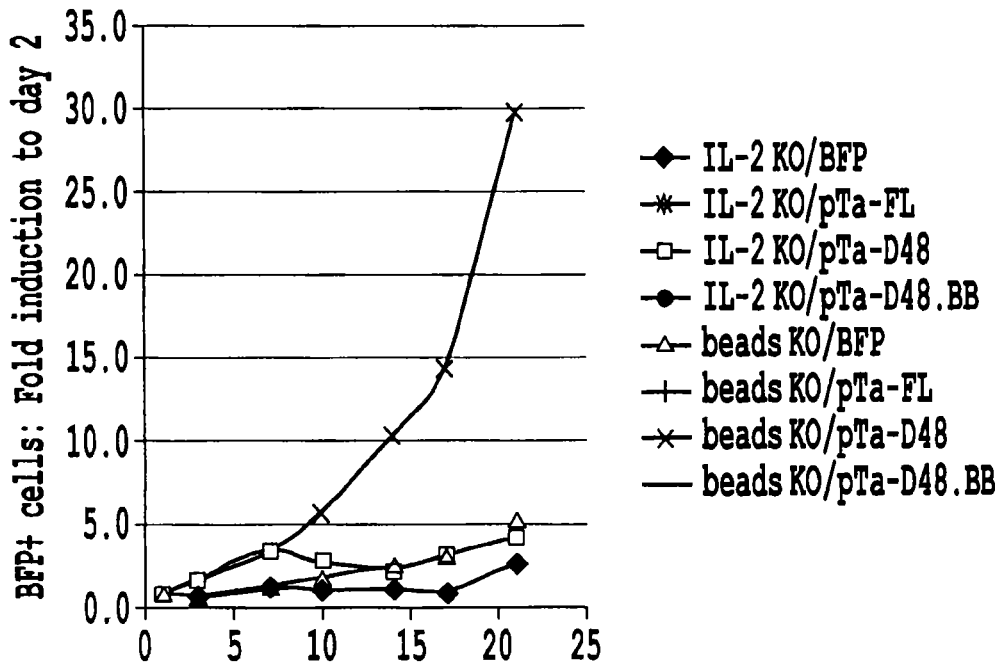
Figure 16B:
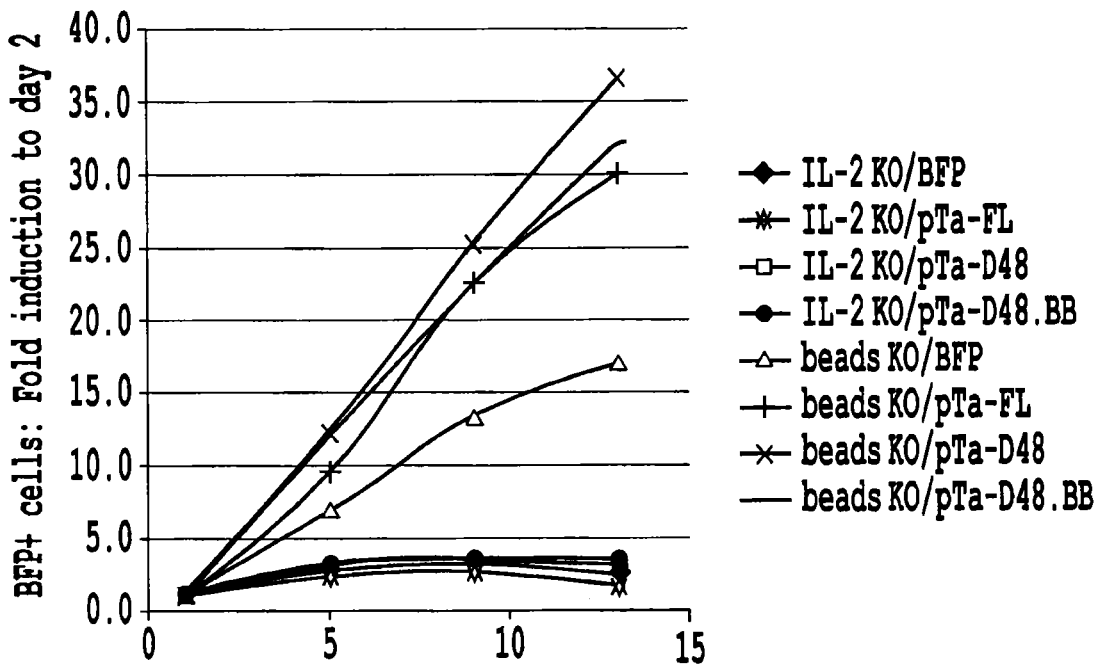

FIG. 16: Cell growth analysis of TCR alpha inactivated cells (KO) transduced with pTalpha-Δ48 (pTaΔ48) or control BFP vector (BFP) maintained in IL2 or in IL2 with anti-CD3/CD28 beads at different time points (x-axis). The BFP+ cells number is estimated at different time points for each condition and the fold induction of these cells (y-axis)

was estimated with respect to the value obtained at day 2 post re-activation. The results are obtained from two independent donors. For the second donor, cell growth was also determined for cells transduced with pTalpha-Δ48.41BB (pTa-Δ48.BB) and full-length pTalpha-(pTa-FL).

Figure 17A:
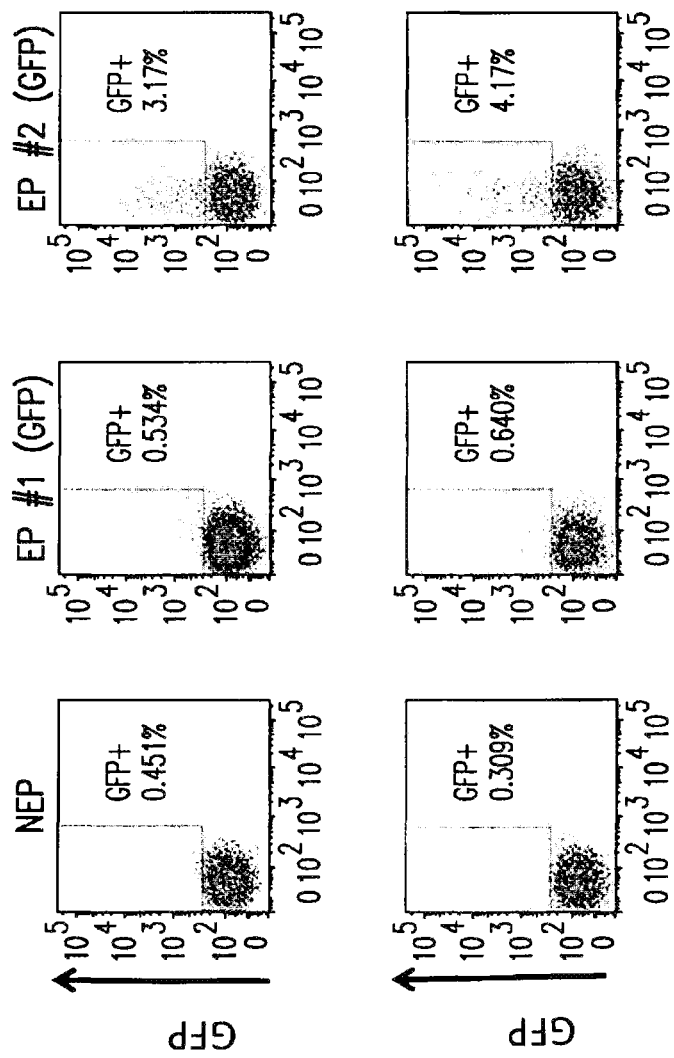
Figure 17B:
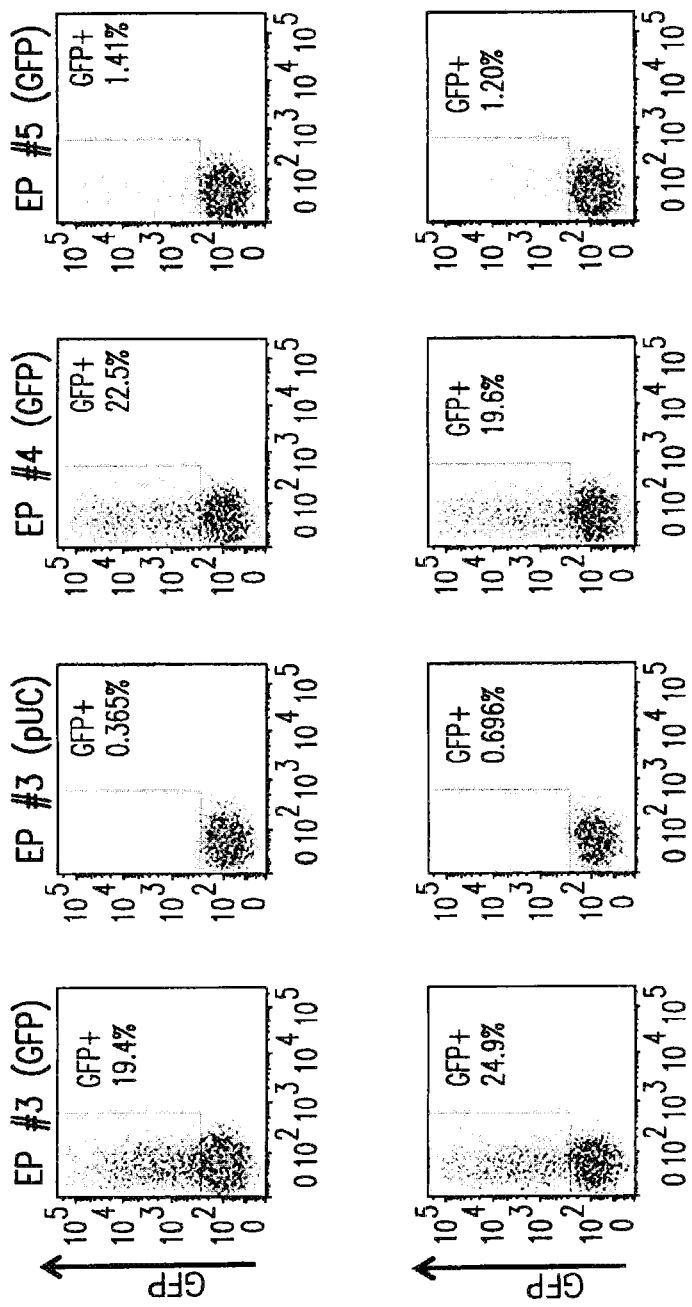

FIG. 17A-B: Flow cytometry analysis of GFP positive cells on PBMCs electroporated with the five different Cytopulse programs. The upper line corresponds to transfection of $6 \times 10^6$ cells per cuvette, while the lower line corresponds to transfection of $3 \times 10^6$ cells per cuvette.

Figure 18A:
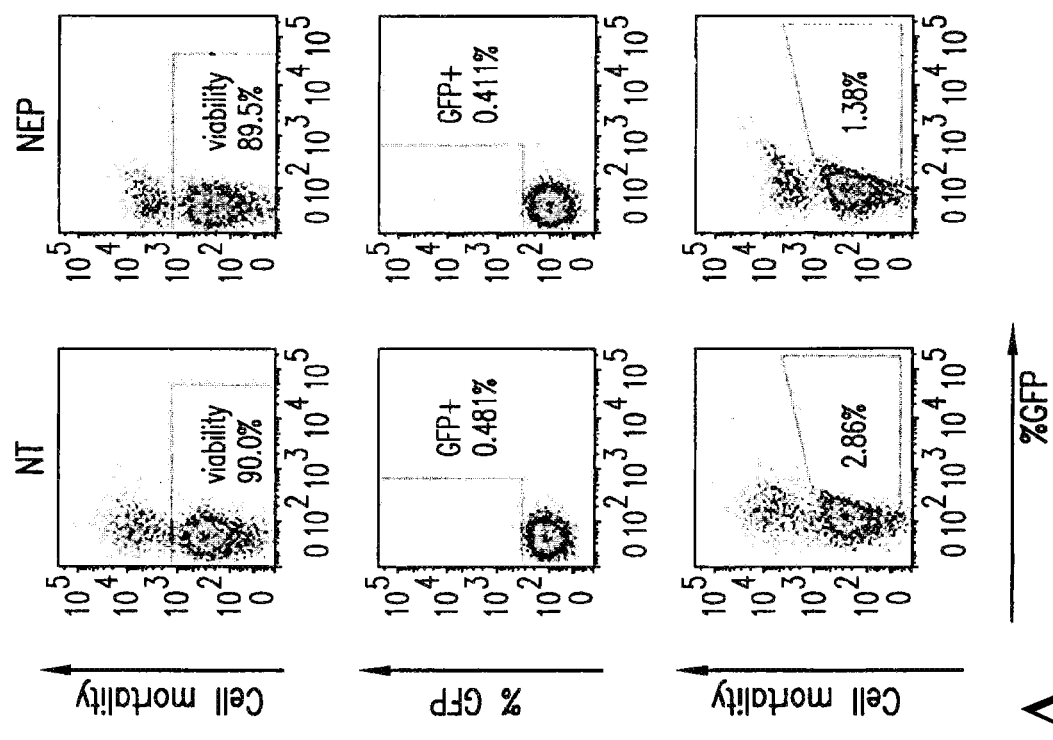
Figure 18B:
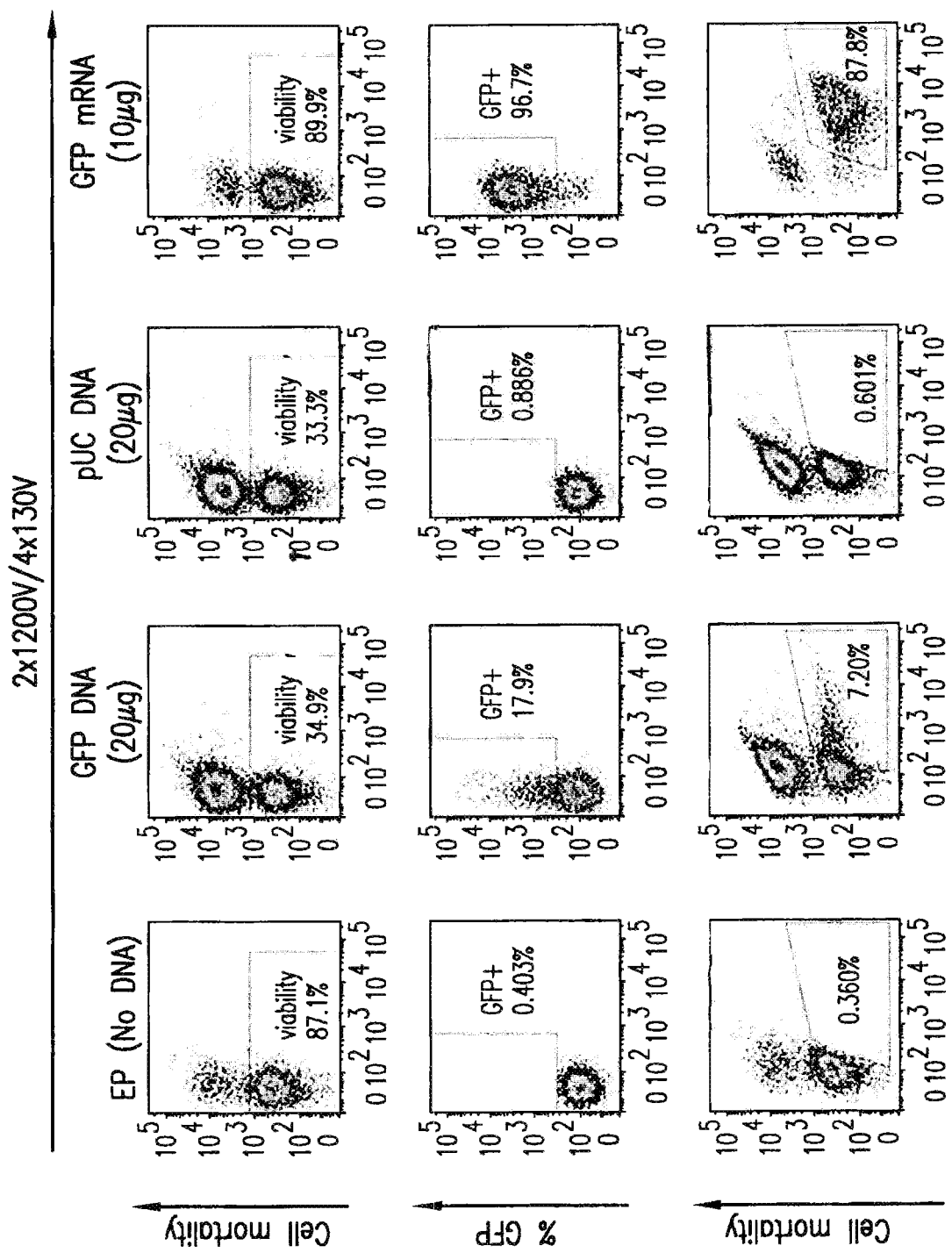

FIG. 18A-B: Flow cytometry analysis of purified T cell mortality using viability dye (eFluor-450) and of GFP positive cells among the viable population after electroporation with GFP mRNA, GFP DNA and control pUC DNA. NEP corresponds to cells that were maintained in electroporation buffer but were not electroporated and NT corresponds to non electroporated cells maintained in culture medium.

Figure 19:
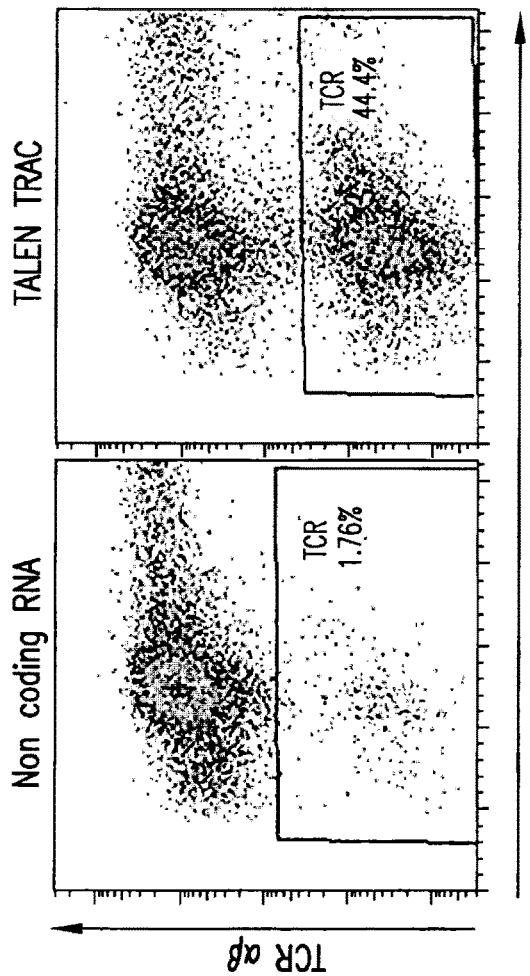

FIG. 19: Flow cytometry analysis of TCR alpha/beta and CD3 expression on human primary T cells following TRAC TALE-nuclease mRNA electroporation (top). Deep sequencing analysis of genomic DNA extracted from human primary T cells following TRAC TALE-nuclease mRNA electroporation (bottom).

Figure 20A:
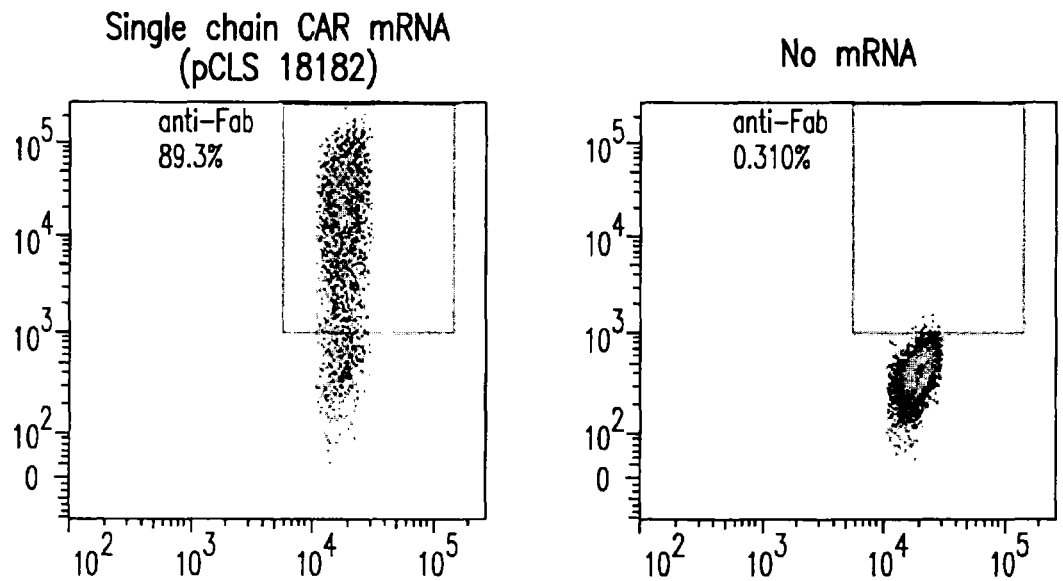
Figure 20B:
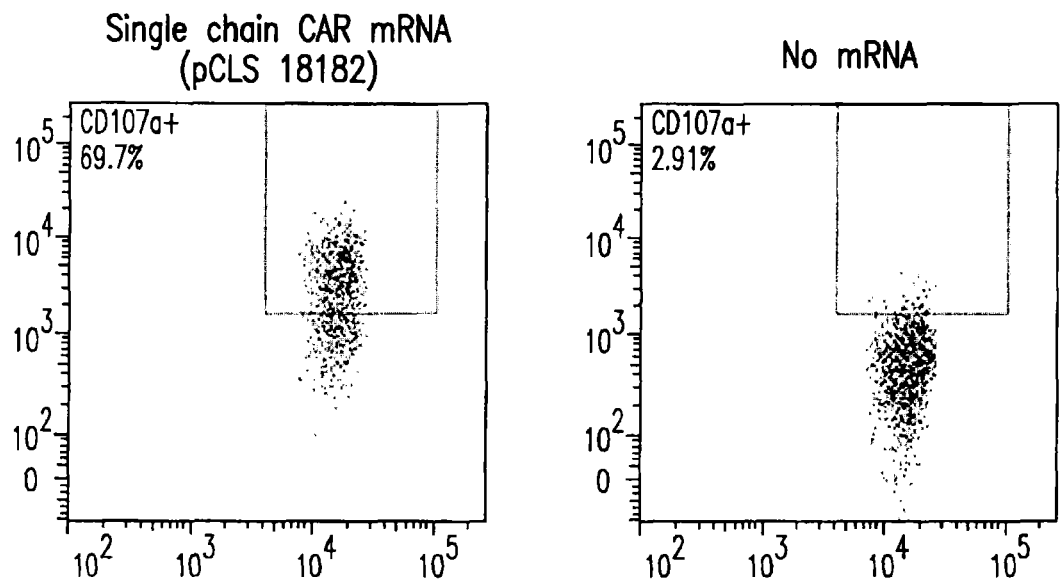

FIG. 20: A. Flow cytometry analysis of CAR expression (anti F(ab')2) after electroporation of T cells with or without mRNA encoding a single chain CAR. B. Flow cytometry analysis of CD107a expression (marker of degranulation) on electroporated T cells cocultured with daudi cells.

Figure 21A:
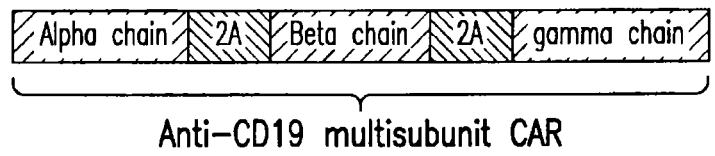
Figure 21B:
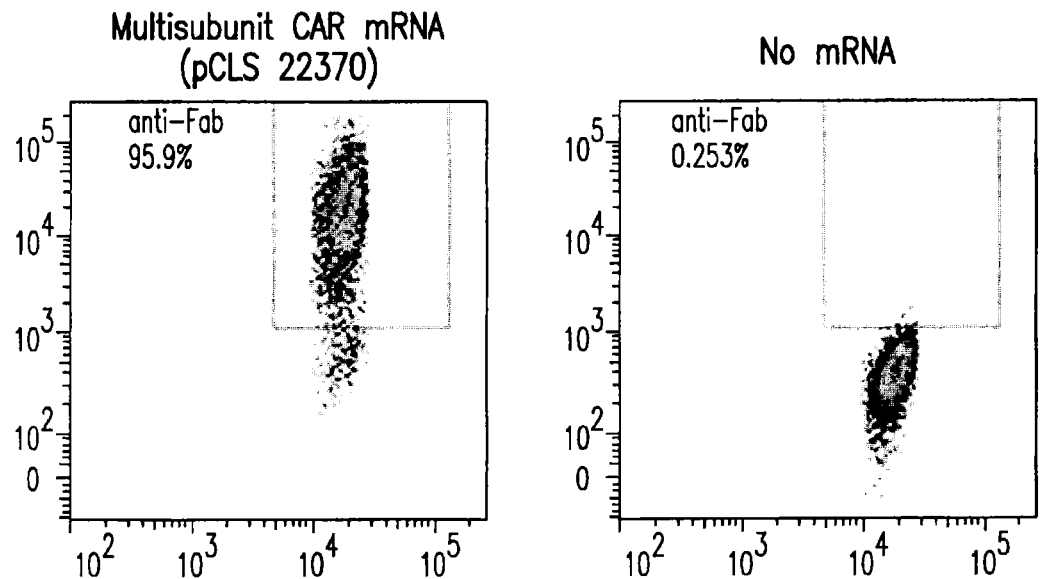
Figure 21C:
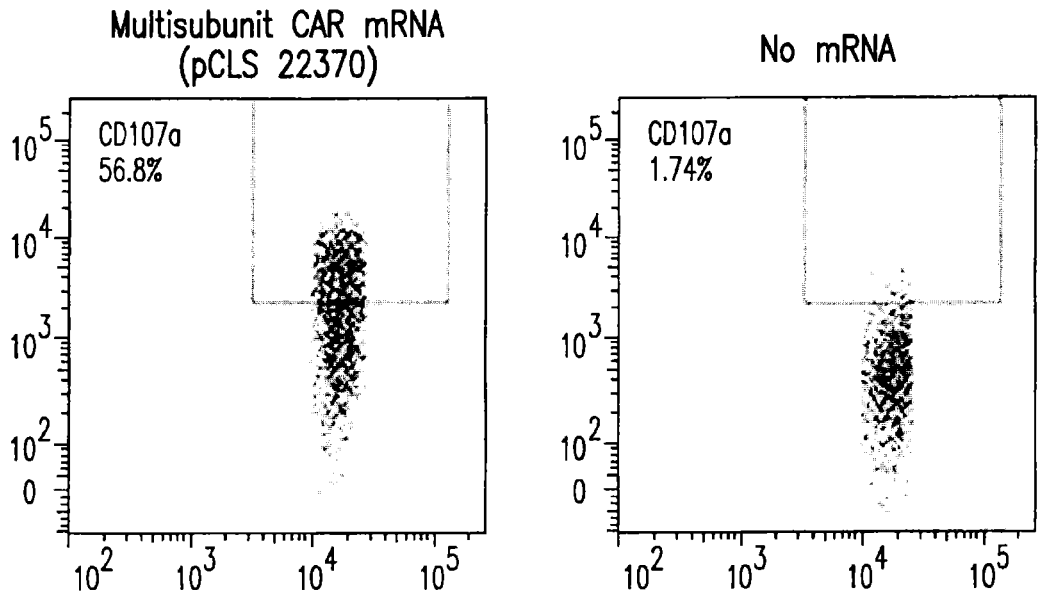

FIG. 21: A. Representation of mRNA encoding a multi-chain CAR. B. Flow cytometry analysis of CAR expression (anti F(ab')2) on viable T cells electroporated with or without a polycistronic mRNA encoding a multi-chain CAR. C. Flow cytometry analysis of CD107a expression (marker of degranulation) on electroporated T cells cocultured with daudi cells.

Figure 22:
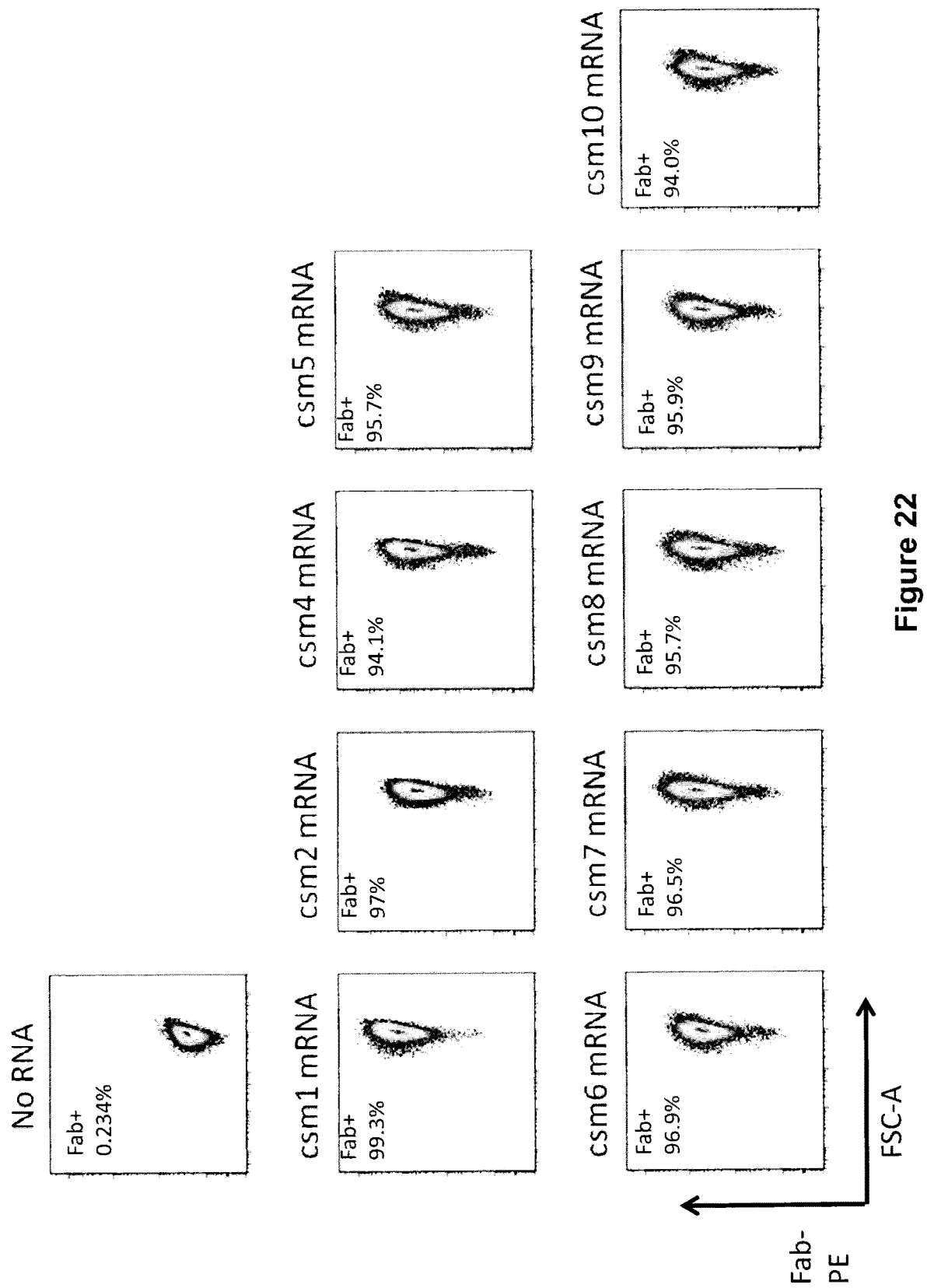

FIG. 22: Multi-chain CARs expression in human T cells after electroporation of polycistronic mRNAs.

Figure 23:
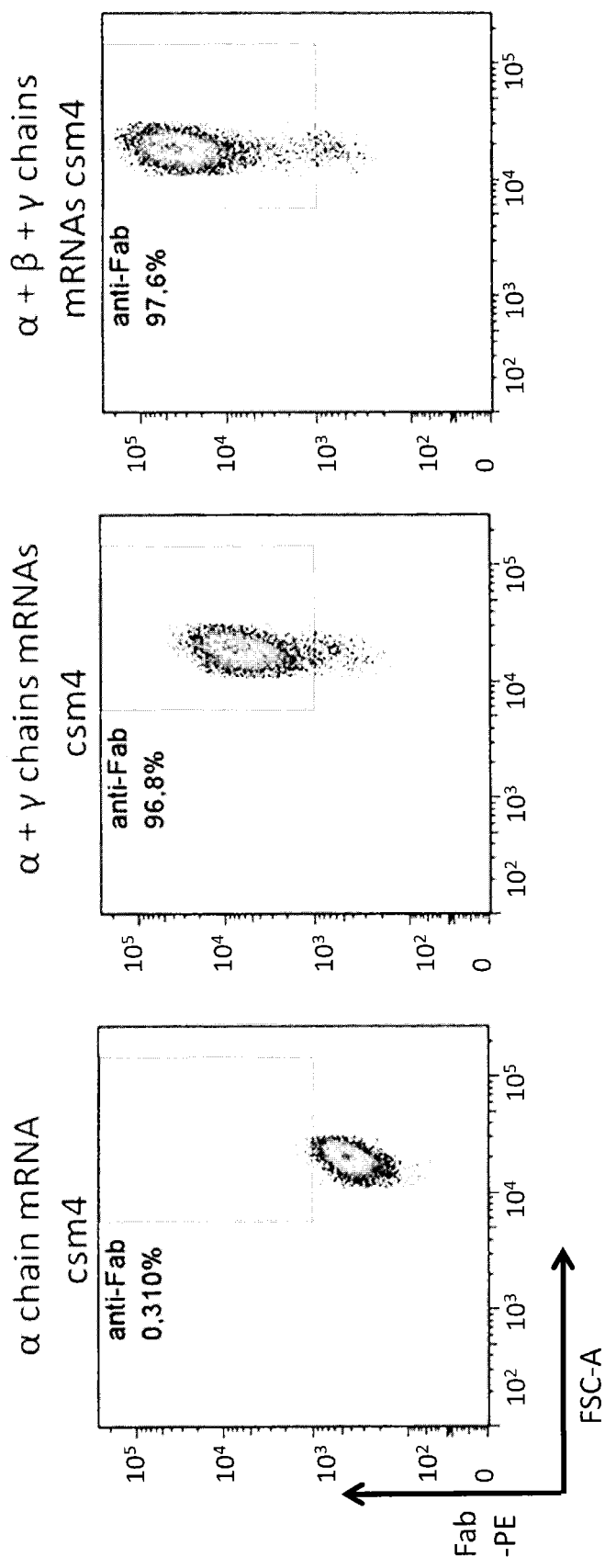

FIG. 23: The expression of the multi-subunit CARs is conditioned by the expression of the three chains: α, β and γ.

Figure 24A:
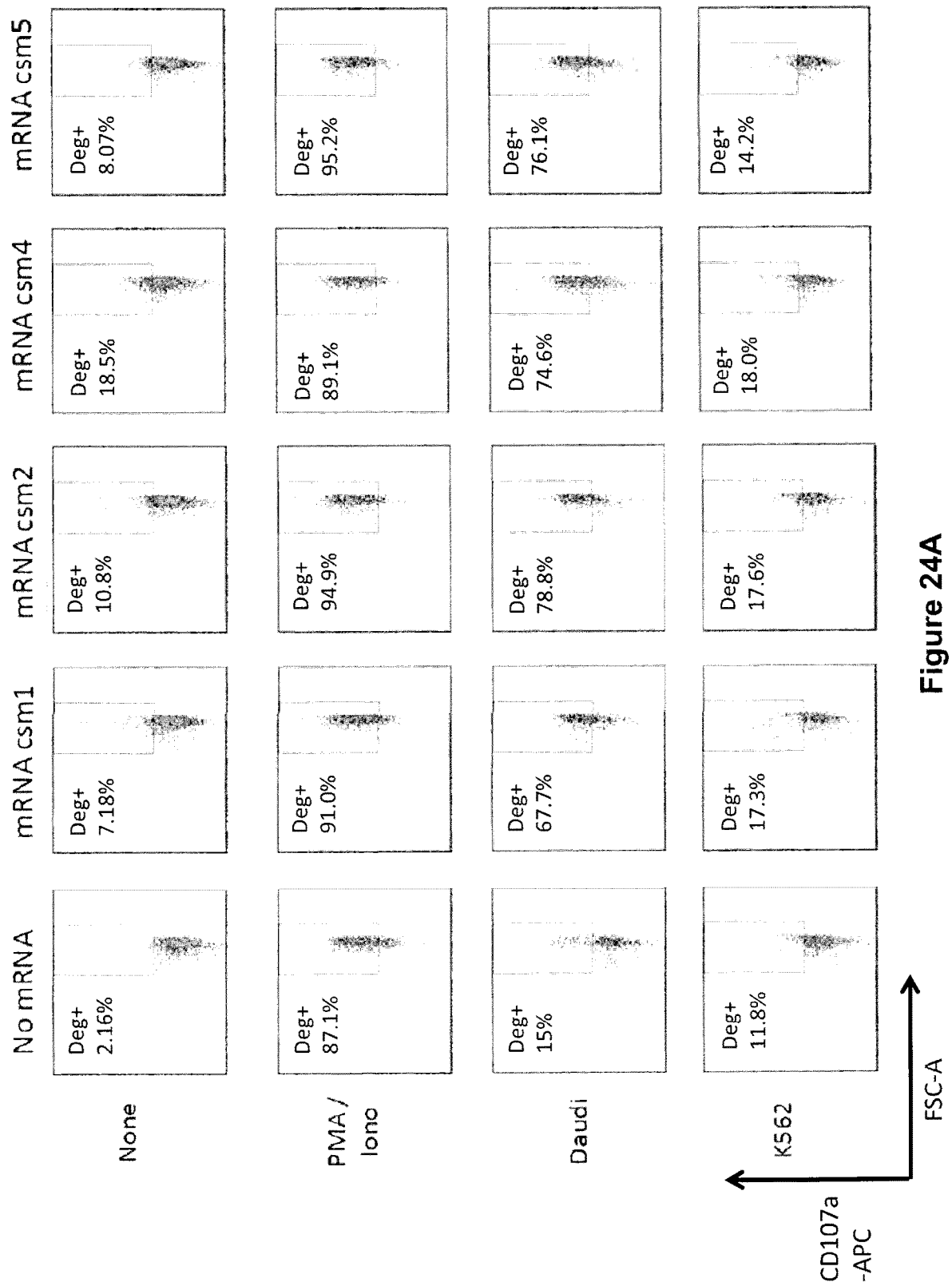
Figure 24B:
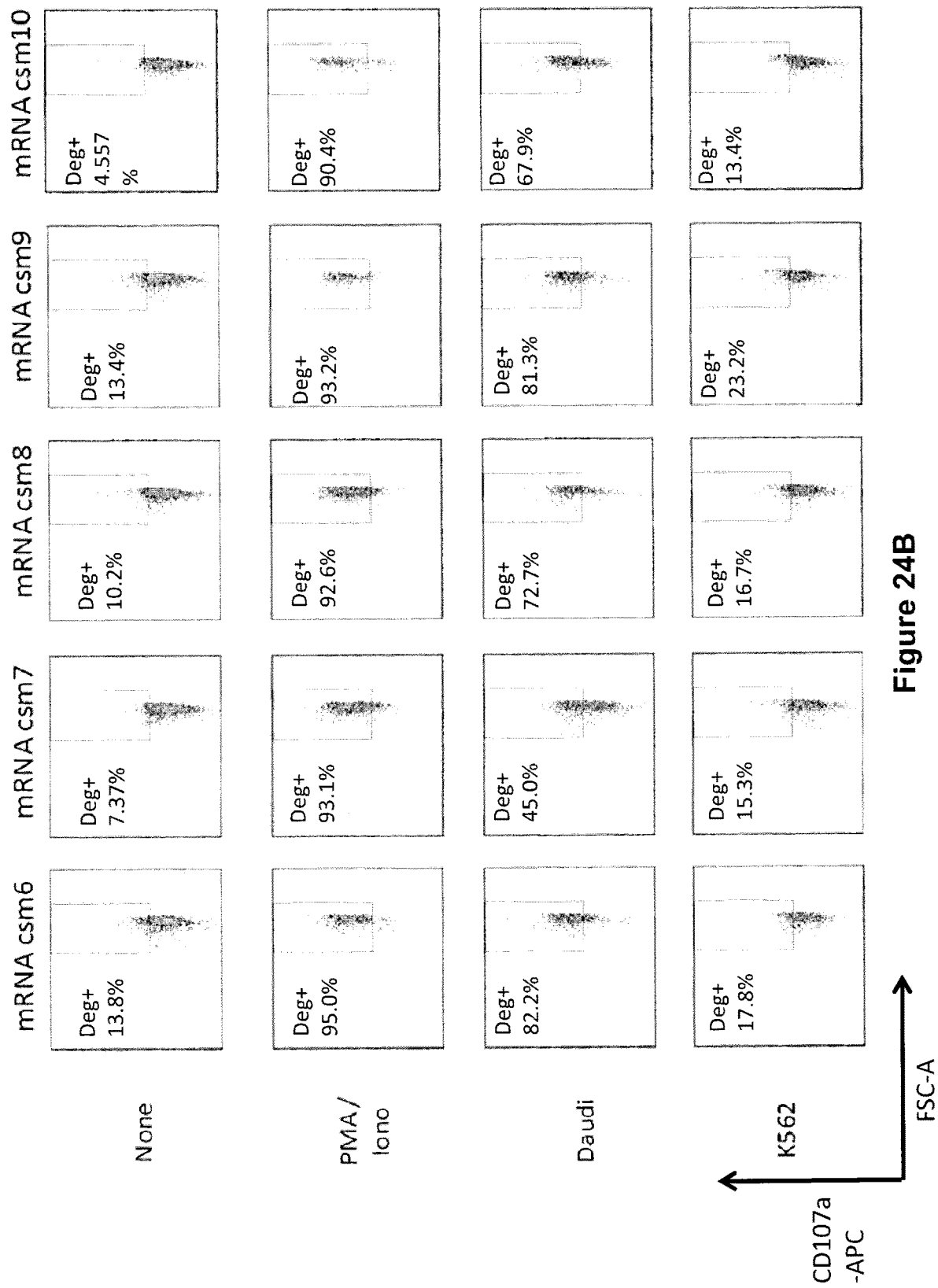

FIG. 24: The human T cells transiently expressing the multi-chain CARs degranulate following coculture with target cells. A: csm1 to csm5 CAR constructs. B: csm6 to csm10 CAR constructs.

Figure 25A:
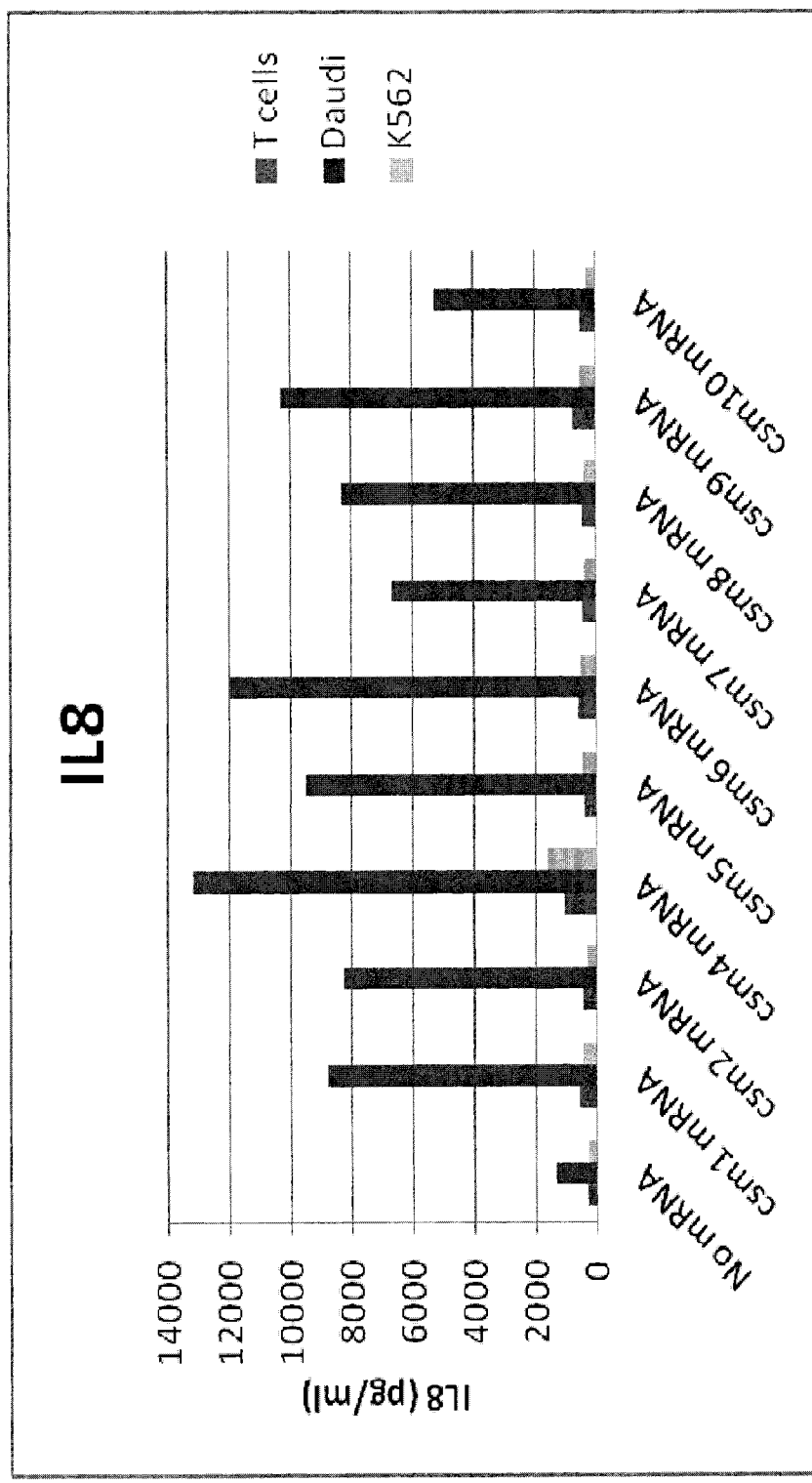
Figure 25B:
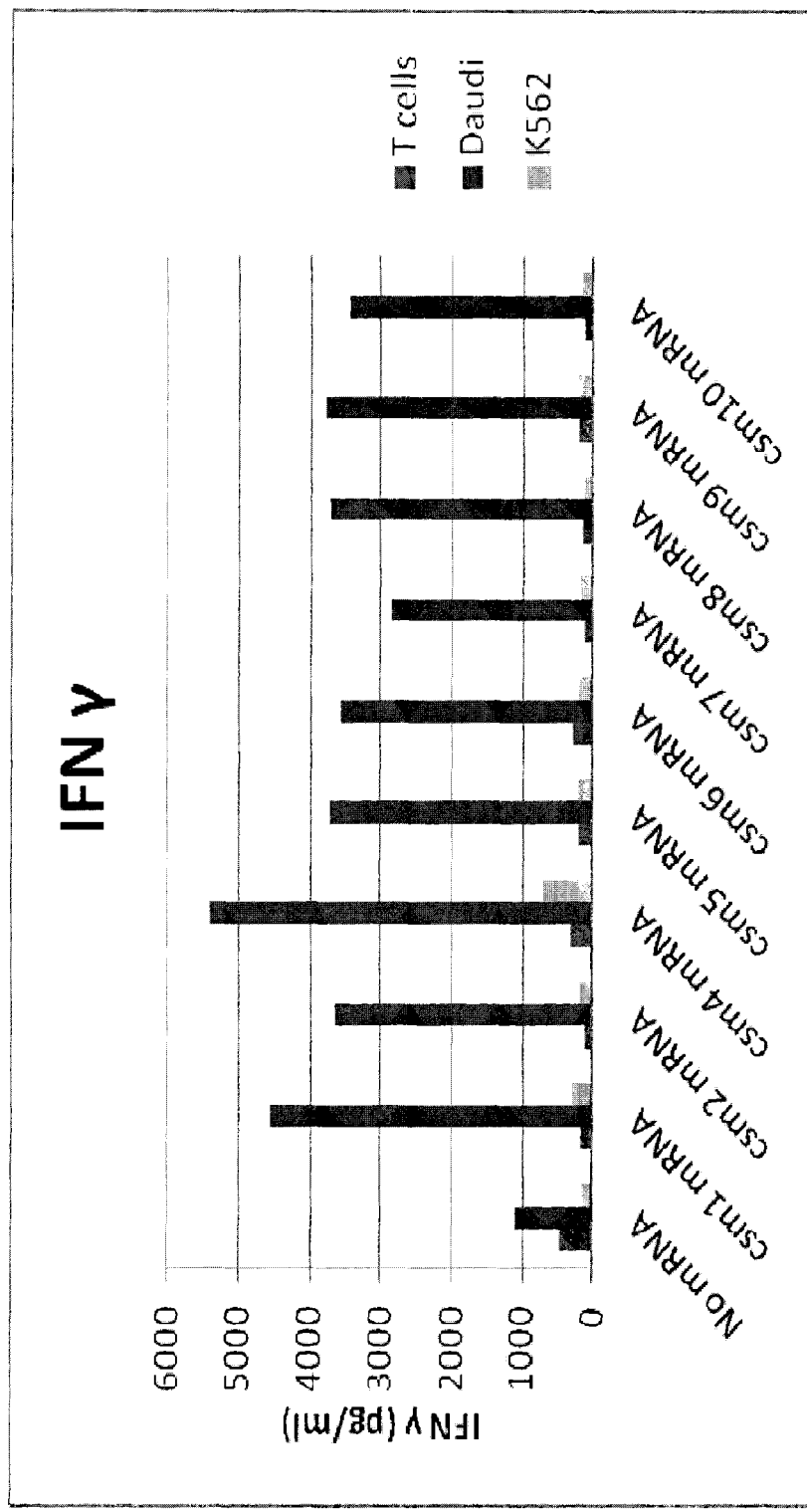
Figure 25C:
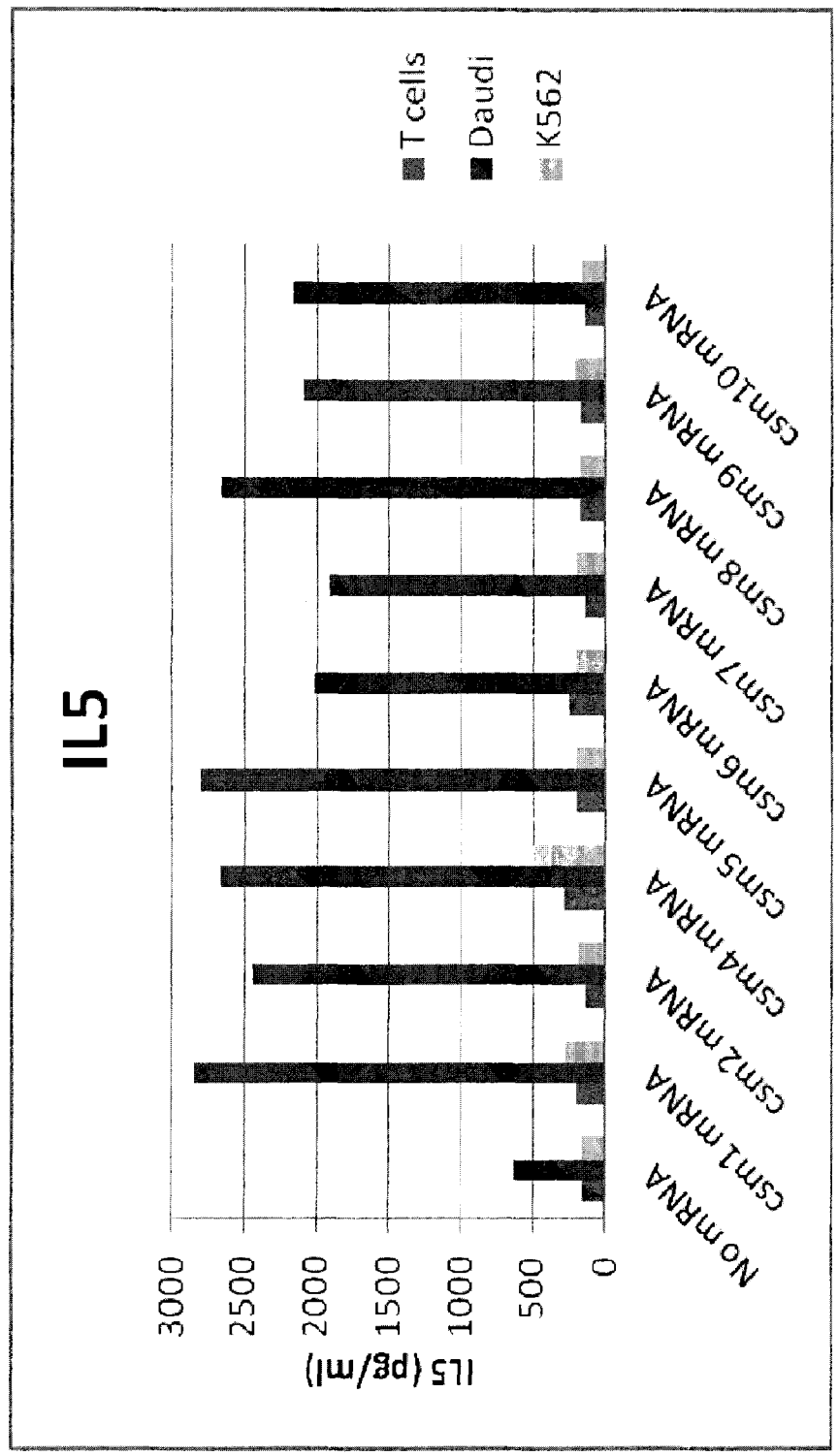

FIG. 25: The human T cells transiently expressing the multi-chain CARs secrete cytokines following coculture with target cells (Tcells vs. Daudi cells or K562). A:IL8 release. B:IFNγ release. C:IL5 release.

Figure 26:
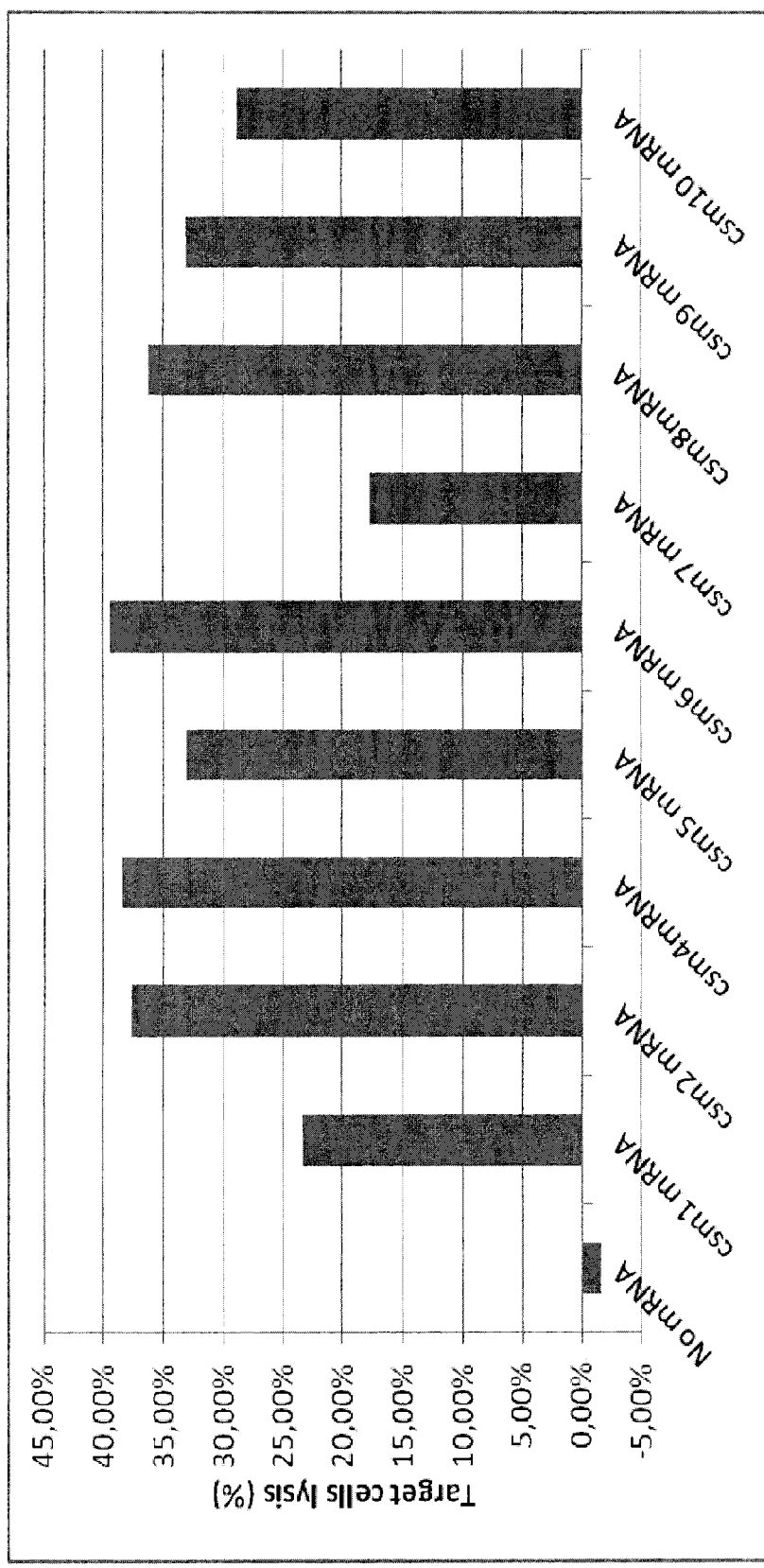

FIG. 26: The human T cells transiently expressing the multi-chain CARs (scm1 to scm10 constructs) lyse target cells.

Figure 27A:
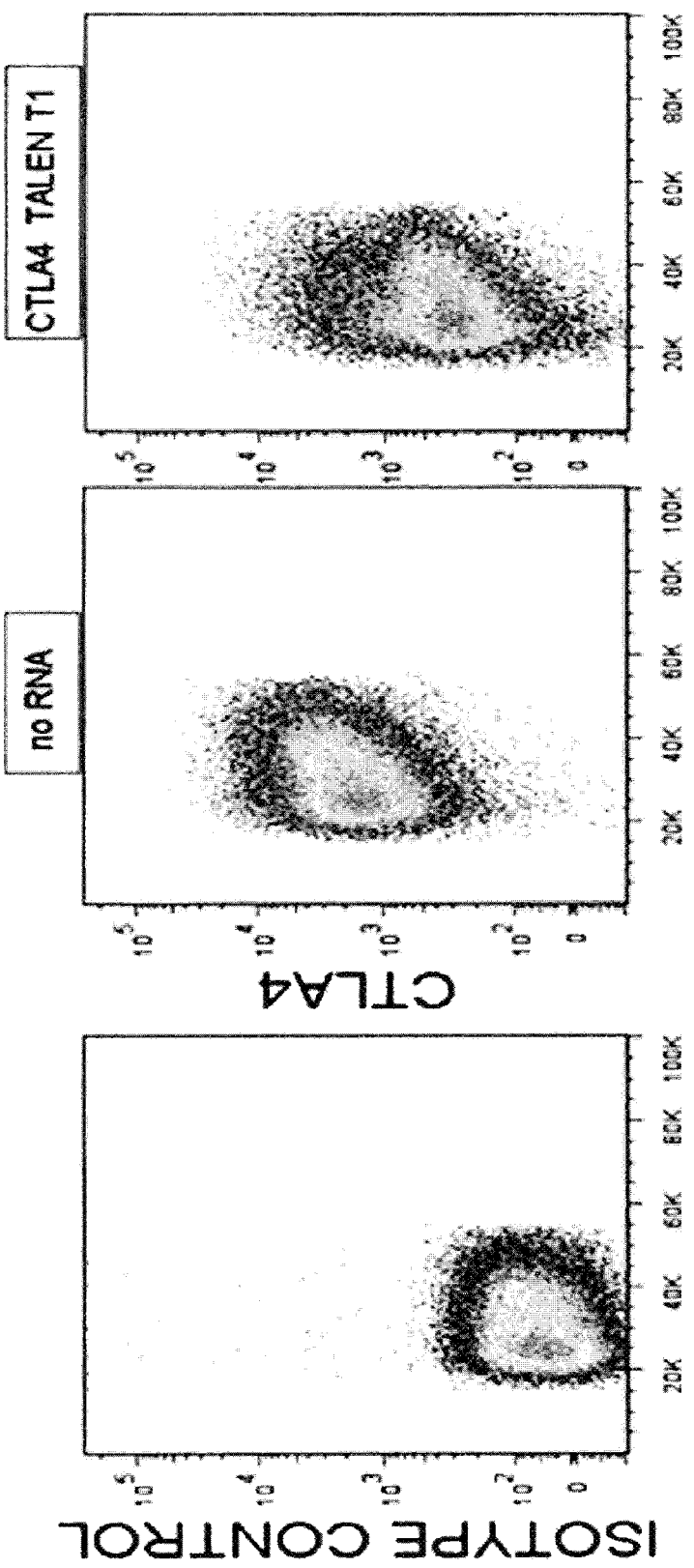
Figure 27B:
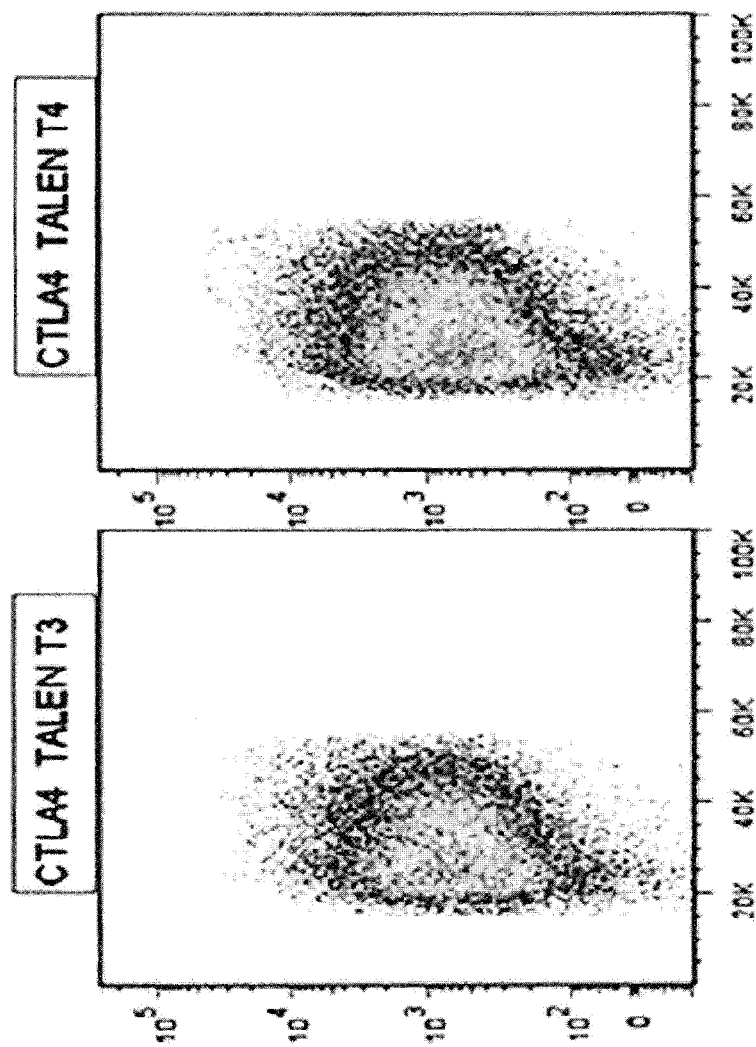

FIG. 27A-B: CTLA4 inactivation in primary T cells measured by intracellular staining using fluorescent antibody and flow cytometry analysis.

Figure 28:
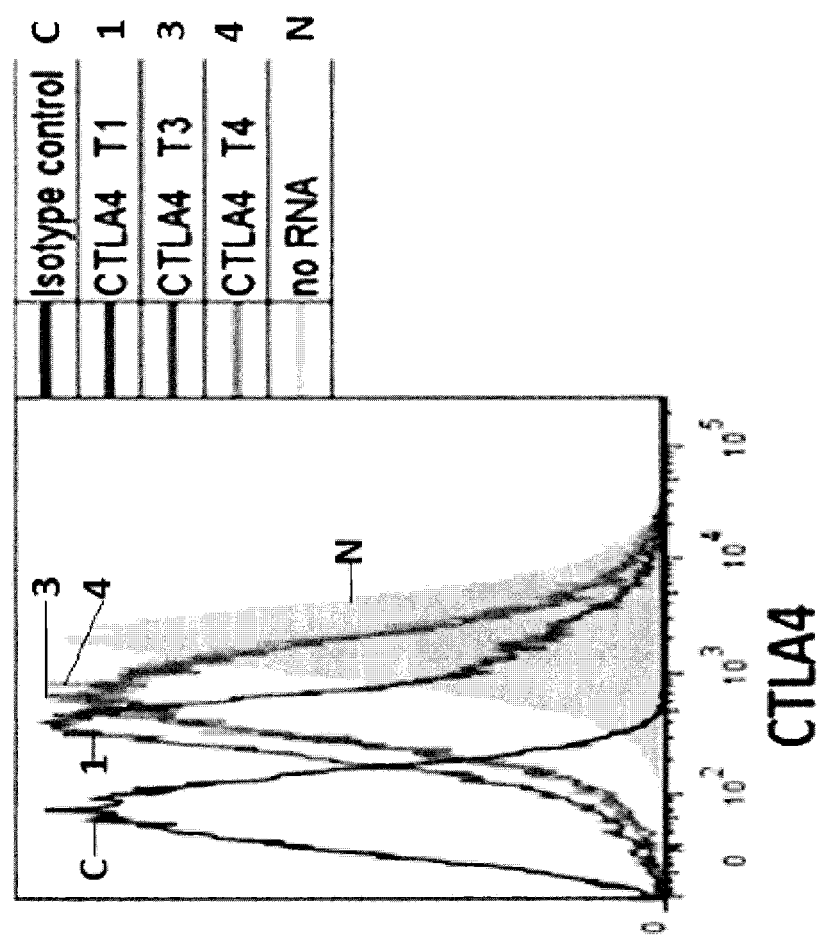

FIG. 28: distribution of fluorescent T-cells expressing CTLA4 upon transfection with TALENs T1, T2 and T3. Proportion of cells expressing CTLA4 is dramatically reduced with respect to control cells.

Figure 29:
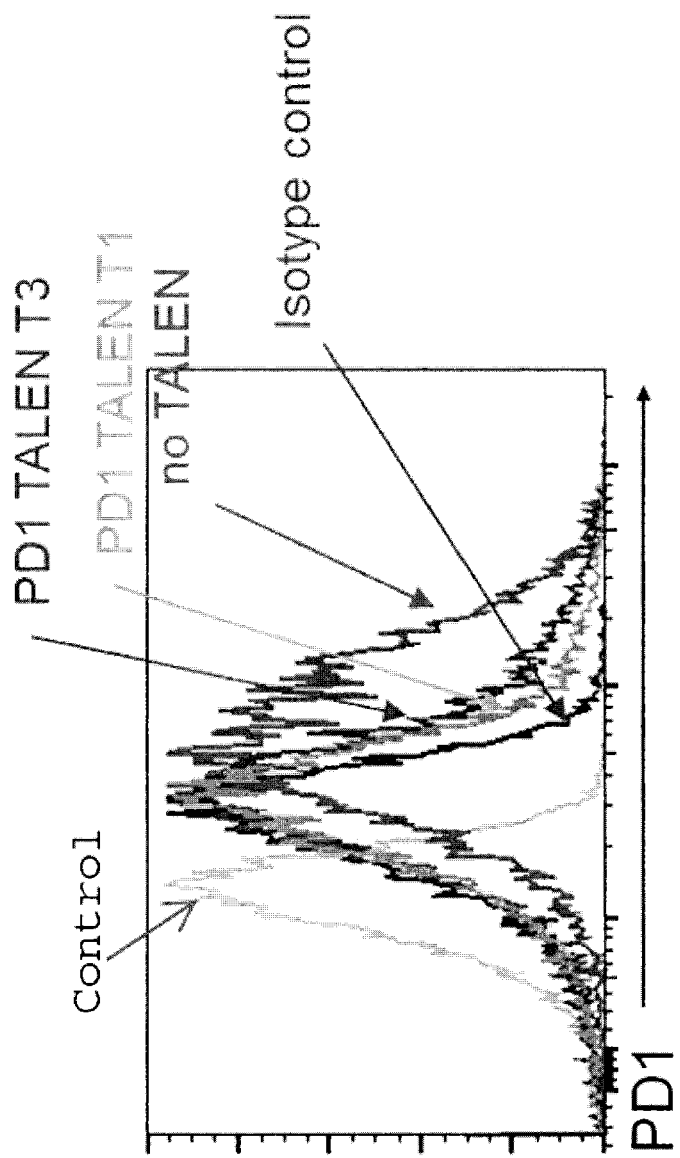

FIG. 29: PD1 inactivation in primary T cells measured by intracellular staining using fluorescent antibody and flow cytometry analysis. Proportion of cells expressing PD1 is dramatically reduced with respect to control cells.

Figure 30:
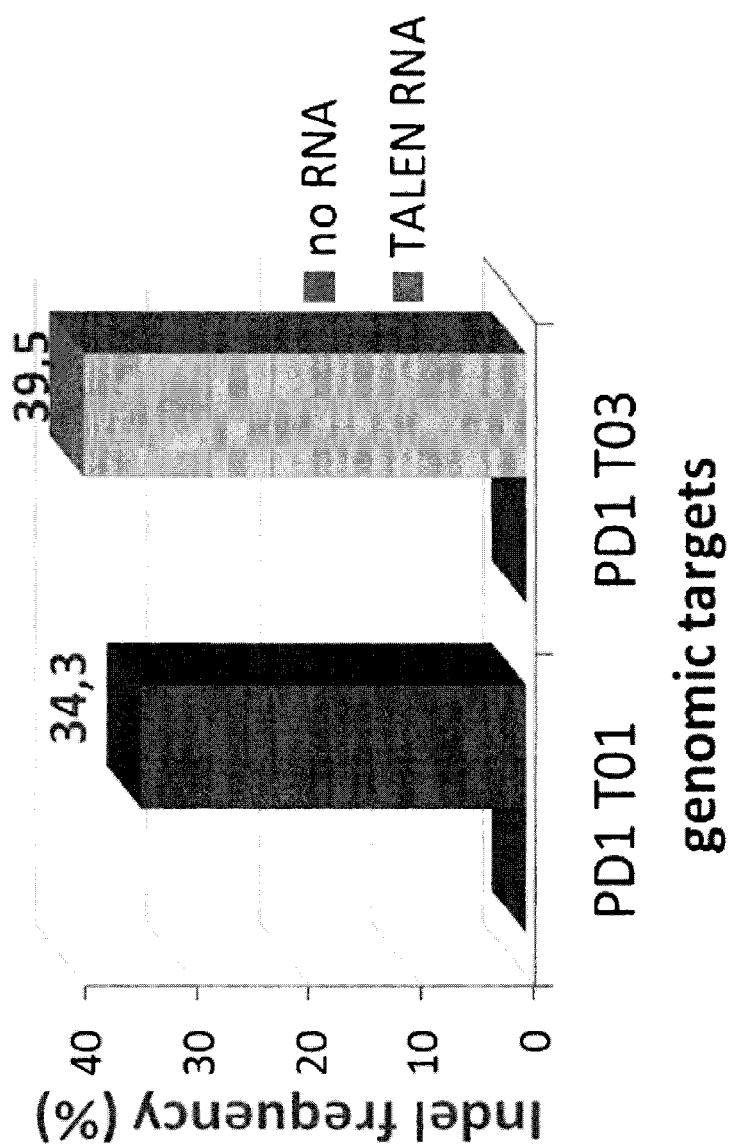

FIG. 30: Diagram showing deletions frequencies observed in T-cells upon transfection with TALEN T01 and T03 targeting PD1 gene.

Figure 31:
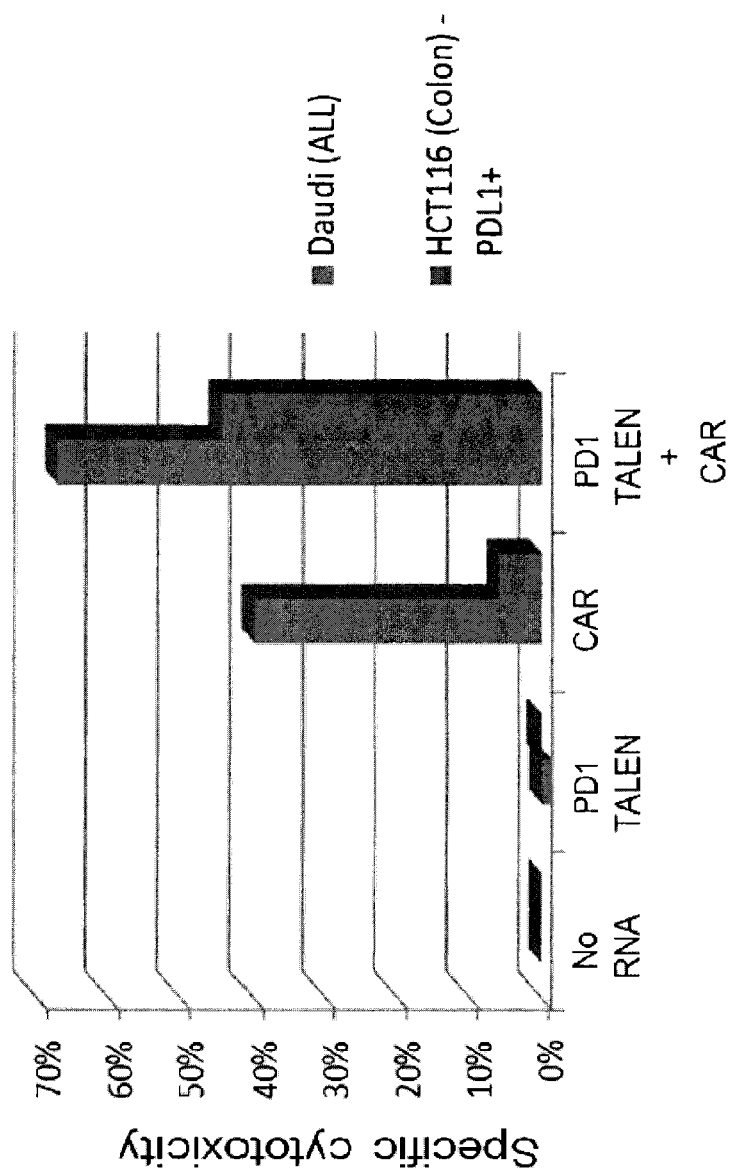

FIG. 31: Diagram showing that cytotoxic activity is enhanced in T-cells disrupted for PD1 as per the experiment described in Example 3.

Table 1: List of immune checkpoint genes identified by the inventors as appropriate to make allogeneic T-cells more active for immunotherapy.

Table2: Description of the GR TALE-nucleases and sequences of the TALE-nucleases target sites in the human GR gene.

Table 3: Cleavage activity of the GR TALE-nucleases in yeast. Values are comprised between 0 and 1. Maximal value is 1.

Table 4: Percentage of targeted mutagenesis at endogenous TALE-nuclease target sites in 293 cells.

Table 5: Percentage of targeted mutagenesis at endogenous TALE-nuclease target sites in primary T lymphocytes.

Table 6: Description of the CD52, TRAC and TRBC TALE-nucleases and sequences of the TALE-nucleases target sites in the human corresponding genes.

Table 7: Additional target sequences for TRAC and CD52 TALE-nucleases.

Table 8: Percentage of indels for TALE-nuclease targeting CD52_T02, TRAC_T01, TRBC_T01 and TRBC_T02 targets.

Table 9: Percentages of CD52-negative, TCR-negative and CD52/TCR-double negative T lymphocytes after transfection of corresponding TALE-nuclease-expressing polynucleotides.

Table 10: Percentages of TCR-negative T lymphocytes after transfection of TRBC TALE-nuclease-expressing polynucleotides.

Table 11: Description of the CTLA4 and PDCD1 TALE-nucleases and sequences of the TALE-nucleases target sites in the human corresponding genes.

Table 12: Description of a subset of pTalpha constructs.

Table 13: Activity of the different pTalpha constructs in Jurkat TCR alpha inactivated cell. Activity was measured by flow cytometry analysis of CD3 expression on jurkat TCR alpha inactivated cell transfected with the different preTalpha constructs.

Table 14: Different cytopulse programs used to determine the minimal voltage required for electroporation in PBMC derived T-cells.

Table 15: Cytopulse program used to electroporate purified T-cells.

Table 16: List of genes encoding immune checkpoint proteins.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety, especially for the subject matter disclosed by each reference that pertains to the subject matter in the adjoining sentence(s), paragraph(s) or section(s) in which the reference is cited. In case of conflict, the present specification, including definitions, will prevail.

Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N. Y., 1986).

In a general aspect, the present invention relates to methods for new adoptive immunotherapy strategies in treating cancer and infections.

Highly Active T Cells for Immunotherapy

According to a first aspect of the present invention, the inventors have identified new genes encoding so-called "immune checkpoints" function that can be individually disrupted to enhance the efficiency of T cells in adoptive immunotherapy. Table 1, below, lists these new targeted genes, which are more particularly involved into the functions of co-inhibitory receptor function, cell death, cytokine signaling, arginine tryptophan starvation, TCR signaling, Induced T-reg repression, transcription factors controlling exhaustion or anergy, and hypoxia mediated tolerance. As previously mentioned, the targeting of one of these later function, through disruption or expression control of one these genes, can be made as part of an autologous or allogeneic scheme treatment The invention thus more particularly relate to engineered T-cells, in which at least one of the genes having identity with one mentioned in Table 1 is disrupted or repressed for the purpose of performing immunotherapy.

T cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signals that fine-tune the response. Although the molecular mechanism for inhibitory signals in most cases has not been defined, studies suggest that negative regulatory components might attenuate T-cell response in more than one way. For example, CTLA-4 can compete with CD28 for costimulatory ligands. In contrast, inhibitory motif-containing molecules such as PD-1 can recruit phosphatases (such as SHP-1, SHP-2 or SHIP) to TCR-proximal signaling complexes and attenuate signaling. Both PD-1 and CTLA-4 can inhibit signaling by the serine-threonine kinase Akt but seem to do so by different molecular mechanisms. Thus, inactivation of one of the genes can be compensated by another negative regulatory pathway. To circumvent this, the present inventors, according to a further aspect of the invention, have sought to inactivate at least two genes encoding immune-checkpoint proteins to sufficiently augment the activity of T-cells for immunotherapy. Based on the classification shown in table 1, they chose different genes encoding proteins preferably involved in different inhibitory pathways that negatively regulate the immune response.

The present invention relates to a method for preparing T-cells for immunotherapy by inactivating in T-cells at least two of the genes encoding immune-checkpoint proteins to sufficiently increase the activity of T-cells for immunotherapy. In particular, the present invention relates to a method of preparing T-cells for immunotherapy comprising:

(a) Modifying T-cells by inactivating at least two genes encoding immune checkpoint proteins;

(b) Expanding said cells.

It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1, (Meyaard, Adema et al. 1997)), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 (Nicoll, Ni et al. 1999), SIGLEC9 (Zhang, Nicoll et al. 2000; Ikehara, Ikehara et al. 2004), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF (Quigley, Pereyra et al. 2010), GUCY1A2, GUCY1A3, GUCY1B2, GUCY1B3 which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune checkpoint, in particular PD1 and/or CTLA-4.

Table 1 below, without being exhaustive, show immune checkpoint genes that can be inactivated according to the teaching of the present invention in order to improve the efficiency and fitness of the engineered T-cells. The immune checkpoints gene are preferably selected from such genes having identity to those listed in this table involved into co-inhibitory receptor function, cell death, cytokine signaling, arginine tryptophan starvation, TCR signaling, Induced T-reg repression, transcription factors controlling exhaustion or anergy, and hypoxia mediated tolerance.

TABLE 1

Immune checkpoint genes appropriate to make allogeneic T-cells more active for immunotherapy

| Pathway | Genes that can be inactivated in pathway | NCBI database gene ID (Homo sapiens) on May 13$^{th}$, 2014 |
|---|---|---|
| Co-inhibitory receptors | LAG3 (CD223) | 3902 |
| | HAVCR2 (TIM3) | 84868 |
| | BTLA (CD272) | 151888 |
| | CD160 (NK1) | 11126 |
| | TIGIT (VSIG9) | 201633 |
| | CD96 (TACTILE) | 10225 |
| | CRTAM (CD355) | 56253 |
| | LAIR1 (CD305) | 3903 |
| | SIGLEC7 (CD328) | 27036 |
| | A2A (IGKV2-29) | 28882 |
| | SIGLEC9 (CD329) | 27180 |
| | CD244 (2B4)) | 51744 |
| Cell death | TNFRSF10B (CD262) | 8795 |
| | TNFRSF10A (CD261) | 8797 |
| | CASP3 | 836 |
| | CASP6 | 839 |
| | CASP7 | 840 |
| | CASP8 | 841 |
| | CASP10 | 843 |
| | Arhgap5 (GFI2) | 394 |
| | Akap8i | 10270 |
| | FADD (GIG3) | 8772 |
| | FAS (RP11) | 355 |
| | Stk17b (DRAK2) | 9262 |
| Cytokine signalling | TGFBRII (AAT3) | 7048 |
| | TGFBRI | 7046 |
| | SMAD2 (JV18) | 4087 |
| | SMAD3 | 4088 |
| | SMAD4 | 4089 |
| | SMAD10 (SMAD7) | 394331 |
| | SKI (SGS) | 6497 |
| | SKIL (SNO) | 6498 |
| | TGIF1 (HPE4) | 7050 |
| | IL10RA (CD210) | 3587 |
| | IL10RB | 3588 |
| | HMOX2 (HO-2) | 3163 |
| | Jun (AP1) | 3725 |
| | Ppp3cc | 5533 |
| | Ppm1g | 5496 |
| | Socs1 | 8651 |
| | Soc3 | 9021 |
| | IL6R (CD126) | 3570 |
| | IL6ST (CD130) | 3572 |
| | Lck | 3932 |
| | Fyn | 2534 |
| | ADAP (FYB) | 2533 |
| | Carma1 (CARD11) | 84433 |
| | Bcl10 | 8915 |
| | Malt1 (IMD12) | 10892 |
| | TAK1 (NR2C2) | 7182 |
| arginine/tryptophan starvation | EIF2AK4 (GCN2) | 440275 |
| | Nuak2 | 81788 |
| TCR signalling | CSK | 1445 |
| | PAG1 (CBP) | 55824 |
| | SIT1 | 27240 |
| | CRTAM (CD355) | 56253 |
| | Egr2 (AT591) | 1959 |
| | DGK-a (DAGK) | 1606 |
| | DGK-z | 8525 |
| | Cblb | 868 |
| | Inpp5b | 3633 |
| | Ptpn2 (PTN2) | 5771 |
| | Vamp7 | 6845 |
| | Mast2 | 23139 |
| | tnk1 | 8711 |
| | stk17b (DRAK2) | 9262 |
| | Mdfic (HIC) | 29969 |
| | F11r (CD321) | 50848 |

TABLE 1-continued

Immune checkpoint genes appropriate to make allogeneic T-cells more active for immunotherapy

| Pathway | Genes that can be inactivated in pathway | NCBI database gene ID (Homo sapiens) on May 13$^{th}$, 2014 |
|---|---|---|
| Induced Treg | FOXP3 (JM2) | 50943 |
| | Entpd1 (CD39) | 953 |
| Transcription factors controlling exhaustion/anergy | PRDM1 (blimp1) | 12142 |
| | BATF | 10538 |
| | Ypel2 | 388403 |
| | Ppp2r2d | 55844 |
| | Rock1 | 6093 |
| | Sbf1 | 6305 |
| | Hipk1 (MYAK) | 204851 |
| | Map3k3 | 4215 |
| | Grk6 | 2870 |
| | Eif2ak3 (PEK) | 9451 |
| | Fyn | 2534 |
| | NFAT1 (NFATC2) | 4773 |
| Hypoxia mediated tolerance | GUCY1A2 | 2977 |
| | GUCY1A3 | 2982 |
| | GUCY1B2 | 2974 |
| | GUCY1B3 | 2983 |

In a preferred embodiment, said two genes encoding immune checkpoint proteins are selected from the group consisting of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3.

In particular embodiments, said two genes encoding immune checkpoint proteins are selected from the group consisting of: BTLA and BATF; CASP10 and BATF; CASP10 and BTLA; CASP3 and BATF; CASP3 and BTLA; CASP3 and CASP10; CASP6 and BATF; CASP6 and BTLA; CASP6 and CASP10; CASP6 and CASP3; CASP7 and BATF; CASP7 and BTLA; CASP7 and CASP10; CASP7 and CASP3; CASP7 and CASP6; CASP8 and BATF; CASP8 and BTLA; CASP8 and CASP10; CASP8 and CASP3; CASP8 and CASP6; CASP8 and CASP7; CD160 and BATF; CD160 and BTLA; CD160 and CASP10; CD160 and CASP3; CD160 and CASP6; CD160 and CASP7; CD160 and CASP8; CD244 and BATF; CD244 and BTLA; CD244 and CASP10; CD244 and CASP3; CD244 and CASP6; CD244 and CASP7; CD244 and CASP8; CD244 and CD160; CD96 and BATF; CD96 and BTLA; CD96 and CASP10; CD96 and CASP3; CD96 and CASP6; CD96 and CASP7; CD96 and CASP8; CD96 and CD160; CD96 and CD244; CRTAM and BATF; CRTAM and BTLA; CRTAM and CASP10; CRTAM and CASP3; CRTAM and CASP6; CRTAM and CASP7; CRTAM and CASP8; CRTAM and CD160; CRTAM and CD244; CRTAM and CD96; CSK and BATF; CSK and BTLA; CSK and CASP10; CSK and CASP3; CSK and CASP6; CSK and CASP7; CSK and CASP8; CSK and CD160; CSK and CD244; CSK and CD96; CSK and CRTAM; CTLA4 and BATF; CTLA4 and BTLA; CTLA4 and CASP10; CTLA4 and CASP3; CTLA4 and CASP6; CTLA4 and CASP7; CTLA4 and CASP8; CTLA4 and CD160; CTLA4 and CD244; CTLA4 and CD96; CTLA4 and CRTAM; CTLA4 and CSK; EIF2AK4 and BATF; EIF2AK4 and BTLA;

EIF2AK4 and CASP10; EIF2AK4 and CASP3; EIF2AK4 and CASP6; EIF2AK4 and CASP7; EIF2AK4 and CASP8; EIF2AK4 and CD160; EIF2AK4 and CD244; EIF2AK4 and CD96; EIF2AK4 and CRTAM; EIF2AK4 and CSK; EIF2AK4 and CTLA4; FADD and BATF; FADD and BTLA; FADD and CASP10; FADD and CASP3; FADD and CASP6; FADD and CASP7; FADD and CASP8; FADD and CD160; FADD and CD244; FADD and CD96; FADD and CRTAM; FADD and CSK; FADD and CTLA4; FADD and EIF2AK4; FAS and BATF; FAS and BTLA; FAS and CASP10; FAS and CASP3; FAS and CASP6; FAS and CASP7; FAS and CASP8; FAS and CD160; FAS and CD244; FAS and CD96; FAS and CRTAM; FAS and CSK; FAS and CTLA4; FAS and EIF2AK4; FAS and FADD; FOXP3 and BATF; FOXP3 and BTLA; FOXP3 and CASP10; FOXP3 and CASP3; FOXP3 and CASP6; FOXP3 and CASP7; FOXP3 and CASP8; FOXP3 and CD160; FOXP3 and CD244; FOXP3 and CD96; FOXP3 and CRTAM; FOXP3 and CSK; FOXP3 and CTLA4; FOXP3 and EIF2AK4; FOXP3 and FADD; FOXP3 and FAS; GUCY1A2 and BATF; GUCY1A2 and BTLA; GUCY1A2 and CASP10; GUCY1A2 and CASP3; GUCY1A2 and CASP6; GUCY1A2 and CASP7; GUCY1A2 and CASP8; GUCY1A2 and CD160; GUCY1A2 and CD244; GUCY1A2 and CD96; GUCY1A2 and CRTAM; GUCY1A2 and CSK; GUCY1A2 and CTLA4; GUCY1A2 and EIF2AK4; GUCY1A2 and FADD; GUCY1A2 and FAS; GUCY1A2 and FOXP3; GUCY1A3 and BATF; GUCY1A3 and BTLA; GUCY1A3 and CASP10; GUCY1A3 and CASP3; GUCY1A3 and CASP6; GUCY1A3 and CASP7; GUCY1A3 and CASP8; GUCY1A3 and CD160; GUCY1A3 and CD244; GUCY1A3 and CD96; GUCY1A3 and CRTAM; GUCY1A3 and CSK; GUCY1A3 and CTLA4; GUCY1A3 and EIF2AK4; GUCY1A3 and FADD; GUCY1A3 and FAS; GUCY1A3 and FOXP3; GUCY1A3 and GUCY1A2; GUCY1B2 and BATF; GUCY1B2 and BTLA; GUCY1B2 and CASP10; GUCY1B2 and CASP3; GUCY1B2 and CASP6; GUCY1B2 and CASP7; GUCY1B2 and CASP8; GUCY1B2 and CD160; GUCY1B2 and CD244; GUCY1B2 and CD96; GUCY1B2 and CRTAM; GUCY1B2 and CSK; GUCY1B2 and CTLA4; GUCY1B2 and EIF2AK4; GUCY1B2 and FADD; GUCY1B2 and FAS; GUCY1B2 and FOXP3; GUCY1B2 and GUCY1A2; GUCY1B2 and GUCY1A3; GUCY1B3 and BATF; GUCY1B3 and BTLA; GUCY1B3 and CASP10; GUCY1B3 and CASP3; GUCY1B3 and CASP6; GUCY1B3 and CASP7; GUCY1B3 and CASP8; GUCY1B3 and CD160; GUCY1B3 and CD244; GUCY1B3 and CD96; GUCY1B3 and CRTAM; GUCY1B3 and CSK; GUCY1B3 and CTLA4; GUCY1B3 and EIF2AK4; GUCY1B3 and FADD; GUCY1B3 and FAS; GUCY1B3 and FOXP3; GUCY1B3 and GUCY1A2; GUCY1B3 and GUCY1A3; GUCY1B3 and GUCY1B2; HAVCR2 and BATF; HAVCR2 and BTLA; HAVCR2 and CASP10; HAVCR2 and CASP3; HAVCR2 and CASP6; HAVCR2 and CASP7; HAVCR2 and CASP8; HAVCR2 and CD160; HAVCR2 and CD244; HAVCR2 and CD96; HAVCR2 and CRTAM; HAVCR2 and CSK; HAVCR2 and CTLA4; HAVCR2 and EIF2AK4; HAVCR2 and FADD; HAVCR2 and FAS; HAVCR2 and FOXP3; HAVCR2 and GUCY1A2; HAVCR2 and GUCY1A3; HAVCR2 and GUCY1B2; HAVCR2 and GUCY1B3; HMOX2 and BATF; HMOX2 and BTLA; HMOX2 and CASP10; HMOX2 and CASP3; HMOX2 and CASP6; HMOX2 and CASP7; HMOX2 and CASP8; HMOX2 and CD160; HMOX2 and CD244; HMOX2 and CD96; HMOX2 and CRTAM; HMOX2 and CSK; HMOX2 and CTLA4; HMOX2 and EIF2AK4; HMOX2 and FADD; HMOX2 and FAS; HMOX2 and FOXP3; HMOX2 and GUCY1A2; HMOX2 and GUCY1A3; HMOX2 and GUCY1B2; HMOX2 and GUCY1B3; HMOX2 and HAVCR2; IL10RA and BATF; IL10RA and BTLA; IL10RA and CASP10; IL10RA and CASP3; IL10RA and CASP6; IL10RA and CASP7; IL10RA and CASP8; IL10RA and CD160; IL10RA and CD244; IL10RA and CD96; IL10RA and CRTAM; IL10RA and CSK; IL10RA and CTLA4; IL10RA and EIF2AK4; IL10RA and FADD; IL10RA and FAS; IL10RA and FOXP3; IL10RA and GUCY1A2; IL10RA and GUCY1A3; IL10RA and GUCY1B2; IL10RA and GUCY1B3; IL10RA and HAVCR2; IL10RA and HMOX2; IL10RB and BATF; IL10RB and BTLA; IL10RB and CASP10; IL10RB and CASP3; IL10RB and CASP6; IL10RB and CASP7; IL10RB and CASP8; IL10RB and CD160; IL10RB and CD244; IL10RB and CD96; IL10RB and CRTAM; IL10RB and CSK; IL10RB and CTLA4; IL10RB and EIF2AK4; IL10RB and FADD; IL10RB and FAS; IL10RB and FOXP3; IL10RB and GUCY1A2; IL10RB and GUCY1A3; IL10RB and GUCY1B2; IL10RB and GUCY1B3; IL10RB and HAVCR2; IL10RB and HMOX2; IL10RB and IL10RA; IL6R and BATF; IL6R and BTLA; IL6R and CASP10; IL6R and CASP3; IL6R and CASP6; IL6R and CASP7; IL6R and CASP8; IL6R and CD160; IL6R and CD244; IL6R and CD96; IL6R and CRTAM; IL6R and CSK; IL6R and CTLA4; IL6R and EIF2AK4; IL6R and FADD; IL6R and FAS; IL6R and FOXP3; IL6R and GUCY1A2; IL6R and GUCY1A3; IL6R and GUCY1B2; IL6R and GUCY1B3; IL6R and HAVCR2; IL6R and HMOX2; IL6R and IL10RA; IL6R and IL10RB; IL6ST and BATF; IL6ST and BTLA; IL6ST and CASP10; IL6ST and CASP3; IL6ST and CASP6; IL6ST and CASP7; IL6ST and CASP8; IL6ST and CD160; IL6ST and CD244; IL6ST and CD96; IL6ST and CRTAM; IL6ST and CSK; IL6ST and CTLA4; IL6ST and EIF2AK4; IL6ST and FADD; IL6ST and FAS; IL6ST and FOXP3; IL6ST and GUCY1A2; IL6ST and GUCY1A3; IL6ST and GUCY1B2; IL6ST and GUCY1B3; IL6ST and HAVCR2; IL6ST and HMOX2; IL6ST and IL10RA; IL6ST and IL10RB; IL6ST and IL6R; LAG3 and BATF; LAG3 and BTLA; LAG3 and CASP10; LAG3 and CASP3; LAG3 and CASP6; LAG3 and CASP7; LAG3 and CASP8; LAG3 and CD160; LAG3 and CD244; LAG3 and CD96; LAG3 and CRTAM; LAG3 and CSK; LAG3 and CTLA4; LAG3 and EIF2AK4; LAG3 and FADD; LAG3 and FAS; LAG3 and FOXP3; LAG3 and GUCY1A2; LAG3 and GUCY1A3; LAG3 and GUCY1B2; LAG3 and GUCY1B3; LAG3 and HAVCR2; LAG3 and HMOX2; LAG3 and IL10RA; LAG3 and IL10RB; LAG3 and IL6R; LAG3 and IL6ST; LAIR1 and BATF; LAIR1 and BTLA; LAIR1 and CASP10; LAIR1 and CASP3; LAIR1 and CASP6; LAIR1 and CASP7; LAIR1 and CASP8; LAIR1 and CD160; LAIR1 and CD244; LAIR1 and CD96; LAIR1 and CRTAM; LAIR1 and CSK; LAIR1 and CTLA4; LAIR1 and EIF2AK4; LAIR1 and FADD; LAIR1 and FAS; LAIR1 and FOXP3; LAIR1 and GUCY1A2; LAIR1 and GUCY1A3; LAIR1 and GUCY1B2; LAIR1 and GUCY1B3; LAIR1 and HAVCR2; LAIR1 and HMOX2; LAIR1 and IL10RA; LAIR1 and IL10RB; LAIR1. and IL6R; LAIR1 and IL6ST; LAIR1 and LAG3; PAG1 and BATF; PAG1 and BTLA; PAG1 and CASP10; PAG1 and CASP3; PAG1 and CASP6; PAG1 and CASP7; PAG1 and CASP8; PAG1 and CD160; PAG1 and CD244; PAG1 and CD96; PAG1 and CRTAM; PAG1 and CSK; PAG1 and CTLA4; PAG1 and EIF2AK4; PAG1 and FADD; PAG1 and FAS; PAG1 and FOXP3; PAG1 and GUCY1A2; PAG1 and GUCY1A3; PAG1 and GUCY1B2; PAG1 and GUCY1B3;

PAG1 and HAVCR2; PAG1 and HMOX2; PAG1 and IL10RA; PAG1 and IL10RB; PAG1 and IL6R; PAG1 and IL6ST; PAG1 and LAG3; PAG1 and LAIR1; PDCD1 and BATF; PDCD1 and BTLA; PDCD1 and CASP10; PDCD1 and CASP3; PDCD1 and CASP6; PDCD1 and CASP7; PDCD1 and CASP8; PDCD1 and CD160; PDCD1 and CD244; PDCD1 and CD96; PDCD1 and CRTAM; PDCD1 and CSK; PDCD1 and CTLA4; PDCD1 and EIF2AK4; PDCD1 and FADD; PDCD1 and FAS; PDCD1 and FOXP3; PDCD1 and GUCY1A2; PDCD1 and GUCY1A3; PDCD1 and GUCY1B2; PDCD1 and GUCY1B3; PDCD1 and HAVCR2; PDCD1 and HMOX2; PDCD1 and IL10RA; PDCD1 and IL10RB; PDCD1 and IL6R; PDCD1 and IL6ST; PDCD1 and LAG3; PDCD1 and LAIR1; PDCD1 and PAG1; PPP2CA and BATF; PPP2CA and BTLA; PPP2CA and CASP10; PPP2CA and CASP3; PPP2CA and CASP6; PPP2CA and CASP7; PPP2CA and CASP8; PPP2CA and CD160; PPP2CA and CD244; PPP2CA and CD96; PPP2CA and CRTAM; PPP2CA and CSK; PPP2CA and CTLA4; PPP2CA and EIF2AK4; PPP2CA and FADD; PPP2CA and FAS; PPP2CA and FOXP3; PPP2CA and GUCY1A2; PPP2CA and GUCY1A3; PPP2CA and GUCY1B2; PPP2CA and GUCY1B3; PPP2CA and HAVCR2; PPP2CA and HMOX2; PPP2CA and IL10RA; PPP2CA and IL10RB; PPP2CA and IL6R; PPP2CA and IL6ST; PPP2CA and LAG3; PPP2CA and LAIR1; PPP2CA and PAG1; PPP2CA and PDCD1; PPP2CB and BATF; PPP2CB and BTLA; PPP2CB and CASP10; PPP2CB and CASP3; PPP2CB and CASP6; PPP2CB and CASP7; PPP2CB and CASP8; PPP2CB and CD160; PPP2CB and CD244; PPP2CB and CD96; PPP2CB and CRTAM; PPP2CB and CSK; PPP2CB and CTLA4; PPP2CB and EIF2AK4; PPP2CB and FADD; PPP2CB and FAS; PPP2CB and FOXP3; PPP2CB and GUCY1A2; PPP2CB and GUCY1A3; PPP2CB and GUCY1B2; PPP2CB and GUCY1B3; PPP2CB and HAVCR2; PPP2CB and HMOX2; PPP2CB and IL10RA; PPP2CB and IL10RB; PPP2CB and IL6R; PPP2CB and IL6ST; PPP2CB and LAG3; PPP2CB and LAIR1; PPP2CB and PAG1; PPP2CB and PDCD1; PPP2CB and PPP2CA; PRDM1 and BATF; PRDM1 and BTLA; PRDM1 and CASP10; PRDM1 and CASP3; PRDM1 and CASP6; PRDM1 and CASP7; PRDM1 and CASP8; PRDM1 and CD160; PRDM1 and CD244; PRDM1 and CD96; PRDM1 and CRTAM; PRDM1 and CSK; PRDM1 and CTLA4; PRDM1 and EIF2AK4; PRDM1 and FADD; PRDM1 and FAS; PRDM1 and FOXP3; PRDM1 and GUCY1A2; PRDM1 and GUCY1A3; PRDM1 and GUCY1B2; PRDM1 and GUCY1B3; PRDM1 and HAVCR2; PRDM1 and HMOX2; PRDM1 and IL10RA; PRDM1 and IL10RB; PRDM1 and IL6R; PRDM1 and IL6ST; PRDM1 and LAG3; PRDM1 and LAIR1; PRDM1 and PAG1; PRDM1 and PDCD1; PRDM1 and PPP2CA; PRDM1 and PPP2CB; PTPN22 and BATF; PTPN22 and BTLA; PTPN22 and CASP10; PTPN22 and CASP3; PTPN22 and CASP6; PTPN22 and CASP7; PTPN22 and CASP8; PTPN22 and CD160; PTPN22 and CD244; PTPN22 and CD96; PTPN22 and CRTAM; PTPN22 and CSK; PTPN22 and CTLA4; PTPN22 and EIF2AK4; PTPN22 and FADD; PTPN22 and FAS; PTPN22 and FOXP3; PTPN22 and GUCY1A2; PTPN22 and GUCY1A3; PTPN22 and GUCY1B2; PTPN22 and GUCY1B3; PTPN22 and HAVCR2; PTPN22 and HMOX2; PTPN22 and IL10RA; PTPN22 and IL10RB; PTPN22 and IL6R; PTPN22 and IL6ST; PTPN22 and LAG3; PTPN22 and LAIR1; PTPN22 and PAG1; PTPN22 and PDCD1; PTPN22 and PPP2CA; PTPN22 and PPP2CB; PTPN22 and PRDM1; PTPN6 and BATF; PTPN6 and BTLA; PTPN6 and CASP10; PTPN6 and CASP3; PTPN6 and CASP6; PTPN6 and CASP7; PTPN6 and CASP8; PTPN6 and CD160; PTPN6 and CD244; PTPN6 and CD96; PTPN6 and CRTAM; PTPN6 and CSK; PTPN6 and CTLA4; PTPN6 and EIF2AK4; PTPN6 and FADD; PTPN6 and FAS; PTPN6 and FOXP3; PTPN6 and GUCY1A2; PTPN6 and GUCY1A3; PTPN6 and GUCY1B2; PTPN6 and GUCY1B3; PTPN6 and HAVCR2; PTPN6 and HMOX2; PTPN6 and IL10RA; PTPN6 and IL10RB; PTPN6 and IL6R; PTPN6 and IL6ST; PTPN6 and LAG3; PTPN6 and LAIR1; PTPN6 and PAG1; PTPN6 and PDCD1; PTPN6 and PPP2CA; PTPN6 and PPP2CB; PTPN6 and PRDM1; PTPN6 and PTPN22; SIGLEC7 and BATF; SIGLEC7 and BTLA; SIGLEC7 and CASP10; SIGLEC7 and CASP3; SIGLEC7 and CASP6; SIGLEC7 and CASP7; SIGLEC7 and CASP8; SIGLEC7 and CD160; SIGLEC7 and CD244; SIGLEC7 and CD96; SIGLEC7 and CRTAM; SIGLEC7 and CSK; SIGLEC7 and CTLA4; SIGLEC7 and EIF2AK4; SIGLEC7 and FADD; SIGLEC7 and FAS; SIGLEC7 and FOXP3; SIGLEC7 and GUCY1A2; SIGLEC7 and GUCY1A3; SIGLEC7 and GUCY1B2; SIGLEC7 and GUCY1B3; SIGLEC7 and HAVCR2; SIGLEC7 and HMOX2; SIGLEC7 and IL10RA; SIGLEC7 and IL10RB; SIGLEC7 and IL6R; SIGLEC7 and IL6ST; SIGLEC7 and LAG3; SIGLEC7 and LAIR1; SIGLEC7 and PAG1; SIGLEC7 and PDCD1; SIGLEC7 and PPP2CA; SIGLEC7 and PPP2CB; SIGLEC7 and PRDM1; SIGLEC7 and PTPN22; SIGLEC7 and PTPN6; SIGLEC9 and BATF; SIGLEC9 and BTLA; SIGLEC9 and CASP10; SIGLEC9 and CASP3; SIGLEC9 and CASP6; SIGLEC9 and CASP7; SIGLEC9 and CASP8; SIGLEC9 and CD160; SIGLEC9 and CD244; SIGLEC9 and CD96; SIGLEC9 and CRTAM; SIGLEC9 and CSK; SIGLEC9 and CTLA4; SIGLEC9 and EIF2AK4; SIGLEC9 and FADD; SIGLEC9 and FAS; SIGLEC9 and FOXP3; SIGLEC9 and GUCY1A2; SIGLEC9 and GUCY1A3; SIGLEC9 and GUCY1B2; SIGLEC9 and GUCY1B3; SIGLEC9 and HAVCR2; SIGLEC9 and HMOX2; SIGLEC9 and IL10RA; SIGLEC9 and IL10RB; SIGLEC9 and IL6R; SIGLEC9 and IL6ST; SIGLEC9 and LAG3; SIGLEC9 and LAIR1; SIGLEC9 and PAG1; SIGLEC9 and PDCD1; SIGLEC9 and PPP2CA; SIGLEC9 and PPP2CB; SIGLEC9 and PRDM1; SIGLEC9 and PTPN22; SIGLEC9 and PTPN6; SIGLEC9 and SIGLEC7; SIT1 and BATF; SIT1 and BTLA; SIT1 and CASP10; SIT1 and CASP3; SIT1 and CASP6; SIT1 and CASP7; SIT1 and CASP8; SIT1 and CD160; SIT1 and CD244; SIT1 and CD96; SIT1 and CRTAM; SIT1 and CSK; SIT1 and CTLA4; SIT1 and EIF2AK4; SIT1 and FADD; SIT1 and FAS; SIT1 and FOXP3; SIT1 and GUCY1A2; SIT1 and GUCY1A3; SIT1 and GUCY1B2; SIT1 and GUCY1B3; SIT1 and HAVCR2; SIT1 and HMOX2; SIT1 and IL10RA; SIT1 and IL10RB; SIT1 and IL6R; SIT1 and IL6ST; SIT1 and LAG3; SIT1 and LAIR1; SIT1 and PAG1; SIT1 and PDCD1; SIT1 and PPP2CA; SIT1 and PPP2CB; SIT1 and PRDM1; SIT1 and PTPN22; SIT1 and PTPN6; SIT1 and SIGLEC7; SIT1 and SIGLEC9; SKI and BATF; SKI and BTLA; SKI and CASP10; SKI and CASP3; SKI and CASP6; SKI and CASP7; SKI and CASP8; SKI and CD160; SKI and CD244; SKI and CD96; SKI and CRTAM; SKI and CSK; SKI and CTLA4; SKI and EIF2AK4; SKI and FADD; SKI and FAS; SKI and FOXP3; SKI and GUCY1A2; SKI and GUCY1A3; SKI and GUCY1B2; SKI and GUCY1B3; SKI and HAVCR2; SKI and HMOX2; SKI and IL10RA; SKI and IL10RB; SKI and IL6R; SKI and IL6ST; SKI and LAG3; SKI and LAIR1; SKI and PAG1; SKI and PDCD1; SKI and PPP2CA; SKI and PPP2CB; SKI and PRDM1; SKI and PTPN22; SKI and PTPN6; SKI and SIGLEC7; SKI and SIGLEC9; SKI and SIT1; SKIL and BATF; SKIL and BTLA; SKIL and CASP10; SKIL and CASP3; SKIL and CASP6; SKIL and CASP7; SKIL and CASP8; SKIL and CD160; SKIL and CD244; SKIL and CD96; SKIL and CRTAM; SKIL and CSK; SKIL and CTLA4; SKIL and EIF2AK4; SKIL and FADD; SKIL and FAS; SKIL and FOXP3; SKIL and GUCY1A2; SKIL and GUCY1A3; SKIL and GUCY1B2; SKIL and GUCY1B3; SKIL and HAVCR2; SKIL and HMOX2; SKIL and IL10RA; SKIL and IL10RB; SKIL and IL6R; SKIL and IL6ST; SKIL and LAG3; SKIL and LAIR1; SKIL and PAG1; SKIL and PDCD1; SKIL and PPP2CA; SKIL and PPP2CB; SKIL and PRDM1; SKIL and PTPN22; SKIL and PTPN6; SKIL and SIGLEC7; SKIL and SIGLEC9; SKIL and SIT1; SKIL and SKI; SMAD10 and BATF; SMAD10 and BTLA; SMAD10 and CASP10; SMAD10 and CASP3; SMAD10 and CASP6; SMAD10 and CASP7; SMAD10 and CASP8; SMAD10 and CD160; SMAD10 and CD244; SMAD10 and CD96; SMAD10 and CRTAM; SMAD10 and CSK; SMAD10 and CTLA4; SMAD10 and EIF2AK4; SMAD10 and FADD; SMAD10 and FAS; SMAD10 and FOXP3; SMAD10 and GUCY1A2; SMAD10 and GUCY1A3; SMAD10 and GUCY1B2; SMAD10 and GUCY1B3; SMAD10 and HAVCR2; SMAD10 and HMOX2; SMAD10 and IL10RA; SMAD10 and IL10RB; SMAD10 and IL6R; SMAD10 and IL6ST; SMAD10 and LAG3; SMAD10 and LAIR1; SMAD10 and PAG1; SMAD10 and PDCD1; SMAD10 and PPP2CA; SMAD10 and PPP2CB; SMAD10 and PRDM1; SMAD10 and PTPN22; SMAD10 and PTPN6; SMAD10 and SIGLEC7; SMAD10 and SIGLEC9; SMAD10 and SIT1; SMAD10 and SKI; SMAD10 and SKIL; SMAD2 and BATF; SMAD2 and BTLA; SMAD2 and CASP10; SMAD2 and CASP3; SMAD2 and CASP6; SMAD2 and CASP7; SMAD2 and CASP8; SMAD2 and CD160; SMAD2 and CD244; SMAD2 and CD96; SMAD2 and CRTAM; SMAD2 and CSK; SMAD2 and CTLA4; SMAD2 and EIF2AK4; SMAD2 and FADD; SMAD2 and FAS; SMAD2 and FOXP3; SMAD2 and GUCY1A2; SMAD2 and GUCY1A3; SMAD2 and GUCY1B2; SMAD2 and GUCY1B3; SMAD2 and HAVCR2; SMAD2 and HMOX2; SMAD2 and IL10RA; SMAD2 and IL10RB; SMAD2 and IL6R; SMAD2 and IL6ST; SMAD2 and LAG3; SMAD2 and LAIR1; SMAD2 and PAG1; SMAD2 and PDCD1; SMAD2 and PPP2CA; SMAD2 and PPP2CB; SMAD2 and PRDM1; SMAD2 and PTPN22; SMAD2 and PTPN6; SMAD2 and SIGLEC7; SMAD2 and SIGLEC9; SMAD2 and SIT1; SMAD2 and SKI; SMAD2 and SKIL; SMAD2 and SMAD10; SMAD3 and BATF; SMAD3 and BTLA; SMAD3 and CASP10; SMAD3 and CASP3; SMAD3 and CASP6; SMAD3 and CASP7; SMAD3 and CASP8; SMAD3 and CD160; SMAD3 and CD244; SMAD3 and CD96; SMAD3 and CRTAM; SMAD3 and CSK; SMAD3 and CTLA4; SMAD3 and EIF2AK4; SMAD3 and FADD; SMAD3 and FAS; SMAD3 and FOXP3; SMAD3 and GUCY1A2; SMAD3 and GUCY1A3; SMAD3 and GUCY1B2; SMAD3 and GUCY1B3; SMAD3 and HAVCR2; SMAD3 and HMOX2; SMAD3 and IL10RA; SMAD3 and IL10RB; SMAD3 and IL6R; SMAD3 and IL6ST; SMAD3 and LAG3; SMAD3 and LAIR1; SMAD3 and PAG1; SMAD3 and PDCD1; SMAD3 and PPP2CA; SMAD3 and PPP2CB; SMAD3 and PRDM1; SMAD3 and PTPN22; SMAD3 and PTPN6; SMAD3 and SIGLEC7; SMAD3 and SIGLEC9; SMAD3 and SIT1; SMAD3 and SKI; SMAD3 and SKIL; SMAD3 and SMAD10; SMAD3 and SMAD2; SMAD4 and BATF; SMAD4 and BTLA; SMAD4 and CASP10; SMAD4 and CASP3; SMAD4 and CASP6; SMAD4 and CASP7; SMAD4 and CASP8; SMAD4 and CD160; SMAD4 and CD244; SMAD4 and CD96; SMAD4 and CRTAM; SMAD4 and CSK; SMAD4 and CTLA4; SMAD4 and EIF2AK4; SMAD4 and FADD; SMAD4 and FAS; SMAD4 and FOXP3; SMAD4 and GUCY1A2; SMAD4 and GUCY1A3; SMAD4 and GUCY1B2; SMAD4 and GUCY1B3; SMAD4 and HAVCR2; SMAD4 and HMOX2; SMAD4 and IL10RA; SMAD4 and IL10RB; SMAD4 and IL6R; SMAD4 and IL6ST; SMAD4 and LAG3; SMAD4 and LAIR1; SMAD4 and PAG1; SMAD4 and PDCD1; SMAD4 and PPP2CA; SMAD4 and PPP2CB; SMAD4 and PRDM1; SMAD4 and PTPN22; SMAD4 and PTPN6; SMAD4 and SIGLEC7; SMAD4 and SIGLEC9; SMAD4 and SIT1; SMAD4 and SKI; SMAD4 and SKIL; SMAD4 and SMAD10; SMAD4 and SMAD2; SMAD4 and SMAD3; TGFBR1 and BATF; TGFBR1 and BTLA; TGFBR1 and CASP10; TGFBR1 and CASP3; TGFBR1 and CASP6; TGFBR1 and CASP7; TGFBR1 and CASP8; TGFBR1 and CD160; TGFBR1 and CD244; TGFBR1 and CD96; TGFBR1 and CRTAM; TGFBR1 and CSK; TGFBR1 and CTLA4; TGFBR1 and EIF2AK4; TGFBR1 and FADD; TGFBR1 and FAS; TGFBR1 and FOXP3; TGFBR1 and GUCY1A2; TGFBR1 and GUCY1A3; TGFBR1 and GUCY1B2; TGFBR1 and GUCY1B3; TGFBR1 and HAVCR2; TGFBR1 and HMOX2; TGFBR1 and IL10RA; TGFBR1 and IL10RB; TGFBR1 and IL6R; TGFBR1 and IL6ST; TGFBR1 and LAG3; TGFBR1 and LAIR1; TGFBR1 and PAG1; TGFBR1 and PDCD1; TGFBR1 and PPP2CA; TGFBR1 and PPP2CB; TGFBR1 and PRDM1; TGFBR1 and PTPN22; TGFBR1 and PTPN6; TGFBR1 and SIGLEC7; TGFBR1 and SIGLEC9; TGFBR1 and SIT1; TGFBR1 and SKI; TGFBR1 and SKIL; TGFBR1 and SMAD10; TGFBR1 and SMAD2; TGFBR1 and SMAD3; TGFBR1 and SMAD4; TGFBR2 and BATF; TGFBR2 and BTLA; TGFBR2 and CASP10; TGFBR2 and CASP3; TGFBR2 and CASP6; TGFBR2 and CASP7; TGFBR2 and CASP8; TGFBR2 and CD160; TGFBR2 and CD244; TGFBR2 and CD96; TGFBR2 and CRTAM; TGFBR2 and CSK; TGFBR2 and CTLA4; TGFBR2 and EIF2AK4; TGFBR2 and FADD; TGFBR2 and FAS; TGFBR2 and FOXP3; TGFBR2 and GUCY1A2; TGFBR2 and GUCY1A3; TGFBR2 and GUCY1B2; TGFBR2 and GUCY1B3; TGFBR2 and HAVCR2; TGFBR2 and HMOX2; TGFBR2 and IL10RA; TGFBR2 and IL10RB; TGFBR2 and IL6R; TGFBR2 and IL6ST; TGFBR2 and LAG3; TGFBR2 and LAIR1; TGFBR2 and PAG1; TGFBR2 and PDCD1; TGFBR2 and PPP2CA; TGFBR2 and PPP2CB; TGFBR2 and PRDM1; TGFBR2 and PTPN22; TGFBR2 and PTPN6; TGFBR2 and SIGLEC7; TGFBR2 and SIGLEC9; TGFBR2 and SIT1; TGFBR2 and SKI; TGFBR2 and SKIL; TGFBR2 and SMAD10; TGFBR2 and SMAD2; TGFBR2 and SMAD3; TGFBR2 and SMAD4; TGFBR2 and TGFBR1; TGIF1 and BATF; TGIF1 and BTLA; TGIF1 and CASP10; TGIF1 and CASP3; TGIF1 and CASP6; TGIF1 and CASP7; TGIF1 and CASP8; TGIF1 and CD160; TGIF1 and CD244; TGIF1 and CD96; TGIF1 and CRTAM; TGIF1 and CSK; TGIF1 and CTLA4; TGIF1 and EIF2AK4; TGIF1 and FADD; TGIF1 and FAS; TGIF1 and FOXP3; TGIF1 and GUCY1A2; TGIF1 and GUCY1A3; TGIF1 and GUCY1B2; TGIF1 and GUCY1B3; TGIF1 and HAVCR2; TGIF1 and HMOX2; TGIF1 and IL10RA; TGIF1 and IL10RB; TGIF1 and IL6R; TGIF1 and IL6ST; TGIF1 and LAG3; TGIF1 and LAIR1; TGIF1 and PAG1; TGIF1 and PDCD1; TGIF1 and PPP2CA; TGIF1 and PPP2CB; TGIF1 and PRDM1; TGIF1 and PTPN22; TGIF1 and PTPN6; TGIF1 and SIGLEC7; TGIF1 and SIGLEC9; TGIF1 and SIT1; TGIF1 and SKI;

TGIF1 and SKIL; TGIF1 and SMAD10; TGIF1 and SMAD2; TGIF1 and SMAD3; TGIF1 and SMAD4; TGIF1 and TGFBR1; TGIF1 and TGFBR2; TIGIT and BATF; TIGIT and BTLA; TIGIT and CASP10; TIGIT and CASP3; TIGIT and CASP6; TIGIT and CASP7; TIGIT and CASP8; TIGIT and CD160; TIGIT and CD244; TIGIT and CD96; TIGIT and CRTAM; TIGIT and CSK; TIGIT and CTLA4; TIGIT and EIF2AK4; TIGIT and FADD; TIGIT and FAS; TIGIT and FOXP3; TIGIT and GUCY1A2; TIGIT and GUCY1A3; TIGIT and GUCY1B2; TIGIT and GUCY1B3; TIGIT and HAVCR2; TIGIT and HMOX2; TIGIT and IL10RA; TIGIT and IL10RB; TIGIT and IL6R; TIGIT and IL6ST; TIGIT and LAG3; TIGIT and LAIR1; TIGIT and PAG1; TIGIT and PDCD1; TIGIT and PPP2CA; TIGIT and PPP2CB; TIGIT and PRDM1; TIGIT and PTPN22; TIGIT and PTPN6; TIGIT and SIGLEC7; TIGIT and SIGLEC9; TIGIT and SIT1; TIGIT and SKI; TIGIT and SKIL; TIGIT and SMAD10; TIGIT and SMAD2; TIGIT and SMAD3; TIGIT and SMAD4; TIGIT and TGFBR1; TIGIT and TGFBR2; TIGIT and TGIF1; TNFRSF10A and BATF; TNFRSF10A and BTLA; TNFRSF10A and CASP10; TNFRSF10A and CASP3; TNFRSF10A and CASP6; TNFRSF10A and CASP7; TNFRSF10A and CASP8; TNFRSF10A and CD160; TNFRSF10A and CD244; TNFRSF10A and CD96; TNFRSF10A and CRTAM; TNFRSF10A and CSK; TNFRSF10A and CTLA4; TNFRSF10A and EIF2AK4; TNFRSF10A and FADD; TNFRSF10A and FAS; TNFRSF10A and FOXP3; TNFRSF10A and GUCY1A2; TNFRSF10A and GUCY1A3; TNFRSF10A and GUCY1B2; TNFRSF10A and GUCY1B3; TNFRSF10A and HAVCR2; TNFRSF10A and HMOX2; TNFRSF10A and IL10RA; TNFRSF10A and IL10RB; TNFRSF10A and IL6R; TNFRSF10A and IL6ST; TNFRSF10A and LAG3; TNFRSF10A and LAIR1; TNFRSF10A and PAG1; TNFRSF10A and PDCD1; TNFRSF10A and PPP2CA; TNFRSF10A and PPP2CB; TNFRSF10A and PRDM1; TNFRSF10A and PTPN22; TNFRSF10A and PTPN6; TNFRSF10A and SIGLEC7; TNFRSF10A and SIGLEC9; TNFRSF10A and SIT1; TNFRSF10A and SKI; TNFRSF10A and SKIL; TNFRSF10A and SMAD10; TNFRSF10A and SMAD2; TNFRSF10A and SMAD3; TNFRSF10A and SMAD4; TNFRSF10A and TGFBR1; TNFRSF10A and TGFBR2; TNFRSF10A and TGIF1; TNFRSF10A and TIGIT; TNFRSF10B and BATF; TNFRSF10B and BTLA; TNFRSF10B and CASP10; TNFRSF10B and CASP3; TNFRSF10B and CASP6; TNFRSF10B and CASP7; TNFRSF10B and CASP8; TNFRSF10B and CD160; TNFRSF10B and CD244; TNFRSF10B and CD96; TNFRSF10B and CRTAM; TNFRSF10B and CSK; TNFRSF10B and CTLA4; TNFRSF10B and EIF2AK4; TNFRSF10B and FADD; TNFRSF10B and FAS; TNFRSF10B and FOXP3; TNFRSF10B and GUCY1A2; TNFRSF10B and GUCY1A3; TNFRSF10B and GUCY1B2; TNFRSF10B and GUCY1B3; TNFRSF10B and HAVCR2; TNFRSF10B and HMOX2; TNFRSF10B and IL10RA; TNFRSF10B and IL10RB; TNFRSF10B and IL6R; TNFRSF10B and IL6ST; TNFRSF10B and LAG3; TNFRSF10B and LAIR1; TNFRSF10B and PAG1; TNFRSF10B and PDCD1; TNFRSF10B and PPP2CA; TNFRSF10B and PPP2CB; TNFRSF10B and PRDM1; TNFRSF10B and PTPN22; TNFRSF10B and PTPN6; TNFRSF10B and SIGLEC7; TNFRSF10B and SIGLEC9; TNFRSF10B and SIT1; TNFRSF10B and SKI; TNFRSF10B and SKIL; TNFRSF10B and SMAD10; TNFRSF10B and SMAD2; TNFRSF10B and SMAD3; TNFRSF10B and SMAD4; TNFRSF10B and TGFBR1; TNFRSF10B and TGFBR2; TNFRSF10B and TGIF1; TNFRSF10B and TIGIT; TNFRSF10B and TNFRSF10A.

By inactivating a gene it is intended that the gene of interest is not expressed in a functional protein form. The gene can be altered or deleted. In a particular embodiment, said protein can be mutated and remains active as a dominant negative form. In another particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art.

In a particular embodiment, said method to engineer cells comprises at least one of the following steps:
(a) providing a T-cell, preferably from a cell culture or from a blood sample;
(b) introducing into said T-cell rare-cutting endonucleases able to selectively inactivate by DNA cleavage, preferably by double-strand break at least two genes encoding immune checkpoint proteins, and
(c) expanding said cells.

Said genes encoding immune checkpoint proteins are preferably selected from the list as described above.

In another embodiment, said rare-cutting endonuclease can be a meganuclease, a Zinc finger nuclease, CRISPR/Cas9 or a TALE-nuclease. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

In the present invention new TALE-nucleases have been designed for precisely targeting relevant genes for adoptive immunotherapy strategies. Preferred TALE-nucleases according to the invention are those recognizing and cleaving the target sequence selected from the group consisting of: SEQ ID NO: 77 and SEQ ID NO: 78 (PD1), SEQ ID NO: 74 to SEQ ID NO: 76 (CTLA-4). The present invention also relates to TALE-nuclease polypeptides which comprise an amino acid sequence selected from the group consisting of SEQ ID NO: 79 to SEQ ID NO: 88.

In another embodiment, additional catalytic domain can be further introduced into the cell with said rare-cutting endonuclease to increase mutagenesis in order to enhance their capacity to inactivate targeted genes. In particular, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), *E. coli* ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX polypeptide (WO2013/009525). Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. In particular, the homologous sequence is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

In particular, said exogenous nucleic acid successively comprises a first region of homology to sequences upstream of said cleavage, a sequence to inactivate one targeted gene selected from the group consisting of immune checkpoint genes and a second region of homology to sequences downstream of the cleavage. Said polynucleotide introduction step can be simultaneous, before or after the introduction or expression of said rare-cutting endonuclease. Depending on the location of the target nucleic acid sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting). As mentioned above, said additional genomic modification step can be an inactivation step comprising:
(a) introducing into said cells at least one rare-cutting endonuclease such that said rare-cutting endonuclease specifically catalyzes cleavage in one targeted sequence of the genome of said cell.
(b) Optionally introducing into said cells a exogenous nucleic acid successively comprising a first region of homology to sequences upstream of said cleavage, a sequence to be inserted in the genome of said cell and a second region of homology to sequences downstream of said cleavage,
wherein said introduced exogenous nucleic acid inactivates a gene and integrates at least one exogenous polynucleotide sequence encoding at least one recombinant protein of interest. In another embodiment, said exogenous polynucleotide sequence is integrated within a gene selected from the group consisting of immune checkpoint genes.

In particular embodiment said method to engineer cell further comprises an additional genomic modification step. By additional genomic modification step, can be intended the introduction into cells to engineer of one protein of interest. Said protein of interest can be, as non limiting examples a Chimeric Antigen Receptor (CAR), a multi-chain CAR, a bispecific antibody as described in the present disclosure. Said method to engineer cell can also further comprise the introduction of rare-cutting endonuclease able to selectively inactivate by DNA cleavage a gene encoding a target for said immunosuppressive agent, TCR genes as described in the present disclosure.

The invention also relates to TALE-nucleases. Generally, the invention relates to TALE-nuclease comprising:
(a) A Transcription Activator-Like Effector (TALE) DNA binding domain that has been engineered to bind a target sequence within genes selected from the group consisting of immune checkpoint genes;
(b) A cleavage domain or a cleavage half-domain.

Preferred TALE-nucleases according to the invention are those recognizing and cleaving the target sequence selected from the group consisting of: SEQ ID NO: 77 and SEQ ID NO: 78 (PD1) and SEQ ID NO: 74 to SEQ ID NO: 76 (CTLA-4).

Said TALE-nucleases preferably comprise a polypeptide sequence selected from the group consisting of SEQ ID NO: 79 to SEQ ID NO: 88 in order to cleave the respective target SEQ ID NO: 74 to 78.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO: 79 to SEQ ID NO: 88.

Are also comprised in the scope of the present invention, polynucleotides, vectors encoding the above described rare-cutting endonucleases according to the invention.

In the scope of the present invention are also encompassed isolated cells or cell lines susceptible to be obtained by said method to engineer cells, in particular T cells, in which at least one gene selected from the group consisting of immune checkpoint genes, preferably genes selected from the group of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3, more preferably, two of the above genes as listed previously have been inactivated. Those genes are preferably inactivated by at least one rare-cutting endonuclease. It has been shown by the inventors that the use of TALE-nucleases was particularly advantageous to achieve double inactivation in T-cells. The invention encompasses also an isolated T-cell comprising at least two polynucleotides, said polynucleotides encoding at least a first and second TALE-nucleases, preferably the TALE-nucleases being directed against at least two genes encoding immune checkpoint proteins, such as CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3. In another embodiment, said isolated cell further comprises one additional genomic modification. In another embodiment, said additional genomic modification is the integration of at least one exogenous polynucleotide sequence.

Non Alloreactive and Highly Active T Cells for Immunotherapy

The current protocol for treatment of patients using adoptive immunotherapy is based on autologous cell transfer. Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Ideally, one would like to use a standardized therapy in which allogeneic therapeutic cells could be pre-manufactured, characterized in detail, and available for immediate administration to patients. However, endogenous TCR specificities of allogeneic cells which recognize the host tissue as foreign, result in graft versus host disease (GvHD), which can lead to serious tissue damage and death. Thus, in order to effectively use allogeneic cells, the inactivation of TCRalpha or TCRbeta can result in the elimination of the TCR from the surface of T cells preventing recognition of alloantigen and thus GVHD.

Thus, in a particular aspect, the present invention can relate to a method of engineering allogeneic T-cells, especially for immunotherapy.

In a particular embodiment, the method comprises:
(a) providing a T cell,
(b) modifying T-cells by inactivating at least:
  a first gene encoding an immune checkpoint protein, and
  a second gene encoding a component of the T-cell receptor (TCR)
(c) expanding said cells.

In a particular embodiment, the genetic modification step of the method relies on the inactivation of one gene, preferably two genes selected from the group consisting of CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT, FOXP3, PRDM1, BATF, GUCY1A2, GUCY1A3, GUCY1B2, GUCY1B3, TCR alpha and TCR beta. In another embodiment, the genetic modification step of the method relies on the inactivation of two genes selected from the group consisting of CTLA4 and TCR alpha, CTLA4 and TCR beta, PPP2CA and TCR alpha, PPP2CB and TCR beta, PTPN6 and TCR alpha, PTPN6 and TCR beta, PTPN22 and TCR alpha, PTPN22 and TCR beta, PDCD1 and TCR alpha, PDCD1 and TCR beta, LAG3 and TCR alpha, LAG3 and TCR beta, HAVCR2 and TCR alpha, HAVCR2 and TCR beta, BTLA and TCR alpha, BTLA and TCR beta, CD160 and TCR alpha, CD160 and TCR beta, TIGIT and TCR alpha, TIGIT and TCR beta, CD96 and TCR alpha, CD96 and TCR beta, CRTAM and TCR alpha, CRTAM and TCR beta, LAIR1 and TCR alpha, LAIR1 and TCR beta, SIGLEC7 and TCR alpha, SIGLEC7 and TCR beta, SIGLEC9 and TCR alpha, SIGLEC9 and TCR beta, CD244 and TCR alpha, CD244 and TCR beta, TNFRSF10B and TCR alpha, TNFRSF10B and TCR beta, TNFRSF10A and TCR alpha, TNFRSF10A and TCR beta, CASP8 and TCR alpha, CASP8 and TCR beta, CASP10 and TCR alpha, CASP10 and TCR beta, CASP3 and TCR alpha, CASP3 and TCR beta, CASP6 and TCR alpha, CASP6 and TCR beta, CASP7 and TCR alpha, CASP7 and TCR beta, FADD and TCR alpha, FADD and TCR beta, FAS and TCR alpha, FAS and TCR beta, TGFBRII and TCR alpha, TGFBRII and TCR beta, TGFRBRI and TCR alpha, TGFRBRI and TCR beta, SMAD2 and TCR alpha, SMAD2 and TCR beta, SMAD3 and TCR alpha, SMAD3 and TCR beta, SMAD4 and TCR alpha, SMAD4 and TCR beta, SMAD10 and TCR alpha, SMAD10 and TCR beta, SKI and TCR alpha, SKIL and TCR beta, TGIF1 and TCR alpha, TGIF1 and TCR beta, IL10RA and TCR alpha, IL10RA and TCR beta, IL10RB and TCR alpha, IL10RB and TCR beta, HMOX2 and TCR alpha, HMOX2 and TCR beta, IL6R and TCR alpha, IL6R and TCR beta, IL6ST and TCR alpha, IL6ST and TCR beta, EIF2AK4 and TCR alpha, EIF2AK4 and TCR beta, CSK and TCR alpha, CSK and TCR beta, PAG1 and TCR alpha, PAG1 and TCR beta, SIT1 and TCR alpha, SIT1 and TCR beta, FOXP3 and TCR alpha, FOXP3 and TCR beta, PRDM1 and TCR alpha, PRDM1 and TCR beta, BATF and TCR alpha, BATF and TCR beta, GUCY1A2 and TCR alpha, GUCY1A2 and TCR beta, GUCY1A3 and TCR alpha, GUCY1A3 and TCR beta, GUCY1B2 and TCR alpha, GUCY1B2 and TCR beta, GUCY1B3 and TCR alpha, GUCY1B3 and TCR beta. In another embodiment, the genetic modification step of the method relies on the inactivation of more than two genes. The genetic modification is preferably operated ex-vivo.

In a particular embodiment, said method to engineer cells comprises at least one of the following steps:
(a) providing a T-cell, preferably from a cell culture or from a blood sample;
(b) introducing into said T-cell a rare-cutting endonuclease able to selectively inactivate by DNA cleavage, preferably by double-strand break respectively:

said gene encoding a immune checkpoint protein, and at least one gene encoding a component of the T-cell receptor (TCR).
(c) expanding said cells.

In a more preferred embodiment, said method comprises:
(a) providing a T-cell, preferably from a cell culture or from a blood sample;
(b) transforming said T cell with nucleic acid encoding a rare-cutting endonuclease able to selectively inactivate by DNA cleavage, preferably by double-strand break respectively:
said gene encoding a immune checkpoint protein and at least one gene encoding a component of the T-cell receptor (TCR)
(c) expressing said rare-cutting endonucleases into said T-cells;
(d) sorting the transformed T-cells, which do not express TCR on their cell surface;
(e) expanding said cells.

In particular embodiment, said rare-cutting endonuclease specifically targets at least one gene, preferably two genes selected from the group consisting of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT, FOXP3, PRDM1, BATF, GUCY1A2, GUCY1A3, GUCY1B2, GUCY1B3, TCR alpha and TCR beta. In another embodiment, more than two rare-cutting endonucleases can be expressed in cells to engineer in order to target and/or inactivate more than two genes.

In another embodiment, said rare-cutting endonuclease can be a meganuclease, a Zinc finger nuclease or a TALE-nuclease. In a preferred embodiment, said rare-cutting endonuclease is a TALE-nuclease.

In the present invention new TALE-nucleases have been designed for precisely targeting relevant genes for adoptive immunotherapy strategies. Preferred TALE-nucleases according to the invention are those recognizing and cleaving the target sequence selected from the group consisting of: SEQ ID NO: 77 and SEQ ID NO: 78 (PD1), SEQ ID NO: 74 to SEQ ID NO: 76 (CTLA-4), SEQ ID NO: 37, 57 to 60 (TCRalpha), SEQ ID NO: 38 or 39 (TCRbeta). The present invention also relates to TALE-nuclease polypeptides which comprise an amino acid sequence selected from the group consisting of SEQ ID NO: 79 to SEQ ID NO: 88 and SEQ ID NO: 41 to 46.

The present invention also relates to polypeptides comprising an amino acid sequence that has at least 70%, preferably at least 80%, more preferably at least 90%, 95% 97% or 99% sequence identity with amino acid sequence selected from the group consisting of SEQ ID NO: 79 to SEQ ID NO: 88. Are also comprised in the scope of the present invention, polynucleotides, vectors encoding the above described rare-cutting endonucleases according to the invention. This method can be associated with any one of the different methods described in the present disclosure.

In preferred embodiment, inactivation of genes from the group consisting of immune checkpoint genes, TCR alpha and TCR beta can be done at a precise genomic location targeted by a specific TALE-nuclease, wherein said specific TALE-nuclease catalyzes a cleavage and wherein an exogenous nucleic acid successively comprising at least a region of homology and a sequence to inactivate one targeted gene selected from the group consisting of immune checkpoint genes, TCR alpha and TCR beta which is integrated by homologous recombination. In another embodiment, several genes can be, successively or at the same time, inactivated by using several TALE-nucleases respectively and specifically targeting one defined gene and several specific polynucleotides for specific gene inactivation.

By additional genomic modification step, can be intended also the inactivation of another gene selected from the group consisting of immune checkpoint genes, TCR alpha and TCR beta. As mentioned above, said additional genomic modification step can be an inactivation step comprising:
(a) introducing into said cells at least one rare-cutting endonuclease such that said rare-cutting endonuclease specifically catalyzes cleavage in one targeted sequence of the genome of said cell.
(b) Optionally introducing into said cells a exogenous nucleic acid successively comprising a first region of homology to sequences upstream of said cleavage, a sequence to be inserted in the genome of said cell and a second region of homology to sequences downstream of said cleavage,
wherein said introduced exogenous nucleic acid inactivates a gene and integrates at least one exogenous polynucleotide sequence encoding at least one recombinant protein of interest. In another embodiment, said exogenous polynucleotide sequence is integrated within a gene selected from the group consisting of immune checkpoint genes, TCR alpha and TCR beta.

In particular embodiment said method to engineer cell further comprises an additional genomic modification step. By additional genomic modification step, can be intended the introduction into cells to engineer of one protein of interest. Said protein of interest can be, as non limiting examples, pTalpha or functional variant thereof, a Chimeric Antigen Receptor (CAR), a multi-chain CAR, a bispecific antibody as described in the present disclosure. Said method to engineer cell can also further comprise the introduction of rare-cutting endonuclease able to selectively inactivate by DNA cleavage a gene encoding a target for said immunosuppressive agent as described in the present disclosure.

Are also comprised in the scope of the present invention, polynucleotides, vectors encoding the above described rare-cutting endonucleases according to the invention. In the scope of the present invention are also encompassed isolated cells or cell lines susceptible to be obtained by said method to engineer cells, in particular T cells, in which at least two genes selected from the group consisting of: CTLA4 and TCR alpha, CTLA4 and TCR beta, PPP2CA and TCR alpha, PPP2CB and TCR beta, PTPN6 and TCR alpha, PTPN6 and TCR beta, PTPN22 and TCR alpha, PTPN22 and TCR beta, PDCD1 and TCR alpha, PDCD1 and TCR beta, LAG3 and TCR alpha, LAG3 and TCR beta, HAVCR2 and TCR alpha, HAVCR2 and TCR beta, BTLA and TCR alpha, BTLA and TCR beta, CD160 and TCR alpha, CD160 and TCR beta, TIGIT and TCR alpha, TIGIT and TCR beta, CD96 and TCR alpha, CD96 and TCR beta, CRTAM and TCR alpha, CRTAM and TCR beta, LAIR1 and TCR alpha, LAIR1 and TCR beta, SIGLEC7 and TCR alpha, SIGLEC7 and TCR beta, SIGLEC9 and TCR alpha, SIGLEC9 and TCR beta, CD244 and TCR alpha, CD244 and TCR beta, TNFRSF10B and TCR alpha, TNFRSF10B and TCR beta, TNFRSF10A and TCR alpha, TNFRSF10A and TCR beta, CASP8 and TCR alpha, CASP8 and TCR beta, CASP10 and TCR alpha, CASP10 and TCR beta, CASP3 and TCR alpha, CASP3 and TCR beta, CASP6 and TCR alpha, CASP6 and TCR beta, CASP7 and TCR alpha, CASP7 and TCR beta, FADD and TCR alpha, FADD and TCR alpha, FAS and TCR alpha, FAS and TCR beta, TGFBRII and TCR alpha, TGFBRII and TCR beta, TGFRBRI and TCR alpha, TGFRBRI and TCR beta, SMAD2 and TCR alpha, SMAD2 and TCR beta, SMAD3 and TCR alpha, SMAD3 and TCR beta, SMAD4 and TCR alpha, SMAD4 and TCR beta, SMAD10 and TCR alpha, SMAD10 and TCR beta, SKI and TCR alpha, SKIL and TCR beta, TGIF1 and TCR alpha, TGIF1 and TCR beta, IL10RA and TCR alpha, IL10RA and TCR beta, IL10RB and TCR alpha, IL10RB and TCR beta, HMOX2 and TCR alpha, HMOX2 and TCR beta, IL6R and TCR alpha, IL6R and TCR beta, IL6ST and TCR alpha, IL6ST and TCR beta, EIF2AK4 and TCR alpha, EIF2AK4 and TCR beta, CSK and TCR alpha, CSK and TCR beta, PAG1 and TCR alpha, PAG1 and TCR beta, SIT1 and TCR alpha, SIT1 and TCR beta, FOXP3 and TCR alpha, FOXP3 and TCR beta, PRDM1 and TCR alpha, PRDM1 and TCR beta, BATF and TCR alpha, BATF and TCR beta, GUCY1A2 and TCR alpha, GUCY1A2 and TCR beta, GUCY1A3 and TCR alpha, GUCY1A3 and TCR beta, GUCY1B2 and TCR alpha, GUCY1B2 and TCR beta, GUCY1B3 and TCR alpha, GUCY1B3 and TCR beta, have been inactivated.

According to the invention, those genes are preferably inactivated by at least one rare-cutting endonuclease. It has been shown by the inventors that the use of TALE-nucleases was particularly advantageous to achieve double inactivation in T-cells. The invention encompasses an isolated T-cell comprising at least two polynucleotides, said polynucleotides encoding at least a first and second TALE-nucleases, preferably the first TALE-nuclease being directed against a gene encoding TCR and the second being directed against a gene encoding a immune checkpoint protein, such as CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3. In another embodiment, said isolated cell further comprises one additional genomic modification. In another embodiment, said additional genomic modification is the integration of at least one exogenous polynucleotide sequence.

Immunosuppressive Resistant T Cells

Allogeneic cells are rapidly rejected by the host immune system. It has been demonstrated that, allogeneic leukocytes present in non-irradiated blood products will persist for no more than 5 to 6 days (Boni, Muranski et al. 2008). Thus, to prevent rejection of allogeneic cells, the host's immune system has to be usually suppressed to some extent. However, in the case of adoptive immunotherapy the use of immunosuppressive drugs also have a detrimental effect on the introduced therapeutic T cells. Therefore, to effectively use an adoptive immunotherapy approach in these conditions, the introduced cells would need to be also resistant to the immunosuppressive treatment. Thus, in particular embodiment, the method according to the present invention further comprises a step of modifying T-cells to make them resistant immunosuppressive agent, preferably by inactivating at least one gene encoding a target for an immunosuppressive agent. An immunosuppressive agent is an agent that suppresses immune function by one of several mechanisms of action. In other words, an immunosuppressive agent is a role played by a compound which is exhibited by a capability to diminish the extent of an immune response. As non limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non limiting examples, targets for immunosuppressive agent can be a receptor for an immunosuppressive agent such as: CD52, glucocorticoid receptor (GR), a FKBP family gene member and a cyclophilin family gene member.

In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. Said rare-cutting endonuclease can be a meganuclease, a Zinc finger nuclease or a TALE-nuclease. Preferred TALE-nucleases according to the invention are those recognizing and cleaving the target sequence selected from the group consisting of: SEQ ID NO: 1 to 6 (GR), and SEQ ID NO: 40, 61 to 65 (CD52). Said TALE-nucleases preferably comprise a polypeptide sequence selected from SEQ ID NO: 7 to SEQ ID NO: 18 and SEQ ID NO: 47 and 48.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO: 7 to SEQ ID NO: 18 and SEQ ID NO: 47 and 48.

Are also comprised in the scope of the present invention, polynucleotides, vectors encoding the above described rare-cutting endonucleases according to the invention.

PreTalpha

Because of the nature of selection of TCRbeta chains through pairing with preTalpha during thymic development, in T cells in which TCRalpha has been inactivated, the heterologous introduction of the pTalpha transgene can result in the formation of a preTCR. This pTCR can serve as a means of T cell activation or stimulation in a manner that is non-MHC dependent, thus for example allowing continued expansion of alpha/beta T-cells following TCRalpha inactivation. Importantly, the pTCR complex displays a similar biochemical composition as the TCR in terms of associated CD3 subunits (Carrasco, Ramiro et al. 2001). In addition, in contrast to the TCR, pre-TCR signaling may occur in part by a ligand independent event. The crystal structure of the pTCR extracellular domain has provided a structural basis for the possible ligand-independence of pTCR signaling. The pTCR has been shown to form a head to tail dimer where two pTalpha-TCRbeta heterodimers associate (Pang, Berry et al. 2010).

In another aspect, the method according to the present invention further comprises introducing into said T-cell pTalpha (also named preTCRα) or a functional variant thereof and expanding said cells, optionally through stimulation of the CD3 complex. In a preferred embodiment, the method comprises:
a) Transforming said cells with nucleic acid encoding at least a fragment of pTalpha to support CD3 surface expression
b) Expressing said pTalpha into said cells
c) Expanding said cells optionally, optionally through stimulation of the CD3 complex.

The invention also relates to a method of preparing T-cells for immunotherapy comprising steps of the method for expansion for T-cell.

In particular embodiment, the pTalpha polynucleotide sequence can be introduced randomly or else through homologous recombination, in particular the insertion could be associated with the inactivation of the TCRalpha gene.

According to the invention, different functional variants of pTalpha are used. A "functional variant" of the peptide refers to a molecule substantially similar to either the entire peptide or a fragment thereof. A "fragment" of the pTalpha or functional variant thereof of the present Invention, refers to any subset of the molecule, that is, a shorter peptide. Preferred pTalpha or functional variants can be full length pTalpha or a C-terminal truncated pTalpha version. C-terminal truncated pTalpha lacks in C-terminal end one or more residues. As non limiting examples, C-terminal truncated pTalpha version lacks 18, 48, 62, 78, 92, 110 or 114 residues from the C-terminus of the protein (SEQ ID NO: 107 to SEQ ID NO: 114). Moreover, amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In preferred embodiment, at least one mutation is introduced in the different pTalpha versions as described above to affect dimerization. As non limiting example, mutated residue can be at least W46R, D22A, K24A, R102A or R117A of the human pTalpha protein or aligned positions using CLUSTALW method on pTalpha family or homologue member. Preferably pTalpha or variant thereof as described above comprise the mutated residue W46R (SEQ ID NO:123) or the mutated residues D22A, K24A, R102A and R117A (SEQ ID NO: 124). In particular embodiment, said pTalpha or variants are also fused to a signal-transducing domain such as CD28, OX40, ICOS, CD27, CD137 (4-1BB) and CD8 as non limiting examples (SEQ ID NO: 115 to SEQ ID NO: 120). The extracellular domain of pTalpha or variants as described above can be fused to a fragment of the TCRalpha protein, particularly the transmembrane and intracellular domain of TCRalpha (SEQ ID NO: 122). pTalpha variants can also be fused to the intracellular domain of TCRalpha (SEQ ID NO:121).

In another embodiment, said pTalpha versions are fused to an extracellular ligand-binding domain and more preferably pTalpha or functional variant thereof is fused to a single chain antibody fragment (scFV) comprising the light ($V_L$) and the heavy ($V_H$) variable fragment of a target antigen specific monoclonal antibody joined by a flexible linker. As a non limiting example, amino acid sequence of pTalpha or functional variant thereof is selected from the group consisting of SEQ ID NO: 107 to SEQ ID NO: 124.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO:107 to SEQ ID NO: 124.

By TCR alpha deficient T cell is intended an isolated T cell that lacks expression of a functional TCR alpha chain. This may be accomplished by different means, as non limiting examples, by engineering a T cell such that it does not express any functional TCR alpha on its cell surface or by engineering a T cell such that it produces very little functional TCR alpha chain on its surface or by engineering a T cell to express mutated or truncated form of TCR alpha chain.

TCR alpha deficient cells can no longer be expanded through CD3 complex. Thus, to overcome this problem and to allow proliferation of TCR alpha deficient cells, pTalpha or functional variant thereof is introduced into said cells, thus restoring a functional CD3 complex. In a preferred embodiment, the method further comprises introducing into said T cells rare-cutting endonucleases able to selectively inactivate by DNA cleavage one gene encoding one component of the T-cell receptor (TCR). In particular embodiment, said rare-cutting endonuclease is a TALE-nucleases. As non limiting examples, TALE-nuclease is directed against one of the gene target sequences of TCRalpha selected from the group consisting of SEQ ID NO: 37 and SEQ ID NO: 57 to 60. Preferably, TALE-nucleases are selected from the group consisting of SEQ ID NO: 41 and SEQ ID NO: 42.

In particular embodiment said method for expansion of TCR alpha deficient T-cells comprises an additional genomic modification step. By additional genomic modification step, can be intended the introduction into cells to engineer of one protein of interest. Said protein of interest can be, as non limiting examples, a Chimeric Antigen Receptor (CAR), particularly CAR comprising amino acid sequence SEQ ID NO: 73, a multi-chain CAR, particularly multi-chain CAR comprising amino acid sequence SEQ ID NO: 125 a bispecific antibody, rare-cutting endonucleases targeting PDCD1 or CTLA-4, particularly targeting nucleic acid sequence SEQ ID NO: 74 to SEQ ID NO: 78 or a rare-cutting endonuclease targeting a target for immunosuppressive agent as described in the present disclosure.

Are also encompassed in the present invention polypeptides encoding pTalpha, particularly functional variants described above. In a preferred embodiment the invention relates to a pTalpha or functional variant thereof fused to a signal transducing domain such as CD28, OX40, ICOS, CD137 and CD8. More particularly, the invention relates to pTalpha functional variant comprising amino acid sequence selected form the group consisting of SEQ ID NO: 107 to SEQ ID NO: 124. Are also encompassed in the present invention polynucleotides, vectors encoding pTalpha or functional variants thereof described above.

In the scope of the present invention are also encompassed isolated cells or cell lines susceptible to be obtained by said method. In particular said isolated cells or cell lines are obtained by introducing into said cells a pTalpha or a functional variant thereof to support CD3 surface expression. In a preferred embodiment, said isolated cell or cell line are further genetically modified by inactivating TCRalpha gene. This gene is preferably inactivating by at least one rare-cutting endonuclease. In a preferred embodiment said rare-cutting endonuclease is TALE-nuclease.

Multi-Chain Chimeric Antigen Receptor (CAR)

In another embodiment, the method according to the present invention further comprises introducing a multi-chain chimeric antigen receptor (CAR) particularly adapted to the production and expansion of engineered T-cells of the present invention. The multi-chain CAR comprising at least two of the following components:
  a) one polypeptide comprising the transmembrembrane domain of FcεRI alpha chain and an extracellular ligand-binding domain,
  b) one polypeptide comprising a part of N- and C-terminal cytoplasmic tail and the transmembrane domain of FcεRI beta chain and/or
  c) two polypeptides comprising each a part of intracytoplasmic tail and the transmembrane domain of FcεRI gamma chain, whereby different polypeptides multimerize together spontaneously to form dimeric, trimeric or tetrameric CAR.

One example of tetrameric CAR is illustrated in FIG. 3. Different versions of multichain CARs are represented in FIG. 4. One example of multi-chain CAR comprises amino acid sequence SEQ ID NO: 125. The term "a part of" used herein refers to any subset of the molecule, that is a shorter peptide. Alternatively, amino acid sequence functional variants of the polypeptide can be prepared by mutations in the DNA which encodes the polypeptide. Such functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity.

In a preferred embodiment, said extracellular ligand-binding domain is a scFv. Other binding domain than scFv can also be used for predefined targeting of lymphocytes, such as camelid single-domain antibody fragments or receptor ligands like a vascular endothelial growth factor polypeptide, an integrin-binding peptide, heregulin or an IL-13 mutein, antibody binding domains, antibody hypervariable loops or CDRs as non limiting examples.

In a preferred embodiment said polypeptide of a) further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

In a preferred embodiment, said polypeptide of a), b) and/or c) further comprises at least one signal-transducing domain. In a most preferred embodiment, said signal-transducing domain is selected from the group consisting of CD28, OX40, ICOS, CD137 and CD8.

In a preferred embodiment, said C-terminal cytoplasmic tail of FcεRI alpha, beta and/or gamma chain fragment further comprises TNFR-associated Factor 2 (TRAF2) binding motifs. In a most preferred embodiment, said C-terminal cytoplasmic tail of FcεRI alpha, beta and/or gamma chain is replaced by intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

In another preferred embodiment said intracytoplasmic domain of FcεRI alpha, beta and/or gamma chain is replaced by intracytoplasmic domain of TCR zeta chain (also named CD3 zeta). In another preferred embodiment, said intracytoplasmic domain of FcεRI alpha, beta and/or gamma chain comprises at least one additional immunoreceptor tyrosine-based activation motif (ITAM). ITAMs are well defined signaling motifs found in the intracytoplasmic tail of a variety of receptors that serve as binding sites for syk/zap70 class tyrosine kinases. Examples of ITAM used in the invention include those derived from TCRzeta, FCRgamma, FCRbeta, CD3gamma, CD3delta, CD3epsilon, CD5, CD22, CD79a, CD79b, and CD66d.

As non limiting example, different versions of multi-chain CAR are illustrated in FIG. 4.

In a preferred embodiment the multi-chain CAR comprise the amino acid sequence SEQ ID NO: 125. The present invention relates to polypeptides comprising a polypeptide sequence that has at least 70%, preferably at least 80%, more preferably at least 90%, 95% 97% or 99% sequence identity with amino acid sequence selected from the group consisting of SEQ ID NO: 125.

Are also comprised in the scope of the present invention, polynucleotides, vectors encoding the above described multi-chain CAR according to the invention. In encompassed particular embodiment, the invention relates to a method of preparing T-cells for immunotherapy comprising introducing into said T-cells the different polypeptides composing said multi-chain CAR and expanding said cells.

In another embodiment, said method further comprises a step of genetically modifying said cells by inactivating at least one gene expressing one component of the TCR and/or a target for an immunosuppressive agent. In a preferred embodiment, said gene is selected from the group consisting of TCRalpha, TCRbeta, CD52 and GR. In a preferred embodiment said method further comprises introducing into said T cells a rare-cutting endonuclease able to selectively inactivate by DNA cleavage said genes. In a more preferred embodiment said rare-cutting endonuclease is TALE-nuclease. Preferred TALE-nucleases according to the invention are those recognizing and cleaving the target sequence selected from the group consisting of: SEQ ID NO: 1 to 6 (GR), SEQ ID NO: 37, 57 to 60 (TCRalpha), SEQ ID NO: 38 or 39 (TCRbeta), and SEQ ID NO: 40, SEQ ID NO: 61 to SEQ ID NO: 65 (CD52).

In particular embodiment said method further comprises an additional genomic modification step. By additional genomic modification step, can be intended the introduction into cells to engineer of one protein of interest. Said protein of interest can be, as non limiting examples a bispecific antibody, rare-cutting endonuclease targeting PDCD1 or CTLA-4, a pTalpha or a functional variant thereof as described in the present disclosure.

The present invention also relates isolated cells or cell lines susceptible to be obtained by said method to engineer cells. In particular said isolated cell comprises exogenous polynucleotide sequences encoding polypeptides composing said multi-chain CAR.

Bispecific Antibodies

According to a further embodiment, engineered T cells obtained by the different methods as previously described can be further exposed with bispecific antibodies. Said T-cells could be exposed to bispecific antibodies ex vivo prior to administration to a patient or in vivo following administration to a patient. Said bispecific antibodies comprise two variable regions with distinct antigen properties that allow bringing the engineered cells into proximity to a target antigen. As a non limiting example, said bispecific antibody is directed against a tumor marker and lymphocyte antigen such as CD3 and has the potential to redirect and activate any circulating T cells against tumors.

Delivery Methods

The different methods described above involve introducing a protein of interest such as rare cutting endonuclease into a cell. As non-limiting example, said protein of interest can be introduced as transgenes preferably encoded by at least one plasmid vector. Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells. Said plasmid vector can comprise a selection marker which provides for identification and/or selection of cells which received said vector. Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme.

A more preferred embodiment of the invention, polynucleotides encoding polypeptides according to the present invention can be mRNA which is introduced directly into the cells, for example by electroporation. The inventors determined the optimal condition for mRNA electroporation in T-cell.

The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell.

Activation and Expansion of T Cells

Whether prior to or after genetic modification of the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell.

Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, -10, -2, IL-15, TGFp, and TNF—or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

Engineered T-Cells

In the scope of the present invention is also encompassed an isolated T cell obtained according to any one of the methods previously described. Said T-cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+T-lymphocytes and CD8+T-lymphocytes. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. In a more particular embodiment, the present invention relates to an isolated T-cell comprising at least two inactivated genes encoding for immune checkpoint proteins, more particularly, at least two genes selected from the group consisting of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3.

In another embodiment, said isolated cell according to the present invention can further comprises one inactivated gene selected from the group consisting of CD52, GR, TCR alpha and TCR beta and/or expresses a CAR, a multi-chain CAR and/or a pTalpha transgene.

Therapeutic Applications

In another embodiment, isolated cell obtained by the different methods or cell line derived from said isolated cell as previously described can be used as a medicament. In another embodiment, said medicament can be used for treating cancer or infections in a patient in need thereof. In another embodiment, said isolated cell according to the invention or cell line derived from said isolated cell can be used in the manufacture of a medicament for treatment of a cancer or a viral infection in a patient in need thereof.

In another aspect, the present invention relies on methods for treating patients in need thereof, said method comprising at least one of the following steps:

(a) providing a T-cell obtainable by any one of the methods previously described;

(b) Administrating said transformed T-cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy. The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^6$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p7056 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Example of Method to Engineer Human Allogeneic Cells for Immunotherapy

For a better understanding of the invention, one example of method to engineer human allogenic cells for immunotherapy is illustrated in FIG. 5. The method comprising a combination of one or several of the following steps:

1. Providing T-cells from a cell culture or from a blood sample from one individual patient or from blood bank and activating said T cells using anti-CD3/C28 activator beads. The beads provide both the primary and co-stimulatory signals that are required for activation and expansion of T cells.
2. a) Transducing said cells with pTalpha or functional variant thereof transgene to support CD3 surface expression and allow cell expansion through stimulation of CD3 complex. TCR disruption is expected to the elimination of the TCR complex and removes alloreactivity (GvHD) but may alter allogenic cells expansion due to the loss of CD3 signaling component. Transduced cells are expected to express pTalpha chain or functional variant thereof. This pTalpha chain pairs with TCRbeta chain and CD3 signaling components to form the preTCR complex and, thus restore a functional CD3 complex and support activation or stimulation of inactivated TCRalpha cells. Transduction of T-cells with pTalpha lentiviral vector can be realized before or after TCRalpha inactivation.
   b) Transducing said cells with multi-chain CARs allow redirecting T cells against antigens expressed at the surface of target cells from various malignancies including lymphomas and solid tumors. To improve the function of co-stimulatory domain, the inventors have designed a multi-chain CAR derived from FcεRI as previously described. Transduction can be realized before or after the inactivation of TCRalpha and the other genes, such as CD52 genes.
3. Engineering non alloreactive and immunosuppressive resistant T cells:
   a) It is possible to Inactivate TCR alpha in said cells to eliminate the TCR from the surface of the cell and prevent recognition of host tissue as foreign by TCR of allogenic and thus to avoid GvHD.
   b) It is also possible to inactive one gene encoding target for immunosuppressive agent to render said cells resistant to immunosuppressive treatment to prevent graft rejection without affecting transplanted T cells. In this example, target of immunosuppressive agents is CD52 and immunosuppressive agent is a humanized monoclonal anti-CD52 antibody.
      It has been shown by the inventors that the use of TALE-nuclease by allowing higher rates of DSB events within T-cells was particularly advantageous to achieve the above double inactivation in T-cells. Preferably, TCRalpha and CD52 genes are inactivated by electoporating T cells with mRNA coding for TALE-nuclease targeting said genes. It has been found by the inventors that using mRNA resulted into high transformation rate was less harmful to T-cells and so, was critical in the process of engineering T-cells. Then, inactivated T cells are sorted using magnetic beads. For example, T cells expressing CD52 are removed by fixation on a solid surface, and inactivated cells are not exposed of the stress of being passed through a column. This gentle method increases the concentration of properly engineered T-cells.
4. Expansion in vitro of engineered T-cells prior to administration to a patient or in vivo following administration to a patient through stimulation of CD3 complex. Before administration step, patients can be subjected to an immunosuppressive treatment such as CAMPATH1-H, a humanized monoclonal antibody anti-CD52.
5. Optionally exposed said cells with bispecific antibodies ex vivo prior to administration to a patient or in vivo following administration to a patient to bring the engineered cells into proximity to a target antigen.

OTHER DEFINITIONS

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of TALE-nuclease targets, targeted genomic sequences generally consist of two 17-bp long sequences (called half targets) separated by a 15-bp spacer. Each half-target is recognized by repeats of TALE-nucleases listed in tables 2, 6, 7 and 11 as non-limiting examples, encoded in plasmids, under the control of EF1-alpha promoter or T7 promoter. The nucleic acid target sequence is defined by the 5' to 3' sequence of one strand of said target, as indicated in tables 1, 5, 6 and 10.

The term "transgene" means a nucleic acid sequence (encoding, e.g., one or more polypeptides), which is partly or entirely heterologous, i.e., foreign, to the host cell into which it is introduced, or, is homologous to an endogenous gene of the host cell into which it is introduced, but which can be designed to be inserted, or can be inserted, into the cell genome in such a way as to alter the genome of the cell into which it is inserted (e.g., it is inserted at a location which differs from that of the natural gene or its insertion results in a knock-out). A transgene can include one or more transcriptional regulatory sequences and any other nucleic acid, such as introns, that may be necessary for optimal expression of the selected nucleic acid encoding polypeptide. The polypeptide encoded by the transgene can be either not expressed, or expressed but not biologically active, in cells in which the transgene is inserted.

By "genome" it is meant the entire genetic material contained in a cell such as nuclear genome, chloroplastic genome, mitochondrial genome.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD19 antigen and can comprise as non limiting example the amino acid sequence: SEQ ID NO: 73

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length. The endonuclease according to the present invention recognizes and cleaves nucleic acid at specific polynucleotide sequences, further referred to as "target sequence". The rare-cutting endonuclease can recognize and generate a single- or double-strand break at specific polynucleotides sequences.

In a particular embodiment, said rare-cutting endonuclease according to the present invention can be a Cas9 endonuclease. Indeed, recently a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010). In the present invention, guide RNA can be designed for example to specifically target a gene encoding a TCR component. Following the pairing between the guide RNA and the target sequence, Cas9 induce a cleavage within TCR gene.

Rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length.

The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease. By modular DNA binding nuclease is meant any fusion proteins comprising at least one catalytic domain of an endonuclease and at least one DNA binding domain or protein specifying a nucleic acid target sequence. The DNA binding domain is generally a RNA or DNA-binding domain formed by an independently folded polypeptide protein domain that contains at least one motif that recognizes double- or single-stranded DNA. Many such polypeptides have been described in the art having the ability to bind specific nucleic acid sequences. Such binding domains often comprise, as non limiting examples, helix-turn helix domains, leucine zipper domains, winged helix domains, helix-loop-helix domains, HMG-box domains, Immunoglobin domains, B3 domain or engineered zinc finger domain.

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base ($T_0$) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

Other engineered DNA binding domains are modular base-per-base specific nucleic acid binding domains (MBBBD) (PCT/US2013/051783). Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). MBBBD proteins comprise modules of about 31 to 33 amino acids that are base specific. These modules display less than 40% sequence identity with *Xanthomonas* TALE common repeats, whereas they present more polypeptides sequence variability. When they are assembled together, these modular polypeptides can although target specific nucleic acid sequences in a quite similar fashion as *Xanthomonas* TALE-nucleases. According to a preferred embodiment of the present invention, said DNA binding domain is an engineered MBBBD binding domain comprising between 10 and 30 modules, preferably between 16 and 20 modules. The different domains from the above proteins (modules, N and C-terminals) from *Burkholderia* and *Xanthomonas* are useful to engineer new proteins or scaffolds having binding properties to specific nucleic acid sequences. In particular, additional N-terminal and C-terminal domains of engineered MBBBD can be derived from natural TALE like AvrBs3, PthXo1, AvrHah1, PthA, Talk as non-limiting examples.

"TALE-nuclease" or "MBBBD-nuclease" refers to engineered proteins resulting from the fusion of a DNA binding domain typically derived from Transcription Activator like Effector proteins (TALE) or MBBBD binding domain, with an endonuclease catalytic domain. Such catalytic domain is preferably a nuclease domain and more preferably a domain having endonuclease activity, like for instance I-TevI, ColE7, NucA and Fok-I. In a particular embodiment, said nuclease is a monomeric TALE-Nuclease or MBBBD-nuclease. A monomeric Nuclease is a nuclease that does not require dimerization for specific recognition and cleavage, such as the fusions of engineered DNA binding domain with the catalytic domain of I-TevI described in WO2012138927. In another particular embodiment, said rare-cutting endonuclease is a dimeric TALE-nuclease or MBBBD-nuclease, preferably comprising a DNA binding domain fused to FokI. TALE-nuclease have been already described and used to stimulate gene targeting and gene modifications. Such engineered TALE-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or down regulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

TALE-Nucleases Cleaving the Human GR Gene 6 heterodimeric TALE-nucleases targeting exons of the human GR gene were designed and produced. Table 2 below indicates the target sequences cleaved by each TALE-nuclease. GR TALE-nuclease was composed of two independent entities (called half TALE-nucleases) each containing a repeat sequence engineered to bind and cleave GR target sequences consisting of two 17-bp long sequences (called half targets) separated by a 15-bp spacer.

TABLE 2

Description of the GR TALE-nucleases and sequences of the TALE-nucleases target sites in the human GR gene.

| Target name | Target sequence | Repeat sequence | Half TALE-nuclease sequence |
|---|---|---|---|
| GRex2 | TATTCACTGATGGACTC caaagaatcattaac TCCTGGTAGAGAAGAAA (SEQ ID NO: 1) | Repeat GRex2-LPT9-L1 (SEQ ID NO: 7) Repeat-GRex2-LPT9-R1 (SEQ ID NO: 8) | GRex2-L TALEN (SEQ ID NO: 19) GRex2-R TALEN (SEQ ID NO: 20) |
| GRex3T2 | TGCCTGGTGTGCTCTGA tgaagcttcaggatg TCATTATGGAGTCTTAA (SEQ ID NO: 2) | Repeat-GRex3T2-L1 (SEQ ID NO: 9) Repeat-GRex3T2-R1 (SEQ ID NO: 10) | GRex3T2-L TALEN (SEQ ID NO: 21) GRex3T2-R TALEN (SEQ ID NO: 22) |
| GRex3T4 | TGCTCTGATGAAGCTTC aggatgtcattatgg AGTCTTAACTTGTGGAA (SEQ ID NO: 3) | Repeat-GRex3T4-L1 (SEQ ID NO: 11) Repeat-GRex3T4-R1 (SEQ ID NO: 12) | GRex3T4-L TALEN (SEQ ID NO: 23) GRex3T4-R TALEN (SEQ ID NO: 24) |
| GRex5T1 | TGGTGTCACTGTTGGAG gttattgaacctgaa GTGTTATATGCAGGATA (SEQ ID NO: 4) | Repeat-GRex5T1-LPT8-L1 (SEQ ID NO: 13) Repeat-GRex5T1-LPT8-R1 (SEQ ID NO: 14) | GRex5T1-L TALEN (SEQ ID NO: 25) GRex5T1-R TALEN (SEQ ID NO: 26) |
| GRex5T2 | TATGATAGCTCTGTTCC agactcaacttggag GATCATGACTACGCTCA (SEQ ID NO: 5) | Repeat-GRex5T2-L1 (SEQ ID NO: 15) Repeat GRex5T2-R1 (SEQ ID NO: 16) | GRex5T2-L TALEN (SEQ ID NO: 27) GRex5T2-R TALEN (SEQ ID NO: 28) |
| GRex5T3 | TTATATGCAGGATATGA tagctctgttccaga CTCAACTTGGAGGATCA (SEQ ID NO: 6) | Repeat-GRex5T3-L1 (SEQ ID NO: 17) Repeat-GRex5T3-R1 (SEQ ID NO: 18) | GRex5T3-L TALEN (SEQ ID NO: 29) GRex5T3-R TALEN (SEQ ID NO: 30) |

The amino acid sequences of the N-terminal, C-terminal domains and repeat are based on the AvrBs3 TALE (ref: GenBank: X16130.1). The C-terminal and the N-terminal domains are separated by two BsmBI restriction sites. The repeat arrays (SEQ ID NO: 7 to 18), targeting the desired sequences (SEQ ID NO: 1 to 6) were synthesized using a solid support method composed of consecutive restriction/ligation/washing steps (International PCT application WO2013/017950). In brief, the first block (coding for a di-repeat) was immobilized on a solid support through biotin/streptavidin interaction, the second block (tri-repeat) was then ligated to the first and after SfaNI digestion a third bloc (tri-repeat) was coupled. The process was repeated using tri- or di-repeat blocks upon obtaining the desired repeat array. The product was then cloned in a classical pAPG10 cloning plasmid for amplification in E. coli and sequenced. The repeat array sequences thus obtained were subcloned in a yeast expression TALE vector using type IIS restriction enzymes BsmBI for the receiving plasmid and BbvI and SfaNI for the inserted repeat sequence. DNA coding for the half TALE-nuclease, containing a TALE derived DNA binding domain fused to the catalytic domain of the FokI restriction enzyme, was amplified in E. coli, recovered by standard miniprep techniques and sequenced to assess the integrity of the insert.

Activity of GR TALE-Nucleases in Yeast:

Nuclease activity of the six GR-TALE-nucleases were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) on targets containing the two TALE target sequences facing each other on the DNA strand separated by a spacer of 15 bps resulting in SEQ ID NO: 1 to 6. All the yeast target reporter plasmids containing the TALE-nuclease DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). TALE-nuclease cleavage activity levels, in yeast, of individual clones on the targets are presented in table 3.

TABLE 3

Cleavage activity of the GR TALE-nucleases in yeast.

| Target | Half TALE-nuclease transfected | yeast gal 37° C. | yeast gal 30° C. |
|---|---|---|---|
| GRex2 | Grex2-L TALEN Grex2-R TALEN | 1 | 1 |
| GRex3T2 | GRex3T2-L TALEN GRex3T2-R TALEN | 0.92 | 0.87 |
| GRex3T4 | GRex3T4-L TALEN GRex3T4-R TALEN | 0.94 | 0.87 |
| GRex5T1 | GRex5T1-L TALEN GRex5T1-R TALEN | 0.48 | 0.36 |
| GRex5T2 | GRex5T2-L TALEN GRex5T2-R TALEN | 0.97 | 0.91 |
| GRex5T3 | GRex5T3-L TALEN GRex5T3-R TALEN | 1 | 0.98 |

Values are comprised between 0 and 1. Maximal value is 1.

Activity of GR TALE-Nucleases in HEK293 Cells:

Each TALE-nuclease construct was subcloned using restriction enzyme digestion in a mammalian expression vector under the control of a pEF1alpha long promoter.

One million HEK293cells were seeded one day prior to transfection. Cells were co-transfected with 2.5 µg of each of two plasmids encoding left and right half of GRex2, GRex3T2, GRex3T4, GRex5T1, GRex5T2 or GRex5T3 TALE-nuclease recognizing the two half targets genomic sequences of interest in the GR gene under the control of EF1alpha promoter using 25ul of lipofectamine (Invitrogen) according to the manufacturer's instructions. As a control, cells were co-transfected with 2.5 µg of each of the two plasmids encoding the left and the right half of TALE-nucleases targeting the T-cell receptor alpha constant chain region (TRAC_T01) target site ((TRAC_01-L and -R TALE-nuclease (SEQ ID NO: 41 and SEQ ID NO: 42, TRAC_T01 target site (SEQ ID NO: 37)) under the control of EF1alpha promoter. The double strand break generated by TALE-nucleases in GR coding sequence induces non homologous end joining (NHEJ), which is an error-prone mechanism. Activity of TALE-nucleases is measured by the frequency of insertions or deletions at the genomic locus targeted.

2 or 7 days post transfection cells were harvested and locus specific PCRs were performed on genomic DNA extracted using the following primers: 5'-CCATCT-CATCCCTGCGTGTCTCCGACTCAG-3' (forward adaptator sequence)-10N (TAG)-locus specific forward sequence for GR exon 2: 5'-GGTTCATTTAACAAGCTGCC-3' (SEQ ID NO: 31), for GR exon 3: 5'-GCATTCTGACTAT-GAAGTGA-3' (SEQ ID NO: 32) and for GR exon 5: 5'-TCAGCAGGCCACTACAGGAGTCTCACAAG-3' (SEQ ID NO: 33) and the reverse primer 5'-CC-TATCCCCTGTGTGCCTTGGCAGTCTCAG-3' (reverse adaptor sequence)-locus specific reverse sequence for GR exon 2: 5'-AGCCAGTGAGGGTGAAGACG-3' (SEQ ID NO: 34), for GR exon 3: 5'-GGGCTTTGCATATAATG-GAA-3' (SEQ ID NO: 35) and for GR exon 5: 5'-CTGACTCTCCCCTTCATAGTCCCCAGAAC-3' (SEQ ID NO: 36).

PCR products were sequenced by a 454 sequencing system (454 Life Sciences). Approximately 10,000 sequences were obtained per PCR product and then analyzed for the presence of site-specific insertion or deletion events. Table 4 indicates the percentage of the sequences showing insertions or deletions at the TALE-nuclease target site among the total number of sequences in the sample. In table 4 are listed for GRex2, GRex3T2 and GRex3T4 the results of a representative experiment.

In all cases tested, the % of mutagenesis was similar at day 7 compared to the one of the sample at day 2 post transfection. The nature of the mutagenic events was also analyzed, revealing a majority of deletions in all cases compared to insertions.

TABLE 4

Percentage of targeted mutagenesis at endogenous TALE-nuclease Target sites in HEK293 cells.

| Target | % Indels at 2 days with GR TALE-nuclease transfection | % Indels at 7 days with GR TALE-nuclease transfection | % Indels at 2 days with TRAC_T01 TALE-nuclease control transfection |
|---|---|---|---|
| GRex2 | 20.3 | 24.9 | 0.5 |
| GRex3T2 | 9.3 | 9.8 | 0 |
| GRex3T4 | 19 | 18.3 | 0.0 |
| GRex5T1 | 11.2 | NA | 0.7 |

TABLE 4-continued

Percentage of targeted mutagenesis at endogenous TALE-nuclease Target sites in HEK293 cells.

| Target | % Indels at 2 days with GR TALE-nuclease transfection | % Indels at 7 days with GR TALE-nuclease transfection | % Indels at 2 days with TRAC_T01 TALE-nuclease control transfection |
|---|---|---|---|
| GRex5T2 | 3.4 | NA | 0 |
| GRex5T3 | 8.3 | NA | 0 |

Activity of GR TALE-Nucleases in Primary T Lymphocytes:

Each TALE-nuclease construct was subcloned using restriction enzyme digestion in an expression vector under the control of a T7 promoter.

mRNA encoding TALE-nucleases cleaving GR genomic sequences were synthesized from each plasmid carrying the coding sequences downstream from the T7 promoter. T lymphocytes isolated from peripheral blood were activated for 5 days using anti-CD3/CD28 activator beads (Life technologies) and 5 million cells were transfected by electroporation with 10 µg of each of 2 mRNAs encoding both half TALE-nucleases using a CytoLVT-P instrument (BTX-Harvard apparatus). T cells transfected with 10 µg of each of the 2 mRNAs encoding both half TALE-nucleases targeting the CD52 gene (CD52_T02-L and -R TALEN (SEQ ID NO: 55 and 56), target sequence CD52_T02 SEQ ID NO: 40) are used as a control.

3 and 7 days after transfection, genomic DNA was isolated from transfected cells and locus specific PCRs were performed using the primers described previously. PCR products were sequenced by a 454 sequencing system (454 Life Sciences). Approximately 10,000 sequences were obtained per PCR product and then analyzed for the presence of site-specific insertion or deletion events; results are in Table 5.

TABLE 5

Percentage of targeted mutagenesis at endogenous TALE-nuclease target sites in primary T lymphocytes.

| Target | % Indels at day 3 with GR TALE-nuclease transfection | % Indels at day 7 with GR TALE-nuclease transfection | % Indels at day 3 with CD52 TALE-nuclease control transfection |
|---|---|---|---|
| GRex2 | 26.2 | 30.7 | 0.7 |
| GRex3T2 | 1.09 | 0.86 | 0.02 |
| GRex3T4 | 6.3 | 6.93 | 0 |
| GRex5T1 | 0.04 | 0.035 | 0.05 |
| GRex5T2 | 1.3 | 1.0 | 0.22 |
| GRex5T3 | 17.4 | NA | 0.41 |

Example 2

TALE-Nucleases Cleaving the Human CD52 Gene, the Human T-Cell Receptor Alpha Constant Chain (TRAC) and the Human T-Cell Receptor Beta Constant Chains 1 and 2 (TRBC)

As described in example 1, heterodimeric TALE-nucleases targeting respectively CD52, TRAC and TRBC genes were designed and produced. The targeted genomic sequences consist of two 17-bp long sequences (called half targets) separated by an 11 or 15-bp spacer. Each half-target is recognized by repeats of half TALE-nucleases listed in table 6. The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. The 2 TRBC targets were chosen in sequences conserved between TRBC1 and TRBC2 so that the corresponding TALE-nuclease would cleave both TRBC1 and TRBC2 at the same time.

TABLE 6

Description of the CD52, TRAC and TRBC TALE-nucleases and sequences of the TALE-nucleases target sites in the human corresponding genes.

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 37) | Repeat TRAC_T01-L (SEQ ID NO: 41) Repeat TRAC_T01-R (SEQ ID NO: 42) | TRAC_T01-L TALEN (SEQ ID NO: 49) TRAC_T01-R TALEN (SEQ ID NO: 50) |
| TRBC_T01 | TGTGTTTGAGCCATCAG aagcagagatctccc ACACCCAAAAGGCCACA (SEQ ID NO: 38) | Repeat TRBC_T01-L (SEQ ID NO: 43) Repeat TRBC_T01-R (SEQ ID NO: 44) | TRBC_T01-L TALEN (SEQ ID NO: 51) TRBC_T01-R TALEN (SEQ ID NO: 52) |
| TRBC_T02 | TTCCCACCCGAGGTCGC tgtgtttgagccatca GAAGCAGAGATCTCCCA (SEQ ID NO: 39) | Repeat TRBC_T02-L (SEQ ID NO: 45) Repeat TRBC_T02-R (SEQ ID NO: 46) | TRBC_T02-L TALEN (SEQ ID NO: 53) TRBC_T02-R TALEN (SEQ ID NO: 54) |
| CD52_T02 | TTCCTCCTACTCACCAT cagcctcctggttat GGTACAGGTAAGAGCAA (SEQ ID NO: 40) | Repeat CD52_T02-L (SEQ ID NO: 47) Repeat CD52_T02-R (SEQ ID NO: 48) | CD52_T02-L TALEN (SEQ ID NO: 55) CD52_T02-R TALEN (SEQ ID NO: 56) |

Other target sequences in TRAC and CD52 genes have been designed, which are displayed in Table 7.

TABLE 7

Additional target sequences for TRAC and CD52 TALE-nucleases.

| Target | Target sequence |
|---|---|
| TRAC_T02 | TTTAGAAAGTTCCTGTG atgtcaagctggtcg AGAAAAGCTTTGAAACA (SEQ ID NO: 57) |
| TRAC_T03 | TCCAGTGACAAGTCTGT ctgcctattcaccga TTTTGATTCTCAAACAA (SEQ ID NO: 58) |
| TRAC_T04 | TATATCACAGACAAAAC tgtgctagacatgag GTCTATGGACTTCAAGA (SEQ ID NO: 59) |
| TRAC_T05 | TGAGGTCTATGGACTTC aagagcaacagtgct GTGGCCTGGAGCAACAA (SEQ ID NO: 60) |
| CD52_T01 | TTCCTCTTCCTCCTAC caccatcagcctcct TTACCTGTACCATAAC (SEQ ID NO: 61) |
| CD52_T04 | TTCCTCCTACTCACCA cagcctcctgg TCTTACCTGTACCATA (SEQ ID NO: 62) |
| CD52_T05 | TCCTACTCACCATCAG ctcctggttat TTGCTCTTACCTGTAC (SEQ ID NO: 63) |
| CD52_T06 | TTATCCCACTTCTCCT ctacagatacaaact TTTTGTCCTGAGAGTC (SEQ ID NO: 64) |
| CD52_T07 | TGGACTCTCAGGACAA acgacaccagccaaa TGCTGAGGGGCTGCTG (SEQ ID NO: 65) |

Activity of CD52-TALE-Nuclease, TRAC-TALE-Nuclease and TRBC-TALE-Nuclease in HEK293 Cells Each TALE-nuclease construct was subcloned using restriction enzyme digestion in a mammalian expression vector under the control of pEF1alpha long promoter. One million HEK293 cells were seeded one day prior to transfection. Cells were co-transfected with 2.5 µg of each of the two plasmids encoding the TALE-nucleases recognizing the two half targets in the genomic sequence of interest in the CD52 gene, T-cell receptor alpha constant chain region (TRAC) or T-cell receptor beta constant chain region (TRBC) under the control of the EF1-alpha promoter or 5 μg of a control pUC vector (pCLS0003) using 25 μl of lipofectamine (Invitrogen) according to the manufacturer's instructions. The double stranded cleavage generated by TALE-nucleases in CD52 or TRAC coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: 5'-CCATCT-CATCCCTGCGTGTCTCCGACTCAG (forward adaptor sequence)-10N (TAG)-locus specific forward sequence for CD52: 5'-CAGATCTGCAGAAAGGAAGC-3' (SEQ ID NO: 66), for TRAC: 5'-ATCACTGGCATCTGGACTCCA-3' (SEQ ID NO: 67), for TRBC1: 5'-AGAGCCCC-TACCAGAACCAGAC-3' (SEQ ID NO: 68), or for TRBC2: 5'-GGACCTAGTAACATAATTGTGC-3' (SEQ ID NO: 69), and the reverse primer 5'-CC-TATCCCCTGTGTGCCTTGGCAGTCTCAG (reverse adaptor sequence)-endogenous locus specific reverse sequence for CD52: 5'-CCTGTTGGAGTCCATCTGCTG-3' (SEQ ID NO: 70), for TRAC: 5'-CCT-CATGTCTAGCACAGTTT-3' (SEQ ID NO: 71), for TRBC1 and TRBC2: 5'-ACCAGCTCAGCTC-CACGTGGT-3' (SEQ ID NO: 72). PCR products were sequenced by a 454 sequencing system (454 Life Sciences). Approximately 10,000 sequences were obtained per PCR product and then analyzed for the presence of site-specific insertion or deletion events; results are in 8.

TABLE 8

Percentages of indels for TALE-nuclease targeting CD52_T02, TRAC_T01, TRBC_T01 and TRBC_T02 targets.

| Target | % Indels with TALE-nuclease transfection | % Indels with pUC control transfection |
| --- | --- | --- |
| CD52_T02 | 28.0 | 0.9 |
| TRAC_T01 | 41.9 | 0.3 |
| TRBC_T01 in constant chain 1 | 3.81 | 0 |
| TRBC_T01 in constant chain 2 | 2.59 | 0 |
| TRBC_T02 in constant chain 1 | 14.7 | 0 |
| TRBC_T02 in constant chain 1 | 5.99 | 0 |

Activity of CD52-TALE-Nuclease, TRBC-TALE-Nuclease and TRAC-TALE-Nuclease in Primary T Lymphocytes Each TALE-nuclease construct was subcloned using restriction enzyme digestion in a mammalian expression vector under the control of the T7 promoter.

mRNA encoding TALE-nuclease cleaving CD52 TRAC and TRBC genomic sequence were synthesized from plasmid carrying the coding sequences downstream from the T7 promoter. T lymphocytes isolated from peripheral blood were activated for 5 days using anti-CD3/CD28 activator beads (Life technologies) and 5 million cells were then transfected by electroporation with 10 μg of each of 2 mRNAs encoding both half TALE-nuclease (or non coding RNA as controls) using a CytoLVT-P instrument. As a consequence of the insertions and deletions induced by NHEJ, the coding sequence for CD52 and/or TRAC will be out of frame in a fraction of the cells resulting in non-functional genes. 5 days after electroporation, cells were labeled with fluorochrome-conjugated anti-CD52 or anti-TCR antibody by flow cytometry for the presence of CD52 or TCR at their cell surface. Since all T lymphocytes expanded from peripheral blood normally express CD52 and TCR, the proportion of CD52-negative or TCR-negative cells is a direct measure of TALE-nuclease activity. In table 9 are listed the results of a representative experiment. The table 9 shows the results of a representative experiment testing the efficiency of TRBC TALE-nucleases.

TABLE 9

Percentages of CD52-negative, TCR-negative and CD52/TCR-double negative T lymphocytes after transfection of corresponding TALE-nuclease-expressing polynucleotides.

| ARN transfected | % CD52-negative cells | % TCR-negative cells | % CD52/ TCR double negative cells |
| --- | --- | --- | --- |
| non coding RNA | 1.21 | 1.531 | 0.111 |
| TALEN CD52_T02 | 49.2 | 1.6 | 0.78 |
| TALEN TRAC_T01 | 2.16 | 44.8 | 0.97 |
| TALEN CD52_T02 + TALEN TRAC_T01 | 29.3 | 39.6 | 15.5 |

TABLE 10

Percentages of TCR-negative T lymphocytes after transfection of TRBC TALE-nuclease-expressing polynucleotides.

| ARN transfected | % TCR-negative cells |
| --- | --- |
| no RNA | 1.22 |
| TALEN TRBC_T01 | 6.52 |
| TALEN TRBC_T02 | 23.5 |

Functional Analysis of T Cells with Targeted CD52 Gene

Figure 6:
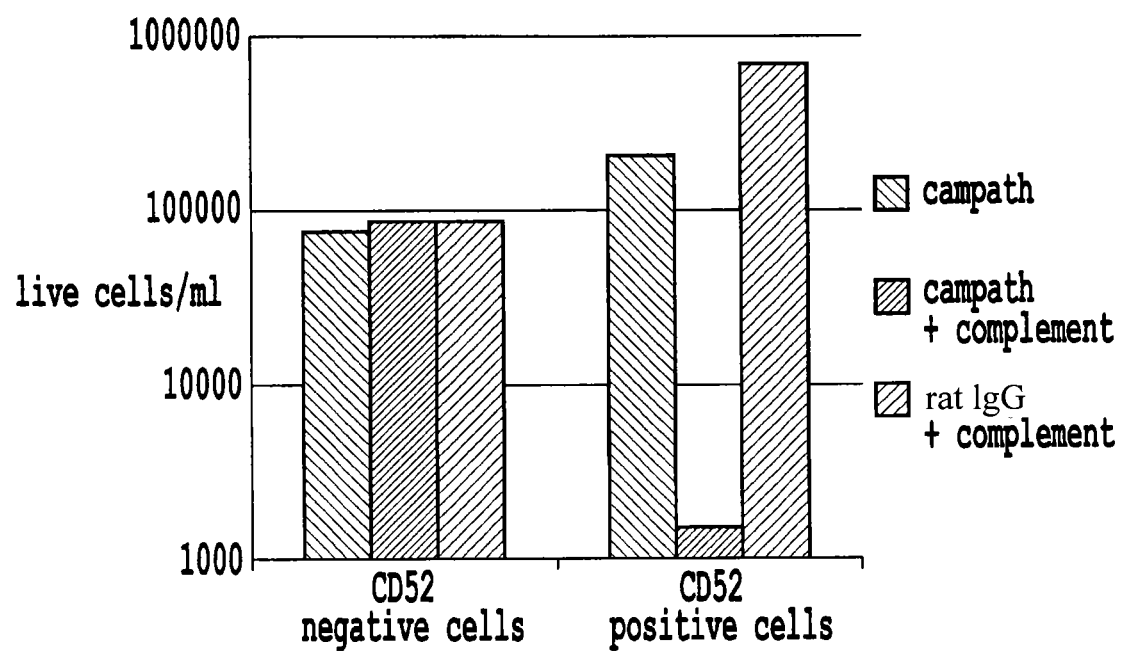

The goal of CD52 gene inactivation is to render T lymphocytes resistant to anti-CD52 antibody mediated immunosuppression. As described in the previous paragraph, T lymphocytes were transfected with mRNA encoding TALE-nuclease cleaving CD52. 7 days after transfection, cells were treated with 50 μg/ml anti-CD52 monoclonal antibody (or rat IgG as control) with or without 30% rabbit complement (Cedarlane). After 2 hours of incubation at 37° C., the cells were labeled with a fluorochrome-conjugated anti-CD52 antibody together with a fluorescent viability dye (eBioscience) and analyzed by flow cytometry to measure the frequency of CD52-positive and CD52-negative cells among live cells. FIG. 6 shows the result of a representative experiment, demonstrating that CD52-negative cells are completely resistant to complement-mediated anti-CD52 antibody toxicity.

Functional Analysis of T Cells with Targeted TRAC Gene

The goal of TRAC gene inactivation is to render T lymphocytes unresponsive to T-cell receptor stimulation. As described in the previous paragraph, T lymphocytes were transfected with mRNA encoding TALE-nuclease cleaving TRAC or CD52. 16 days after transfection, cells were treated with up to 5 μg/ml of phytohemagglutinin (PHA, Sigma-Aldrich), a T-cell mitogen acting through the T cell receptor. Cells with a functional T-cell receptor should increase in size following PHA treatment. After three days of incubation, cells were labeled with a fluorochrome-conjugated anti-CD52 or anti-TCR antibody and analyzed by flow cytometry to compare the cell size distribution between TCR-positive and TCR-negative cells, or between CD52-positive and CD52-negative cells. FIG. 7 shows that TCR-positive cells significantly increase in size after PHA treatment whereas TCR-negative cells have the same size as untreated cells indicating that TRAC inactivation rendered them unresponsive to TCR-signaling. By contrast, CD52-positive and CD52-negative increase in size to same extent.
Functional Analysis of T Cells with Targeted CD52 and TRAC Genes To verify that genome engineering did not affect the ability of T cells to present anti-tumor activity when provided with a chimeric antigen receptor (CAR), we transfected T cells that had been targeted with CD52-TALE-nuclease and TRAC-TALE-nuclease with 10 μg of RNA encoding an anti-CD19 CAR (SEQ ID NO: 73). 24 hours later, T cells were incubated for 4 hours with CD19 expressing Daudi cells. The cell surface upregulation of CD107a, a marker of cytotoxic granule release by T lymphocytes (called degranulation) was measured by flow cytometry analysis (Betts, Brenchley et al. 2003). The results are included in FIG. 8 and show that CD52-negative/TCRαβ-negative cells and CD52-positive/TCRαβ-positive have the same ability to degranulate in response to PMA/ionomycin (positive control) or CD19+Daudi cells. CD107 upregulation is dependent on the presence of a CD19+. These data suggest that genome engineering has no negative impact on the ability of T cells to mount a controlled anti-tumor response.

Genomic Safety of CD52-TALE-Nuclease and TRAC-TALE-Nuclease in Primary T Lymphocytes As our constructs include nuclease subunits, an important question is whether multiple TALE-nuclease transfection can lead to genotoxicity and off-target cleavage at 'close match' target sequences or by mispairing of half-TALE-nucleases. To estimate the impact of TRAC-TALE-nuclease and CD52-TALE-nuclease on the integrity of the cellular genomes, we listed sequences in the human genome that presented the potential for off-site cleavage. To generate this list, we identified all the sequences in the genome with up to 4 substitutions compared to the original half targets and then identified the pairs of potential half targets in a head to head orientation with a spacer of 9 to 30 bp from each other. This analysis included sites potentially targeted by homodimers of one half-TALE-nuclease molecule or heterodimers formed by one CD52 half TALE-nuclease and one TRAC half-TALE-nuclease. We scored the potential off-site targets based on the specificity data taking into account the cost of individual substitutions and the position of the substitutions (where mismatches are better tolerated for bases at the 3' end of the half target). We obtained 173 unique sequences with a score reflecting an estimation of the likelihood of cleavage. We selected the 15 top scores and analyzed by deep sequencing the frequency of mutations found at these loci in T cells simultaneously transfected with CD52 and TRAC TALE-nuclease and purified by magnetic separation as CD52-negative, TCRαβ-negative. Results are in FIG. 9. The highest frequency of insertion/deletion is $7 \times 10^{-4}$. These results make the putative offsite target at least 600 times less likely to be mutated than the intended targets. The TALE-nuclease reagents used in this study therefore appear extremely specific.

Example 3

TALE-Nucleases Cleaving the Human CTLA4 Gene and the Human PDCD1 Gene

As described in example 1, heterodimeric TALE-nucleases targeting respectively PDCD1 and CTLA4 genes were designed and produced. The targeted genomic sequences consist of two 17-bp long sequences (called half targets) separated by an 11 or 15-bp spacer. Each half-target is recognized by repeats of half TALE-nucleases listed in table 11.

TABLE 11

Description of the CTLA4 and PDCD1 TALE-nucleases and sequences of the TALE-nucleases target sites in the human corresponding genes.

| Target | Target sequence | Repeat sequence | Half TALE-nuclease |
|---|---|---|---|
| CTLA4_T01 | TGGCCCTGCACTCTCCT gtttttctttctctt CATCCCTGTCTTCTGCA (SEQ ID NO: 74) | Repeat CTLA4_T01-L (SEQ ID NO: 79) Repeat CTLA4_T01-R (SEQ ID NO: 80) | CTLA4_T01-L TALEN (SEQ ID NO: 89) CTLA4_T01-R TALEN (SEQ ID NO: 90) |
| CTLA4_T03 | TTTTCCATGCTAGCAAT gcacgtggcccagcc TGCTGTGGTACTGGCCA (SEQ ID NO : 75) | Repeat CTLA4_T03-L (SEQ ID NO: 81) Repeat CTLA4_T03-R (SEQ ID NO: 82) | CTLA4_T03-L TALEN (SEQ ID NO: 91) CTLA4_T03-R TALEN (SEQ ID NO: 92) |
| CTLA4_T04 | TCCATGCTAGCAATGCA cgtggcccagcctgc TGTGGTACTGGCCAGCA (SEQ ID NO: 76) | Repeat CTLA4_T04-L (SEQ ID NO: 84) Repeat CTLA4_T04-R (SEQ ID NO: 85) | CTLA4_T04-L TALEN (SEQ ID NO: 93) CTLA4_T04-R TALEN (SEQ ID NO: 94) |
| PDCD1_T01 | TTCTCCCCAGCCCTGCT cgtggtgaccgaagg GGACAACGCCACCTTCA (SEQ ID NO: 77) | Repeat PDCD1_T01-L (SEQ ID NO: 86) Repeat PDCD1_T01-R (SEQ ID NO: 87) | PDCD1_T01-L TALEN (SEQ ID NO: 95) PDCD1_T01-R TALEN (SEQ ID NO: 96) |
| PDCD1_T03 | TACCTCTGTGGGGCCAT ctccctggcccccaa GGCGCAGATCAAAGAGA (SEQ ID NO: 78) | Repeat PDCD1_T03-L (SEQ ID NO: 88) Repeat PDCD1_T03-R (SEQ ID NO: 89) | PDCD1_T03-L TALEN (SEQ ID NO: 97) PDCD1_T03-R TALEN (SEQ ID NO: 98) |

Activity of CTLA4-TALE-Nuclease and PDCD1-TALE-Nuclease in HEK293 Cells

Each TALE-nuclease construct was subcloned using restriction enzyme digestion in a mammalian expression vector under the control of the pEF1alpha long promoter. One million HEK293 cells were seeded one day prior to transfection. Cells were co-transfected with 2.5 µg of each of two plasmids encoding the TALE-nucleases recognizing the two half targets in the genomic sequence of interest in the PDCD1 and CTLA-4 gene under the control of the EF1-alpha promoter or 5 µg of a control pUC vector (pCLS0003) using 25 µl of lipofectamine (Invitrogen) according to the manufacturer's instructions. The double stranded cleavage generated by TALE-nucleases in PDCD1 or CTLA-4 coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: 5'-CCATCT-CATCCCTGCGTGTCTCCGACTCAG (forward adaptor sequence)-10N (TAG)-locus specific forward sequence for CTLA4_T01: 5'-CTCTACTTCCTGAAGACCTG-3' (SEQ ID NO: 99), for CTLA4_T03/T04: 5'-ACAGTT-GAGAGATGGAGGGG-3' (SEQ ID NO: 100), for PDCD1_T01: 5'-CCACAGAGGTAGGTGCCGC-3' (SEQ ID NO: 101) or for PDCD1_T03: 5'-GACAGAGATGCCGGTCACCA-3' (SEQ ID NO: 102) and the reverse primer 5'-CC-TATCCCTGTGTGCCTTGGCAGTCTCAG (reverse adaptor sequence)-endogenous locus specific reverse sequence for CTLA4_T01: 5'-TGGAATACAGAGCCAGC-CAA-3' (SEQ ID NO: 103), for CTLA4_T03/T04: 5'-GGTGCCCGTGCAGATGGAAT-3' (SEQ ID NO: 104), for PDCD1_T01: 5'-GGCTCTGCAGTGGAGGCCAG-3' (SEQ ID NO: 105) or for PDCD1_T03: 5'-GGACAACGC-CACCTTCACCT-3' (SEQ ID NO: 106).

PCR products were analyzed by T7-endonuclease assay: briefly, after denaturation and reannealing of the PCR product, T7 endonuclease will specifically digest mismatched DNA composed of wild type and mutated strands. The digestion product is then resolved by polyacrylamide gel electrophoresis. The presence of a digested product is indicative of mutated sequences induced by TALE-nuclease activity. Results are displayed in FIG. 10 where arrows point to the digested PCR products. They demonstrate that PDCD1_T1, PDCD1_T3, CTLA4_T1, CTLA4_T3 and CTLA4_T4 TALE-nucleases all exhibit mutagenic nuclease activity at their target sites.

CTLA4 Inactivation in Primary T Cells:

Human primary T cells were activated with CD3/28 beads. Five days later, 5×10⁶ cells were electroporated with 20 µg of RNA encoding one of three TALEN™ (T1, T2 and T3) designed with respect to CTLA4 gene or without RNA as control. Three days post electroporation, CTLA4 expression was measured by intracellular staining using fluorescent antibody and flow cytometry analysis (FIGS. 27 and 28).

All three TALEN™ induced downregulation of CTLA4 expression in a manner correlated with their efficiency in HEK293 cell lines (T1 was more efficient than T3 and T4).

Deep sequencing analysis of genomic DNA isolated from transfected cells using 454 technology (Roche) revealed than 96% of CTLA4 alleles were mutated in TALEN T1-treated cells compared to 0.1% in the control sample without TALEN.

PD1 Inactivation in Primary T Cells:

Human primary T cells were activated with CD3/28 beads. Five days later 5×10⁶ cells were electroporated with 20 µg of RNA encoding one of two TALENs specific for human PD1 gene or without RNA as control. Ten days later, cells were re-activated and 3 days post re-activation, PD1 expression was measured by surface staining using fluorescent antibody and flow cytometry analysis (see FIG. 29).

Both TALENs induced significant downregulation of PD1 expression. Deep sequencing analysis of genomic DNA isolated from cells transfected with TALEN T1 and TALEN T03 respectively using 454 technology (Roche) revealed than 34% and 39% of PD1 alleles were mutated respectively (results shown in FIG. 30).

Enhanced Anti-Tumor Activity PD1-TALEN Treated Cells:

Human primary T cells were activated with CD3/28 beads. Five days later 5×10⁶ cells were electroporated with 20 µg of RNA encoding a TALEN specific for human PD1 gene or without RNA as control. A week later, cells were electroporated with mRNA encoding a chimeric antigen receptor specific for human CD19 or no RNA as negative control. The next day, their antitumor activity was measured in cellular cytotoxicity assay using CD19+Daudi cells (vs. K562 as control) or HCT116 cells, which express PD1ligand 1 (PDL1) transduced with CD19 expression vector (vs. parental HCT116 cells as control). Cytotoxic activity was determined by comparing viability of target cells and control cells. Results are shown in the diagrams of FIG. 31. PD1 TALEN transfection restored cytotoxic activity against PDL1-expressing HCT116 cells and improved cytotoxic activity against Daudi cells.

Example 4 pTalpha Permits CD3 Surface Expression in Inactivated TCR Alpha T Lymphocytes

Description of the Different preTalpha Versions:

The human pTalpha gene encodes a transmembrane glycoprotein comprising an extracellular Ig-like domain, a hydrophobic transmembrane domain and a large C-terminal intracytoplasmic tail. Different versions derived from human pTalpha glycoprotein have been designed and are described in Table 12 and represented in FIG. 11.

TABLE 12

Description of a subset of pTalpha constructs

| PTalpha versions | Description | SEQ ID |
|---|---|---|
| pTalpha-FL | Full-length of human pTalpha glycoprotein | 107 |
| pTalpha-Δ18 | Truncated Human pTalpha glycoprotein lacking 18 residues from the C-terminus. | 108 |
| pTalpha-Δ48 | Truncated Human pTalpha glycoprotein lacking 48 residues from the C-terminus. | 109 |
| pTalpha-Δ62 | Truncated Human pTalpha glycoprotein lacking 62 residues from the C-terminus. | 110 |
| pTalpha-Δ78 | Truncated Human pTalpha glycoprotein lacking 78 residues from the C-terminus. | 111 |

TABLE 12-continued

Description of a subset of pTalpha constructs

| PTalpha versions | Description | SEQ ID |
|---|---|---|
| pTalpha-Δ92 | Truncated Human pTalpha glycoprotein lacking 92 residues from the C-terminus. | 112 |
| pTalpha-Δ110 | Truncated Human pTalpha glycoprotein lacking 110 residues from the C-terminus. | 113 |
| pTalpha-Δ114 | Truncated Human pTalpha glycoprotein lacking 114 residues from the C-terminus. | 114 |
| pTalpha-FL-CD28 | Full-length of human pTalpha glycoprotein fused in C-terminus with CD28 activation domain. | 115 |
| pTalpha-FL-CD8 | Full-length of human pTalpha glycoprotein fused in C-terminus with CD8 activation domain. | 116 |
| pTalpha-FL-4-1BB | Full-length of human pTalpha glycoprotein fused in C-terminus with 4-1BB activation domain.. | 117 |
| pTalpha-Δ48-CD28 | pTalpha-Δ48 glycoprotein fused in C-terminus with CD28 activation domain. | 118 |
| pTalpha-Δ48-CD8 | pTalpha-Δ48 glycoprotein fused in C-terminus with CD8 activation domain. | 119 |
| pTalpha-Δ48-41BB | pTalpha-Δ48 glycoprotein fused in C-terminus with 4-1BB activation domain. | 120 |
| pTalpha-Δ114/TCRα.IC | pTalpha-Δ114 glycoprotein fused in C-terminus with the intracellular domain of TCRalpha | 121 |
| pTalpha-EC/TCRα.TM.IC | pTalpha extracellular domain fused in C-terminus with the transmembrane and intracellular domain of TCRalpha. | 122 |
| pTalpha-Δ48-1xMUT | pTalpha-Δ48 glycoprotein with mutated residue W46R. | 123 |
| preTalpha-Δ48-4xMUT | pTalpha-Δ48 glycoprotein with mutated residues D22A, K24A, R102A, R117A | 124 |

The different preTalpha constructs tested include:
1) pTalpha deletion mutants: Different deletions were generated in the intracellular cytoplasmic tail of the human pTalpha protein (which comprises 114 amino acids) (SEQ ID NO: 107). The constructs tested include the full length version of the protein (FL) and mutants in which 18, 48, 62, 78, 92, 110 and 114 amino acids were deleted from the C-terminus of the protein (SEQ ID NO: 108 to SEQ ID NO: 114).
2) pTalpha mutants containing intracellular activation domains: The FL and Δ48 variants where fused to the CD8, CD28 or 4166 intracellular activation domains at their C-terminus (SEQ ID NO: 115 to SEQ ID NO: 120).
3) pTalpha/TCRα chimeric mutants: In one of the constructs, the TCRα intracellular domain (IC) was fused to a tail-less version (Δ114) of pTalpha (SEQ ID NO: 121). A second construct was also generated in which the pTalpha extracellular domain was fused to the transmembrane (TM) and the IC domains from TCRα (SEQ ID NO: 122).
4) pTalpha dimerization mutants: Some mutations have been described in the literature as being capable to alter the oligomerisation/dimerisation ability of the preTCR complex. These mutants are proposed to allow preTCR expression at the cell surface, without inducing the constitutive signaling (supposed to be induced upon preTCR oligomerization). The mutations have been introduced in the pTalphaΔ48 variant and are:
1xMUT: W46R (SEQ ID NO: 123)
4xMUT: D22A, K24A, R102A, R117A (SEQ ID NO: 124)

Activity of Different preTalpha Constructs in TRAC Inactivated Jurkat Cells:

In order to screen different pTalpha variants for their ability to restore CD3 surface expression in TCRalpha inactivated cells, a cell line was generated in which the TCRalpha gene was disrupted using TALEN targeting TRAC. Jurkat cells (a T-cell leukemia cell line) were transfected with plasmids coding for the TALEN cleaving TRAC using CytoPulse electroporation, and the KO cells ($TCR_{\alpha/\beta}^{NEG}$; $CD3^{NEG}$) where then purified by negative selection using CD3 magnetic beads. The KO population (JKT_KOx3 cells) was amplified and used for screening of the different pTalpha variants. Screening was performed by transfection of one million of JKT_KOx3 cells with 15 μg of plasmid coding the different pTalpha variants under control of the EF1α promoter, followed by analysis by flow cytometry of CD3 cell surface expression 48 h after transfection. FIG. 12 is a representative example of the transfection efficiencies (% of BFP+ cells) and activity of the FL, Δ18 and Δ48 pTalpha constructs in JKT_KOx3 cells, based on the % of CD3+ cells, determined by flow cytometry. The results from the different constructs are grouped in Table 13.

TABLE 13

Activity of the different pTalpha constructs in Jurkat TCR alpha inactivated cells. Activity was measured by flow cytometry analysis of CD3 expression in jurkat TCR alpha inactivated cells transfected with the different preTalpha constructs.

| Mutant | ID | % $CD3_{LOW}$ | SD |
|---|---|---|---|
| 0 | NEG | 4.69 | 1.53 |
| 1 | preTCRa-FL | 31.18 | 4.15 |

TABLE 13-continued

Activity of the different pTalpha constructs in Jurkat TCR alpha inactivated cells. Activity was measured by flow cytometry analysis of CD3 expression in jurkat TCR alpha inactivated cells transfected with the different preTalpha constructs.

| Mutant | ID | % CD3$_{LOW}$ | SD |
| --- | --- | --- | --- |
| 2 | preTCRα-Δ18 | 20.13 | 4.56 |
| 3 | preTCRα-Δ48 | 44.86 | 3.90 |
| 4 | preTCRα-Δ62 | 32.42 | 2.95 |
| 5 | preTCRα-Δ78 | 24.75 | 3.87 |
| 6 | preTCRα-Δ92 | 20.63 | 3.70 |
| 7 | preTCRα-Δ110 | 18.18 | 3.49 |
| 8 | preTCRα-Δ114 | 4.29 | 2.74 |
| 9 | preTCRα-FL-CD8 | 18.16 | 5.30 |
| 10 | preTCRα-FL-CD28 | 5.67 | 2.77 |
| 11 | preTCRα-FL-41BB | 27.27 | 3.66 |
| 12 | preTCRα-Δ48-CD8 | 11.56 | 6.01 |
| 13 | preTCRα-Δ48-CD28 | 12.22 | 4.72 |
| 14 | preTCRα-Δ48-41BB | 35.93 | 4.55 |
| 15 | preTCRα-Δ114/TCRα.IC | 3.94 | 1.95 |
| 16 | preTCRα-EC/TCRα.TM.IC | 17.80 | 4.47 |
| 17 | preTCRα-Δ48-1xMUT | 26.88 | 4.37 |
| 18 | preTCRα-Δ48-4xMUT | 7.59 | 1.06 |

Activity of pTalpha-FL and pTalpha-Δ48 in TCR Alpha Inactivated Primary T Lymphocytes:

In order to test the ability of pTalpha-FL and pTalpha-Δ48 versions to induce CD3 surface expression in TCR alpha inactivated T lymphocytes, pTalpha-FL and pTalpha-Δ48 coding sequences were cloned into a self-inactivating pLV-SFFV-BFP-2A-PCTRA lentiviral vector that codes for Blue Fluorescent protein (BFP) under the SFFV promoter followed by the self-cleaving T2A peptide (FIG. 13).

T lymphocytes isolated from peripheral blood were activated for 72 hours using anti-CD3/CD28 activator beads (Life technologies) and 4.5 million cells were transfected by electroporation with 10 µg mRNA encoding the TALE-nuclease targeting TCR alpha constant chain region (TRAC) using a CytoLVT-S instrument (BTX-Harvard Harbour). Two days after electroporation, T cells were transduced with either the LV-SFFV-BFP-2A-pTalpha-Δ48 or LV-SFFV-BFP-2A-control lentiviral vectors. CD3 negative and CD3low T cells were then purified using anti-CD3 magnetic beads (Miltenyi Biotech). This experimental protocol is represented in FIG. 14A.

FIG. 14B represents flow cytometry analysis of TCRalpha/beta, CD3 cell surface expression, and BFP expression on TCRalpha inactivated T cells (KO) transduced with either BFP-2A-pTalphaΔ48 (KO/Δ48) or control BFP lentiviral vector (KO/BFP) before and after purification with CD3 beads. TCRalpha inactivated T cells transduced with the BFP-T2A-pTalpha-Δ48 vector (BFP+ cells) show higher levels of CD3 compared to non transduced cells (BFP− cells). No differences are observed among cells transduced with the control BFP vector. These results indicate that pTalpha mediates restoration of CD3 expression at the cell surface of TCRalpha inactivated cells. In contrast, TCRalpha/beta staining remains, as expected, unchanged in cells transduced or not with the pTalpha-Δ48 expressing vector.

pTalpha-Mediated CD3 Expression Supports Activation of TCR-Deficient T-Cells:

To determine the capacity of pTalpha to transduce cell activation signals, expression of early and later activation markers was analyzed on TCR alpha inactivated T cells transduced with pTalpha-Δ48 and pTalpha-Δ48.41BB. TCR alpha inactivated T cells transduced with pTalpha-Δ48 and pTalpha-Δ48.41BB were generated from primary human T-cells as described in previous section and in FIG. 14A.

Figure 15A:
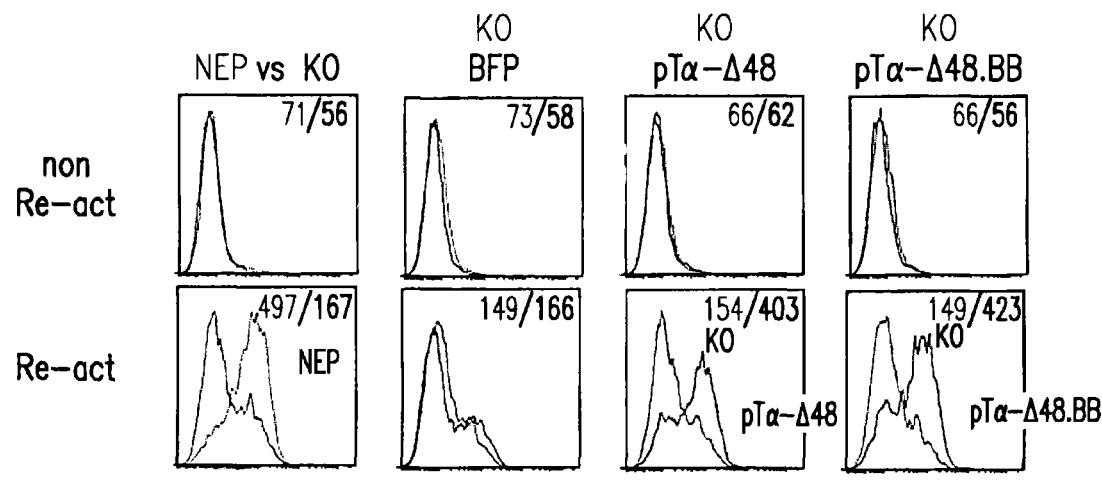
Figure 15B:
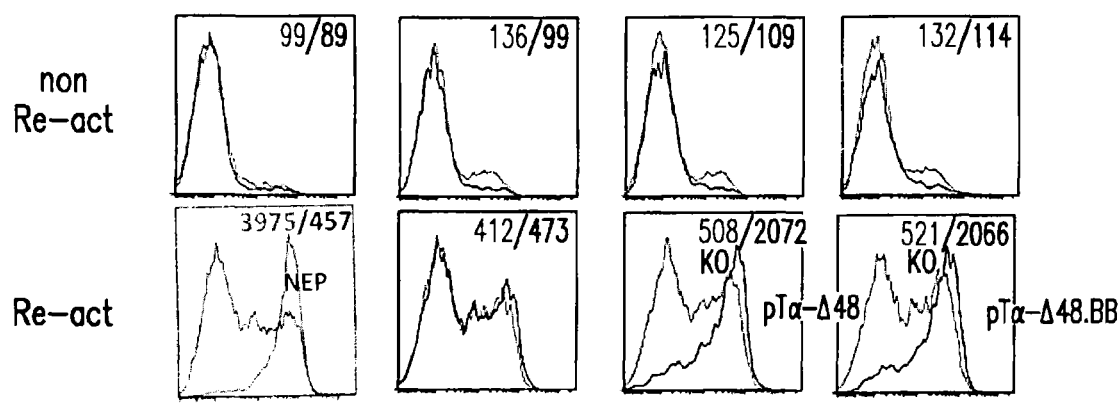

To detect signaling via CD3, cells were re-activated using anti-CD3/CD28-coated beads 3 days after purification of TCR alpha inactivated T cells with CD3 beads (FIG. 14A). Cells were stained with fluorochrome-conjugated anti-CD69 (early activation marker) and anti-CD25 (late activation marker), 24 and 48 hours after re-activation respectively and analyzed by flow cytometry (FIG. 15A-B). As represented in FIG. 15A-B, TCR alpha inactivated cells expressing pTalpha-Δ48 (KO/pTα-Δ48) or pTalpha-Δ48.41BB (KO/pTα-Δ48.BB) show upregulation of the activation markers, to levels similar to those observed in TCRalpha/beta expressing cells (NEP: non electroporated cells).

Figure 15C:
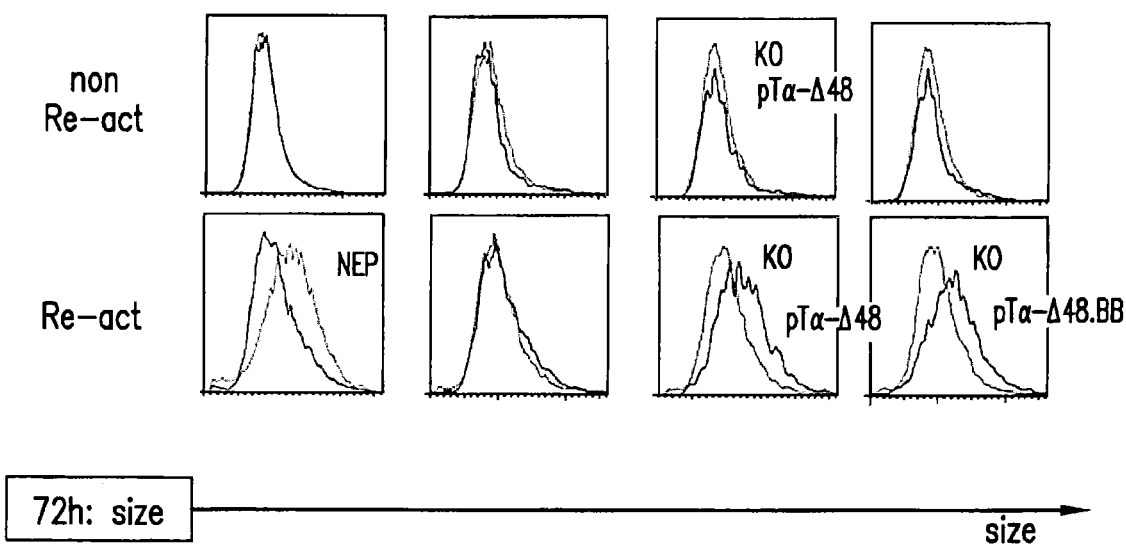

Another indicator of T cell activation is an increase in cell size which is sometimes referred to as "blasting". The capacity of the preTCR complexes to induce "blasting" was measured by flow cytometry analysis of the cell size 72 hours after re-activation using anti-CD3/CD28-beads (FIG. 15C). Stimulation with anti-CD3/CD28 beads induced comparable increases in cell size in cells expressing TCRalpha/beta complexes vs. cells expressing pTalpha-Δ48 or pTalpha-Δ48.41BB. Taken together, these results suggest that preTCR complexes are competent to transduce signals that efficiently couple to the mechanisms mediating activation marker upregulation.

pTalpha Mediated CD3 Expression Supports Expansion of TCR-Deficient Primary T-Cells Using Stimulatory Anti-CD3/CD28 Antibodies To evaluate the capacity of preTCR complexes to support long term cell proliferation, proliferation of cells generated as previously described was measured. Ten days after the initial activation, cells were maintained in IL2 (non-Re-act) or in IL2 with anti-CD3/CD28 beads (Re-act). For each condition, cells were counted and analyzed by flow cytometry at the different time points to estimate the number of BFP+ cells. The growth of TCRalpha inactivated cells (KO) transduced with BFP or BFP-T2A-preTCRα-Δ48 vectors was compared, and the fold induction of these cells was estimated with respect to the value obtained at day 2 post re-activation. FIG. 16 shows the results obtained with two independent donors. In both cases, TCRalpha inactivated cells expressing pTalpha-Δ48 displayed greater expansion than TCR alpha inactivated cells expressing only the BFP control vector. For the second donor, TCRalpha inactivated cells expressing pTalpha-Δ48.41BB or full-length pTalpha were also included, displaying also greater expansion than TCRalpha inactivated cells expressing only the BFP control vector.

Example 5

Optimization of mRNA Transfection in T Cells Using Cytopulse Technology

Determination of the Optimized Cytopulse Program

A first set of experiments were performed on non activated PBMCs in order to determine a voltage range in which cells could be transfected. Five different programs were tested as described in Table 14.

TABLE 13

Different cytopulse programs used to determine the minimal voltage required for electroporation in PBMC derived T-cells.

| Cyto-pulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

3 or 6 million of cells were electroporated in 0.4 cm gap cuvette (30 or $15 \times 10^6$ cells/ml) with 20 µg of plasmids encoding GFP and control plasmids pUC using the different Cytopulse programs. 24 hours post electroporation, GFP expression was analyzed in electroporated cells by flow cytometry to determine the efficiency of transfection. The data shown in FIG. 17 indicates the minimal voltage required for plasmid electroporation in PBMC derived T cells. These results demonstrate that the cytopulse program 3 and 4 allow an efficient transformation of T cells (EP#3 and #4).

Electroporation of mRNA of Purified Tcells Activated

After determining the best cytopulse program that allows an efficient DNA electroporation of T cells, we tested whether this method was applicable to the mRNA electroporation.

$5 \times 10^6$ purified T cells preactivated 6 days with PHA/IL2 were resupended in cytoporation buffer T (BTX-Harvard apparatus) and electroporated in 0.4 cm cuvettes with 10 µg of mRNA encoding GFP or 20 µg of plasmids encoding GFP or pUC using the preferred cytopulse program as determined in the previous section (table 14).

TABLE 15

Cytopulse program used to electroporate purified T-cells.

| Cyto-pulse program | Group 1 | | | | Group 2 | | | | Group 3 | | | |
|---|---|---|---|---|---|---|---|---|---|---|---|---|
| | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

48 h after transfection cells were stained with viability dye (eFluor-450) and the cellular viability and % of viable GFP+ cells was determined by flow cytometry analysis (FIG. 18).

The data shown in FIG. 18 indicates that the electroporation of RNA with the optimal condition determined here is no toxic and allows transfection of more than 95% of the viable cells.

In synthesis, the whole dataset shows that T-cells can be efficiently transfected either with DNA or RNA. In particular, RNA transfection has no impact on cellular viability and allows uniform expression levels of the transfected gene of interest in the cellular population.

Efficient transfection can be achieved early after cellular activation, independently of the activation method used (PHA/IL-2 or CD3/CD28-coated-beads). The inventors have succeeded in transfecting cells from 72 h after activation with efficiencies of >95%. In addition, efficient transfection of T cells after thawing and activation can also be obtained using the same electroporation protocol.

mRNA Electroporation in Primary Human T Cells for TALE-Nuclease Functional Expression After demonstrating that mRNA electroporation allow efficient expression of GFP in primary human T cells, we tested whether this method was applicable to the expression of other proteins of interest. Transcription activator-like effector nucleases (TALE-nuclease) are site-specific nucleases generated by the fusion of a TAL DNA binding domain to a DNA cleavage domain. They are powerful genome editing tools as they induce double-strand breaks at practically any desired DNA sequence. These double-strand breaks activate Non-homologous end-joining (NHEJ), an error-prone DNA repair mechanism, potentially leading to inactivation of any desired gene of interest. Alternatively, if an adequate repair template is introduced into the cells at the same time, TALE-nuclease-induced DNA breaks can be repaired by homologous recombination, therefore offering the possibility of modifying at will the gene sequence.

We have used mRNA electroporation to express a TALE-nuclease designed to specifically cleave a sequence in the human gene coding for the alpha chain of the T cell antigen receptor (TRAC). Mutations induced in this sequence are expected to result in gene inactivation and loss of TCRαβ complex from the cell surface. TRAC TALE-nuclease RNA or non coding RNA as control are transfected into activated primary human T lymphocytes using Cytopulse technology. The electroporation sequence consisted in 2 pulses of 1200 V followed by four pulses of 130 V as described in Table 15.

By flow cytometry analysis of TCR surface expression 7 days post electroporation (FIG. 19, top panel), we observed that 44% of T cells lost the expression of TCRαβ. We analyzed the genomic DNA of the transfected cells by PCR amplification of the TRAC locus followed by 454 high throughput sequencing. 33% of alleles sequenced (727 out of 2153) contained insertion or deletion at the site of TALE-nuclease cleavage. FIG. 19 (bottom panel) shows examples of the mutated alleles.

These data indicate that electroporation of mRNA using cytopulse technology results in functional expression of TRAC TALE-nuclease.

Electroporation of T Cells with a Monocistronic mRNA Encoding for an Anti-CD19 Single Chain Chimeric Antigen Receptor (CAR):

$5 \times 10^6$ T cells preactivated several days (3-5) with anti-CD3/CD28 coated beads and IL2 were resuspended in cytoporation buffer T, and electroporated in 0.4 cm cuvettes without mRNA or with 10 µg of mRNA encoding a single chain CAR (SEQ ID NO: 73) using the program described in Table 15.

24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 20. A indicates that the vast majority of the live T cells electroporated with the monocitronic mRNA described previously express the CAR at their surface. 24 hours post electroporation, T cells were cocultured with Daudi (CD19+) cells for 6 hours and analyzed by flow cytometry to detect the expression of the degranulation marker CD107a at their surface (Betts, Brenchley et al. 2003).

The data shown in FIG. 20 indicates that the majority of the cells electroporated with the monocistronic mRNA described previously degranulate in the presence of target cells expressing CD19. These results clearly demonstrate that the CAR expressed at the surface of electroporated T cells is active.

Figure 4A:
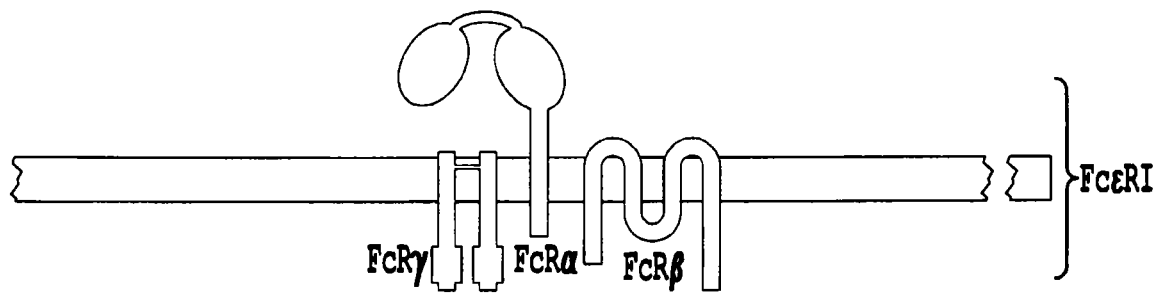
Figure 4B:
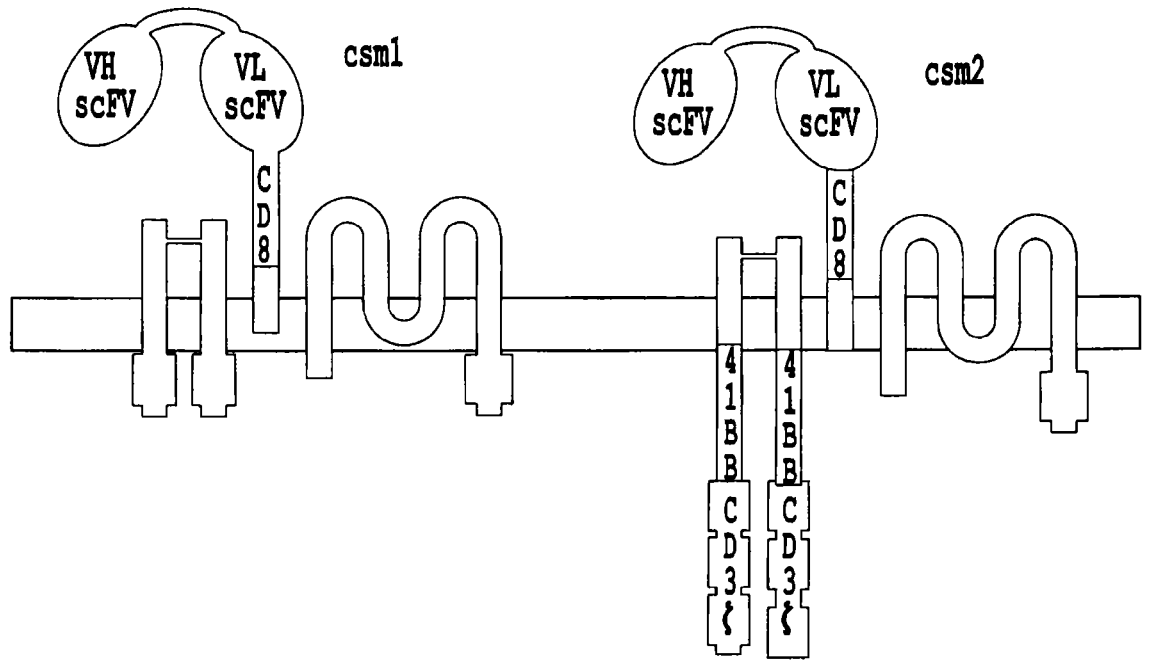
Figure 4B:
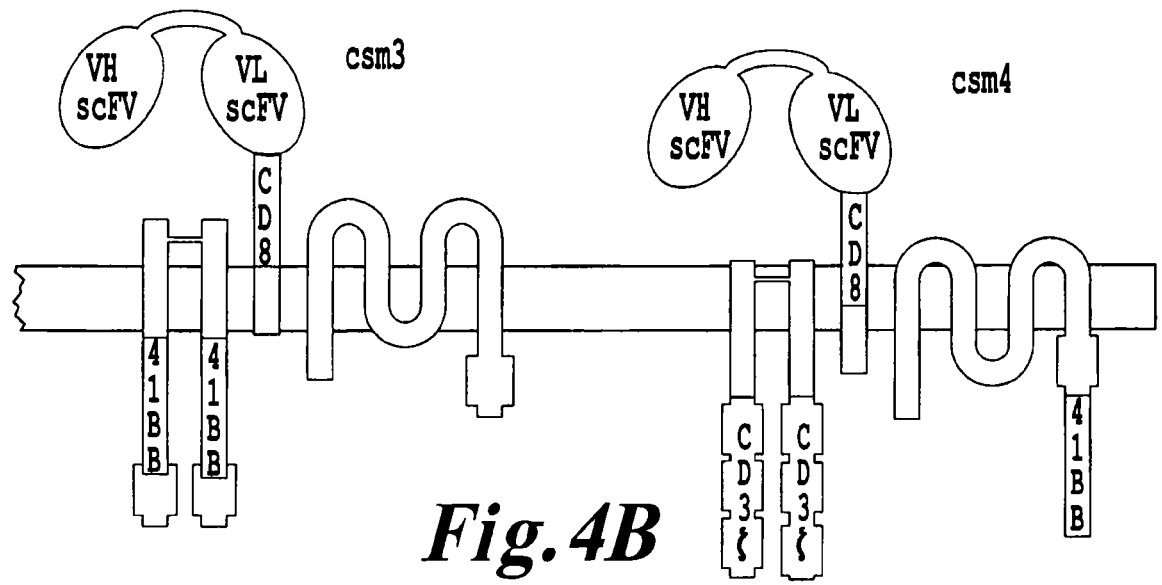
Figure 4C:
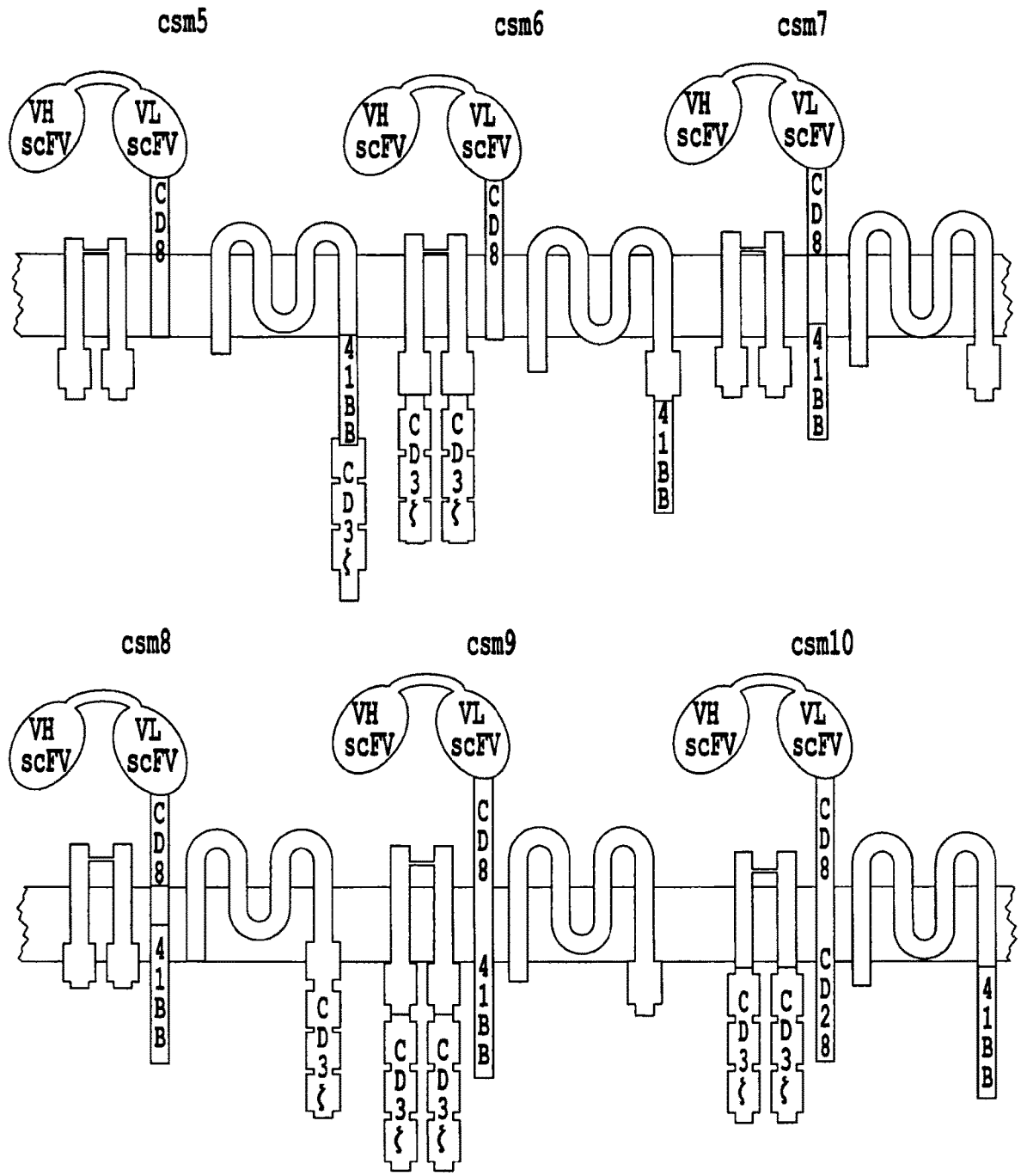

Electroporation of T Cells with a Polycistronic mRNA Encoding for an Anti-CD19 Multisubunit Chimeric Antigen Receptor (CAR):

$5 \times 10^6$ T cells preactivated several days (3-5) with anti CD3/CD28 coated beads and IL2 were electroporated in cytoporation buffer T, and electroporated in 0.4 cm cuvettes without mRNA or with 45 µg of mRNA encoding a multi-chain CAR (SEQ ID NO: 125, encoded by SEQ ID NO: 126, FIG. 21A and FIG. 4B (csm4)) using the program as described in Table 15.

24 hours post electroporation, cells were stained with a fixable viability dye eFluor-780 and a PE-conjugated goat anti mouse IgG F(ab')2 fragment specific to assess the cell surface expression of the CAR on the live cells. The data shown in FIG. 21 indicates that the vast majority of the live T cells electroporated with the polycistronic mRNA described previously express the CAR at their surface.

24 hours post electroporation, T cells were cocultured with Daudi (CD19+) for 6 hours and analyzed by flow cytometry to detect the expression of the degranulation marker CD107a at their surface. The data shown in FIG. 21 indicates that the majority of the cells electroporated with the polycistronic mRNA described previously degranulate in the presence of target cells expressing CD19. These results clearly demonstrate that the CAR expressed at the surface of electroporated T cells is active.

LIST OF REFERENCES

Arnould, S., P. Chames, et al. (2006). "Engineering of large numbers of highly specific homing endonucleases that induce recombination on novel DNA targets." *J Mol Biol* 355(3): 443-58.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type Ill effectors." *Science* 326(5959): 1509-12.

Boni, A., P. Muranski, et al. (2008). "Adoptive transfer of allogeneic tumor-specific T cells mediates effective regression of large tumors across major histocompatibility barriers." *Blood* 112(12): 4746-54.

Brahmer, J. R., C. G. Drake, et al. (2010). "Phase I study of single-agent anti-programmed death-1 (MDX-1106) in refractory solid tumors: safety, clinical activity, pharmacodynamics, and immunologic correlates." *J Clin Oncol* 28(19): 3167-75.

Bucks, C. M., J. A. Norton, et al. (2009). "Chronic antigen stimulation alone is sufficient to drive CD8+ T cell exhaustion." *J Immunol* 182(11): 6697-708.

Carrasco, Y. R., A. R. Ramiro, et al. (2001). "An endoplasmic reticulum retention function for the cytoplasmic tail of the human pre-T cell receptor (TCR) alpha chain: potential role in the regulation of cell surface pre-TCR expression levels." *J Exp Med* 193(9): 1045-58.

Cermak, T., E. L. Doyle, et al. (2011). "Efficient design and assembly of custom TALEN and other TAL effector-based constructs for DNA targeting." *Nucleic Acids Res* 39(12): e82.

Chames, P., J. C. Epinat, et al. (2005). "In vivo selection of engineered homing endonucleases using double-strand break induced homologous recombination." *Nucleic Acids Res* 33(20): e178.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Deltcheva, E., K. Chylinski, et al. (2011). "CRISPR RNA maturation by trans-encoded small RNA and host factor RNase Ill." *Nature* 471(7340): 602-7.

Deng, D., C. Yan, et al. (2012). "Structural basis for sequence-specific recognition of DNA by TAL effectors." *Science* 335(6069): 720-3.

Dessarthe, B., A. Thedrez, et al. (2013). "CRTAM receptor engagement by NecI-2 on tumor cells triggers cell death of activated Vgamma9Vdelta2 T cells." *J Immunol* 190 (9): 4868-76.

Epinat, J. C., S. Arnould, et al. (2003). "A novel engineered meganuclease induces homologous recombination in yeast and mammalian cells." *Nucleic Acids Res* 31(11): 2952-62.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Geissler, R., H. Scholze, et al. (2011). "Transcriptional activators of human genes with programmable DNA-specificity." *PLoS One* 6(5): e19509.

Grange, M., G. Verdeil, et al. (2013). "Active STATS regulates T-bet and eomesodermin expression in CD8 T cells and imprints a T-bet-dependent Tc1 program with repressed IL-6/TGF-beta1 signaling." *J Immunol* 191(7): 3712-24.

Heinrich, P. C., I. Behrmann, et al. (2003). "Principles of interleukin (IL)-6-type cytokine signalling and its regulation." *Biochem J* 374(Pt 1): 1-20.

Huang, P., A. Xiao, et al. (2011). "Heritable gene targeting in zebrafish using customized TALENs." *Nat Biotechnol* 29(8): 699-700.

Ikehara, Y., S. K. Ikehara, et al. (2004). "Negative regulation of T cell receptor signaling by Siglec-7 (p70/AIRM) and Siglec-9." *J Biol Chem* 279(41): 43117-25.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Lackner, G., N. Moebius, et al. (2011). "Complete genome sequence of *Burkholderia rhizoxinica*, an Endosymbiont of *Rhizopus microsporus.*" *J Bacteriol* 193(3): 783-4.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "Modularly assembled designer TAL effector nucleases for targeted gene knockout and gene replacement in eukaryotes." *Nucleic Acids Res* 39(14): 6315-25.

Lozano, E., M. Dominguez-Villar, et al. (2011). "The TIGIT/CD226 axis regulates human T cell function." *J Immunol* 188(8): 3869-75.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Mali, P., L. Yang, et al. (2013). "RNA-guided human genome engineering via Cas9." *Science* 339(6121): 823-6.

Meyaard, L., G. J. Adema, et al. (1997). "LAIR-1, a novel inhibitory receptor expressed on human mononuclear leukocytes." *Immunity* 7(2): 283-90.

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Nicoll, G., J. Ni, et al. (1999). "Identification and characterization of a novel siglec, siglec-7, expressed by human natural killer cells and monocytes." *J Biol Chem* 274(48): 34089-95.

Pang, S. S., R. Berry, et al. (2010). "The structural basis for autonomous dimerization of the pre-T-cell antigen receptor." *Nature* 467(7317): 844-8.

Pardoll, D. and C. Drake (2012). "Immunotherapy earns its spot in the ranks of cancer therapy." *J Exp Med* 209(2): 201-9.

Pardoll, D. M. (2012). "The blockade of immune checkpoints in cancer immunotherapy." *Nat Rev Cancer* 12(4): 252-64.

Park, T. S., S. A. Rosenberg, et al. (2011). "Treating cancer with genetically engineered T cells." *Trends Biotechnol* 29(11): 550-7.

Quigley, M., F. Pereyra, et al. (2010). "Transcriptional analysis of HIV-specific CD8+ T cells shows that PD-1 inhibits T cell function by upregulating BATF." *Nat Med* 16(10): 1147-51.

Robert, C. and C. Mateus (2011). "[Anti-CTLA-4 monoclonal antibody: a major step in the treatment of metastatic melanoma]." *Med Sci* (Paris) 27(10): 850-8.

Rodriguez, P. C., D. G. Quiceno, et al. (2007). "L-arginine availability regulates T-lymphocyte cell-cycle progression." *Blood* 109(4): 1568-73.

Sander, J. D., L. Cade, et al. (2011). "Targeted gene disruption in somatic zebrafish cells using engineered TALENs." *Nat Biotechnol* 29(8): 697-8.

Shin, H., S. D. Blackburn, et al. (2009). "A role for the transcriptional repressor Blimp-1 in CD8(+) T cell exhaustion during chronic viral infection." *Immunity* 31(2): 309-20.

Smith, J., S. Grizot, et al. (2006). "A combinatorial approach to create artificial homing endonucleases cleaving chosen sequences." *Nucleic Acids Res* 34(22): e149.

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Tesson, L., C. Usal, et al. (2011). "Knockout rats generated by embryo microinjection of TALENs." *Nat Biotechnol* 29(8): 695-6.

Thaventhiran, J. E., A. Hoffmann, et al. (2012). "Activation of the Hippo pathway by CTLA-4 regulates the expression of Blimp-1 in the CD8+ T cell." *Proc Natl Acad Sci USA* 109(33): E2223-9.

Weber, E., R. Gruetzner, et al. (2011). "Assembly of designer TAL effectors by Golden Gate cloning." *PLoS One* 6(5): e19722.

Wolchok, J. D., H. Kluger, et al. "Nivolumab plus ipilimumab in advanced melanoma." *N Engl J Med* 369(2): 122-33.

Zhang, F., L. Cong, et al. (2011). "Efficient construction of sequence-specific TAL effectors for modulating mammalian transcription." *Nat Biotechnol* 29(2): 149-53.

Zhang, J. Q., G. Nicoll, et al. (2000). "Siglec-9, a novel sialic acid binding member of the immunoglobulin superfamily expressed broadly on human blood leukocytes." *J Biol Chem* 275(29): 22121-6.

The invention claimed is:

1. A population of isolated primary human T cells comprising at least $10^5$ isolated primary human T cells that:
   a) express a chimeric antigen receptor (CAR), wherein the CAR comprises the amino acid sequence of SEQ ID NO:73;
   b) have the TCRα or TCRβ alleles in the cells inactivated; and
   c) have the PD-1 gene inactivated,
   wherein inactivation of the PD1 gene enhances the anti-tumor activity of the population of isolated primary human T cells.

2. The population of isolated primary human T cells of claim 1, having the TCRa alleles in the cells inactivated.

3. The population of isolated primary human T cells of claim 1, having the TCRβ alleles in the cells inactivated.

4. The population of isolated primary human T cells of claim 1, having the TCRα alleles and the TCRβ alleles in the cells inactivated.

5. The population of isolated primary human T cells of claim 1, further having the CD52 alleles in the cells inactivated.

6. The population of isolated primary human T cells of claim 1, further having the glucocorticoid receptor alleles in the cells inactivated.

7. The population of isolated primary human T cells of claim 2, further expressing a fragment of preTalpha sufficient to support CD3 surface expression.

8. The population of isolated primary human T cells of claim 1, having the PD-1 gene and CTLA-4 alleles in the cells inactivated.

9. A population of isolated primary human T cells comprising at least $10^5$ isolated primary human T cells that:
   a) express a chimeric antigen receptor (CAR),
   wherein the CAR comprises the amino acid sequence of SEQ ID NO:73;
   b) have the TCRa or TCRβ alleles in the cells inactivated; and
   c) have the PD-1 or CTLA-4 alleles in the cells inactivated,
   wherein inactivation of the PD1 alleles enhances the anti-tumor activity of the population of isolated primary human T cells.

10. The population of isolated primary human T cells of claim 9, having the TCRα alleles in the cells inactivated.

11. The population of isolated primary human T cells of claim 9, having the TCRβ alleles in the cells inactivated.

12. The population of isolated primary human T cells of claim 9, having the TCRα alleles and the TCRβ alleles in the cells inactivated.

13. The population of isolated primary human T cells of claim 9, further having the CD52 alleles in the cells inactivated.

14. The population of isolated primary human T cells of claim 9, further having the glucocorticoid receptor alleles in the cells inactivated.

15. The population of isolated primary human T cells of claim 9, further expressing a fragment of preTalpha sufficient to support CD3 surface expression.

* * * * *

SEQUENCE LISTING

```
<160> NUMBER OF SEQ ID NOS: 126

<210> SEQ ID NO 1
<211> LENGTH: 49
<212> TYPE: DNA
<213> ORGANISM: Artificial Sequence
<220> FEATURE:
<223> OTHER INFORMATION: GRex2

<400> SEQUENCE: 1
tattcactga tggactccaa agaatcatta actcctggta gagaagaaa          49

<210> SEQ ID NO 2
<211> LENGTH: 49
<212> TYPE: DNA
<213> ORGANISM: Artificial Sequence
<220> FEATURE:
<223> OTHER INFORMATION: GRex3T2

<400> SEQUENCE: 2
tgcctggtgt gctctgatga agcttcagga tgtcattatg gagtcttaa           49

<210> SEQ ID NO 3
<211> LENGTH: 49
<212> TYPE: DNA
<213> ORGANISM: Artificial Sequence
<220> FEATURE:
<223> OTHER INFORMATION: GRex3T4

<400> SEQUENCE: 3
tgctctgatg aagcttcagg atgtcattat ggagtcttaa cttgtggaa           49

<210> SEQ ID NO 4
<211> LENGTH: 49
<212> TYPE: DNA
<213> ORGANISM: Artificial Sequence
<220> FEATURE:
<223> OTHER INFORMATION: GRex5T1

<400> SEQUENCE: 4
tggtgtcact gttggaggtt attgaacctg aagtgttata tgcaggata           49

<210> SEQ ID NO 5
<211> LENGTH: 49
<212> TYPE: DNA
<213> ORGANISM: Artificial Sequence
<220> FEATURE:
<223> OTHER INFORMATION: GRex5T2

<400> SEQUENCE: 5
tatgatagct ctgttccaga ctcaacttgg aggatcatga ctacgctca           49

<210> SEQ ID NO 6
<211> LENGTH: 49
<212> TYPE: DNA
<213> ORGANISM: Artificial Sequence
<220> FEATURE:
<223> OTHER INFORMATION: GRex5T3

<400> SEQUENCE: 6
ttatatgcag gatatgatag ctctgttcca gactcaactt ggaggatca           49

<210> SEQ ID NO 7
<211> LENGTH: 530
<212> TYPE: PRT
<213> ORGANISM: Artificial Sequence
```

<220> FEATURE:
<223> OTHER INFORMATION: Repeat-GRex2-LPT9-L1

<400> SEQUENCE: 7

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65              70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
130                 135                 140

Ile Ala Ser Asn Ile Gly Gly Lys Gln Ala Leu Glu Thr Val Gln Ala
145             150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
210                 215                 220

Thr Val Gln Arg Leu Leu Pro Val Leu Cys Gln Ala His Gly Leu Thr
225             230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
290                 295                 300

His Gly Leu Thr Pro Gln Gln Val Val Ala Ile Ala Ser Asn Gly Gly
305             310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385             390                 395                 400

```
Pro Val Leu Cys Gln Ala His Gly Leu Thr Pro Glu Gln Val Val Ala
            405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
            435                 440                 445
Val Ala Ile Ala Ser His Asp Gly Gly Lys Gln Ala Leu Glu Thr Val
            450                 455                 460
Gln Arg Leu Leu Pro Val Leu Cys Gln Ala His Gly Leu Thr Pro Gln
465                 470                 475                 480
Gln Val Val Ala Ile Ala Ser Asn Gly Gly Lys Gln Ala Leu Glu
            485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
            515                 520                 525
Leu Glu
    530

<210> SEQ ID NO 8
<211> LENGTH: 530
<212> TYPE: PRT
<213> ORGANISM: Artificial Sequence
<220> FEATURE:
<223> OTHER INFORMATION: Repeat-GRex2-LPT9-R1

<400> SEQUENCE: 8

Leu Thr Pro Gln Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Gly Gly
            35                  40                  45
Gly Lys Gln Ala Leu Glu Thr Val Gln Arg Leu Leu Pro Val Leu Cys
        50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
            85                  90                  95
Leu Cys Gln Ala His Gly Leu Thr Pro Gln Gln Val Val Ala Ile Ala
            100                 105                 110
Ser Asn Gly Gly Gly Lys Gln Ala Leu Glu Thr Val Gln Arg Leu Leu
            115                 120                 125
Pro Val Leu Cys Gln Ala His Gly Leu Thr Pro Gln Gln Val Val Ala
            130                 135                 140
Ile Ala Ser Asn Gly Gly Gly Lys Gln Ala Leu Glu Thr Val Gln Arg
145                 150                 155                 160
Leu Leu Pro Val Leu Cys Gln Ala His Gly Leu Thr Pro Glu Gln Val
            165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
            195                 200                 205
Gln Val Val Ala Ile Ala Ser Asn Gly Gly Gly Lys Gln Ala Leu Glu
            210                 215                 220
```

```
Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Lys
            275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530

<210> SEQ ID NO 9
<211> LENGTH: 530
<212> TYPE: PRT
<213> ORGANISM: Artificial Sequence
<220> FEATURE:
<223> OTHER INFORMATION: Repeat-GRex3T2-L1

<400> SEQUENCE: 9

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45
```

```
Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
             85                  90                  95

Leu Cys Gln Ala His Gly Leu Thr Pro Gln Gln Val Val Ala Ile Ala
                100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
        130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
        370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
        450                 455                 460
```

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
    530

<210> SEQ ID NO 10
<211> LENGTH: 530
<212> TYPE: PRT
<213> ORGANISM: Artificial Sequence
<220> FEATURE:
<223> OTHER INFORMATION: Repeat-GRex3T2-R1

<400> SEQUENCE: 10

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

```
Gln Ala Leu Glu Thr Val Gln Arg Leu Leu Pro Val Leu Cys Gln Ala
    290                 295                 300
His Gly Leu Thr Pro Glu Gln Val Val Ala Ile Ala Ser Asn Ile Gly
305                 310                 315                 320
Gly Lys Gln Ala Leu Glu Thr Val Gln Ala Leu Leu Pro Val Leu Cys
                325                 330                 335
Gln Ala His Gly Leu Thr Pro Gln Gln Val Val Ala Ile Ala Ser Asn
            340                 345                 350
Gly Gly Gly Lys Gln Ala Leu Glu Thr Val Gln Arg Leu Leu Pro Val
        355                 360                 365
Leu Cys Gln Ala His Gly Leu Thr Pro Glu Gln Val Val Ala Ile Ala
370                 375                 380
Ser Asn Ile Gly Gly Lys Gln Ala Leu Glu Thr Val Gln Ala Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Gln Gln Val
        435                 440                 445
Val Ala Ile Ala Ser Asn Gly Gly Gly Lys Gln Ala Leu Glu Thr Val
450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530

<210> SEQ ID NO 11
<211> LENGTH: 530
<212> TYPE: PRT
<213> ORGANISM: Artificial Sequence
<220> FEATURE:
<223> OTHER INFORMATION: Repeat-GRex3T4-L1

<400> SEQUENCE: 11

Leu Thr Pro Gln Gln Val Val Ala Ile Ala Ser Asn Asn Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Glu Gln Val Val Ala Ile Ala Ser His Asp Gly
            35                  40                  45
Gly Lys Gln Ala Leu Glu Thr Val Gln Arg Leu Leu Pro Val Leu Cys
        50                  55                  60
Gln Ala His Gly Leu Thr Pro Gln Gln Val Val Ala Ile Ala Ser Asn
65                  70                  75                  80
Gly Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
```

```
Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Asn Gly Gly Lys
    275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser Asn
        340                 345                 350

Ile Gly Gly Lys Gln Ala Leu Glu Thr Val Gln Ala Leu Leu Pro Val
    355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
        420                 425                 430

Leu Leu Pro Val Leu Cys Gln Ala His Gly Leu Thr Pro Gln Gln Val
    435                 440                 445

Val Ala Ile Ala Ser Asn Gly Gly Gly Lys Gln Ala Leu Glu Thr Val
450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
```

<210> SEQ ID NO 12
<211> LENGTH: 530
<212> TYPE: PRT
<213> ORGANISM: Artificial Sequence
<220> FEATURE:
<223> OTHER INFORMATION: Repeat-GRex3T4-R1

<400> SEQUENCE: 12

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
```

```
                355                 360                 365
Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser Asn Ile Gly Gly Lys Gln Ala Leu Glu Thr Val
                450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
                515                 520                 525

Leu Glu
530

<210> SEQ ID NO 13
<211> LENGTH: 530
<212> TYPE: PRT
<213> ORGANISM: Artificial Sequence
<220> FEATURE:
<223> OTHER INFORMATION: Repeat-GRex5T1-LPT8-L1

<400> SEQUENCE: 13

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
        130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
```

```
                180              185              190
Gln Arg Leu Leu Pro Val Leu Cys Gln Ala His Gly Leu Thr Pro Glu
            195              200              205
Gln Val Val Ala Ile Ala Ser Asn Ile Gly Gly Lys Gln Ala Leu Glu
            210              215              220
Thr Val Gln Ala Leu Leu Pro Val Leu Cys Gln Ala His Gly Leu Thr
225              230              235              240
Pro Glu Gln Val Val Ala Ile Ala Ser His Asp Gly Gly Lys Gln Ala
                245              250              255
Leu Glu Thr Val Gln Arg Leu Leu Pro Val Leu Cys Gln Ala His Gly
            260              265              270
Leu Thr Pro Gln Gln Val Val Ala Ile Ala Ser Asn Gly Gly Lys
            275              280              285
Gln Ala Leu Glu Thr Val Gln Arg Leu Leu Pro Val Leu Cys Gln Ala
            290              295              300
His Gly Leu Thr Pro Gln Gln Val Val Ala Ile Ala Ser Asn Asn Gly
305              310              315              320
Gly Lys Gln Ala Leu Glu Thr Val Gln Arg Leu Leu Pro Val Leu Cys
            325              330              335
Gln Ala His Gly Leu Thr Pro Gln Gln Val Val Ala Ile Ala Ser Asn
            340              345              350
Gly Gly Lys Gln Ala Leu Glu Thr Val Gln Arg Leu Leu Pro Val
            355              360              365
Leu Cys Gln Ala His Gly Leu Thr Pro Gln Gln Val Val Ala Ile Ala
            370              375              380
Ser Asn Gly Gly Lys Gln Ala Leu Glu Thr Val Gln Arg Leu Leu
385              390              395              400
Pro Val Leu Cys Gln Ala His Gly Leu Thr Pro Gln Gln Val Val Ala
                405              410              415
Ile Ala Ser Asn Asn Gly Gly Lys Gln Ala Leu Glu Thr Val Gln Arg
            420              425              430
Leu Leu Pro Val Leu Cys Gln Ala His Gly Leu Thr Pro Gln Gln Val
            435              440              445
Val Ala Ile Ala Ser Asn Asn Gly Gly Lys Gln Ala Leu Glu Thr Val
            450              455              460
Gln Arg Leu Leu Pro Val Leu Cys Gln Ala His Gly Leu Thr Pro Glu
465              470              475              480
Gln Val Val Ala Ile Ala Ser Asn Ile Gly Gly Lys Gln Ala Leu Glu
                485              490              495
Thr Val Gln Ala Leu Leu Pro Val Leu Cys Gln Ala His Gly Leu Thr
            500              505              510
Pro Gln Gln Val Val Ala Ile Ala Ser Asn Gly Gly Arg Pro Ala
            515              520              525
Leu Glu
    530

<210> SEQ ID NO 14
<211> LENGTH: 530
<212> TYPE: PRT
<213> ORGANISM: Artificial Sequence
<220> FEATURE:
<223> OTHER INFORMATION: Repeat-GRex5T1-LPT8-R1

<400> SEQUENCE: 14

Leu Thr Pro Glu Gln Val Val Ala Ile Ala Ser Asn Ile Gly Gly Lys
```

-continued

```
1               5                   10                  15
Gln Ala Leu Glu Thr Val Gln Ala Leu Leu Pro Val Leu Cys Gln Ala
                20                  25                  30

His Gly Leu Thr Pro Gln Gln Val Val Ala Ile Ala Ser Asn Gly Gly
                35                  40                  45

Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
                115                 120                 125

Pro Val Leu Cys Gln Ala His Gly Leu Thr Pro Gln Gln Val Val Ala
                130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
                180                 185                 190

Gln Arg Leu Leu Pro Val Leu Cys Gln Ala His Gly Leu Thr Pro Glu
                195                 200                 205

Gln Val Val Ala Ile Ala Ser His Asp Gly Gly Lys Gln Ala Leu Glu
                210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Gly Gly Lys
                275                 280                 285

Gln Ala Leu Glu Thr Val Gln Arg Leu Leu Pro Val Leu Cys Gln Ala
                290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
                340                 345                 350

Gly Gly Gly Lys Gln Ala Leu Glu Thr Val Gln Arg Leu Leu Pro Val
                355                 360                 365

Leu Cys Gln Ala His Gly Leu Thr Pro Glu Gln Val Val Ala Ile Ala
                370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430
```

-continued

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
            485                 490                 495

Thr Val Gln Ala Leu Leu Pro Val Leu Cys Gln Ala His Gly Leu Thr
        500                 505                 510

Pro Gln Gln Val Val Ala Ile Ala Ser Asn Gly Gly Arg Pro Ala
        515                 520                 525

Leu Glu
    530

<210> SEQ ID NO 15
<211> LENGTH: 530
<212> TYPE: PRT
<213> ORGANISM: Artificial Sequence
<220> FEATURE:
<223> OTHER INFORMATION: Repeat-GRex5T2-L1

<400> SEQUENCE: 15

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Lys
        275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 16
<211> LENGTH: 530
<212> TYPE: PRT
<213> ORGANISM: Artificial Sequence
<220> FEATURE:
<223> OTHER INFORMATION: Repeat-GRex5T2-R1

<400> SEQUENCE: 16

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

```
Asn Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
                100                 105                 110
Ser His Asp Gly Gly Lys Gln Ala Leu Glu Thr Val Gln Arg Leu Leu
                115                 120                 125
Pro Val Leu Cys Gln Ala His Gly Leu Thr Pro Gln Gln Val Val Ala
        130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Gln Gln Val
                165                 170                 175
Val Ala Ile Ala Ser Asn Gly Gly Gly Lys Gln Ala Leu Glu Thr Val
                180                 185                 190
Gln Arg Leu Leu Pro Val Leu Cys Gln Ala His Gly Leu Thr Pro Glu
                195                 200                 205
Gln Val Val Ala Ile Ala Ser Asn Ile Gly Gly Lys Gln Ala Leu Glu
                210                 215                 220
Thr Val Gln Ala Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
                260                 265                 270
Leu Thr Pro Gln Gln Val Val Ala Ile Ala Ser Asn Gly Gly Gly Lys
                275                 280                 285
Gln Ala Leu Glu Thr Val Gln Arg Leu Leu Pro Val Leu Cys Gln Ala
        290                 295                 300
His Gly Leu Thr Pro Glu Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
                340                 345                 350
Ile Gly Gly Lys Gln Ala Leu Glu Thr Val Gln Ala Leu Leu Pro Val
                355                 360                 365
Leu Cys Gln Ala His Gly Leu Thr Pro Gln Gln Val Val Ala Ile Ala
        370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
                420                 425                 430
Leu Leu Pro Val Leu Cys Gln Ala His Gly Leu Thr Pro Glu Gln Val
                435                 440                 445
Val Ala Ile Ala Ser Asn Ile Gly Gly Lys Gln Ala Leu Glu Thr Val
                450                 455                 460
Gln Ala Leu Leu Pro Val Leu Cys Gln Ala His Gly Leu Thr Pro Gln
465                 470                 475                 480
Gln Val Val Ala Ile Ala Ser Asn Gly Gly Gly Lys Gln Ala Leu Glu
                485                 490                 495
```

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
        515                 520                 525

Leu Glu
    530

<210> SEQ ID NO 17
<211> LENGTH: 530
<212> TYPE: PRT
<213> ORGANISM: Artificial Sequence
<220> FEATURE:
<223> OTHER INFORMATION: Repeat-GRex5T3-L1

<400> SEQUENCE: 17

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser Asn Ile Gly Gly Lys Gln Ala Leu Glu Thr Val Gln Ala Leu Leu
            115                 120                 125

Pro Val Leu Cys Gln Ala His Gly Leu Thr Pro Gln Gln Val Val Ala
        130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Asn Gly
305                 310                 315                 320

```
Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Val Ala Ile Ala
        370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
            450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530
```

<210> SEQ ID NO 18
<211> LENGTH: 530
<212> TYPE: PRT
<213> ORGANISM: Artificial Sequence
<220> FEATURE:
<223> OTHER INFORMATION: Repeat-GRex5T3-R1

<400> SEQUENCE: 18

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
            130                 135                 140
```

```
Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
            165                 170                 175

Val Ala Ile Ala Ser Asn Gly Gly Lys Gln Ala Leu Glu Thr Val
        180                 185                 190

Gln Arg Leu Leu Pro Val Leu Cys Gln Ala His Gly Leu Thr Pro Glu
    195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 19
<211> LENGTH: 2814
<212> TYPE: DNA
```

<213> ORGANISM: Artificial Sequence
<220> FEATURE:
<223> OTHER INFORMATION: GRex2-L TALEN

<400> SEQUENCE: 19

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agcaatattg gtggcaagca ggcgctggag    540
acggtgcagg cgctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc cccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag caatattggt ggcaagcagg cgctggagac ggtgcaggcg    960
ctgttgccgg tgctgtgcca ggcccacggc ttgaccccgg agcaggtggt ggccatcgcc   1020
agccacgatg cggcaagca ggcgctggag acggtccagc ggctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caatggcggt   1440
ggcaagcagg cgctggagac ggtccagcgg ctgttgccgg tgctgtgcca ggcccacggc   1500
ttgacccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtc aggcgctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccccag   1920
caggtggtgg ccatcgccag caatggcggt ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
```

```
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gcctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 20
<211> LENGTH: 2832
<212> TYPE: DNA
<213> ORGANISM: Artificial Sequence
<220> FEATURE:
<223> OTHER INFORMATION: GRex2-R TALEN

<400> SEQUENCE: 20
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caatggcggt     540
ggcaagcagg cgctggagac ggtccagcgg ctgttgccgg tgctgtgcca ggcccacggc     600
ttgacccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccccagcagg tggtggccat cgccagcaat     840
ggcggtggca agcaggcgct ggagacggtc cagcggctgt tgccggtgct gtgccaggcc     900
cacggcttga ccccccagca ggtggtggcc atcgccagca atggcggtgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ggagcaggtg gtggccatcg ccagccacga tggcggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt tgccggtgct gtgccaggcc cacggcttga ccccggagca ggtggtggcc    1440
```

```
atcgccagca atattggtgg caagcaggcg ctggagacgg tgcaggcgct gttgccggtg    1500
ctgtgccagg cccacggctt gaccccggag caggtggtgg ccatcgccag ccacgatggc    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccccagcagg tggtggccat cgccagcaat    1860
aatggtggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctgat gcagtgaaaa agggattggg ggatcctatc     2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacagggc     2400 aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg     2640
tccggccact tcaagggcaa ctacaaggcc agctgacca ggctgaacca catcaccaac     2700
tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                        2832

<210> SEQ ID NO 21
<211> LENGTH: 2814
<212> TYPE: DNA
<213> ORGANISM: Artificial Sequence
<220> FEATURE:
<223> OTHER INFORMATION: GRex3T2-L TALEN

<400> SEQUENCE: 21
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccc agcaggtggt ggccatcgcc agcaataatg gtggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
```

```
ccggtgctgt gccaggccca cggcttgacc ccggagcagg tggtggccat cgccagccac    720
gatggcggca agcaggcgct ggagacggtc agcggctgt tgccggtgct gtgccaggcc    780
cacggcttga ccccccagca ggtggtggcc atcgccagca atggcggtgg caagcaggcg    840
ctggagacgt ccagcggct gttgccggtg ctgtgccagg cccacggctt gaccccccag    900
caggtggtgg ccatcgccag caataatggt ggcaagcagg cgctggagac ggtccagcgg    960
ctgttgccgg tgctgtgcca ggcccacggc ttgaccccc agcaggtggt ggccatcgcc   1020
agcaataatg gtggcaagca ggcgctggag acggtccagc ggctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccccagca ggtggtggcc   1320
atcgccagca atggcggtgg caagcaggcg ctggagacgg tccagcggct gttgccggtg   1380
ctgtgccagg cccacggctt gacccccag caggtggtgg ccatcgccag caataatggt   1440
ggcaagcagg cgctggagac ggtccagcgg ctgttgccgg tgctgtgcca ggcccacggc   1500
ttgaccccgg agcaggtggt ggccatcgcc agccacgatg gcggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc agcggctgt tgccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gacccccag   1920 caggtggtgg ccatcgccag caataatggt ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctcccccca tcgactacgg cgtgatcgtg   2460
gacaccaagg cctactccgg cggctacaac ctgcccatcg ccaggccgga cgaaatgcag   2520
aggtacgtgg aggagaacca gaccaggaac aagcacatca ccccaacga gtggtggaag   2580 gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gacctggag   2760 gaggtgagga ggaagttcaa caacggcgag atcaacttcg cggccgactg ataa         2814
```

<210> SEQ ID NO 22
<211> LENGTH: 2832
<212> TYPE: DNA
<213> ORGANISM: Artificial Sequence
<220> FEATURE:

<223> OTHER INFORMATION: GRex3T2-R TALEN

<400> SEQUENCE: 22

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caatggcggt     540
ggcaagcagg cgctggagac ggtccagcgg ctgttgccgg tgctgtgcca ggcccacggc     600
ttgaccccgg agcaggtggt ggccatcgcc agcaatattg gtggcaagca ggcgctggag     660
acggtgcagg cgctgttgcc ggtgctgtgc caggcccacg gcttgacccc ggagcaggtg     720
gtggccatcg ccagcaatat tggtggcaag caggcgctgg agacggtgca ggcgctgttg     780
ccggtgctgt gccaggccca cggcttgacc cccagcagg tggtggccat cgccagcaat     840
aatggtggca agcaggcgct ggagacggtc agcggctgt tgccggtgct gtgccaggcc     900
cacggcttga ccccggagca ggtggtggcc atcgccagca atattggtgg caagcaggcg     960
ctggagacgt gcaggcgct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ggagcaggtg gtggccatcg ccagccacga tggcggcaag    1260
caggcgctgg agacggtcca gcggctgttg ccggtgctgt gccaggccca cggcttgacc    1320
ccggagcagg tggtggccat cgccagccac gatggcggca agcaggcgct ggagacggtc    1380
cagcggctgt tgccggtgct gtgccaggcc cacggcttga ccccggagca ggtggtggcc    1440
atcgccagca atattggtgg caagcaggcg ctggagacgg tgcaggcgct gttgccggtg    1500
ctgtgccagg cccacggctt gaccccccag caggtggtgg ccatcgccag caatggcggt    1560
ggcaagcagg cgctggagac ggtccagcgg ctgttgccgg tgctgtgcca ggcccacggc    1620
ttgaccccgg agcaggtggt ggccatcgcc agcaatattg gtggcaagca ggcgctggag    1680
acggtgcagg cgctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc cccagcagg tggtggccat cgccagcaat    1860
ggcggtggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgt ccagcggct gttgccggtg ctgtgccagg cccacggctt gaccccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga aatccgagtt gaggcacaag    2280
```

```
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc agctgaccag gctgaaccca catcaccaac    2700
tgcaacggcg ccgtgctgtc cgtgaggagc tcctgatcgc gggcgagat gatcaaggcc    2760 ggcaccctga ccctggagga ggtgaggagg aagttcaaca acggcgagat caacttcgcg    2820
gccgactgat aa                                                       2832
```

<210> SEQ ID NO 23
<211> LENGTH: 2814
<212> TYPE: DNA
<213> ORGANISM: Artificial Sequence
<220> FEATURE:
<223> OTHER INFORMATION: GRex3T4-L TALEN

<400> SEQUENCE: 23

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480 ttgaccccc agcaggtggt ggccatcgcc agcaataatg gtggcaagca ggcgctggag     540
acggtccagc ggctgttgcc ggtgctgtgc caggcccacg gcttgacccc ggagcaggtg     600
gtggccatcg ccagccacga tggcggcaag caggcgctgg agacggtcca gcggctgttg     660
ccggtgctgt gccaggccca cggcttgacc ccccagcagg tggtggccat cgccagcaat     720
ggcggtggca agcaggcgct ggagacggtc agcggctgt tgccggtgct gtgccaggcc     780
cacggcttga ccccggagca ggtggtggcc atcgccagcc acgatggcgg caagcaggcg     840
ctggagacgg tccagcggct gttgccggtg ctgtgccagg cccacggctt gaccccccag     900
caggtggtgg ccatcgccag caatggcggt ggcaagcagg cgctggagac ggtccagcgg     960
ctgttgccgg tgctgtgcca ggcccacggc ttgaccccc agcaggtggt ggccatcgcc    1020
agcaataatg gtggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccagcccca cggcttgacc    1200
ccccagcagg tggtggccat cgccagcaat ggcggtggca agcaggcgct ggagacggtc    1260
cagcggctgt tgccggtgct gtgccaggcc cacggcttga ccccccagca ggtggtggcc    1320
atcgccagca ataatggtgg caagcaggcg ctggagacgg tccagcggct gttgccggtg    1380
ctgtgccagg cccacggctt gaccccggag caggtggtgg ccatcgccag caatattggt    1440
```

| | |
|---|---|
| ggcaagcagg cgctggagac ggtgcaggcg ctgttgccgg tgctgtgcca ggcccacggc | 1500 |
| ttgaccccgg agcaggtggt ggccatcgcc agcaatattg gtggcaagca ggcgctggag | 1560 |
| acggtgcagg cgctgttgcc ggtgctgtgc caggcccacg gcttgacccc ccagcaggtg | 1620 |
| gtggccatcg ccagcaataa tggtggcaag caggcgctgg agacggtcca gcggctgttg | 1680 |
| ccggtgctgt gccaggccca cggcttgacc ccggagcagg tggtggccat cgccagccac | 1740 |
| gatggcggca gcaggcgct ggagacggtc agcggctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccgtg ctgtgccagg cccacggctt gaccccccag | 1920 |
| caggtggtgg ccatcgccag caatggcggt ggcaagcagg cgctggagac ggtccagcgg | 1980 |
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg ccaggcgga cgaaatgcag | 2520 |
| aggtacgtgg aggagaacca gaccaggaac aagcacatca accccaacga gtggtggaag | 2580 |
| gtgtaccccc tccagcgtga ccgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gacctggag | 2760 |
| gaggtgagga ggaagttcaa caacggcgag atcaacttcg cggccgactg ataa | 2814 |

<210> SEQ ID NO 24
<211> LENGTH: 2832
<212> TYPE: DNA
<213> ORGANISM: Artificial Sequence
<220> FEATURE:
<223> OTHER INFORMATION: GRex3T4-R TALEN

<400> SEQUENCE: 24

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg agagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caatggcggt | 540 |
| ggcaagcagg cgctggagac ggtccagcgg ctgttgccgg tgctgtgcca ggcccacggc | 600 |
| ttgaccccgg agcaggtggt ggccatcgcc agccacgatg cggcaagca ggcgctggag | 660 |
| acggtccagc ggctgttgcc ggtgctgtgc caggcccacg gcttgacccc ggagcaggtg | 720 |

```
gtggccatcg ccagccacga tggcggcaag caggcgctgg agacggtcca gcggctgttg      780
ccggtgctgt gccaggccca cggcttgacc ccggagcagg tggtggccat cgccagcaat      840
attggtggca agcaggcgct ggagacggtg caggcgctgt tgccggtgct gtgccaggcc      900
cacggcttga ccccggagca ggtggtggcc atcgccagcc acgatggcgg caagcaggcg      960
ctggagacgg tccagcggct gttgccggtg ctgtgccagg cccacggctt gaccccggag     1020
caggtggtgg ccatcgccag caatattggt ggcaagcagg cgctggagac ggtgcaggcg     1080
ctgttgccgg tgctgtgcca ggcccacggc ttgaccccgg agcaggtggt ggccatcgcc     1140
agcaatattg gtggcaagca ggcgctggag acggtgcagg cgctgttgcc ggtgctgtgc     1200
caggcccacg gcttgacccc cagcaggtg gtggccatcg ccagcaataa tggtggcaag     1260
```

<223> OTHER INFORMATION: GRex5T1-L TALEN

<400> SEQUENCE: 25

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccggcag cgttagggac cgtcgctgtc    240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgaccccc agcaggtggt ggccatcgcc agcaataatg gtggcaagca ggcgctggag    540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc cccagcagg tggtggccat cgccagcaat    720
ggcggtggca agcaggcgct ggagacggtc agcggctgt tgccggtgct gtgccaggcc    780
cacggcttga ccccccagca ggtggtggcc atcgccagca ataatggtgg caagcaggcg   840
ctggagacgt ccagcggct gttgccggtg ctgtgccagg cccacggctt gacccccag    900
caggtggtgg ccatcgccag caatggcggt ggcaagcagg cgctggagac ggtccagcgg   960
ctgttgccgg tgctgtgcca ggcccacggc ttgaccccgg agcaggtggt ggccatcgcc  1020
agccacgatg gcggcaagca ggcgctggag acggtccagc ggctgttgcc ggtgctgtgc  1080
caggcccacg gcttgacccc ggagcaggtg gtggccatcg ccagcaatat tggtggcaag  1140
caggcgctgg agacggtgca ggcgctgttg ccggtgctgt gccaggccca cggcttgacc  1200
ccggagcagg tggtggccat cgccagccac gatggcggca agcaggcgct ggagacggtc  1260
cagcggctgt tgccggtgct gtgccaggcc cacggcttga ccccccagca ggtggtggcc  1320
atcgccagca atggcggtgg caagcaggcg ctggagacgg tccagcggct gttgccggtg  1380
ctgtgccagg cccacggctt gaccccccag caggtggtgg ccatcgccag caataatggt  1440
ggcaagcagg cgctggagac ggtccagcgg ctgttgccgg tgctgtgcca ggcccacggc  1500
ttgaccccc agcaggtggt ggccatcgcc agcaatggcg gtggcaagca ggcgctggag   1560
acggtccagc ggctgttgcc ggtgctgtgc caggcccacg gcttgacccc ccagcaggtg  1620
gtggccatcg ccagcaatgg cggtggcaag caggcgctgg agacggtcca gcggctgttg  1680
ccggtgctgt gccaggccca cggcttgacc cccagcagg tggtggccat cgccagcaat   1740
aatggtggca agcaggcgct ggagacggtc agcggctgt tgccggtgct gtgccaggcc   1800
cacggcttga ccccccagca ggtggtggcc atcgccagca ataatggtgg caagcaggcg  1860
ctggagacgg tccagcggct gttgccggtg ctgtgccagg cccacggctt gaccccggag  1920
caggtggtgg ccatcgccag caatattggt ggcaagcagg cgctggagac ggtgcaggcg  1980
ctgttgccgg tgctgtgcca ggcccacggc ttgaccccctc agcaggtggt ggccatcgcc  2040
agcaatggcg gcggcaggcc ggcgctggag agcattgttg cccagttatc tcgccctgat  2100
ccggcgttgg ccgcgttgac caacgaccac ctcgtcgcct tggcctgcct cggcgggcgt  2160
cctgcgctga tgcagtgaa aagggattg ggggatccta tcagccgttc ccagctggtg   2220
aagtccgagc tggaggagaa gaaatccgag ttgaggcaca agctgaagta cgtgccccac  2280
```

```
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca ccccaacga gtggtggaag    2580 gtgtaccccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agtcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 26
<211> LENGTH: 2832
<212> TYPE: DNA
<213> ORGANISM: Artificial Sequence
<220> FEATURE:
<223> OTHER INFORMATION: GRex5T1-R TALEN

<400> SEQUENCE: 26

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag caatattggt    540
ggcaagcagg cgctggagac ggtgcaggcg ctgttgccgg tgctgtgcca ggcccacggc    600 ttgaccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagccac    840
gatggcggca agcaggcgct ggagacggtc agcggctgt gccggtgct gtgccaggcc    900 cacggcttga ccccccagca ggtggtggcc atcgccagca atggcggtgg caagcaggcg    960
ctggagacgt ccagcggct gttgccggtg ctgtgccagg cccacggctt gaccccccag   1020
caggtggtgg ccatcgccag caataatggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctga gacggtgca ggcgctgttg ccggtgctgt gccaggccca cggcttgacc   1320
ccccagcagg tggtggccat cgccagcaat ggcggtggca agcaggcgct ggagacggtc   1380
cagcggctgt gccggtgct gtgccaggcc cacggcttga ccccgagca ggtggtggcc   1440 atcgccagca atattggtgg caagcaggcg ctggagacgg tgcaggcgct gttgccggtg   1500
```

| | |
|---|---|
| ctgtgccagg cccacggctt gacccccag caggtggtgg ccatcgccag caatggcggt | 1560 |
| ggcaagcagg cgctggagac ggtccagcgg ctgttgccgg tgctgtgcca ggcccacggc | 1620 |
| ttgaccccgg agcaggtggt ggccatcgcc agcaatattg gtggcaagca ggcgctggag | 1680 |
| acggtgcagg cgctgttgcc ggtgctgtgc caggcccacg gcttgacccc ggagcaggtg | 1740 |
| gtggccatcg ccagcaatat tggtggcaag caggcgctgg agacggtgca ggcgctgttg | 1800 |
| ccggtgctgt gccaggccca cggcttgacc ccggagcagg tggtggccat cgccagccac | 1860 |
| gatggcggca agcaggcgct ggagacggtc agcggctgt tgccggtgct gtgccaggcc | 1920 |
| cacggcttga ccccggagca ggtggtggcc atcgccagca atattggtgg caagcaggcg | 1980 |
| ctggagacgg tgcaggcgct gttgccggtg ctgtgccagg cccacggctt gacccctcag | 2040 |
| caggtggtgg ccatcgccag caatggcggc ggcaggccgg cgctggagag cattgttgcc | 2100 |
| cagttatctc gccctgatcc ggcgttggcc gcgttgacca acgaccacct cgtcgccttg | 2160 |
| gcctgcctcg gcgggcgtcc tgcgctggat gcagtgaaaa agggattggg ggatcctatc | 2220 |
| agccgttccc agctggtgaa gtccgagctg gaggagaaga atccgagtt gaggcacaag | 2280 |
| ctgaagtacg tgccccacga gtacatcgag ctgatcgaga tcgcccggaa cagcacccag | 2340 |
| gaccgtatcc tggagatgaa ggtgatggag ttcttcatga aggtgtacgg ctacaggggc | 2400 |
| aagcacctgg gcggctccag gaagcccgac ggcgccatct acaccgtggg ctcccccatc | 2460 |
| gactacggcg tgatcgtgga caccaaggcc tactccggcg gctacaacct gcccatcggc | 2520 |
| caggccgacg aaatgcagag gtacgtggag gagaaccaga ccaggaacaa gcacatcaac | 2580 |
| cccaacgagt ggtggaaggt gtacccctcc agcgtgaccg agttcaagtt cctgttcgtg | 2640 |
| tccggccact tcaagggcaa ctacaaggcc cagctgacca ggctgaacca catcaccaac | 2700 |
| tgcaacggcg ccgtgctgtc cgtggaggag ctcctgatcg gcggcgagat gatcaaggcc | 2760 |
| ggcaccctga ccctggagga ggtgaggagg aagttcaaca acggcgagat caacttcgcg | 2820 |
| gccgactgat aa | 2832 |

<210> SEQ ID NO 27
<211> LENGTH: 2814
<212> TYPE: DNA
<213> ORGANISM: Artificial Sequence
<220> FEATURE:
<223> OTHER INFORMATION: GRex5T2-L TALEN

<400> SEQUENCE: 27

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccgg agcaggtggt ggccatcgcc agcaatattg gtggcaagca ggcgctggag | 540 |
| acggtgcagg cgctgttgcc ggtgctgtgc caggcccacg gcttgacccc ggagcaggtg | 600 |
| gtggccatcg ccagcaatgg cggtggcaag caggcgctgg agacggtcca gcggctgttg | 660 |
| ccggtgctgt gccaggccca cggcttgacc cccagcagg tggtggccat cgccagcaat | 720 |

```
aatggtggca agcaggcgct ggagacggtc agcggctgt tgccggtgct gtgccaggcc      780
cacggcttga ccccggagca ggtggtggcc atcgccagca atattggtgg caagcaggcg      840
ctggagacgg tgcaggcgct gttgccggtg ctgtgccagg cccacggctt gaccccccag      900
caggtggtgg ccatcgccag caatggcggt ggcaagcagg cgctggagac ggtccagcgg      960
ctgttgccgg tgctgtgcca ggcccacggc ttgaccccgg agcaggtggt ggccatcgcc     1020
agcaatattg gtggcaagca ggcgctggag acggtgcagg cgctgttgcc ggtgctgtgc     1080
caggcccacg gcttgacccc cagcaggtg gtggccatcg ccagcaataa tggtggcaag     1140
caggcgctgg agacggtcca gcggctgttg ccggtgctgt gccaggccca cggcttgacc     1200
ccggagcagg tggtggccat cgccagccac gatggcggca agcaggcgct ggagacggtc     1260
cagcggctgt tgccggtgct gtgccaggcc cacggcttga ccccccagca ggtggtggcc     1320
atcgccagca atggcggtgg caagcaggcg ctggagacgg tccagcggct gttgccggtg     1380
ctgtgccagg cccacggctt gaccccggag caggtggtgg ccatcgccag ccacgatggc     1440
ggcaagcagg cgctggagac ggtccagcgg ctgttgccgg tgctgtgcca ggcccacggc     1500
ttgaccccc agcaggtggt ggccatcgcc agcaatggcg gtggcaagca ggcgctggag     1560
acggtccagc ggctgttgcc ggtgctgtgc caggcccacg gcttgacccc cagcaggtg     1620
gtggccatcg ccagcaataa tggtggcaag caggcgctgg agacggtcca gcggctgttg     1680
ccggtgctgt gccaggccca cggcttgacc cccagcagg tggtggccat cgccagcaat     1740
ggcggtggca agcaggcgct ggagacggtc agcggctgt tgccggtgct gtgccaggcc     1800
cacggcttga ccccccagca ggtggtggcc atcgccagca atggcggtgg caagcaggcg     1860
ctggagacgg tccagcggct gttgccggtg ctgtgccagg cccacggctt gaccccggag     1920
caggtggtgg ccatcgccag ccacgatggc ggcaagcagg cgctggagac ggtccagcgg     1980
ctgttgccgg tgctgtgcca ggcccacggc ttgaccccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatgg agttcttcat gaaggtgtac ggctacaggg gcaagcacct gggcggctcc     2400
aggaagcccg acgcgccat ctacaccgtg gctcccccca tcgactacgg cgtgatcgtg     2460
gacaccaagg cctactccgg cggctacaac ctgcccatcg ccaggcggcga cgaaatgcag     2520
aggtacgtga aggagaacca gaccaggaac aagcacatca cccccaacga gtggtggaag     2580
gtgtaccct ccagcgtgac cgagttcaag ttcctgttcg tgtccggcca cttcaagggc     2640
aactacaagg cccagctgac caggctgaac cacatcacca actgcaacgg cgccgtgctg     2700
tccgtggagg agctcctgat cggcggcgag atgatcaagg ccggcaccct gacccttgag     2760
gaggtgagga ggaagttcaa caacggcgag atcaacttcg cggccgactg ataa          2814
```

<210> SEQ ID NO 28
<211> LENGTH: 2832
<212> TYPE: DNA
<213> ORGANISM: Artificial Sequence
<220> FEATURE:
<223> OTHER INFORMATION: GRex5T2-R TALEN

<400> SEQUENCE: 28

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gacccccag caggtggtgg ccatcgccag caataatggt     540
ggcaagcagg cgctggagac ggtccagcgg ctgttgccgg tgctgtgcca ggcccacggc     600
ttgaccccgg agcaggtggt ggccatcgcc agcaatattg gtggcaagca ggcgctggag     660
acggtgcagg cgctgttgcc ggtgctgtgc caggcccacg gcttgacccc ccagcaggtg     720
gtggccatcg ccagcaataa tggtggcaag caggcgctgg agacggtcca gcggctgttg     780
ccggtgctgt gccaggccca cggcttgacc ccggagcagg tggtggccat cgccagccac     840
gatggcggca agcaggcgct ggagacggtc agcggctgt tgccggtgct gtgccaggcc     900
cacggcttga ccccccagca ggtggtggcc atcgccagca ataatggtgg caagcaggcg     960
ctggagacgg tccagcggct gttgccggtg ctgtgccagg cccacggctt gaccccccag    1020
caggtggtgg ccatcgccag caatggcggt ggcaagcagg cgctggagac ggtccagcgg    1080
ctgttgccgg tgctgtgcca ggcccacggc ttgaccccgg agcaggtggt ggccatcgcc    1140
agcaatattg gtggcaagca ggcgctggag acggtgcagg cgctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt gccggtgct gtgccaggcc acggcttga ccccgagca ggtggtggcc    1440
atcgccagcc acgatggcgg caagcaggcg ctggagacgg tccagcggct gttgccggtg    1500
ctgtgccagg cccacggctt gacccggag caggtggtgg ccatcgccag caatattggt    1560
ggcaagcagg cgctggagac ggtgcaggcg ctgttgccgg tgctgtgcca ggcccacggc    1620
ttgacccccc agcaggtggt ggccatcgcc agcaatggcg gtggcaagca ggcgctggag    1680
acggtccagc ggctgttgcc ggtgctgtgc caggcccacg gcttgacccc ccagcaggtg    1740
gtggccatcg ccagcaataa tggtggcaag caggcgctgg agacggtcca gcggctgttg    1800
ccggtgctgt gccaggccca cggcttgacc ccggagcagg tggtggccat cgccagcaat    1860
attggtggca agcaggcgct ggagacggtg caggcgctgt gccggtgct gtgccaggcc    1920
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga aatccgagtt gaggcacaag    2280
ctgaagtacg tgccccacga gtacatcgag ctgatcgaga tcgcccggaa cagcacccag    2340
```

```
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc   2760 ggcacccctga ccctggagga ggtgaggagg aagttcaaca cggcgagat caacttcgcg    2820 gccgactgat aa                                                       2832
```

<210> SEQ ID NO 29  
<211> LENGTH: 2814  
<212> TYPE: DNA  
<213> ORGANISM: Artificial Sequence  
<220> FEATURE:  
<223> OTHER INFORMATION: GRex5T3-L TALEN

<400> SEQUENCE: 29

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccggcag cgttagggac cgtcgctgtc      240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca gattgcaaa acgtggcggc      420 gtgaccgcag tggaggcagt gcatgcatgg cgcaatgcac tgacgggtgc cccgctcaac     480
ttgacccccc agcaggtggt ggccatcgcc agcaatggcg gtggcaagca ggcgctggag     540
acggtccagc ggctgttgcc ggtgctgtgc caggcccacg gcttgacccc ggagcaggtg     600
gtggccatcg ccagcaatat tggtggcaag caggcgctgg agacggtgca ggcgctgttg     660
ccggtgctgt gccaggccca cggcttgacc cccagcagg tggtggccat cgccagcaat      720
ggcggtggca agcaggcgct ggagacggtc agcggctgt gccggtgct gtgccaggcc       780 cacggcttga ccccggagca ggtggtggcc atcgccagca atattggtgg caagcaggcg     840
ctggagacgt gcaggcgct gttgccggtg ctgtgccagg cccacggctt gacccccag       900 caggtggtgg ccatcgccag caatggcggt ggcaagcagg cgctggagac ggtccagcgg     960
ctgttgccgg tgctgtgcca ggcccacggc ttgaccccc agcaggtggt ggccatcgcc     1020
agcaataatg gtggcaagca ggcgctggag acggtccagc ggctgttgcc ggtgctgtgc    1080
caggcccacg gcttgacccc ggagcaggtg gtggccatcg ccagccacga tggcggcaag    1140
caggcgctgg agacggtcca gcggctgttg ccggtgctgt gccaggccca cggcttgacc    1200
ccggagcagg tggtggccat cgccagcaat attggtggca agcaggcgct ggagacggtg    1260
caggcgctgt tgccggtgct gtgccaggcc cacggcttga ccccccagca ggtggtggcc    1320
atcgccagca ataatggtgg caagcaggcg ctggagacgg tccagcggct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
```

| | |
|---|---:|
| ttgaccccgg agcaggtggt ggccatcgcc agcaatattg gtggcaagca ggcgctggag | 1560 |
| acggtgcagg cgctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtg caggcgctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccccag | 1920 |
| caggtggtgg ccatcgccag caataatggt ggcaagcagg cgctggagac ggtccagcgg | 1980 |
| ctgttgccgg tgctgtgcca ggcccacggc ttgaccccte agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg caagcacct gggcggctcc | 2400 |
| aggaagcccg acggcgccat ctacaccgtg ggctcccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca ccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 30
<211> LENGTH: 2832
<212> TYPE: DNA
<213> ORGANISM: Artificial Sequence
<220> FEATURE:
<223> OTHER INFORMATION: GRex5T3-R TALEN

<400> SEQUENCE: 30

| | |
|---|---:|
| atgggcgatc taaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgaccccgg agcaggtggt ggccatcgcc agcaatattg gtggcaagca ggcgctggag | 660 |
| acggtgcagg cgctgttgcc ggtgctgtgc caggcccacg gcttgacccc ccagcaggtg | 720 |
| gtggccatcg ccagcaatgg cggtggcaag caggcgctgg agacggtcca gcggctgttg | 780 |

```
ccggtgctgt gccaggccca cggcttgacc ccggagcagg tggtggccat cgccagccac   840
gatggcggca agcaggcgct ggagacggtc agcggctgt tgccggtgct gtgccaggcc    900
cacggcttga ccccggagca ggtggtggcc atcgccagcc acgatggcgg caagcaggcg   960
ctggagacgg tccagcggct gttgccggtg ctgtgccagg cccacggctt gaccccccag   1020
caggtggtgg ccatcgccag caatggcggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccggagcagg tggtggccat cgccagcaat attggtggca agcaggcgct ggagacggtg   1380
caggcgctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gaccccccag caggtggtgg ccatcgccag caataatggt   1560
ggcaagcagg cgctggagac ggtccagcgg ctgttgccgg tgctgtgcca ggcccacggc   1620 ttgaccccccc agcaggtggt ggccatcgcc agcaatggcg gtggcaagca ggcgctggag   1680
acggtccagc ggctgttgcc ggtgctgtgc caggcccacg gcttgacccc ccagcaggtg   1740
gtggccatcg ccagcaatgg cggtggcaag caggcgctgg agacggtcca gcggctgttg   1800
ccggtgctgt gccaggccca cggcttgacc ccccagcagg tggtggccat cgccagcaat   1860
aatggtggca agcaggcgct ggagacggtc agcggctgt tgccggtgct gtgccaggcc    1920
cacggcttga ccccggagca ggtggtggcc atcgccagca atattggtgg caagcaggcg   1980
ctggagacgg tgcaggcgct gttgccggtg ctgtgccagg cccacggctt gaccccctcag  2040 caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctctc cagcgtgacc agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa   2832
```

<210> SEQ ID NO 31
<211> LENGTH: 60
<212> TYPE: DNA
<213> ORGANISM: Artificial Sequence
<220> FEATURE:
<223> OTHER INFORMATION: Forward primer GR exon 2
<220> FEATURE:

```
<221> NAME/KEY: misc_feature
<222> LOCATION: (31)..(40)
<223> OTHER INFORMATION: n is a or c or t or g

<400> SEQUENCE: 31
ccatctcatc cctgcgtgtc tccgactcag nnnnnnnnnn ggttcattta acaagctgcc    60

<210> SEQ ID NO 32
<211> LENGTH: 60
<212> TYPE: DNA
<213> ORGANISM: Artificial Sequence
<220> FEATURE:
<223> OTHER INFORMATION: Forward primer GR exon 3
<220> FEATURE:
<221> NAME/KEY: misc_feature
<222> LOCATION: (31)..(40)
<223> OTHER INFORMATION: n is a or c or t or g

<400> SEQUENCE: 32
ccatctcatc cctgcgtgtc tccgactcag nnnnnnnnnn gcattctgac tatgaagtga    60

<210> SEQ ID NO 33
<211> LENGTH: 69
<212> TYPE: DNA
<213> ORGANISM: Artificial Sequence
<220> FEATURE:
<223> OTHER INFORMATION: Forward primer GR exon 5
<220> FEATURE:
<221> NAME/KEY: misc_feature
<222> LOCATION: (31)..(40)
<223> OTHER INFORMATION: n is a or c or t or g

<400> SEQUENCE: 33
ccatctcatc cctgcgtgtc tccgactcag nnnnnnnnnn tcagcaggcc actacaggag    60
tctcacaag                                                            69

<210> SEQ ID NO 34
<211> LENGTH: 50
<212> TYPE: DNA
<213> ORGANISM: Artificial Sequence
<220> FEATURE:
<223> OTHER INFORMATION: Reverse primer GR exon 2

<400> SEQUENCE: 34
cctatcccct gtgtgccttg gcagtctcag agccagtgag ggtgaagacg              50

<210> SEQ ID NO 35
<211> LENGTH: 50
<212> TYPE: DNA
<213> ORGANISM: Artificial Sequence
<220> FEATURE:
<223> OTHER INFORMATION: Reverse primer GR exon 3

<400> SEQUENCE: 35
cctatcccct gtgtgccttg gcagtctcag gggctttgca tataatggaa              50

<210> SEQ ID NO 36
<211> LENGTH: 59
<212> TYPE: DNA
<213> ORGANISM: Artificial Sequence
<220> FEATURE:
<223> OTHER INFORMATION: Reverse primer GR exon 5

<400> SEQUENCE: 36
cctatcccct gtgtgccttg gcagtctcag ctgactctcc cttcatagt ccccagaac     59
```

```
<210> SEQ ID NO 37
<211> LENGTH: 49
<212> TYPE: DNA
<213> ORGANISM: Artificial Sequence
<220> FEATURE:
<223> OTHER INFORMATION: TRAC_T01

<400> SEQUENCE: 37
ttgtcccaca gatatccaga accctgaccc tgccgtgtac cagctgaga          49

<210> SEQ ID NO 38
<211> LENGTH: 49
<212> TYPE: DNA
<213> ORGANISM: Artificial Sequence
<220> FEATURE:
<223> OTHER INFORMATION: TRBC_T01

<400> SEQUENCE: 38
tgtgtttgag ccatcagaag cagagatctc ccacacccaa aaggccaca          49

<210> SEQ ID NO 39
<211> LENGTH: 50
<212> TYPE: DNA
<213> ORGANISM: Artificial Sequence
<220> FEATURE:
<223> OTHER INFORMATION: TRBC_T02

<400> SEQUENCE: 39
ttcccacccg aggtcgctgt gtttgagcca tcagaagcag agatctccca          50

<210> SEQ ID NO 40
<211> LENGTH: 49
<212> TYPE: DNA
<213> ORGANISM: Artificial Sequence
<220> FEATURE:
<223> OTHER INFORMATION: CD52_T02

<400> SEQUENCE: 40
ttcctcctac tcaccatcag cctcctggtt atggtacagg taagagcaa           49

<210> SEQ ID NO 41
<211> LENGTH: 530
<212> TYPE: PRT
<213> ORGANISM: Artificial Sequence
<220> FEATURE:
<223> OTHER INFORMATION: Repeat TRAC_T01-L

<400> SEQUENCE: 41

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
```

```
            115                 120                 125
Pro Val Leu Cys Gln Ala His Gly Leu Thr Pro Glu Gln Val Val Ala
            130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Glu
        195                 200                 205
Gln Val Val Ala Ile Ala Ser Asn Ile Gly Gly Lys Gln Ala Leu Glu
        210                 215                 220
Thr Val Gln Ala Leu Leu Pro Val Leu Cys Gln Ala His Gly Leu Thr
225                 230                 235                 240
Pro Glu Gln Val Val Ala Ile Ala Ser His Asp Gly Gly Lys Gln Ala
                245                 250                 255
Leu Glu Thr Val Gln Arg Leu Leu Pro Val Leu Cys Gln Ala His Gly
            260                 265                 270
Leu Thr Pro Glu Gln Val Val Ala Ile Ala Ser Asn Ile Gly Gly Lys
        275                 280                 285
Gln Ala Leu Glu Thr Val Gln Ala Leu Leu Pro Val Leu Cys Gln Ala
290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Gln Gln Val Val Ala Ile Ala
370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Gln Gln Val
        435                 440                 445
Val Ala Ile Ala Ser Asn Gly Gly Lys Gln Ala Leu Glu Thr Val
            450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
530
```

<210> SEQ ID NO 42
<211> LENGTH: 530
<212> TYPE: PRT
<213> ORGANISM: Artificial Sequence
<220> FEATURE:
<223> OTHER INFORMATION: Repeat TRAC_T01-R

<400> SEQUENCE: 42

```
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365
```

Leu Cys Gln Ala His Gly Leu Thr Pro Glu Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 43
<211> LENGTH: 530
<212> TYPE: PRT
<213> ORGANISM: Artificial Sequence
<220> FEATURE:
<223> OTHER INFORMATION: Repeat TRBC_T01-L

<400> SEQUENCE: 43

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
            245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
            370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
            405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
            485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 44
<211> LENGTH: 530
<212> TYPE: PRT
<213> ORGANISM: Artificial Sequence
<220> FEATURE:
<223> OTHER INFORMATION: Repeat TRBC_T01-R

<400> SEQUENCE: 44

Leu Thr Pro Gln Gln Val Val Ala Ile Ala Ser Asn Asn Gly Gly Lys
1               5                   10                  15

```
Gln Ala Leu Glu Thr Val Gln Arg Leu Leu Pro Val Leu Cys Gln Ala
            20                  25                  30

His Gly Leu Thr Pro Gln Gln Val Ala Ile Ala Ser Asn Gly Gly
        35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
 65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Lys Gln Ala
        245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Lys
        275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Asn Gly Gly Lys Gln Ala Leu Glu Thr Val Gln Arg
        420                 425                 430
```

```
Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 45
<211> LENGTH: 530
<212> TYPE: PRT
<213> ORGANISM: Artificial Sequence
<220> FEATURE:
<223> OTHER INFORMATION: Repeat TRBC_T02-L

<400> SEQUENCE: 45

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255
```

-continued

```
Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 46
<211> LENGTH: 530
<212> TYPE: PRT
<213> ORGANISM: Artificial Sequence
<220> FEATURE:
<223> OTHER INFORMATION: Repeat TRBC_T02-R

<400> SEQUENCE: 46

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80
```

Asn Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
        100                 105                 110

Ser Asn Ile Gly Gly Lys Gln Ala Leu Glu Thr Val Gln Ala Leu Leu
    115                 120                 125

Pro Val Leu Cys Gln Ala His Gly Leu Thr Pro Gln Gln Val Val Ala
130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr 500                 505                 510
Pro Gln Gln Val Val Ala Ile Ala Ser Asn Gly Gly Gly Arg Pro Ala
            515                 520                 525

Leu Glu
    530

<210> SEQ ID NO 47
<211> LENGTH: 530
<212> TYPE: PRT
<213> ORGANISM: Artificial Sequence
<220> FEATURE:
<223> OTHER INFORMATION: Repeat CD52_T02-L

<400> SEQUENCE: 47

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys

```
                     325                 330                 335
Gln Ala His Gly Leu Thr Pro Glu Gln Val Ala Ile Ala Ser His
            340                 345                 350
Asp Gly Gly Lys Gln Ala Leu Glu Thr Val Gln Arg Leu Leu Pro Val
            355                 360                 365
Leu Cys Gln Ala His Gly Leu Thr Pro Glu Gln Val Val Ala Ile Ala
        370                 375                 380
Ser Asn Ile Gly Gly Lys Gln Ala Leu Glu Thr Val Gln Ala Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Glu
465                 470                 475                 480
Gln Val Val Ala Ile Ala Ser Asn Ile Gly Gly Lys Gln Ala Leu Glu
                485                 490                 495
Thr Val Gln Ala Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
            515                 520                 525
Leu Glu
    530

<210> SEQ ID NO 48
<211> LENGTH: 530
<212> TYPE: PRT
<213> ORGANISM: Artificial Sequence
<220> FEATURE:
<223> OTHER INFORMATION: Repeat CD52_T02-R

<400> SEQUENCE: 48

Leu Thr Pro Gln Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Asn Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Gln Gln Val Val Ala Ile Ala
            100                 105                 110
Ser Asn Gly Gly Gly Lys Gln Ala Leu Glu Thr Val Gln Arg Leu Leu
        115                 120                 125
Pro Val Leu Cys Gln Ala His Gly Leu Thr Pro Glu Gln Val Val Ala
    130                 135                 140
Ile Ala Ser His Asp Gly Gly Lys Gln Ala Leu Glu Thr Val Gln Arg
```

```
             145                 150                 155                 160
Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 49
<211> LENGTH: 2814
<212> TYPE: DNA
<213> ORGANISM: Artificial Sequence
```

<220> FEATURE:
<223> OTHER INFORMATION: TRAC_T01-L TALEN

<400> SEQUENCE: 49

| | | | | | |
|---|---|---|---|---|---|
| atgggcgatc | ctaaaaagaa | acgtaaggtc | atcgattacc | catacgatgt | tccagattac | 60 |
| gctatcgata | tcgccgatct | acgcacgctc | ggctacagcc | agcagcaaca | ggagaagatc | 120 |
| aaaccgaagg | ttcgttcgac | agtggcgcag | caccacgagg | cactggtcgg | ccacgggttt | 180 |
| acacacgcgc | acatcgttgc | gttaagccaa | cacccggcag | cgttagggac | cgtcgctgtc | 240 |
| aagtatcagg | acatgatcgc | agcgttgcca | gaggcgacac | acgaagcgat | cgttggcgtc | 300 |
| ggcaaacagt | ggtccggcgc | acgcgctctg | gaggccttgc | tcacggtggc | gggagagttg | 360 |
| agaggtccac | cgttacagtt | ggacacaggc | caacttctca | agattgcaaa | acgtggcggc | 420 |
| gtgaccgcag | tggaggcagt | gcatgcatgg | cgcaatgcac | tgacgggtgc | cccgctcaac | 480 |
| ttgacccccc | agcaggtggt | ggccatcgcc | agcaatggcg | gtggcaagca | ggcgctggag | 540 |
| acggtccagc | ggctgttgcc | ggtgctgtgc | caggcccacg | gcttgacccc | ccagcaggtg | 600 |
| gtggccatcg | ccagcaataa | tggtggcaag | caggcgctgg | agacggtcca | gcggctgttg | 660 |
| ccggtgctgt | gccaggccca | cggcttgacc | ccccagcagg | tggtggccat | cgccagcaat | 720 |
| ggcggtggca | agcaggcgct | ggagacggtc | cagcggctgt | tgccggtgct | gtgccaggcc | 780 |
| cacggcttga | ccccggagca | ggtggtggcc | atcgccagcc | acgatggcgg | caagcaggcg | 840 |
| ctggagacgg | tccagcggct | gttgccggtg | ctgtgccagg | cccacggctt | gaccccggag | 900 |
| caggtggtgg | ccatcgccag | ccacgatggc | ggcaagcagg | cgctggagac | ggtccagcgg | 960 |
| ctgttgccgg | tgctgtgcca | ggcccacggc | ttgaccccgg | agcaggtggt | ggccatcgcc | 1020 |
| agccacgatg | cggcaagca | ggcgctggag | acggtccagc | ggctgttgcc | ggtgctgtgc | 1080 |
| caggcccacg | gcttgacccc | ggagcaggtg | gtggccatcg | ccagcaatat | tggtggcaag | 1140 |
| caggcgctgg | agacggtgca | ggcgctgttg | ccggtgctgt | gccaggccca | cggcttgacc | 1200 |
| ccggagcagg | tggtggccat | cgccagccac | gatggcggca | agcaggcgct | ggagacggtc | 1260 |
| cagcggctgt | tgccggtgct | gtgccaggcc | cacggcttga | ccccggagca | ggtggtggcc | 1320 |
| atcgccagca | atattggtgg | caagcaggcg | ctggagacgg | tgcaggcgct | gttgccggtg | 1380 |
| ctgtgccagg | cccacggctt | gaccccccag | caggtggtgg | ccatcgccag | caataatggt | 1440 |
| ggcaagcagg | cgctggagac | ggtccagcgg | ctgttgccgg | tgctgtgcca | ggcccacggc | 1500 |
| ttgaccccgg | agcaggtggt | ggccatcgcc | agcaatattg | gtggcaagca | ggcgctggag | 1560 |
| acggtgcagg | cgctgttgcc | ggtgctgtgc | caggcccacg | gcttgacccc | ccagcaggtg | 1620 |
| gtggccatcg | ccagcaatgg | cgtggcaag | caggcgctgg | agacggtcca | gcggctgttg | 1680 |
| ccggtgctgt | gccaggccca | cggcttgacc | ccggagcagg | tggtggccat | cgccagcaat | 1740 |
| attggtggca | agcaggcgct | ggagacggtg | caggcgctgt | tgccggtgct | gtgccaggcc | 1800 |
| cacggcttga | ccccccagca | ggtggtggcc | atcgccagca | atggcggtgg | caagcaggcg | 1860 |
| ctggagacgg | tccagcggct | gttgccggtg | ctgtgccagg | cccacggctt | gaccccggag | 1920 |
| caggtggtgg | ccatcgccag | ccacgatggc | ggcaagcagg | cgctggagac | ggtccagcgg | 1980 |
| ctgttgccgg | tgctgtgcca | ggcccacggc | ttgaccccct | cagcaggtgt | ggccatcgcc | 2040 |
| agcaatggcg | gcggcaggcc | ggcgctggag | agcattgttg | cccagttatc | tcgccctgat | 2100 |
| ccggcgttgg | ccgcgttgac | caacgaccac | ctcgtcgcct | tggcctgcct | cggcgggcgt | 2160 |
| cctgcgctgg | atgcagtgaa | aaagggattg | ggggatccta | tcagccgttc | ccagctggtg | 2220 |

| | |
|---|---|
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acgcgccat ctacaccgtg ggctccccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 50
<211> LENGTH: 2832
<212> TYPE: DNA
<213> ORGANISM: Artificial Sequence
<220> FEATURE:
<223> OTHER INFORMATION: TRAC_T01-R TALEN

<400> SEQUENCE: 50

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatct tggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gaccccggag caggtggtgg ccatcgccag ccacgatggc | 540 |
| ggcaagcagg cgctggagac ggtccagcgg ctgttgccgg tgctgtgcca ggcccacggc | 600 |
| ttgaccccc agcaggtggt ggccatcgcc agcaatggcg gtggcaagca ggcgctggag | 660 |
| acggtccagc ggctgttgcc ggtgctgtgc caggcccacg gcttgacccc ggagcaggtg | 720 |
| gtggccatcg ccagccacga tggcggcaag caggcgctgg agacggtcca gcggctgttg | 780 |
| ccggtgctgt gccaggccca cggcttgacc ccggagcagg tggtggccat cgccagcaat | 840 |
| attggtggca gcaggcgct ggagacggtg caggcgctgt gccggtgct gtgccaggcc | 900 |
| cacggcttga ccccccagca ggtggtggcc atcgccagca ataatggtgg caagcaggcg | 960 |
| ctggagacgg tccagcggct gttgccggtg ctgtgccagg cccacggctt gaccccggag | 1020 |
| caggtggtgg ccatcgccag ccacgatggc ggcaagcagg cgctggagac ggtccagcgg | 1080 |
| ctgttgccgg tgctgtgcca ggcccacggc ttgaccccc agcaggtggt ggccatcgcc | 1140 |
| agcaatggcg gtggcaagca ggcgctggag acggtccagc ggctgttgcc ggtgctgtgc | 1200 |
| caggcccacg gcttgacccc ccagcaggtg gtggccatcg ccagcaataa tggtggcaag | 1260 |
| caggcgctgg agacggtcca gcggctgttg ccggtgctgt gccaggccca cggcttgacc | 1320 |
| ccccagcagg tggtggccat cgccagcaat aatggtggca gcaggcgct ggagacggtc | 1380 |
| cagcggctgt tgccggtgct gtgccaggcc cacggcttga ccccccagca ggtggtggcc | 1440 |
| atcgccagca atggcggtgg caagcaggcg ctggagacgg tccagcggct gttgccggtg | 1500 |

```
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc cggagcagg tggtggccat cgccagccac    1860
gatggcggca gcaggcgct ggagacggtc agcggctgt tgccggtgct gtgccaggcc    1920
cacggcttga cccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga atccgagtt gaggcacaag    2280 ctgaagtacg tgccccacga gtacatcgag ctgatcgaga tcgcccggaa cagcaccccag    2340 gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760 ggcacctga ccctggagga ggtgaggagg aagttcaaca acggcgagat caacttcgcg    2820
gccgactgat aa                                                       2832

<210> SEQ ID NO 51
<211> LENGTH: 2814
<212> TYPE: DNA
<213> ORGANISM: Artificial Sequence
<220> FEATURE:
<223> OTHER INFORMATION: TRBC_T01-L TALEN

<400> SEQUENCE: 51
atgggcgatc taaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgacccccc agcaggtggt ggccatcgcc agcaataatg gtggcaagca ggcgctggag     540
acggtccagc ggctgttgcc ggtgctgtgc caggcccacg gcttgacccc ccagcaggtg     600
gtggccatcg ccagcaatgg cggtggcaag caggcgctgg agacggtcca gcggctgttg     660
```

```
ccggtgctgt gccaggccca cggcttgacc ccccagcagg tggtggccat cgccagcaat    720
aatggtggca agcaggcgct ggagacggtc agcggctgt tgccggtgct gtgccaggcc     780
cacggcttga ccccccagca ggtggtggcc atcgccagca atggcggtgg caagcaggcg    840
ctggagacgg tccagcggct gttgccggtg ctgtgccagg cccacggctt gaccccccag    900
caggtggtgg ccatcgccag caatggcggt ggcaagcagg cgctggagac ggtccagcgg    960
ctgttgccgg tgctgtgcca ggcccacggc ttgacccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccggagcagg tggtggccat cgccagcaat attggtggca agcaggcgct ggagacggtg   1260
caggcgctgt gccggtgct gtgccaggcc cacggcttga ccccccagca ggtggtggcc    1320
atcgccagca ataatggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgaccccgg agcaggtggt ggccatcgcc agccacgatg cggcaagca ggcgctggag    1560
acggtccagc ggctgttgcc ggtgctgtgc caggcccacg gcttgacccc ggagcaggtg   1620
gtggccatcg ccagcaatat tggtggcaag caggcgctgg agacggtgca ggcgctgttg   1680
ccggtgctgt gccaggccca cggcttgacc ccccagcagg tggtggccat cgccagcaat   1740
ggcggtggca agcaggcgct ggagacggtc agcggctgt tgccggtgct gtgccaggcc    1800
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatga gttcttcat gaaggtgtac ggctacaggg gcaagcacct gggcggctcc    2400
aggaagcccg acggcgccat ctacaccgtg gctccccca tcgactacgg cgtgatcgtg     2460
gacaccaagg cctactccgg cggctacaac ctgcccatcg ccaggccga cgaaatgcag    2520
aggtacgtgg aggagaacca gaccaggaac aagcacatca ccccaacga gtggtggaag    2580
gtgtacccct ccagcgtgac cgagttcaag ttcctgttcg tgtccggcca cttcaagggc   2640
aactacaagg cccagctgac caggctgaac cacatcacca ctgcaacgg cgccgtgctg    2700
tccgtggagg agctcctgat cggcggcgag atgatcaagg ccggcaccct gaccctggag   2760
gaggtgagga ggaagttcaa caacggcgag atcaacttcg cggccgactg ataa          2814
```

<210> SEQ ID NO 52
<211> LENGTH: 2832
<212> TYPE: DNA
<213> ORGANISM: Artificial Sequence
<220> FEATURE:
<223> OTHER INFORMATION: TRBC_T01-R TALEN

<400> SEQUENCE: 52

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcac cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caataatggt     540
ggcaagcagg cgctggagac ggtccagcgg ctgttgccgg tgctgtgcca ggcccacggc     600
ttgaccccc agcaggtggt ggccatcgcc agcaatggcg gtggcaagca ggcgctggag     660
acggtccagc ggctgttgcc ggtgctgtgc caggcccacg gcttgacccc ccagcaggtg     720
gtggccatcg ccagcaataa tggtggcaag caggcgctgg agacggtcca gcggctgttg     780
ccggtgctgt gccaggccca cggcttgacc cccagcagg tggtggccat cgccagcaat     840
aatggtggca agcaggcgct ggagacggtc agcggctgt tgccggtgct gtgccaggcc     900
cacggcttga ccccggagca ggtggtggcc atcgccagcc acgatggcgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaatgg cggtggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt tgccggtgct gtgccaggcc acggcttga ccccccagca ggtggtggcc    1440
atcgccagca atggcggtgg caagcaggcg ctggagacgg tccagcggct gttgccggtg    1500
ctgtgccagg cccacggctt gaccccccag caggtggtgg ccatcgccag caataatggt    1560
ggcaagcagg cgctggagac ggtccagcgg ctgttgccgg tgctgtgcca ggcccacggc    1620
ttgaccccc agcaggtggt ggccatcgcc agcaataatg gtggcaagca ggcgctggag    1680
acggtccagc ggctgttgcc ggtgctgtgc caggcccacg gcttgacccc ccagcaggtg    1740
gtggccatcg ccagcaataa tgtggcaag caggcgctgg agacggtcca gcggctgttg    1800
ccggtgctgt gccaggccca cggcttgacc cccagcagg tggtggccat cgccagcaat    1860
ggcggtggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga aatccgagtt gaggcacaag    2280
```

```
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacctga ccctggagga ggtgaggagg aagttcaaca acggcgagat caacttcgcg    2820
gccgactgat aa                                                       2832

<210> SEQ ID NO 53
<211> LENGTH: 2814
<212> TYPE: DNA
<213> ORGANISM: Artificial Sequence
<220> FEATURE:
<223> OTHER INFORMATION: TRBC_T02-L TALEN

<400> SEQUENCE: 53
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc atcgttgc gttaagccaa caccggcag cgttagggac cgtcgctgtc       240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccgg agcaggtggt ggccatcgcc agccacgatg gcggcaagca ggcgctggag     540
acggtccagc ggctgttgcc ggtgctgtgc caggcccacg gcttgacccc ggagcaggtg     600
gtggccatcg ccagccacga tggcggcaag caggcgctgg agacggtcca gcggctgttg     660
ccggtgctgt gccaggccca cggcttgacc ccggagcagg tggtggccat cgccagccac     720
gatggcggca agcaggcgct ggagacggtc agcggctgt tgccggtgct gtgccaggcc      780
cacggcttga ccccggagca ggtggtggcc atcgccagca atattggtgg caagcaggcg     840
ctggagacgg tgcaggcgct gttgccggtg ctgtgccagg cccacggctt gaccccggag     900
caggtggtgg ccatcgccag ccacgatggc ggcaagcagg cgctggagac ggtccagcgg     960
ctgttgccgg tgctgtgcca ggcccacggc ttgaccccgg agcaggtggt ggccatcgcc    1020
agccacgatg cggcaagca ggcgctggag acggtccagc ggctgttgcc ggtgctgtgc      1080
caggcccacg gcttgacccc ggagcaggtg gtggccatcg ccagccacga tggcggcaag    1140
caggcgctgg agacggtcca gcggctgttg ccggtgctgt gccaggccca cggcttgacc    1200
ccccagcagg tggtggccat cgccagcaat aatggtggca agcaggcgct ggagacggtc    1260
cagcggctgt tgccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gacccccag caggtggtgg ccatcgccag caataatggt     1440
ggcaagcagg cgctggagac ggtccagcgg ctgttgccgg tgctgtgcca ggcccacggc    1500
```

```
ttgacccccc agcaggtggt ggccatcgcc agcaataatg gtggcaagca ggcgctggag    1560
acggtccagc ggctgttgcc ggtgctgtgc caggcccacg gcttgacccc ccagcaggtg    1620
gtggccatcg ccagcaatgg cgtggcaag caggcgctgg agacggtcca gcggctgttg    1680
ccggtgctgt gccaggccca cggcttgacc ccggagcagg tggtggccat cgccagccac    1740
gatggcggca agcaggcgct ggagacggtc cagcggctgt tgccggtgct gtgccaggcc    1800
cacggcttga ccccccagca ggtggtggcc atcgccagca ataatggtgg caagcaggcg    1860
ctggagacgg tccagcggct gttgccggtg ctgtgccagg cccacggctt gaccccggag    1920
caggtggtgc ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgcctgat    2100 ccggcgttgg ccgcgttgac caacgaccac ctcgtcgcct tggcctgcct cggcgggcgt    2160
cctgcgctga tgcagtgaa aaagggattg ggggatccta tcagccgttc ccagctggtg    2220
aagtccgagc tggaggagaa gaaatccgag ttgaggcaca agctgaagta cgtgcccac    2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gctccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca accccaacga gtggtggaag    2580
gtgtaccccc ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gacccctgag    2760
gaggtgagga ggaagttcaa caacggcgag atcaacttcg cggccgactg ataa          2814
```

<210> SEQ ID NO 54
<211> LENGTH: 2832
<212> TYPE: DNA
<213> ORGANISM: Artificial Sequence
<220> FEATURE:
<223> OTHER INFORMATION: TRBC_T02-R TALEN

<400> SEQUENCE: 54

```
atgggcgatc ctaaaaagaa acgtaaggtc atcgataagg agaccgccgc tgccaagttc    60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatct tggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caataatggt    540
ggcaagcagg cgctggagac ggtccagcgg ctgttgccgg tgctgtgcca ggcccacggc    600 ttgaccccc agcaggtggt ggccatcgcc agcaataatg gtggcaagca ggcgctggag    660
acggtccagc ggctgttgcc ggtgctgtgc caggcccacg gcttgacccc ccagcaggtg    720
```

```
gtggccatcg ccagcaataa tggtggcaag caggcgctgg agacggtcca gcggctgttg      780
ccggtgctgt gccaggccca cggcttgacc ccggagcagg tggtggccat cgccagcaat      840
attggtggca agcaggcgct ggagacggtg caggcgctgt tgccggtgct gtgccaggcc      900
cacggcttga ccccccagca ggtggtggcc atcgccagca ataatggtgg caagcaggcg      960
ctggagacgg tccagcggct gttgccggtg ctgtgccagg cccacggctt gaccccggag     1020
caggtggtgg ccatcgccag caatattggt ggcaagcagg cgctggagac ggtgcaggcg     1080
ctgttgccgg tgctgtgcca ggcccacggc ttgaccccc  agcaggtggt ggccatcgcc     1140
agcaatggcg gtggcaagca ggcgctggag acggtccagc ggctgttgcc ggtgctgtgc     1200
caggcccacg gcttgacccc ggagcaggtg gtggccatcg ccagccacga tggcggcaag     1260
caggcgctgg agacggtcca gcggctgttg ccggtgctgt gccaggccca cggcttgacc     1320
ccccagcagg tggtggccat cgccagcaat ggcggtggca agcaggcgct ggagacggtc     1380
cagcggctgt tgccggtgct gtgccaggcc cacggcttga ccccggagca ggtggtggcc     1440
atcgccagcc acgatggcgg caagcaggcg ctggagacgg tccagcggct gttgccggtg     1500
ctgtgccagg cccacggctt gaccccccag caggtggtgg ccatcgccag caatggcggt     1560
ggcaagcagg cgctggagac ggtccagcgg ctgttgccgg tgctgtgcca ggcccacggc     1620
ttgaccccc  agcaggtggt ggccatcgcc agcaataatg gtggcaagca ggcgctggag     1680
acggtccagc ggctgttgcc ggtgctgtgc caggcccacg gcttgacccc ggagcaggtg     1740
gtggccatcg ccagccacga tggcggcaag caggcgctgg agacggtcca gcggctgttg     1800
ccggtgctgt gccaggccca cggcttgacc ccccagcagg tggtggccat cgccagcaat     1860
ggcggtggca agcaggcgct ggagacggtc cagcggctgt tgccggtgct gtgccaggcc     1920
cacggcttga ccccccagca ggtggtggcc atcgccagca atggcggtgg caagcaggcg     1980
ctggagacgg tccagcggct gttgccggtg ctgtgccagg cccacggctt gaccccctcag    2040
caggtggtgg ccatcgccag caatggcggc ggcaggccgg cgctggagag cattgttgcc     2100
cagttatctc gccctgatcc ggcgttggcc gcgttgacca acgaccacct cgtcgccttg     2160
gcctgcctcg gcgggcgtcc tgcgctggat gcagtgaaaa agggattggg ggatcctatc     2220
agccgttccc agctggtgaa gtccgagctg aggagaaga  aatccgagtt gaggcacaag     2280
ctgaagtacg tgccccacga gtacatcgag ctgatcgaga tcgcccggaa cagcaccccag    2340
gaccgtatcc tggagatgaa ggtgatggag ttcttcatga aggtgtacgg ctacaggggc     2400
aagcacctgg gcggctccag gaagcccgac ggcgccatct acaccgtggg ctcccccatc     2460
gactacggcg tgatcgtgga caccaaggcc tactccggcg gctacaacct gcccatcggc     2520
caggccgacg aaatgcagag gtacgtggag gagaaccaga ccaggaacaa gcacatcaac     2580
cccaacgagt ggtggaaggt gtaccctcc  agcgtgaccg agttcaagtt cctgttcgtg     2640
tccggccact tcaagggcaa ctacaaggcc agctgacca  ggctgaacca catcaccaac     2700
tgcaacggcg ccgtgctgtc cgtggaggag ctcctgatcg gcggcgagat gatcaaggcc     2760
ggcacccctga ccctggagga ggtgaggagg aagttcaaca acggcgagat caacttcgcg     2820
gccgactgat aa                                                        2832
```

<210> SEQ ID NO 55
<211> LENGTH: 2814
<212> TYPE: DNA
<213> ORGANISM: Artificial Sequence
<220> FEATURE:
<223> OTHER INFORMATION: CD52_T02-L TALEN

<400> SEQUENCE: 55

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccggagcagg tggtggccat cgccagccac   720
gatgcggca agcaggcgct ggagacggtc agcggctgt tgccggtgct gtgccaggcc   780
cacggcttga ccccccagca ggtggtggcc atcgccagca atggcggtgg caagcaggcg   840
ctggagacgg tccagcggct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg cggcaagca ggcgctggag acggtccagc ggctgttgcc ggtgctgtgc  1080
caggcccacg gcttgacccc ccagcaggtg gtggccatcg ccagcaatgg cggtggcaag  1140
caggcgctgg agacggtcca gcggctgttg ccggtgctgt gccaggccca cggcttgacc  1200
ccggagcagg tggtggccat cgccagcaat attggtggca agcaggcgct ggagacggtg  1260
caggcgctgt tgccggtgct gtgccaggcc cacggcttga ccccggagca ggtggtggcc  1320
atcgccagcc acgatggcgg caagcaggcg ctggagacgg tccagcggct gttgccggtg  1380
ctgtgccagg cccacggctt gaccccccag caggtggtgg ccatcgccag caatggcggt  1440
ggcaagcagg cgctggagac ggtccagcgg ctgttgccgg tgctgtgcca ggcccacggc  1500
ttgacccccgg agcaggtggt ggccatcgcc agccacgatg cggcaagca ggcgctggag  1560
acggtccagc ggctgttgcc ggtgctgtgc caggcccacg gcttgacccc ggagcaggtg  1620
gtggccatcg ccagcaatat tggtggcaag caggcgctgg agacggtgca ggcgctgttg  1680
ccggtgctgt gccaggccca cggcttgacc ccggagcagg tggtggccat cgccagccac  1740
gatgcggca agcaggcgct ggagacggtc agcggctgt tgccggtgct gtgccaggcc  1800
cacggcttga ccccggagca ggtggtggcc atcgccagcc acgatggcgg caagcaggcg  1860
ctggagacgg tccagcggct gttgccggtg ctgtgccagg cccacggctt gaccccggag  1920
caggtggtgg ccatcgccag caatattggt ggcaagcagg cgctggagac ggtgcaggcg  1980
ctgttgccgg tgctgtgcca ggcccacggc ttgaccccctc agcaggtggt ggccatcgcc  2040
agcaatggcg gcggcaggcc ggcgctggag agcattgttg cccagttatc tcgccctgat  2100
ccggcgttgg ccgcgttgac caacgaccac ctcgtcgcct tggcctgcct cggcgggcgt  2160
cctgcgctgg atgcagtgaa aaagggattg ggggatccta tcagccgttc ccagctggtg  2220
aagtccgagc tggaggagaa gaaatccgag ttgaggcaca agctgaagta cgtgccccac  2280
```

```
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag     2520 aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gacccctgga    2760
                                                                   g
gaggtgagga ggaagttcaa caacggcgag atcaacttcg cggccgactg ataa           2814
```

<210> SEQ ID NO 56
<211> LENGTH: 2832
<212> TYPE: DNA
<213> ORGANISM: Artificial Sequence
<220> FEATURE:
<223> OTHER INFORMATION: CD52_T02-R TALEN

<400> SEQUENCE: 56

```
atgggcgatc taaaaagaa acgtaaggtc atcgataagg agaccgccgc tgccaagttc       60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcac cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caatggcggt     540
ggcaagcagg cgctggagac ggtccagcgg ctgttgccgg tgctgtgcca ggcccacggc     600
ttgacccccc agcaggtggt ggccatcgcc agcaataatg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccccagcagg tggtggccat cgccagcaat     840
ggcggtggca gcaggcgct ggagacggtc agcggctgt tgccggtgct gtgccaggcc      900
cacggcttga ccccggagca ggtggtggcc atcgccagcc acgatggcgg caagcaggcg     960
ctggagacgg tccagcggct gttgccggtg ctgtgccagg cccacggctt gacccccag    1020 caggtggtgg ccatcgccag caatggcggt ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctga gacggtgca ggcgctgttg ccggtgctgt gccaggccca cggcttgacc    1320
ccggagcagg tggtggccat cgccagccac gatggcggca agcaggcgct ggagacggtc   1380
cagcggctgt tgccggtgct gtgccaggcc cacggcttga ccccggagca ggtggtggcc   1440
atcgccagcc acgatggcgg caagcaggcg ctggagacgg tccagcggct gttgccggtg   1500
ctgtgccagg cccacggctt gacccccag caggtggtgg ccatcgccag caatggcggt    1560
```

```
ggcaagcagg cgctggagac ggtccagcgg ctgttgccgg tgctgtgcca ggcccacggc    1620
ttgacccccc agcaggtggt ggccatcgcc agcaataatg gtggcaagca ggcgctggag    1680
acggtccagc ggctgttgcc ggtgctgtgc caggcccacg gcttgacccc ccagcaggtg    1740
gtggccatcg ccagcaatgg cggtggcaag caggcgctgg agacggtcca gcggctgttg    1800
ccggtgctgt gccaggccca cggcttgacc ccggagcagg tggtggccat cgccagcaat    1860
attggtggca agcaggcgct ggagacggtg caggcgctgt gccggtgct gtgccaggcc     1920 cacggcttga ccccggagca ggtggtggcc atcgccagcc acgatggcgg caagcaggcg    1980
ctggagacgg tccagcggct gttgccggtg ctgtgccagg cccacggctt gaccccctcag   2040 caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg cggcgagat gatcaaggcc    2760 ggcacccctga ccctggagga ggtgaggagg aagttcaaca cggcgagat caacttcgcg   2820 gccgactgat aa                                                        2832

<210> SEQ ID NO 57
<211> LENGTH: 49
<212> TYPE: DNA
<213> ORGANISM: Artificial Sequence
<220> FEATURE:
<223> OTHER INFORMATION: TRAC_T02

<400> SEQUENCE: 57
tttagaaagt tcctgtgatg tcaagctggt cgagaaaagc tttgaaaca               49

<210> SEQ ID NO 58
<211> LENGTH: 49
<212> TYPE: DNA
<213> ORGANISM: Artificial Sequence
<220> FEATURE:
<223> OTHER INFORMATION: TRAC_T03

<400> SEQUENCE: 58
tccagtgaca agtctgtctg cctattcacc gattttgatt ctcaaacaa               49

<210> SEQ ID NO 59
<211> LENGTH: 49
<212> TYPE: DNA
<213> ORGANISM: Artificial Sequence
<220> FEATURE:
<223> OTHER INFORMATION: TRAC_T04

<400> SEQUENCE: 59
```
tatatcacag acaaaactgt gctagacatg aggtctatgg acttcaaga 49

<210> SEQ ID NO 60
<211> LENGTH: 49
<212> TYPE: DNA
<213> ORGANISM: Artificial Sequence
<220> FEATURE:
<223> OTHER INFORMATION: TRAC_T05

<400> SEQUENCE: 60
tgaggtctat ggacttcaag agcaacagtg ctgtggcctg agcaacaa 49

<210> SEQ ID NO 61
<211> LENGTH: 47
<212> TYPE: DNA
<213> ORGANISM: Artificial Sequence
<220> FEATURE:
<223> OTHER INFORMATION: CD52_T01

<400> SEQUENCE: 61
ttcctcttcc tcctaccacc atcagcctcc tttacctgta ccataac 47

<210> SEQ ID NO 62
<211> LENGTH: 43
<212> TYPE: DNA
<213> ORGANISM: Artificial Sequence
<220> FEATURE:
<223> OTHER INFORMATION: CD52_T04

<400> SEQUENCE: 62
ttcctcctac tcaccacagc ctcctggtct tacctgtacc ata 43

<210> SEQ ID NO 63
<211> LENGTH: 43
<212> TYPE: DNA
<213> ORGANISM: Artificial Sequence
<220> FEATURE:
<223> OTHER INFORMATION: CD52_T05

<400> SEQUENCE: 63
tcctactcac catcagctcc tggttatttg ctcttacctg tac 43

<210> SEQ ID NO 64
<211> LENGTH: 47
<212> TYPE: DNA
<213> ORGANISM: Artificial Sequence
<220> FEATURE:
<223> OTHER INFORMATION: CD52_T06

<400> SEQUENCE: 64
ttatcccact tctcctctac agatacaaac tttttgtcct gagagtc 47

<210> SEQ ID NO 65
<211> LENGTH: 47
<212> TYPE: DNA
<213> ORGANISM: Artificial Sequence
<220> FEATURE:
<223> OTHER INFORMATION: CD52_T07

<400> SEQUENCE: 65
tggactctca ggacaaacga caccagccaa atgctgaggg gctgctg 47

<210> SEQ ID NO 66
<211> LENGTH: 60
<212> TYPE: DNA
<213> ORGANISM: Artificial Sequence

```
<220> FEATURE:
<223> OTHER INFORMATION: Forward primer CD52
<220> FEATURE:
<221> NAME/KEY: misc_feature
<222> LOCATION: (31)..(40)
<223> OTHER INFORMATION: n is a or c or t or g

<400> SEQUENCE: 66
ccatctcatc cctgcgtgtc tccgactcag nnnnnnnnnn cagatctgca gaaaggaagc      60

<210> SEQ ID NO 67
<211> LENGTH: 61
<212> TYPE: DNA
<213> ORGANISM: Artificial Sequence
<220> FEATURE:
<223> OTHER INFORMATION: Forward primer TRAC
<220> FEATURE:
<221> NAME/KEY: misc_feature
<222> LOCATION: (31)..(40)
<223> OTHER INFORMATION: n is a or c or t or g

<400> SEQUENCE: 67
ccatctcatc cctgcgtgtc tccgactcag nnnnnnnnnn atcactggca tctggactcc      60
a                                                                     61

<210> SEQ ID NO 68
<211> LENGTH: 62
<212> TYPE: DNA
<213> ORGANISM: Artificial Sequence
<220> FEATURE:
<223> OTHER INFORMATION: Forward primer TRBC1
<220> FEATURE:
<221> NAME/KEY: misc_feature
<222> LOCATION: (31)..(40)
<223> OTHER INFORMATION: n is a or c or t or g

<400> SEQUENCE: 68
ccatctcatc cctgcgtgtc tccgactcag nnnnnnnnnn agagccccta ccagaaccag      60
ac                                                                    62

<210> SEQ ID NO 69
<211> LENGTH: 62
<212> TYPE: DNA
<213> ORGANISM: Artificial Sequence
<220> FEATURE:
<223> OTHER INFORMATION: Forward primer TRBC2
<220> FEATURE:
<221> NAME/KEY: misc_feature
<222> LOCATION: (31)..(40)
<223> OTHER INFORMATION: n is a or c or t or g

<400> SEQUENCE: 69
ccatctcatc cctgcgtgtc tccgactcag nnnnnnnnnn ggacctagta acataattgt      60
gc                                                                    62

<210> SEQ ID NO 70
<211> LENGTH: 51
<212> TYPE: DNA
<213> ORGANISM: Artificial Sequence
<220> FEATURE:
<223> OTHER INFORMATION: Reverse primer GR CD52

<400> SEQUENCE: 70
cctatcccct gtgtgccttg gcagtctcag cctgttggag tccatctgct g              51

<210> SEQ ID NO 71
```

```
<211> LENGTH: 50
<212> TYPE: DNA
<213> ORGANISM: Artificial Sequence
<220> FEATURE:
<223> OTHER INFORMATION: Reverse primer GR TRAC

<400> SEQUENCE: 71
cctatcccct gtgtgccttg gcagtctcag cctcatgtct agcacagttt            50

<210> SEQ ID NO 72
<211> LENGTH: 51
<212> TYPE: DNA
<213> ORGANISM: Artificial Sequence
<220> FEATURE:
<223> OTHER INFORMATION: Reverse primer GR TRBC1-2

<400> SEQUENCE: 72
cctatcccct gtgtgccttg gcagtctcag accagctcag ctccacgtgg t          51

<210> SEQ ID NO 73
<211> LENGTH: 495
<212> TYPE: PRT
<213> ORGANISM: Artificial Sequence
<220> FEATURE:
<223> OTHER INFORMATION: anti-CD19 CAR

<400> SEQUENCE: 73
```

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
    210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
              260                 265                 270

Thr Thr Thr Pro Ala Pro Arg Pro Thr Pro Ala Pro Thr Ile Ala
    275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Ser Leu Val
              325                 330                 335

Ile Thr Leu Tyr Cys Lys Arg Gly Arg Lys Lys Leu Leu Tyr Ile Phe
              340                 345                 350

Lys Gln Pro Phe Met Arg Pro Val Gln Thr Thr Gln Glu Glu Asp Gly
              355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
              405                 410                 415

Val Leu Asp Lys Arg Arg Gly Arg Asp Pro Glu Met Gly Gly Lys Pro
              420                 425                 430

Arg Arg Lys Asn Pro Gln Glu Gly Leu Tyr Asn Glu Leu Gln Lys Asp
              435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
              485                 490                 495

<210> SEQ ID NO 74
<211> LENGTH: 49
<212> TYPE: DNA
<213> ORGANISM: Artificial Sequence
<220> FEATURE:
<223> OTHER INFORMATION: CTLA4_T01

<400> SEQUENCE: 74
tggccctgca ctctcctgtt ttttcttctc ttcatccctg tcttctgca                    49

<210> SEQ ID NO 75
<211> LENGTH: 49
<212> TYPE: DNA
<213> ORGANISM: Artificial Sequence
<220> FEATURE:
<223> OTHER INFORMATION: CTLA4_T03

<400> SEQUENCE: 75
ttttccatgc tagcaatgca cgtggcccag cctgctgtgg tactggcca                    49

<210> SEQ ID NO 76
<211> LENGTH: 49
<212> TYPE: DNA
<213> ORGANISM: Artificial Sequence
<220> FEATURE:
<223> OTHER INFORMATION: CTLA4_T04

<400> SEQUENCE: 76

```
tccatgctag caatgcacgt ggcccagcct gctgtggtac tggccagca          49
```

<210> SEQ ID NO 77
<211> LENGTH: 49
<212> TYPE: DNA
<213> ORGANISM: Artificial Sequence
<220> FEATURE:
<223> OTHER INFORMATION: PDCD1_T01

<400> SEQUENCE: 77

```
ttctccccag ccctgctcgt ggtgaccgaa ggggacaacg ccaccttca          49
```

<210> SEQ ID NO 78
<211> LENGTH: 49
<212> TYPE: DNA
<213> ORGANISM: Artificial Sequence
<220> FEATURE:
<223> OTHER INFORMATION: PDCD1_T03

<400> SEQUENCE: 78

```
tacctctgtg gggccatctc cctggccccc aaggcgcaga tcaaagaga          49
```

<210> SEQ ID NO 79
<211> LENGTH: 530
<212> TYPE: PRT
<213> ORGANISM: Artificial Sequence
<220> FEATURE:
<223> OTHER INFORMATION: Repeat CTLA4_T01-L

<400> SEQUENCE: 79

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser Asn Ile Gly Gly Lys
            275                 280                 285

Gln Ala Leu Glu Thr Val Gln Ala Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Gly Gly Gly Lys Gln Ala Leu Glu Thr Val Gln Arg
        420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Arg Pro Ala
            515                 520                 525

Leu Glu
    530

<210> SEQ ID NO 80
<211> LENGTH: 530
<212> TYPE: PRT
<213> ORGANISM: Artificial Sequence
<220> FEATURE:
<223> OTHER INFORMATION: Repeat CTLA4_T01-R

<400> SEQUENCE: 80

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

```
Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser Asn
 65                  70                  75                  80

Ile Gly Gly Lys Gln Ala Leu Glu Thr Val Gln Ala Leu Leu Pro Val
                 85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser Asn Ile Gly Gly Lys Gln Ala Leu Glu Thr Val
        450                 455                 460

Gln Ala Leu Leu Pro Val Leu Cys Gln Ala His Gly Leu Thr Pro Gln
```

```
                465                 470                 475                 480
Gln Val Val Ala Ile Ala Ser Asn Gly Gly Gly Lys Gln Ala Leu Glu
                    485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
                515                 520                 525

Leu Glu
    530

<210> SEQ ID NO 81
<211> LENGTH: 530
<212> TYPE: PRT
<213> ORGANISM: Artificial Sequence
<220> FEATURE:
<223> OTHER INFORMATION: RepeatCTLA4_T03-L

<400> SEQUENCE: 81

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
                180                 185                 190

Gln Ala Leu Leu Pro Val Leu Cys Gln Ala His Gly Leu Thr Pro Gln
            195                 200                 205

Gln Val Val Ala Ile Ala Ser Asn Gly Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
                260                 265                 270

Leu Thr Pro Glu Gln Val Val Ala Ile Ala Ser His Asp Gly Gly Lys
            275                 280                 285

Gln Ala Leu Glu Thr Val Gln Arg Leu Leu Pro Val Leu Cys Gln Ala
```

```
                290                 295                 300
His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Ile Gly Gly Lys Gln Ala Leu Glu Thr Val Gln Ala Leu Leu Pro Val
                355                 360                 365

Leu Cys Gln Ala His Gly Leu Thr Pro Gln Gln Val Val Ala Ile Ala
                370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser Asn Ile Gly Gly Lys Gln Ala Leu Glu Thr Val
                450                 455                 460

Gln Ala Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
                500                 505                 510

Pro Gln Gln Val Val Ala Ile Ala Ser Asn Gly Gly Arg Pro Ala
                515                 520                 525

Leu Glu
    530

<210> SEQ ID NO 82
<211> LENGTH: 530
<212> TYPE: PRT
<213> ORGANISM: Artificial Sequence
<220> FEATURE:
<223> OTHER INFORMATION: Repeat CTLA4_T03-R

<400> SEQUENCE: 82

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
                35                  40                  45

Gly Lys Gln Ala Leu Glu Thr Val Gln Arg Leu Leu Pro Val Leu Cys
                50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
```

```
                115                 120                 125
Pro Val Leu Cys Gln Ala His Gly Leu Thr Pro Glu Gln Val Val Ala
            130                 135                 140
Ile Ala Ser Asn Ile Gly Gly Lys Gln Ala Leu Glu Thr Val Gln Ala
145                 150                 155                 160
Leu Leu Pro Val Leu Cys Gln Ala His Gly Leu Thr Pro Gln Gln Val
                165                 170                 175
Val Ala Ile Ala Ser Asn Asn Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Glu Gln Val Val Ala Ile Ala Ser Asn Ile Gly Gly Lys Gln Ala
                245                 250                 255
Leu Glu Thr Val Gln Ala Leu Leu Pro Val Leu Cys Gln Ala His Gly
            260                 265                 270
Leu Thr Pro Glu Gln Val Val Ala Ile Ala Ser His Asp Gly Gly Lys
        275                 280                 285
Gln Ala Leu Glu Thr Val Gln Arg Leu Leu Pro Val Leu Cys Gln Ala
    290                 295                 300
His Gly Leu Thr Pro Glu Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
    370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Gln Gln Val
        435                 440                 445
Val Ala Ile Ala Ser Asn Asn Gly Gly Lys Gln Ala Leu Glu Thr Val
    450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530
```

<210> SEQ ID NO 83
<211> LENGTH: 530
<212> TYPE: PRT
<213> ORGANISM: Artificial Sequence
<220> FEATURE:
<223> OTHER INFORMATION: Repeat CTLA4_T04-L

<400> SEQUENCE: 83

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

```
Leu Cys Gln Ala His Gly Leu Thr Pro Glu Gln Val Val Ala Ile Ala
            370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
            515                 520                 525

Leu Glu
    530

<210> SEQ ID NO 84
<211> LENGTH: 530
<212> TYPE: PRT
<213> ORGANISM: Artificial Sequence
<220> FEATURE:
<223> OTHER INFORMATION: Repeat CTLA4_T04-R

<400> SEQUENCE: 84

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190
```

Gln Arg Leu Leu Pro Val Leu Cys Gln Ala His Gly Leu Thr Pro Glu
            195                 200                 205

Gln Val Val Ala Ile Ala Ser His Asp Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
            245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Glu Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser Asn Ile Gly Gly Lys Gln Ala Leu Glu Thr Val
            450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 85
<211> LENGTH: 530
<212> TYPE: PRT
<213> ORGANISM: Artificial Sequence
<220> FEATURE:
<223> OTHER INFORMATION: Repeat PDCD1_T01-L

<400> SEQUENCE: 85

Leu Thr Pro Gln Gln Val Val Ala Ile Ala Ser Asn Gly Gly Gly Lys
1               5                   10                  15

```
Gln Ala Leu Glu Thr Val Gln Arg Leu Leu Pro Val Leu Cys Gln Ala
            20                  25                  30

His Gly Leu Thr Pro Glu Gln Val Ala Ile Ala Ser His Asp Gly
        35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
            195                 200                 205

Gln Val Val Ala Ile Ala Ser His Asp Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
            245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
        370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Gly Gly Gly Lys Gln Ala Leu Glu Thr Val Gln Arg
            420                 425                 430
```

```
Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 86
<211> LENGTH: 529
<212> TYPE: PRT
<213> ORGANISM: Artificial Sequence
<220> FEATURE:
<223> OTHER INFORMATION: Repeat PDCD1_T01-R

<400> SEQUENCE: 86

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255
```

-continued

```
Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Lys Gln
            275                 280                 285

Ala Leu Glu Thr Val Gln Arg Leu Leu Pro Val Leu Cys Gln Ala His
            290                 295                 300

Gly Leu Thr Pro Gln Gln Val Val Ala Ile Ala Ser Asn Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Gly
            340                 345                 350

Gly Gly Lys Gln Ala Leu Glu Thr Val Gln Arg Leu Leu Pro Val Leu
            355                 360                 365

Cys Gln Ala His Gly Leu Thr Pro Gln Gln Val Val Ala Ile Ala Ser
            370                 375                 380

Asn Gly Gly Lys Gln Ala Leu Glu Thr Val Gln Arg Leu Leu Pro
385                 390                 395                 400

Val Leu Cys Gln Ala His Gly Leu Thr Pro Gln Gln Val Val Ala Ile
                405                 410                 415

Ala Ser Asn Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
            435                 440                 445

Ala Ile Ala Ser Asn Gly Gly Lys Gln Ala Leu Glu Thr Val Gln
450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
            515                 520                 525

Glu

<210> SEQ ID NO 87
<211> LENGTH: 530
<212> TYPE: PRT
<213> ORGANISM: Artificial Sequence
<220> FEATURE:
<223> OTHER INFORMATION: Repeat PDCD1_T03-L

<400> SEQUENCE: 87

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
```

```
                        85                    90                    95
Leu Cys Gln Ala His Gly Leu Thr Pro Gln Gln Val Val Ala Ile Ala
                100                   105                   110

Ser Asn Gly Gly Gly Lys Gln Ala Leu Glu Thr Val Gln Arg Leu Leu
                115                   120                   125

Pro Val Leu Cys Gln Ala His Gly Leu Thr Pro Glu Gln Val Val Ala
130                   135                   140

Ile Ala Ser His Asp Gly Gly Lys Gln Ala Leu Glu Thr Val Gln Arg
145                   150                   155                   160

Leu Leu Pro Val Leu Cys Gln Ala His Gly Leu Thr Pro Gln Gln Val
                165                   170                   175

Val Ala Ile Ala Ser Asn Gly Gly Lys Gln Ala Leu Glu Thr Val
                180                   185                   190

Gln Arg Leu Leu Pro Val Leu Cys Gln Ala His Gly Leu Thr Pro Gln
                195                   200                   205

Gln Val Val Ala Ile Ala Ser Asn Asn Gly Gly Lys Gln Ala Leu Glu
                210                   215                   220

Thr Val Gln Arg Leu Leu Pro Val Leu Cys Gln Ala His Gly Leu Thr
225                   230                   235                   240

Pro Gln Gln Val Val Ala Ile Ala Ser Asn Gly Gly Lys Gln Ala
                245                   250                   255

Leu Glu Thr Val Gln Arg Leu Leu Pro Val Leu Cys Gln Ala His Gly
                260                   265                   270

Leu Thr Pro Gln Gln Val Val Ala Ile Ala Ser Asn Asn Gly Gly Lys
                275                   280                   285

Gln Ala Leu Glu Thr Val Gln Arg Leu Leu Pro Val Leu Cys Gln Ala
                290                   295                   300

His Gly Leu Thr Pro Gln Gln Val Val Ala Ile Ala Ser Asn Asn Gly
305                   310                   315                   320

Gly Lys Gln Ala Leu Glu Thr Val Gln Arg Leu Leu Pro Val Leu Cys
                325                   330                   335

Gln Ala His Gly Leu Thr Pro Gln Gln Val Val Ala Ile Ala Ser Asn
                340                   345                   350

Asn Gly Gly Lys Gln Ala Leu Glu Thr Val Gln Arg Leu Leu Pro Val
                355                   360                   365

Leu Cys Gln Ala His Gly Leu Thr Pro Gln Gln Val Val Ala Ile Ala
                370                   375                   380

Ser Asn Asn Gly Gly Lys Gln Ala Leu Glu Thr Val Gln Arg Leu Leu
385                   390                   395                   400

Pro Val Leu Cys Gln Ala His Gly Leu Thr Pro Glu Gln Val Val Ala
                405                   410                   415

Ile Ala Ser His Asp Gly Gly Lys Gln Ala Leu Glu Thr Val Gln Arg
                420                   425                   430

Leu Leu Pro Val Leu Cys Gln Ala His Gly Leu Thr Pro Glu Gln Val
                435                   440                   445

Val Ala Ile Ala Ser His Asp Gly Gly Lys Gln Ala Leu Glu Thr Val
                450                   455                   460

Gln Arg Leu Leu Pro Val Leu Cys Gln Ala His Gly Leu Thr Pro Glu
465                   470                   475                   480

Gln Val Val Ala Ile Ala Ser Asn Ile Gly Gly Lys Gln Ala Leu Glu
                485                   490                   495

Thr Val Gln Ala Leu Leu Pro Val Leu Cys Gln Ala His Gly Leu Thr
                500                   505                   510
```

```
Pro Gln Gln Val Val Ala Ile Ala Ser Asn Gly Gly Arg Pro Ala
        515                 520                 525

Leu Glu
    530

<210> SEQ ID NO 88
<211> LENGTH: 529
<212> TYPE: PRT
<213> ORGANISM: Artificial Sequence
<220> FEATURE:
<223> OTHER INFORMATION: Repeat PDCD1_T03-R

<400> SEQUENCE: 88

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65              70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335
```

Gln Ala His Gly Leu Thr Pro Gln Gln Val Val Ala Ile Ala Ser Asn
                    340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
                435                 440                 445

Ala Ile Ala Ser Asn Asn Gly Gly Lys Gln Ala Leu Glu Thr Val Gln
            450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
            515                 520                 525

Glu

<210> SEQ ID NO 89
<211> LENGTH: 2814
<212> TYPE: DNA
<213> ORGANISM: Artificial Sequence
<220> FEATURE:
<223> OTHER INFORMATION: CTLA4_T01-L  TALEN

<400> SEQUENCE: 89

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgacccccc agcaggtggt ggccatcgcc agcaataatg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc ccggagcagg tggtggccat cgccagccac     720
gatggcggca gcaggcgct ggagacggtc cagcggctgt tgccggtgct gtgccaggcc     780
cacggcttga ccccggagca ggtggtggcc atcgccagcc acgatggcgg caagcaggcg     840
ctggagacgg tccagcggct gttgccggtg ctgtgccagg cccacggctt gaccccggag     900
```

```
caggtggtgg ccatcgccag ccacgatggc ggcaagcagg cgctggagac ggtccagcgg      960
ctgttgccgg tgctgtgcca ggcccacggc ttgaccccc  agcaggtggt ggccatcgcc     1020
agcaatggcg gtggcaagca ggcgctggag acggtccagc ggctgttgcc ggtgctgtgc     1080
caggcccacg gcttgacccc ccagcaggtg gtggccatcg ccagcaataa tggtggcaag     1140
caggcgctgg agacggtcca gcggctgttg ccggtgctgt gccaggccca cggcttgacc     1200
ccggagcagg tggtggccat cgccagccac gatggcggca agcaggcgct ggagacggtc     1260
cagcggctgt tgccggtgct gtgccaggcc cacggcttga ccccggagca ggtggtggcc     1320
atcgccagca atattggtgg caagcaggcg ctggagacgg tgcaggcgct gttgccggtg     1380
ctgtgccagg cccacggctt gaccccggag caggtggtgg ccatcgccag ccacgatggc     1440
ggcaagcagg cgctggagac ggtccagcgg ctgttgccgg tgctgtgcca ggcccacggc     1500
ttgacccccc agcaggtggt ggccatcgcc agcaatggcg gtggcaagca ggcgctggag     1560
acggtccagc ggctgttgcc ggtgctgtgc caggcccacg gcttgacccc ggagcaggtg     1620
gtggccatcg ccagccacga tggcggcaag caggcgctgg agacggtcca gcggctgttg     1680
ccggtgctgt gccaggccca cggcttgacc cccagcagg  tggtggccat cgccagcaat     1740
ggcggtggca agcaggcgct ggagacggtc agcggctgt tgccggtgct gtgccaggcc     1800
cacggcttga ccccggagca ggtggtggcc atcgccagcc acgatggcgg caagcaggcg     1860
ctggagacgg tccagcggct gttgccggtg ctgtgccagg cccacggctt gaccccggag     1920
caggtggtgg ccatcgccag ccacgatggc ggcaagcagg cgctggagac ggtccagcgg     1980
ctgttgccgg tgctgtgcca ggcccacggc ttgacccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatgg agttcttcat gaaggtgtac ggctacaggg gcaagcacct gggcggctcc     2400
aggaagcccg acggcgccat ctacaccgtg gctcccccca tcgactacgg cgtgatcgtg     2460
gacaccaagg cctactccgg cggctacaac ctgcccatcg ccaggcccga cgaaatgcag     2520
aggtacgtgg aggagaacca gaccaggaac aagcacatca ccccaacga gtggtggaag     2580 gtgtaccccct ccagcgtgac cgagttcaag ttcctgttcg tgtccggcca cttcaagggc     2640
aactacaagg cccagctgac caggctgaac cacatcacca ctgcaacgg cgccgtgctg     2700 tccgtggagg agctcctgat cggcggcgag atgatcaagg ccggcaccct gaccctggag     2760
gaggtgagga ggaagttcaa caacggcgag atcaacttcg cggccgactg ataa           2814
```

<210> SEQ ID NO 90
<211> LENGTH: 2832
<212> TYPE: DNA
<213> ORGANISM: Artificial Sequence
<220> FEATURE:
<223> OTHER INFORMATION: CTLA4_T01-R TALEN

<400> SEQUENCE: 90

```
atgggcgatc ctaaaaagaa acgtaaggtc atcgataagg agaccgccgc tgccaagttc       60
gagagacagc acatggacag catcgatatc gccgatctac gcacgctcgg ctacagccag      120
cagcaacagg agaagatcaa accgaaggtt cgttcgacag tggcgcagca ccacgaggca      180
```

```
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360 acggtggcg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agccacgatg gcggcaagca ggcgctggag    660
acggtccagc ggctgttgcc ggtgctgtgc caggcccacg gcttgaccccc ggagcaggtg    720 gtggccatcg ccagcaatat tggtggcaag caggcgctgg agacggtgca ggcgctgttg    780
ccggtgctgt gccaggccca cggcttgacc cccagcagg tggtggccat cgccagcaat    840
aatggtggca agcaggcgct ggagacggtc agcggctgt tgccggtgct gtgccaggcc    900
cacggcttga ccccggagca ggtggtggcc atcgccagca atattggtgg caagcaggcg    960
ctggagacgg tgcaggcgct gttgccggtg ctgtgccagg cccacggctt gaccccggag   1020
caggtggtgg ccatcgccag caatattggt ggcaagcagg cgctggagac ggtgcaggcg   1080
ctgttgccgg tgctgtgcca ggcccacggc ttgaccccccc agcaggtggt ggccatcgcc   1140
agcaataatg gtggcaagca ggcgctggag acggtccagc ggctgttgcc ggtgctgtgc   1200
caggcccacg gcttgaccccc ggagcaggtg gtggccatcg ccagcaatat tggtggcaag   1260
caggcgctgg agacggtgca ggcgctgttt ccggtgctgt gccaggccca cggcttgacc   1320
ccggagcagg tggtggccat cgccagccac gatggcggca agcaggcgct ggagacggtc   1380
cagcggctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gacccccag caggtggtgg ccatcgccag caataatggt   1560
ggcaagcagg cgctggagac ggtccagcgg ctgttgccgg tgctgtgcca ggcccacggc   1620 ttgaccccccc agcaggtggt ggccatcgcc agcaataatg gtggcaagca ggcgctggag   1680
acggtccagc ggctgttgcc ggtgctgtgc caggcccacg gcttgaccccc cagcaggtg   1740 gtggccatcg ccagcaataa tggtggcaag caggcgctgg agacggtcca gcggctgttg   1800
ccggtgctgt gccaggccca cggcttgacc ccggagcagg tggtggccat cgccagcaat   1860
attggtggca agcaggcgct ggagacggtc aggcgctgt tgccggtgct gtgccaggcc   1920
cacggcttga ccccccagca ggtggtggcc atcgccagca atggcggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
```

```
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc agctgacca ggctgaacca catcaccaac     2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                        2832

<210> SEQ ID NO 91
<211> LENGTH: 2814
<212> TYPE: DNA
<213> ORGANISM: Artificial Sequence
<220> FEATURE:
<223> OTHER INFORMATION: CTLA4_T03-L TALEN

<400> SEQUENCE: 91
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480 ttgaccccc agcaggtggt ggccatcgcc agcaatggcg gtggcaagca ggcgctggag    540
acggtccagc ggctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc cccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc    1020
agcaatattg gtggcaagca ggcgctggag acggtgcagg cgctgttgcc ggtgctgtgc    1080
caggcccacg gcttgacccc ccagcaggtg gtggccatcg ccagcaatgg cggtggcaag    1140
caggcgctgg agacggtcca gcggctgttg ccggtgctgt gccaggccca cggcttgacc    1200
ccccagcagg tggtggccat cgccagcaat aatggtggca agcaggcgct ggagacggtc    1260
cagcggctgt tgccggtgct gtgccaggcc acggcttga ccccggagca ggtggtggcc    1320
atcgccagcc acgatggcgg caagcaggcg ctggagacgg tccagcggct gttgccggtg    1380
ctgtgccagg cccacggctt gaccccccag caggtggtgg ccatcgccag caatggcggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaataa tggtggcaag caggcgctgg agacggtcca gcggctgttg    1680
ccggtgctgt gccaggccca cggcttgacc ccggagcagg tggtggccat cgccagccac    1740
```

```
gatggcggca agcaggcgct ggagacggtc agcggctgt tgccggtgct gtgccaggcc   1800
cacggcttga ccccggagca ggtggtggcc atcgccagca atattggtgg caagcaggcg   1860
ctggagacgg tgcaggcgct gttgccggtc tgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctga tgcagtgaa aaagggattg ggggatccta tcagccgttc ccagctggtg   2220
aagtccgagc tggaggagaa gaaatccgag ttgaggcaca gctgaagta cgtgccccac   2280 gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acgcgccat ctacaccgtg gctcccccca tcgactacgg cgtgatcgtg   2460
gacaccaagg cctactccgg cggctacaac ctgcccatcg ccaggccga cgaaatgcag   2520 aggtacgtgg aggagaacca gaccaggaac aagcacatca ccccaacga gtggtggaag   2580 gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa          2814

<210> SEQ ID NO 92
<211> LENGTH: 2832
<212> TYPE: DNA
<213> ORGANISM: Artificial Sequence
<220> FEATURE:
<223> OTHER INFORMATION: CTLA4_T03-RTALEN

<400> SEQUENCE: 92
atgggcgatc ctaaaaagaa acgtaaggtc atcgataagg agaccgccgc tgccaagttc    60
gagagacagc acatggacag catcgatatc gccgatctac gcacgctcgg ctacagccag   120
cagcaacagg agaagatcaa accgaaggtt cgttcgacag tggcgcagca ccacgaggca   180
ctggtcggcc acgggtttac acacgcgcac atcgttgcgt taagccaaca cccggcagcg   240
ttagggaccg tcgctgtcaa gtatcaggac atgatcgcag cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttgg acacaggcca acttctcaag   420
attgcaaaac gtgcggcgt gaccgcagtg gaggcagtgc atgcatggcg caatgcactg   480
acgggtgccc cgctcaactt gacccccag caggtggtgg ccatcgccag caataatggt   540
ggcaagcagg cgctggagac ggtccagcgg ctgttgccgg tgctgtgcca ggcccacggc   600 ttgaccccc agcaggtggt ggccatcgcc agcaataatg gtggcaagca ggcgctggag   660
acggtccagc ggctgttgcc ggtgctgtgc caggcccacg gcttgacccc ggagcaggtg   720
gtggccatcg ccagccacga tggcggcaag caggcgctgg agacggtcca gcggctgttg   780
ccggtgctgt gccagcccca cggcttgacc ccggagcagg tggtggccat cgccagccac   840
gatggcggca agcaggcgct ggagacggtc agcggctgt tgccggtgct gtgccaggcc   900
cacggcttga ccccggagca ggtggtggcc atcgccagca atattggtgg caagcaggcg   960
```

```
ctggagacgg tgcaggcgct gttgccggtg ctgtgccagg cccacggctt gacccccag    1020 caggtggtgg ccatcgccag caataatggt ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ggagcaggtg gtggccatcg ccagcaatat tggtggcaag    1260
caggcgctgg agacggtgca ggcgctgttg ccggtgctgt gccaggccca cggcttgacc    1320
ccggagcagg tggtggccat cgccagccac gatggcggca agcaggcgct ggagacggtc    1380
cagcggctgt tgccggtgct gtgccaggcc acggcttga ccccggagca ggtggtggcc    1440
atcgccagcc acgatggcgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc cccagcagg tggtggccat cgccagcaat    1860
aatggtggca agcaggcgct ggagacggtc agcggctgt tgccggtgct gtgccaggcc    1920
cacggcttga ccccggagca ggtggtggcc atcgccagcc acgatggcgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                         2832
```

<210> SEQ ID NO 93
<211> LENGTH: 2814
<212> TYPE: DNA
<213> ORGANISM: Artificial Sequence
<220> FEATURE:
<223> OTHER INFORMATION: CTLA4_T04-L TALEN

<400> SEQUENCE: 93

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt    180
```

-continued

```
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agccacgatg gcggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagcaat    720
attggtggca agcaggcgct ggagacggtg caggcgctgt gccggtgct gtgccaggcc     780
cacggcttga ccccccagca ggtggtggcc atcgccagca atggcggtgg caagcaggcg    840
ctggagacgg tccagcggct gttgccggtg ctgtgccagg cccacggctt gacccccag    900
caggtggtgg ccatcgccag caataatggt ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccggagcagg tggtggccat cgccagcaat attggtggca agcaggcgct ggagacggtg   1260
caggcgctgt gccggtgct gtgccaggcc cacggcttga ccccccagca ggtggtggcc    1320
atcgccagca ataatggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtcagg cgctgttgcc ggtgctgtgc caggcccacg gcttgacccc ggagcaggtg    1620
gtggccatcg ccagcaatat tggtggcaag caggcgctgg agacggtgca ggcgctgttg   1680
ccggtgctgt gccaggccca cggcttgacc ccccagcagg tggtggccat cgccagcaat   1740
ggcggtggca agcaggcgct ggagacggtc agcggctgt tgccggtgct gtgccaggcc    1800
cacggcttga ccccccagca ggtggtggcc atcgccagca ataatggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgaccccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acgcgccat ctacaccgtg ggctcccca tcgactacgg cgtgatcgtg    2460
gacaccaagg cctactccgg cggctacaac ctgcccatcg ccaggccga cgaaatgcag    2520
```

```
aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 94
<211> LENGTH: 2832
<212> TYPE: DNA
<213> ORGANISM: Artificial Sequence
<220> FEATURE:
<223> OTHER INFORMATION: CTLA4_T04-R TALEN

<400> SEQUENCE: 94
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacga tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcac gttgccaga ggcgacacac      300 gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agccacgatg gcggcaagca ggcgctggag    660
acggtccagc ggctgttgcc ggtgctgtgc caggcccacg gcttgacccc ccagcaggtg    720
gtggccatcg ccagcaatgg cggtggcaag caggcgctgg agacggtcca gcggctgttg    780
ccggtgctgt gccaggccca cggcttgacc cccagcagg tggtggccat cgccagcaat    840
aatggtggca gcaggcgct ggagacggtc agcggctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccgg agcaggtggt ggccatcgcc    1140
agccacgatg gcggcaagca ggcgctggag acggtccagc ggctgttgcc ggtgctgtgc    1200
caggcccacg gcttgacccc ggagcaggtg gtggccatcg ccagcaatat tggtggcaag    1260
caggcgctgg agacggtgca ggcgctgttg ccggtgctgt gccaggccca cggcttgacc    1320
ccccagcagg tggtggccat cgccagcaat aatggtggca gcaggcgct ggagacggtc    1380 cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagccacga tgcggcaag caggcgctgg agacggtcca gcggctgttg    1800
```

-continued

| | |
|---|---|
| ccggtgctgt gccaggccca cggcttgacc ccggagcagg tggtggccat cgccagcaat | 1860 |
| attggtggca agcaggcgct ggagacggtg caggcgctgt tgccggtgct gtgccaggcc | 1920 |
| cacggcttga ccccggagca ggtggtggcc atcgccagcc acgatggcgg caagcaggcg | 1980 |
| ctggagacgg tccagcggct gttgccggtg ctgtgccagg cccacggctt gacccctcag | 2040 |
| caggtggtgg ccatcgccag caatggcggc ggcaggccgg cgctggagag cattgttgcc | 2100 |
| cagttatctc gccctgatcc ggcgttggcc gcgttgacca acgaccacct cgtcgccttg | 2160 |
| gcctgcctcg gcgggcgtcc tgcgctggat gcagtgaaaa agggattggg ggatcctatc | 2220 |
| agccgttccc agctggtgaa gtccgagctg aggagaaga aatccgagtt gaggcacaag | 2280 |
| ctgaagtacg tgccccacga gtacatcgag ctgatcgaga tcgcccggaa cagcacccag | 2340 |
| gaccgtatcc tggagatgaa ggtgatggag ttcttcatga aggtgtacgg ctacaggggc | 2400 |
| aagcacctgg gcggctccag gaagcccgac ggcgccatct acaccgtggg ctcccccatc | 2460 |
| gactacggcg tgatcgtgga caccaaggcc tactccggcg gctacaacct gcccatcggc | 2520 |
| caggccgacg aaatgcagag gtacgtggag gagaaccaga ccaggaacaa gcacatcaac | 2580 |
| cccaacgagt ggtggaaggt gtaccccctcc agcgtgaccg agttcaagtt cctgttcgtg | 2640 |
| tccggccact tcaagggcaa ctacaaggcc cagctgacca ggctgaacca tatcaccaac | 2700 |
| tgcaacggcg ccgtgctgtc cgtggaggag ctcctgatcg gcggcgagat gatcaaggcc | 2760 |
| ggcacccctga ccctggagga ggtgaggagg aagttcaaca acggcgagat caacttcgcg | 2820 |
| gccgactgat aa | 2832 |

<210> SEQ ID NO 95
<211> LENGTH: 2814
<212> TYPE: DNA
<213> ORGANISM: Artificial Sequence
<220> FEATURE:
<223> OTHER INFORMATION: PDCD1_T01-L TALEN

<400> SEQUENCE: 95

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccc agcaggtggt ggccatcgcc agcaatggcg gtggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccccagcagg tggtggccat cgccagcaat | 720 |
| ggcggtggca agcaggcgct ggagacggtc cagcggctgt tgccggtgct gtgccaggcc | 780 |
| cacggcttga ccccggagca ggtggtggcc atcgccagcc acgatggcgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |

-continued

```
ctgttgccgg tgctgtgcca ggcccacggc ttgaccccgg agcaggtggt ggccatcgcc    1020
agccacgatg gcggcaagca ggcgctggag acggtccagc ggctgttgcc ggtgctgtgc    1080
caggcccacg gcttgacccc ggagcaggtg gtggccatcg ccagccacga tggcggcaag    1140
caggcgctgg agacggtcca gcggctgttg ccggtgctgt gccaggccca cggcttgacc    1200
ccggagcagg tggtggccat cgccagcaat attggtggca agcaggcgct ggagacggtg    1260
caggcgctgt tgccggtgct gtgccaggcc acggcttga ccccccagca ggtggtggcc    1320
atcgccagca ataatggtgg caagcaggcg ctggagacgg tccagcggct gttgccggtg    1380
ctgtgccagg cccacggctt gaccccggag caggtggtgg ccatcgccag ccacgatggc    1440
ggcaagcagg cgctggagac ggtccagcgg ctgttgccgg tgctgtgcca ggcccacggc    1500
ttgaccccgg agcaggtggt ggccatcgcc agccacgatg gcggcaagca ggcgctggag    1560
acggtccagc ggctgttgcc ggtgctgtgc caggcccacg gcttgacccc ggagcaggtg    1620
gtggccatcg ccagccacga tggcggcaag caggcgctgg agacggtcca gcggctgttg    1680
ccggtgctgt gccaggccca cggcttgacc ccccagcagg tggtggccat cgccagcaat    1740
ggcggtggca agcaggcgct ggagacggtc agcggctgt tgccggtgct gtgccaggcc    1800
cacggcttga ccccccagca ggtggtggcc atcgccagca ataatggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgaccccct cagcaggtgg tggccatcgcc    2040 agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctga tgcagtgaa aagggattg ggggatccta tcagccgttc ccagctggtg    2220
aagtccgagc tggaggagaa gaaatccgag ttgaggcaca gctgaagta cgtgccccac    2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acgcgccat ctacaccgtg gctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca cccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 96
<211> LENGTH: 2829
<212> TYPE: DNA
<213> ORGANISM: Artificial Sequence
<220> FEATURE:
<223> OTHER INFORMATION: PDCD1_T01-R TALEN

<400> SEQUENCE: 96

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
```

```
ttagggaccg tcgctgtcaa gtatcaggac atgatcgcag cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttgg acacaggcca acttctcaag   420
attgcaaaac gtggcggcgt gaccgcagtg gaggcagtgc atgcatggcg caatgcactg   480
acgggtgccc cgctcaactt gaccccccag caagtcgtcg caatcgccag caataacgga   540
gggaagcaag ccctcgaaac cgtgcagcgg ttgcttcctg tgctctgcca ggcccacggc   600
cttacccctg agcaggtggt ggccatcgca agtaacattg gaggaaagca agccttggag   660
acagtgcagg ccctgttgcc cgtgctgtgc caggcacacg gcctcacacc agagcaggtc   720
gtggccattg cctccaacat cgggggaaa caggctctgg agaccgtcca ggccctgctg   780
cccgtcctct gtcaagctca cggcctgact ccccaacaag tggtcgccat cgcctctaat   840
aacggcggga agcaggcact ggaaacagtg cagagactgc tccctgtgct tgccaagct   900
catgggttga ccccccaaca ggtcgtcgct attgcctcaa caacggggg caagcaggcc   960
cttgagactg tgcagaggct gttgccagtg ctgtgtcagg ctcacgggct cactccacaa  1020
caggtggtcg caattgccag caacggcggc ggaaagcaag ctcttgaaac cgtgcaacgc  1080
ctcctgcccg tgctctgtca ggctcatggc ctgacaccac aacaagtcgt ggccatcgcc  1140
agtaataatg gcgggaaaca ggctcttgag accgtccaga ggctgctccc agtgctctgc  1200
caggcacacg gctgaccc ccagcaggtg gtggctatcg ccagcaataa tgggggcaag  1260
caggccctgg aaacagtcca gcgcctgctg ccagtgcttt gccaggctca cgggctcact  1320
cccgaacagg tcgtggcaat cgcctccaac ggagggaagc aggctctgga gaccgtgcag  1380
agactgctgc ccgtcttgtg ccaggcccac ggactcacac ctcagcaggt cgtcgccatt  1440
gcctctaaca acggggcaa acaagccctg gagacagtgc agcggctgtt gcctgtgttg  1500
tgccaagccc acggcttgac tcctcaacaa gtggtcgcca tcgctcaaa tggcggcgga  1560
aaacaagctc tggagacagt gcagaggttg ctgcccgtcc tctgccaagc ccacggcctg  1620
actccccaac aggtcgtcgc cattgccagc aacggcggag gaaagcaggc tctcgaaact  1680
gtgcagcggc tgcttcctgt gctgtgtcag gctcatgggc tgacccccca gcaagtggtg  1740
gctattgcct ctaacaatgg aggcaagcaa gcccttgaga cagtccagag gctgttgcca  1800
gtgctgtgcc aggcccacgg gctcacaccc agcaggtgg tcgccatcgc cagtaacggc  1860
ggggcaaac aggcattgga aaccgtccag cgcctgcttc cagtgctctg ccaggcacac  1920
ggactgacac ccgaacaggt ggtggccatt gcatcccatg atgggggcaa gcaggccctg  1980
agaccgtgc agagactcct gccagtgttg tgccaagctc acggcctcac ccctcagcaa  2040
gtcgtggcca tcgcctcaaa cggggggc cggcctgcac tggagagcat tgttgcccag  2100
ttatctcgcc ctgatccggc gttggccgcg ttgaccaacg accacctcgt cgccttggcc  2160
tgcctcggcg ggcgtcctgc gctggatgca gtgaaaaagg gattgggggga tcctatcagc  2220
cgttcccagc tggtgaagtc cgagctggag gagaagaaat ccgagttgag gcacaagctg  2280
aagtacgtgc cccacgagta catcgagctg atcgagatcg cccggaacag caccaggac  2340
cgtatcctgg agatgaaggt gatggagttc ttcatgaagg tgtacggcta caggggcaag  2400
cacctgggcg gctccaggaa gcccgacggc gccatctaca ccgtgggctc ccccatcgac  2460
tacgcgtga tcgtggacac caaggcctac tccggcggct acaacctgcc catcggccag  2520
gccgacgaaa tgcagaggta cgtggaggag aaccagacca ggaacaagca catcaacccc  2580
```

| | |
|---|---:|
| aacgagtggt ggaaggtgta cccctccagc gtgaccgagt tcaagttcct gttcgtgtcc | 2640 |
| ggccacttca agggcaacta caaggcccag ctgaccaggc tgaaccacat caccaactgc | 2700 |
| aacggcgccg tgctgtccgt ggaggagctc ctgatcggcg gcgagatgat caaggccggc | 2760 |
| accctgaccc tggaggaggt gaggaggaag ttcaacaacg gcgagatcaa cttcgcggcc | 2820 |
| gactgataa | 2829 |

<210> SEQ ID NO 97
<211> LENGTH: 2814
<212> TYPE: DNA
<213> ORGANISM: Artificial Sequence
<220> FEATURE:
<223> OTHER INFORMATION: PDCD1_T03-L TALEN

<400> SEQUENCE: 97

| | |
|---|---:|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca gattgcaaa acgtggcggc | 420 |
| gtgaccgcag tggaggcagt gcatgcatgg cgcaatgcac tgacgggtgc cccgctcaac | 480 |
| ttgaccccgg agcaggtggt ggccatcgcc agcaatattg gtggcaagca ggcgctggag | 540 |
| acggtgcagg cgctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagccac | 720 |
| gatggcggca agcaggcgct ggagacggtc agcggctgt tgccggtgct gtgccaggcc | 780 |
| cacggcttga ccccccagca ggtggtggcc atcgccagca atggcggtgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccc agcaggtggt ggccatcgcc | 1020 |
| agcaatggcg gtggcaagca ggcgctggag acggtccagc ggctgttgcc ggtgctgtgc | 1080 |
| caggcccacg gcttgacccc ccagcaggtg gtggccatcg ccagcaataa tggtggcaag | 1140 |
| caggcgctgg agacggtcca gcggctgttg ccggtgctgt gccaggccca cggcttgacc | 1200 |
| ccccagcagg tggtggccat cgccagcaat ggcggtggca agcaggcgct ggagacggtc | 1260 |
| cagcggctgt tgccggtgct gtgccaggcc cacggcttga ccccccagca ggtggtggcc | 1320 |
| atcgccagca ataatggtgg caagcaggcg ctggagacgg tccagcggct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccc agcaggtggt ggccatcgcc agcaataatg gtggcaagca ggcgctggag | 1560 |
| acggtccagc ggctgttgcc ggtgctgtgc caggcccacg gcttgacccc ccagcaggtg | 1620 |
| gtggccatcg ccagcaataa tggtggcaag caggcgctgg agacggtcca gcggctgttg | 1680 |
| ccggtgctgt gccaggccca cggcttgacc ccggagcagg tggtggccat cgccagccac | 1740 |
| gatggcggca agcaggcgct ggagacggtc agcggctgt tgccggtgct gtgccaggcc | 1800 |

```
cacggcttga ccccggagca ggtggtggcc atcgccagcc acgatggcgg caagcaggcg      1860
ctggagacgg tccagcggct gttgccggtg ctgtgccagg cccacggctt gaccccggag      1920
caggtggtgg ccatcgccag caatattggt ggcaagcagg cgctggagac ggtgcaggcg      1980
ctgttgccgg tgctgtgcca ggcccacggc ttgacccctc agcaggtggt ggccatcgcc      2040
agcaatggcg gcggcaggcc ggcgctggag agcattgttg cccagttatc tcgccctgat      2100
ccggcgttgg ccgcgttgac caacgaccac ctcgtcgcct tggcctgcct cggcgggcgt      2160
cctgcgctgg atgcagtgaa aaagggattg ggggatccta tcagccgttc ccagctggtg      2220
aagtccgagc tggaggagaa gaaatccgag ttgaggcaca agctgaagta cgtgccccac      2280
gagtacatcg agctgatcga gatcgcccgg aacagcaccc aggaccgtat cctggagatg      2340
aaggtgatga gttcttcat gaaggtgtac ggctacaggg gcaagcacct gggcggctcc      2400
aggaagcccg acggcgccat ctacaccgtg ggctcccca tcgactacgg cgtgatcgtg      2460
gacaccaagg cctactccgg cggctacaac ctgcccatcg ccaggccga cgaaatgcag      2520 aggtacgtgg aggagaacca gaccaggaac aagcacatca ccccaacga gtggtggaag      2580 gtgtacccct ccagcgtgac cgagttcaag ttcctgttcg tgtccggcca cttcaagggc      2640
aactacaagg cccagctgac caggctgaac cacatcacca actgcaacgg cgccgtgctg      2700
tccgtggagg agctcctgat cggcggcgag atgatcaagg ccggcaccct gaccctggag      2760
gaggtgagga ggaagttcaa caacggcgag atcaacttcg cggccgactg ataa           2814
```

<210> SEQ ID NO 98
<211> LENGTH: 2829
<212> TYPE: DNA
<213> ORGANISM: Artificial Sequence
<220> FEATURE:
<223> OTHER INFORMATION: PDCD1_T03-R TALEN

<400> SEQUENCE: 98

```
atgggcgatc taaaaagaa acgtaaggtc atcgataagg agaccgccgc tgccaagttc        60
gagagacagc acatggacag catcgatatc gccgatctac gcacgctcgg ctacagccag      120
cagcaacagg agaagatcaa accgaaggtt cgttcgacag tggcgcagca ccacgaggca      180
ctggtcggcc acgggtttac acacgcgcac atcgttgcgt taagccaaca cccggcagcg      240
ttagggaccg tcgctgtcaa gtatcaggac atgatcgcac cgttgccaga ggcgacacac      300
gaagcgatcg ttggcgtcgg caaacagtgg tccggcgcac gcgctctgga ggccttgctc      360
acggtggcgg gagagttgag aggtccaccg ttacagttgg acacaggcca acttctcaag      420
attgcaaaac gtggcggcgt gaccgcagtg gaggcagtgc atgcatggcg caatgcactg      480
acgggtgccc cgctcaactt gaccccgag caagtcgtcg caatcgccag ccatgatgga      540
gggaagcaag ccctcgaaac cgtgcagcgg ttgcttcctg tgctctgcca ggcccacggc      600 cttaccccctc agcaggtggt ggccatcgca agtaacggag gaggaaagca agccttggag      660
acagtgcagc gcctgttgcc cgtgctgtgc caggcacacg gcctcacacc agagcaggtc      720
gtggccattg cctcccatga cgggggaaa caggctctgg agaccgtcca gaggctgctg      780
cccgtcctct gtcaagctca cggcctgact ccccaacaag tggtcgccat cgcctctaat      840
ggcggcggga agcaggcact ggaaacagtg cagagactgc tccctgtgct ttgccaagct      900
catgggttga ccccccaaca ggtcgtcgct attgcctcaa acggggggg caagcaggcc      960 cttgagactg tgcagaggct gttgccagtg ctgtgtcagg ctcacgggct cactccacaa     1020
```

```
caggtggtcg caattgccag caacggcggc ggaaagcaag ctcttgaaac cgtgcaacgc   1080
ctcctgcccg tgctctgtca ggctcatggc ctgacaccac aacaagtcgt ggccatcgcc   1140
agtaataatg gcgggaaaca ggctcttgag accgtccaga ggctgctccc agtgctctgc   1200
caggcacacg ggctgacccc cgagcaggtg gtggctatcg ccagcaatat tgggggcaag   1260
caggccctgg aaacagtcca ggccctgctg ccagtgcttt gccaggctca cgggctcact   1320
ccccagcagg tcgtggcaat cgcctccaac ggcggaggga agcaggctct ggagaccgtg   1380
cagagactgc tgcccgtctt gtgccaggcc cacggactca cacctgaaca ggtcgtcgcc   1440
attgcctctc acgatggggg caaacaagcc ctggagacag tgcagcggct gttgcctgtg   1500
ttgtgccaag cccacggctt gactcctcaa caagtggtcg ccatcgcctc aaatggcggc   1560
ggaaaacaag ctctggagac agtgcagagg ttgctgcccg tcctctgcca agcccacggc   1620
ctgactcccc aacaggtcgt cgccattgcc agcaacaacg gaggaaagca ggctctcgaa   1680
actgtgcagc ggctgcttcc tgtgctgtgt caggctcatg ggctgacccc cgagcaagtg   1740
gtggctattg cctctaatgg aggcaagcaa gcccttgaga cagtccagag gctgttgcca   1800
gtgctgtgcc aggcccacgg gctcacaccc cagcaggtgg tcgccatcgc cagtaacaac   1860
gggggcaaac aggcattgga aaccgtccag cgcctgcttc cagtgctctg ccaggcacac   1920
ggactgacac ccgaacaggt ggtggccatt gcatcccatg atggggcaa gcaggccctg   1980 gagaccgtgc agagactcct gccagtgttg tgccaagctc acggcctcac ccctcagcaa   2040
gtcgtggcca tcgcctcaaa cggggggggc cggcctgcac tggagagcat tgttgcccag   2100
ttatctcgcc ctgatccggc gttggccgcg ttgaccaacg accacctcgt cgccttggcc   2160
tgcctcggcg ggcgtcctgc gctggatgca gtgaaaaagg gattgggga tcctatcagc   2220 cgttcccagc tggtgaagtc cgagctggag gagaagaaat ccgagttgag gcacaagctg   2280
aagtacgtgc cccacgagta catcgagctg atcgagatcg cccggaacag caccccaggac   2340 cgtatcctgg agatgaaggt gatggagttc ttcatgaagg tgtacggcta cagggggcaag   2400 cacctgggcg gctccaggaa gcccgacggc gccatctaca ccgtgggctc ccccatcgac   2460 tacgcgtga tcgtggacac caaggcctac tccggcggct acaacctgcc catcggccag   2520
gccgacgaaa tgcagaggta cgtggaggag aaccagacca ggaacaagca catcaaccc c   2580 aacgagtggt ggaaggtgta cccctccagc gtgaccgagt tcaagttcct gttcgtgtcc   2640
ggccacttca agggcaacta caaggcccag ctgaccaggc tgaaccacat caccaactgc   2700
aacggcgccg tgctgtccgt ggaggagctc ctgatcggcg gcgagatgat caaggccggc   2760
accctgaccc tggaggaggt gaggaggaag ttcaacaacg gcgagatcaa cttcgcggcc   2820
gactgataa                                                          2829
```

<210> SEQ ID NO 99
<211> LENGTH: 60
<212> TYPE: DNA
<213> ORGANISM: Artificial Sequence
<220> FEATURE:
<223> OTHER INFORMATION: Forward primer CTLA4_T01
<220> FEATURE:
<221> NAME/KEY: misc_feature
<222> LOCATION: (31)..(40)
<223> OTHER INFORMATION: n is a or c or t or g

<400> SEQUENCE: 99

```
ccatctcatc cctgcgtgtc tccgactcag nnnnnnnnnn ctctacttcc tgaagacctg    60
```

<210> SEQ ID NO 100
<211> LENGTH: 60
<212> TYPE: DNA
<213> ORGANISM: Artificial Sequence
<220> FEATURE:
<223> OTHER INFORMATION: Forward primer CTLA4_T03/T04
<220> FEATURE:
<221> NAME/KEY: misc_feature
<222> LOCATION: (31)..(40)
<223> OTHER INFORMATION: n is a or c or t or g

<400> SEQUENCE: 100
ccatctcatc cctgcgtgtc tccgactcag nnnnnnnnnn acagttgaga gatggagggg    60

<210> SEQ ID NO 101
<211> LENGTH: 59
<212> TYPE: DNA
<213> ORGANISM: Artificial Sequence
<220> FEATURE:
<223> OTHER INFORMATION: Forward primer PDCD1_T01
<220> FEATURE:
<221> NAME/KEY: misc_feature
<222> LOCATION: (31)..(40)
<223> OTHER INFORMATION: n is a or c or t or g

<400> SEQUENCE: 101
ccatctcatc cctgcgtgtc tccgactcag nnnnnnnnnn ccacagaggt aggtgccgc    59

<210> SEQ ID NO 102
<211> LENGTH: 60
<212> TYPE: DNA
<213> ORGANISM: Artificial Sequence
<220> FEATURE:
<223> OTHER INFORMATION: Forward primer PDCD1_T03
<220> FEATURE:
<221> NAME/KEY: misc_feature
<222> LOCATION: (31)..(40)
<223> OTHER INFORMATION: n is a or c or t or g

<400> SEQUENCE: 102
ccatctcatc cctgcgtgtc tccgactcag nnnnnnnnnn gacagagatg ccggtcacca    60

<210> SEQ ID NO 103
<211> LENGTH: 50
<212> TYPE: DNA
<213> ORGANISM: Artificial Sequence
<220> FEATURE:
<223> OTHER INFORMATION: Reverse primer CTLA4_T01

<400> SEQUENCE: 103
cctatcccct gtgtgccttg gcagtctcag tggaatacag agccagccaa    50

<210> SEQ ID NO 104
<211> LENGTH: 50
<212> TYPE: DNA
<213> ORGANISM: Artificial Sequence
<220> FEATURE:
<223> OTHER INFORMATION: Reverse primer CTLA4_T03/04

<400> SEQUENCE: 104
cctatcccct gtgtgccttg gcagtctcag ggtgcccgtg cagatggaat    50

<210> SEQ ID NO 105
<211> LENGTH: 50
<212> TYPE: DNA
<213> ORGANISM: Artificial Sequence
<220> FEATURE:
<223> OTHER INFORMATION: Reverse primer PDCD1_T01

<400> SEQUENCE: 105
cctatcccct gtgtgccttg gcagtctcag ggctctgcag tggaggccag                50

<210> SEQ ID NO 106
<211> LENGTH: 50
<212> TYPE: DNA
<213> ORGANISM: Artificial Sequence
<220> FEATURE:
<223> OTHER INFORMATION: Reverse primer PDCD1_T03

<400> SEQUENCE: 106
cctatcccct gtgtgccttg gcagtctcag ggacaacgcc accttcacct                50

<210> SEQ ID NO 107
<211> LENGTH: 281
<212> TYPE: PRT
<213> ORGANISM: Artificial Sequence
<220> FEATURE:
<223> OTHER INFORMATION: pTalpha-FL

<400> SEQUENCE: 107

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
        130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
            260                 265                 270

Pro Pro Pro Leu Gln Ala Gly Ala Ala
        275                 280
```

<210> SEQ ID NO 108
<211> LENGTH: 263
<212> TYPE: PRT
<213> ORGANISM: Artificial Sequence
<220> FEATURE:
<223> OTHER INFORMATION: pTalpha-Delta18

<400> SEQUENCE: 108

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
            195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser
            260
```

<210> SEQ ID NO 109
<211> LENGTH: 233
<212> TYPE: PRT
<213> ORGANISM: Artificial Sequence
<220> FEATURE:
<223> OTHER INFORMATION: pTalpha-Delta48

<400> SEQUENCE: 109

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
```

```
             35                  40                  45
Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly Gly Arg Glu Ala Thr
                195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val
225                 230

<210> SEQ ID NO 110
<211> LENGTH: 219
<212> TYPE: PRT
<213> ORGANISM: Artificial Sequence
<220> FEATURE:
<223> OTHER INFORMATION: pTalpha-Delta62

<400> SEQUENCE: 110

Met Ala Gly Thr Trp Leu Leu Leu Leu Ala Leu Gly Cys Pro Ala
 1               5                  10                  15

Leu Pro Thr Gly Val Gly Gly Thr Pro Phe Pro Ser Leu Ala Pro Pro
                 20                  25                  30

Ile Met Leu Leu Val Asp Gly Lys Gln Gln Met Val Val Cys Leu
                 35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
```

```
                    165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly Gly Arg Glu Ala Thr
                195                 200                 205

Ser Ser Pro Arg Pro Gln Pro Arg Asp Arg Arg
            210                 215

<210> SEQ ID NO 111
<211> LENGTH: 203
<212> TYPE: PRT
<213> ORGANISM: Artificial Sequence
<220> FEATURE:
<223> OTHER INFORMATION: pTalpha-Delta78

<400> SEQUENCE: 111

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly
                195                 200

<210> SEQ ID NO 112
<211> LENGTH: 189
<212> TYPE: PRT
<213> ORGANISM: Artificial Sequence
<220> FEATURE:
<223> OTHER INFORMATION: pTalpha-Delta92

<400> SEQUENCE: 112

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Val Cys Leu
            35                  40                  45
```

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg
                180                 185

<210> SEQ ID NO 113
<211> LENGTH: 171
<212> TYPE: PRT
<213> ORGANISM: Artificial Sequence
<220> FEATURE:
<223> OTHER INFORMATION: pTalpha-Delta110

<400> SEQUENCE: 113

Met Ala Gly Thr Trp Leu Leu Leu Leu Ala Leu Gly Cys Pro Ala
 1               5                  10                  15

Leu Pro Thr Gly Val Gly Gly Thr Pro Phe Pro Ser Leu Ala Pro Pro
                 20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys
                165                 170

<210> SEQ ID NO 114
<211> LENGTH: 167
<212> TYPE: PRT
<213> ORGANISM: Artificial Sequence
<220> FEATURE:
<223> OTHER INFORMATION: pTalpha-Delta114

<400> SEQUENCE: 114

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
            85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu
                165

<210> SEQ ID NO 115
<211> LENGTH: 344
<212> TYPE: PRT
<213> ORGANISM: Artificial Sequence
<220> FEATURE:
<223> OTHER INFORMATION: pTalpha-FL-CD28

<400> SEQUENCE: 115

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
            85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
            245                 250                 255

Leu Arg Ala Pro Ser Ser Leu Gly Ala Phe Phe Arg Gly Asp Leu
        260                 265                 270

Pro Pro Pro Leu Gln Ala Gly Ala Ala Ser Gly Gly Val Leu Ala
            275                 280                 285

Cys Tyr Ser Leu Leu Val Thr Val Ala Phe Ile Ile Phe Trp Val Arg
        290                 295                 300

Ser Lys Arg Ser Arg Gly Gly His Ser Asp Tyr Met Asn Met Thr Pro
305                 310                 315                 320

Arg Arg Pro Gly Pro Thr Arg Lys His Tyr Gln Pro Tyr Ala Pro Pro
                325                 330                 335

Arg Asp Phe Ala Ala Tyr Arg Ser
            340

<210> SEQ ID NO 116
<211> LENGTH: 311
<212> TYPE: PRT
<213> ORGANISM: Artificial Sequence
<220> FEATURE:
<223> OTHER INFORMATION: pTalpha-FL-CD8

<400> SEQUENCE: 116

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

```
Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Leu Gly Ala Phe Phe Arg Gly Asp Leu
            260                 265                 270

Pro Pro Pro Leu Gln Ala Gly Ala Ala Ala Ser His Arg Asn Arg Arg
        275                 280                 285

Arg Val Cys Lys Cys Pro Arg Pro Val Val Lys Ser Gly Asp Lys Pro
    290                 295                 300

Ser Leu Ser Ala Arg Tyr Val
305                 310

<210> SEQ ID NO 117
<211> LENGTH: 325
<212> TYPE: PRT
<213> ORGANISM: Artificial Sequence
<220> FEATURE:
<223> OTHER INFORMATION: pTalpha-FL-41BB

<400> SEQUENCE: 117

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255
```

```
Leu Arg Ala Pro Ser Ser Leu Gly Ala Phe Phe Arg Gly Asp Leu
            260                 265                 270
Pro Pro Pro Leu Gln Ala Gly Ala Gly Ser Lys Arg Gly Arg Lys
            275                 280                 285
Lys Leu Leu Tyr Ile Phe Lys Gln Pro Phe Met Arg Pro Val Gln Thr
            290                 295                 300
Thr Gln Glu Glu Asp Gly Cys Ser Cys Arg Phe Pro Glu Glu Glu
305                 310                 315                 320
Gly Gly Cys Glu Leu
                325

<210> SEQ ID NO 118
<211> LENGTH: 296
<212> TYPE: PRT
<213> ORGANISM: Artificial Sequence
<220> FEATURE:
<223> OTHER INFORMATION: pTalpha-Delta48-CD28

<400> SEQUENCE: 118

Met Ala Gly Thr Trp Leu Leu Leu Leu Ala Leu Gly Cys Pro Ala
1               5                   10                  15
Leu Pro Thr Gly Val Gly Gly Thr Pro Phe Pro Ser Leu Ala Pro Pro
                20                  25                  30
Ile Met Leu Leu Val Asp Gly Lys Gln Gln Met Val Val Val Cys Leu
            35                  40                  45
Val Leu Asp Val Ala Pro Pro Gly Leu Asp Ser Pro Ile Trp Phe Ser
50                  55                  60
Ala Gly Asn Gly Ser Ala Leu Asp Ala Phe Thr Tyr Gly Pro Ser Pro
65                  70                  75                  80
Ala Thr Asp Gly Thr Trp Thr Asn Leu Ala His Leu Ser Leu Pro Ser
                85                  90                  95
Glu Glu Leu Ala Ser Trp Glu Pro Leu Val Cys His Thr Gly Pro Gly
            100                 105                 110
Ala Glu Gly His Ser Arg Ser Thr Gln Pro Met His Leu Ser Gly Glu
        115                 120                 125
Ala Ser Thr Ala Arg Thr Cys Pro Gln Glu Pro Leu Arg Gly Thr Pro
130                 135                 140
Gly Gly Ala Leu Trp Leu Gly Val Leu Arg Leu Leu Leu Phe Lys Leu
145                 150                 155                 160
Leu Leu Phe Asp Leu Leu Leu Thr Cys Ser Cys Leu Cys Asp Pro Ala
                165                 170                 175
Gly Pro Leu Pro Ser Pro Ala Thr Thr Thr Arg Leu Arg Ala Leu Gly
            180                 185                 190
Ser His Arg Leu His Pro Ala Thr Glu Thr Gly Gly Arg Glu Ala Thr
        195                 200                 205
Ser Ser Pro Arg Pro Gln Pro Arg Asp Arg Arg Trp Gly Asp Thr Pro
210                 215                 220
Pro Gly Arg Lys Pro Gly Ser Pro Val Ala Ser Gly Gly Val Leu Ala
225                 230                 235                 240
Cys Tyr Ser Leu Leu Val Thr Val Ala Phe Ile Ile Phe Trp Val Arg
                245                 250                 255
Ser Lys Arg Ser Arg Gly Gly His Ser Asp Tyr Met Asn Met Thr Pro
            260                 265                 270
Arg Arg Pro Gly Pro Thr Arg Lys His Tyr Gln Pro Tyr Ala Pro Pro
        275                 280                 285
```

Arg Asp Phe Ala Ala Tyr Arg Ser
    290                 295

<210> SEQ ID NO 119
<211> LENGTH: 263
<212> TYPE: PRT
<213> ORGANISM: Artificial Sequence
<220> FEATURE:
<223> OTHER INFORMATION: pTalpha-Delta48-CD8

<400> SEQUENCE: 119

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Ala Ser His Arg Asn Arg Arg
225                 230                 235                 240

Arg Val Cys Lys Cys Pro Arg Pro Val Val Lys Ser Gly Asp Lys Pro
                245                 250                 255

Ser Leu Ser Ala Arg Tyr Val
            260

<210> SEQ ID NO 120
<211> LENGTH: 277
<212> TYPE: PRT
<213> ORGANISM: Artificial Sequence
<220> FEATURE:
<223> OTHER INFORMATION: pTalpha-Delta48-41BB

<400> SEQUENCE: 120

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro

```
                    20                  25                  30
Ile Met Leu Leu Val Asp Gly Lys Gln Gln Met Val Val Cys Leu
                35                  40                  45
Val Leu Asp Val Ala Pro Pro Gly Leu Asp Ser Pro Ile Trp Phe Ser
 50                  55                  60
Ala Gly Asn Gly Ser Ala Leu Asp Ala Phe Thr Tyr Gly Pro Ser Pro
 65                  70                  75                  80
Ala Thr Asp Gly Thr Trp Thr Asn Leu Ala His Leu Ser Leu Pro Ser
                85                  90                  95
Glu Glu Leu Ala Ser Trp Glu Pro Leu Val Cys His Thr Gly Pro Gly
                100                 105                 110
Ala Glu Gly His Ser Arg Ser Thr Gln Pro Met His Leu Ser Gly Glu
                115                 120                 125
Ala Ser Thr Ala Arg Thr Cys Pro Gln Glu Pro Leu Arg Gly Thr Pro
                130                 135                 140
Gly Gly Ala Leu Trp Leu Gly Val Leu Arg Leu Leu Phe Lys Leu
145                 150                 155                 160
Leu Leu Phe Asp Leu Leu Leu Thr Cys Ser Cys Leu Cys Asp Pro Ala
                165                 170                 175
Gly Pro Leu Pro Ser Pro Ala Thr Thr Thr Arg Leu Arg Ala Leu Gly
                180                 185                 190
Ser His Arg Leu His Pro Ala Thr Glu Thr Gly Gly Arg Glu Ala Thr
                195                 200                 205
Ser Ser Pro Arg Pro Gln Pro Arg Asp Arg Arg Trp Gly Asp Thr Pro
                210                 215                 220
Pro Gly Arg Lys Pro Gly Ser Pro Val Gly Ser Lys Arg Gly Arg Lys
225                 230                 235                 240
Lys Leu Leu Tyr Ile Phe Lys Gln Pro Phe Met Arg Pro Val Gln Thr
                245                 250                 255
Thr Gln Glu Glu Asp Gly Cys Ser Cys Arg Phe Pro Glu Glu Glu Glu
                260                 265                 270
Gly Gly Cys Glu Leu
                275

<210> SEQ ID NO 121
<211> LENGTH: 172
<212> TYPE: PRT
<213> ORGANISM: Artificial Sequence
<220> FEATURE:
<223> OTHER INFORMATION: pTalpha-Delta114-TCRalpha.IC

<400> SEQUENCE: 121

Met Ala Gly Thr Trp Leu Leu Leu Leu Ala Leu Gly Cys Pro Ala
 1               5                  10                  15
Leu Pro Thr Gly Val Gly Gly Thr Pro Phe Pro Ser Leu Ala Pro Pro
                20                  25                  30
Ile Met Leu Leu Val Asp Gly Lys Gln Gln Met Val Val Cys Leu
                35                  40                  45
Val Leu Asp Val Ala Pro Pro Gly Leu Asp Ser Pro Ile Trp Phe Ser
 50                  55                  60
Ala Gly Asn Gly Ser Ala Leu Asp Ala Phe Thr Tyr Gly Pro Ser Pro
 65                  70                  75                  80
Ala Thr Asp Gly Thr Trp Thr Asn Leu Ala His Leu Ser Leu Pro Ser
                85                  90                  95
Glu Glu Leu Ala Ser Trp Glu Pro Leu Val Cys His Thr Gly Pro Gly
```

```
                    100                 105                 110
Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
        130                 135                 140

Gly Gly Ala Leu Trp Leu Gly Val Leu Arg Leu Leu Leu Phe Lys Leu
145                 150                 155                 160

Leu Leu Phe Asp Leu Leu Leu Arg Leu Trp Ser Ser
                165                 170
```

<210> SEQ ID NO 122
<211> LENGTH: 173
<212> TYPE: PRT
<213> ORGANISM: Artificial Sequence
<220> FEATURE:
<223> OTHER INFORMATION: pTalpha.EC-TCRalpha.TM.IC

<400> SEQUENCE: 122

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Leu Ser Val Ile Gly Phe Arg Ile Leu Leu Leu Lys Val Ala
145                 150                 155                 160

Gly Phe Asn Leu Leu Met Thr Leu Arg Leu Trp Ser Ser
                165                 170
```

<210> SEQ ID NO 123
<211> LENGTH: 233
<212> TYPE: PRT
<213> ORGANISM: Artificial Sequence
<220> FEATURE:
<223> OTHER INFORMATION: pTalpha.EC-Delta48-1xMUT

<400> SEQUENCE: 123

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Arg Phe Ser
    50                  55                  60
```

```
Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
    195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val
225                 230

<210> SEQ ID NO 124
<211> LENGTH: 233
<212> TYPE: PRT
<213> ORGANISM: Artificial Sequence
<220> FEATURE:
<223> OTHER INFORMATION: pTalpha.EC-Delta48-4xMUT

<400> SEQUENCE: 124

Met Ala Gly Thr Trp Leu Leu Leu Leu Ala Leu Gly Cys Pro Ala
  1               5                  10                  15

Leu Pro Thr Gly Val Gly Gly Thr Pro Phe Pro Ser Leu Ala Pro Pro
                 20                  25                  30

Ile Met Leu Leu Val Ala Gly Ala Gln Gln Met Val Val Cys Leu
             35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Ala Ser Thr Gln Pro Met His Leu Ser Gly Glu
        115                 120                 125

Ala Ser Thr Ala Ala Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190
```

```
Ser His Arg Leu His Pro Ala Thr Glu Thr Gly Gly Arg Glu Ala Thr
            195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val
225                 230

<210> SEQ ID NO 125
<211> LENGTH: 848
<212> TYPE: PRT
<213> ORGANISM: Artificial Sequence
<220> FEATURE:
<223> OTHER INFORMATION: Multi-chain CAR

<400> SEQUENCE: 125

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320
```

-continued

```
Asp Phe Phe Ile Pro Leu Leu Val Val Ile Leu Phe Ala Val Asp Thr
                325                 330                 335
Gly Leu Phe Ile Ser Thr Gln Gln Val Thr Phe Leu Leu Lys Ile
            340                 345                 350
Lys Arg Thr Arg Lys Gly Phe Arg Leu Leu Asn Pro His Pro Lys Pro
        355                 360                 365
Asn Pro Lys Asn Asn Arg Ala Glu Gly Arg Gly Ser Leu Leu Thr Cys
370                 375                 380
Gly Asp Val Glu Glu Asn Pro Gly Pro Met Asp Thr Glu Ser Asn Arg
385                 390                 395                 400
Arg Ala Asn Leu Ala Leu Pro Gln Glu Pro Ser Ser Val Pro Ala Phe
                405                 410                 415
Glu Val Leu Glu Ile Ser Pro Gln Glu Val Ser Ser Gly Arg Leu Leu
            420                 425                 430
Lys Ser Ala Ser Ser Pro Pro Leu His Thr Trp Leu Thr Val Leu Lys
        435                 440                 445
Lys Glu Gln Glu Phe Leu Gly Val Thr Gln Ile Leu Thr Ala Met Ile
    450                 455                 460
Cys Leu Cys Phe Gly Thr Val Val Cys Ser Val Leu Asp Ile Ser His
465                 470                 475                 480
Ile Glu Gly Asp Ile Phe Ser Ser Phe Lys Ala Gly Tyr Pro Phe Trp
                485                 490                 495
Gly Ala Ile Phe Phe Ser Ile Ser Gly Met Leu Ser Ile Ile Ser Glu
            500                 505                 510
Arg Arg Asn Ala Thr Tyr Leu Val Arg Gly Ser Leu Gly Ala Asn Thr
        515                 520                 525
Ala Ser Ser Ile Ala Gly Gly Thr Gly Ile Thr Ile Leu Ile Ile Asn
530                 535                 540
Leu Lys Lys Ser Leu Ala Tyr Ile His Ile His Ser Cys Gln Lys Phe
545                 550                 555                 560
Phe Glu Thr Lys Cys Phe Met Ala Ser Phe Ser Thr Glu Ile Val Val
                565                 570                 575
Met Met Leu Phe Leu Thr Ile Leu Gly Leu Gly Ser Ala Val Ser Leu
            580                 585                 590
Thr Ile Cys Gly Ala Gly Glu Glu Leu Lys Gly Asn Lys Val Pro Glu
        595                 600                 605
Lys Arg Gly Arg Lys Lys Leu Leu Tyr Ile Phe Lys Gln Pro Phe Met
    610                 615                 620
Arg Pro Val Gln Thr Thr Gln Glu Glu Asp Gly Cys Ser Cys Arg Phe
625                 630                 635                 640
Pro Glu Glu Glu Glu Gly Gly Cys Glu Leu Gly Ser Gly Val Lys Gln
                645                 650                 655
Thr Leu Asn Phe Asp Leu Leu Lys Leu Ala Gly Asp Val Glu Ser Asn
            660                 665                 670
Pro Gly Pro Met Ile Pro Ala Val Val Leu Leu Leu Leu Leu Leu Val
        675                 680                 685
Glu Gln Ala Ala Ala Leu Gly Glu Pro Gln Leu Cys Tyr Ile Leu Asp
    690                 695                 700
Ala Ile Leu Phe Leu Tyr Gly Ile Val Leu Thr Leu Leu Tyr Cys Arg
705                 710                 715                 720
Leu Lys Ile Gln Val Arg Lys Ala Ala Ile Thr Ser Tyr Glu Lys Ser
                725                 730                 735
Arg Val Lys Phe Ser Arg Ser Ala Asp Ala Pro Ala Tyr Gln Gln Gly
```

|   |   | 740 |   |   | 745 |   |   | 750 |   |
|---|---|---|---|---|---|---|---|---|---|

Gln Asn Gln Leu Tyr Asn Glu Leu Asn Leu Gly Arg Arg Glu Glu Tyr
                755                 760                 765

Asp Val Leu Asp Lys Arg Arg Gly Arg Asp Pro Glu Met Gly Gly Lys
            770                 775                 780

Pro Arg Arg Lys Asn Pro Gln Glu Gly Leu Tyr Asn Glu Leu Gln Lys
785                 790                 795                 800

Asp Lys Met Ala Glu Ala Tyr Ser Glu Ile Gly Met Lys Gly Glu Arg
                805                 810                 815

Arg Arg Gly Lys Gly His Asp Gly Leu Tyr Gln Gly Leu Ser Thr Ala
            820                 825                 830

Thr Lys Asp Thr Tyr Asp Ala Leu His Met Gln Ala Leu Pro Pro Arg
            835                 840                 845

```
<210> SEQ ID NO 126
<211> LENGTH: 2547
<212> TYPE: DNA
<213> ORGANISM: Artificial Sequence
<220> FEATURE:
<223> OTHER INFORMATION: Multi-chain CAR

<400> SEQUENCE: 126
atggctcctg ccatggaatc ccctactcta ctgtgtgtag ccttactgtt cttcgctcca      60
gatggcgtgt tagcagaggt gcagttgcag cagtcagggc cagagttgat taagcccgga     120
gcctccgtca gatgtcctg caaggccagc gggtacactt tcaccagcta cgtcatgcat     180
tgggtgaagc agaagccagg ccaggggctt gagtggattg gtacatcaa ccccctacaac    240 gacgggacca atacaacga gaaattcaag gcaaagcca cactcacctc cgataagtcc      300
tcctctaccg cctacatgga gctcagctcc ctgacctccg aggatagcgc tgtgtattac      360
tgcgcaaggg gcacatacta ctatggctct agggtgttcg actactgggg gcagggcact      420
actctcacag tgagctcagg cggaggaggc agtggcggag gggaagtgg gggcggcggc      480 agcgatattg tcatgaccca ggcagcccct agtatccctg tgactccagg cgagagcgtg      540
agcatcagct gccggtccag caagagcctg ctgaacagta cggaaacac ataccttctac      600 tggtttctgc agaggcccgg ccagagccct cagctgctga tttaccgcat gtcaaatctt      660
gcctctgggg tgcccgatag atttagtggg agcggatccg gcacagcttt tacattgcgg      720
atctccagag tcgaggccga agacgtgggg gtctattact gtatgcaaca cctggaatac      780
ccctttacct tcggagccgg cacaaagctg gagctgaagc gggctgacac acaaccccc      840 gctccaaggc ccctacccc cgcaccaact attgcctccc agccactctc actgcggcct      900
gaggcctgtc ggcccgctgc tggaggcgca gtgcatacaa ggggcctcga tttcgcctgc      960
gattttttta tcccattgtt ggtggtgatt ctgtttgctg tggacacagg attatttatc     1020
tcaactcagc agcaggtcac atttctcttg aagattaaga gaaccaggaa aggcttcaga     1080
cttctgaacc cacatcctaa gccaaacccc aaaaacaaca gagccgaggg cagaggcagc     1140
ctgctgacct gcggcgacgt ggaggagaac ccaggcccca tggacacaga aagtaatagg     1200
agagcaaatc ttgctctccc acaggagcct tccagtgtgc ctgcatttga agtcttggaa     1260
atatctcccc aggaagtatc ttcaggcaga ctattgaagt cggcctcatc cccaccactg     1320
catacatggc tgacagtttt gaaaaaagag caggagttcc tggggtaac acaaattctg     1380 actgctatga tatgcctttg ttttggaaca gttgtctgct ctgtacttga tatttcacac      1440
attgagggag acatttttc atcatttaaa gcaggttatc cattctgggg agccatattt      1500
```

```
tttctatttt ctggaatgtt gtcaattata tctgaaagga gaaatgcaac atatctggtg    1560
agaggaagcc tgggagcaaa cactgccagc agcatagctg ggggaacggg aattaccatc    1620
ctgatcatca acctgaagaa gagcttggcc tatatccaca tccacagttg ccagaaattt    1680
tttgagacca agtgctttat ggcttccttt tccactgaaa ttgtagtgat gatgctgttt    1740
ctcaccattc tgggacttgg tagtgctgtg tcactcacaa tctgtggagc tggggaagaa    1800
ctcaaaggaa acaaggttcc agagaaacgg ggccggaaga agctcctcta cattttttaag  1860 cagcctttca tgcggccagt gcagacaacc caagaggagg atgggtgttc ctgcagattc    1920
cctgaggaag aggaaggcgg gtgcgagctg ggttctggcg tgaaacagac tttgaatttt    1980
gaccttctca agttggcggg agacgtggag tccaacccag ggcccatgat tccagcagtg    2040
gtcttgctct tactccttt ggttgaacaa gcagcggccc tgggagagcc tcagctctgc    2100
tatatcctgg atgccatcct gtttctgtat ggaattgtcc tcaccctcct ctactgtcga    2160
ctgaagatcc aagtgcgaaa ggcagctata accagctatg agaaatcaag agtgaagttc    2220
tccaggagcg cagatgcccc cgcctatcaa cagggccaga accagctcta caacgagctt    2280
aacctcggga ggcgcgaaga atacgacgtg ttggataaga aaggggggcg ggaccccgag    2340
atgggaggaa agccccggag gaagaaccct caggagggcc tgtacaacga gctgcagaag    2400
gataagatgg ccgaggccta ctcagagatc gggatgaagg gggagcggcg ccgcgggaag    2460
gggcacgatg ggctctacca ggggctgagc acagccacaa aggacacata cgacgccttg    2520
cacatgcagg cccttccacc ccggtga                                       2547
```